(12) United States Patent
Jones et al.

(10) Patent No.: US 10,894,787 B2
(45) Date of Patent: Jan. 19, 2021

(54) MODULATORS OF THE GPR119 RECEPTOR AND THE TREATMENT OF DISORDERS RELATED THERETO

(75) Inventors: Robert M. Jones, San Diego, CA (US); Juerg Lehmann, San Diego, CA (US); Weichao Chen, San Diego, CA (US); Jeffrey Edwards, San Diego, CA (US); Glen Marquez, San Jose, CA (US); Michael E. Morgan, San Diego, CA (US); Abu J. M. Sadeque, San Diego, CA (US); Sun Hee Kim, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 1838 days.

(21) Appl. No.: 13/825,601

(22) PCT Filed: Sep. 21, 2011

(86) PCT No.: PCT/US2011/052478
§ 371 (c)(1),
(2), (4) Date: Nov. 8, 2013

(87) PCT Pub. No.: WO2012/040279
PCT Pub. Date: Mar. 29, 2012

(65) Prior Publication Data
US 2014/0051629 A1 Feb. 20, 2014

Related U.S. Application Data

(60) Provisional application No. 61/385,410, filed on Sep. 22, 2010, provisional application No. 61/478,262, filed on Apr. 22, 2011.

(51) Int. Cl.
*A61K 38/00* (2006.01)
*C07D 413/14* (2006.01)
*A61K 31/506* (2006.01)
*A61K 45/06* (2006.01)

(52) U.S. Cl.
CPC .......... *C07D 413/14* (2013.01); *A61K 31/506* (2013.01); *A61K 45/06* (2013.01)

(58) Field of Classification Search
None
See application file for complete search history.

(56) References Cited

U.S. PATENT DOCUMENTS

| | | |
|---|---|---|
| 3,503,963 A | 3/1970 | Schweizer et al. |
| 3,592,932 A | 7/1971 | Duerr et al. |
| 3,598,801 A | 8/1971 | Beffa et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,948,914 A | 4/1976 | Fischer |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,101,541 A | 7/1978 | Petipierre et al. |
| 4,139,705 A | 2/1979 | Dunbar et al. |
| 4,189,427 A | 2/1980 | Komorowski |
| 4,189,579 A | 2/1980 | Dunbar et al. |
| 4,242,507 A | 12/1980 | Itoh et al. |
| 4,267,174 A | 5/1981 | Berger et al. |
| 4,273,870 A | 6/1981 | Endo et al. |
| 4,275,148 A | 6/1981 | Endo et al. |
| 4,343,804 A | 8/1982 | Munison et al. |

(Continued)

FOREIGN PATENT DOCUMENTS

| | | |
|---|---|---|
| AT | 327605 | 6/2006 |
| AU | 492126 | 11/1975 |

(Continued)

OTHER PUBLICATIONS

The Pocket Oxford American Dictionary of Current English, "Advise" and "Prescribe" Oxford University Press, New York: 2002, pp. 11 and 623.*
"Glucose Metabolism Disorders" http://www.nlm.nih.gov/cgi/mesh/2011/MB_cgi?mode=&term=Glucose+Metabolism+Disorders&field=entry, accessed Jan. 11, 2011, 3 pp.
Abbott et al., "Blockade of the neuropeptide Y Y2 receptor with the specific antagonist BIIE0246 attenuates the effect of endogenous and exogenous peptide YY (3-36) on food intake," *Brain Res.*, 2005, 1043, 139-144.
Abdalla et al., "Synthesis and reaction of 3-cyano 2-(1H)-pyridones," *Pakistan J. Sci. Indus. Res.*, 1977, 30(3), 139-149.

(Continued)

*Primary Examiner* — Jeanette M Lieb
(74) *Attorney, Agent, or Firm* — Fish & Richardson P.C.

(57) ABSTRACT

The present invention relates to the GPR119 receptor agonists: 3-fluoro-4-(5-fluoro-6-(4-3-(2-fluoropropan-2-yl)-1,2,4-oxadiazol-5-yl)piperidin-1-yl)pyrimidin-4-ylamino)-N,N-imethylbenzamide; 3-fluoro-4-(5-fluoro-6-(4-(3-(2-fluoropropan-2-yl)-1,2,4-oxadiazol-5-yl)piperidin-1-yl) pyrimidin-4-ylamino)-N-methylbenzamide; and 3-fluoro-4-(5-fluoro-6-(4-(3-(2-fluoropropan-2-yl)-1,2,4-oxadiazol-5-yl)piperidin-1-yl)pyrimidin-4-ylamino)benzamide, and pharmaceutically acceptable salts, solvates, and hydrates thereof, that are useful as a single pharmaceutical agent or in combination with one or more additional pharmaceutical agents, such as, a DPP-IV inhibitor, a biguanide, an alpha-glucosidase inhibitor, an insulin analogue, a sulfonylurea, an SGLT2 inhibitor, a meglitinide, a thiazolidinedione, or an anti-diabetic peptide analogue, in the treatment of, for example, a disorder selected from: a GPRI19-receptor-related disorder; a condition ameliorated by increasing secretion of an incretin; a condition ameliorated by increasing a blood incretin level; a condition characterized by low bone mass; a neurological disorder; a metabolic-related disorder; type 2 diabetes; obesity; and complications related thereto.

35 Claims, 11 Drawing Sheets

(56) References Cited

U.S. PATENT DOCUMENTS

| | | |
|---|---|---|
| 4,397,848 A | 8/1983 | Bosies et al. |
| 4,493,726 A | 1/1985 | Burdeska et al. |
| 4,517,183 A | 5/1985 | Bosies et al. |
| 4,643,995 A | 2/1987 | Engel et al. |
| 4,766,213 A | 8/1988 | Juraszyk et al. |
| 4,880,932 A | 11/1989 | Moriya et al. |
| 5,571,815 A | 11/1996 | Schaper et al. |
| 5,624,941 A | 4/1997 | Barth et al. |
| 5,691,364 A | 11/1997 | Buckman et al. |
| 5,849,759 A | 12/1998 | Arnaiz et al. |
| 5,948,786 A | 9/1999 | Fujwara et al. |
| 5,952,504 A | 9/1999 | Yoo et al. |
| 5,962,479 A | 10/1999 | Chen |
| 6,008,234 A | 12/1999 | Kochanny et al. |
| 6,060,478 A | 5/2000 | Gilligan |
| 6,107,301 A | 8/2000 | Aldrich et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,267,985 B1 | 7/2001 | Chen et al. |
| 6,294,671 B1 | 9/2001 | Frietze |
| 6,350,750 B1 | 2/2002 | Den Hartog et al. |
| 6,414,002 B1 | 7/2002 | Cheng et al. |
| 6,506,762 B1 | 1/2003 | Horvath et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,552,192 B1 | 4/2003 | Hanus et al. |
| 6,569,879 B2 | 5/2003 | Liu et al. |
| 6,583,154 B1 | 6/2003 | Norman et al. |
| 6,620,821 B2 | 9/2003 | Robl et al. |
| 6,660,744 B1 | 12/2003 | Hirst et al. |
| 6,713,508 B2 | 3/2004 | Sahoo et al. |
| 6,787,542 B2 | 9/2004 | Wang et al. |
| 6,844,351 B1 | 1/2005 | Chen et al. |
| 6,849,636 B2 | 2/2005 | Waddell et al. |
| 6,956,047 B1 | 10/2005 | Chen et al. |
| 7,056,942 B2 | 6/2006 | Hildeasheim et al. |
| 7,057,046 B2 | 6/2006 | Sher et al. |
| 7,083,933 B1 | 8/2006 | Griffin |
| 7,098,235 B2 | 8/2006 | Sher et al. |
| 7,132,426 B2 | 11/2006 | Jones et al. |
| 7,276,249 B2 | 10/2007 | Ryde et al. |
| 7,417,039 B2 | 8/2008 | Davis |
| 7,425,630 B2 | 9/2008 | Gharbaoui et al. |
| 7,470,699 B2 | 12/2008 | Jones et al. |
| 7,625,906 B2 | 12/2009 | Jones et al. |
| 7,763,278 B2 | 7/2010 | Cooper et al. |
| 7,812,159 B2 | 10/2010 | Gharbaoui et al. |
| 7,838,525 B2 | 11/2010 | Jones et al. |
| 8,293,751 B2 | 10/2012 | Jones et al. |
| 8,362,248 B2 | 1/2013 | Jones et al. |
| 8,410,119 B2 | 4/2013 | Jones et al. |
| 2002/0058026 A1 | 5/2002 | Hammerly |
| 2002/0137755 A1 | 9/2002 | Bilodeau et al. |
| 2002/0156081 A1 | 10/2002 | Hirst et al. |
| 2003/0224058 A1 | 12/2003 | Ryde et al. |
| 2004/0110241 A1 | 6/2004 | Segal |
| 2005/0043327 A1 | 2/2005 | Coe et al. |
| 2005/0070562 A1 | 3/2005 | Jones et al. |
| 2005/0182067 A1 | 8/2005 | Balan et al. |
| 2005/0197353 A1 | 9/2005 | Ritzeler et al. |
| 2005/0209251 A1 | 9/2005 | Linker et al. |
| 2006/0154866 A1 | 7/2006 | Chu et al. |
| 2006/0155128 A1 | 7/2006 | Jones et al. |
| 2006/0217379 A1 | 9/2006 | Jones et al. |
| 2007/0066590 A1 | 3/2007 | Jones et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0167413 A1 | 7/2007 | Srinivas et al. |
| 2007/0167473 A1 | 7/2007 | Jones et al. |
| 2007/0225351 A1 | 9/2007 | Tuomilehto et al. |
| 2007/0259928 A1* | 11/2007 | Yoshida et al. ............... 514/359 |
| 2009/0036434 A1 | 2/2009 | Jones et al. |
| 2009/0203676 A1 | 8/2009 | Barba et al. |
| 2009/0270409 A1 | 10/2009 | Alper et al. |
| 2009/0286816 A1 | 11/2009 | Jones et al. |
| 2010/0004272 A1 | 1/2010 | Jones et al. |
| 2010/0029650 A1 | 2/2010 | Fang et al. |
| 2010/0160359 A1 | 6/2010 | Jones et al. |
| 2011/0082134 A1 | 4/2011 | Jones et al. |
| 2011/0112060 A1 | 5/2011 | Jones et al. |
| 2011/0230457 A1 | 9/2011 | Berghausen et al. |
| 2012/0016119 A1 | 1/2012 | Tsubol et al. |
| 2013/0023494 A1 | 1/2013 | Jones et al. |
| 2013/0023527 A1 | 1/2013 | Jones et al. |

FOREIGN PATENT DOCUMENTS

| | | |
|---|---|---|
| BE | 829845 | 12/1975 |
| BE | 868796 | 1/1979 |
| CA | 2499497 | 4/2004 |
| CH | 560197 | 3/1975 |
| CN | 1212117 C | 7/2005 |
| DE | 2048375 | 4/1971 |
| DE | 2223644 | 11/1972 |
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| DE | 19602095 | 7/1997 |
| DE | 19737723 | 2/1999 |
| DE | 19962936 | 6/2001 |
| EP | 0014976 | 9/1980 |
| EP | 0053678 | 10/1981 |
| EP | 0050671 | 5/1982 |
| EP | 0055693 | 7/1982 |
| EP | 0123402 | 10/1984 |
| EP | 0149088 | 12/1984 |
| EP | 0154190 | 9/1985 |
| EP | 0191603 | 8/1986 |
| EP | 0193249 | 9/1986 |
| EP | 0283261 | 9/1988 |
| EP | 0324426 | 7/1989 |
| EP | 0518675 | 12/1992 |
| EP | 0526004 | 2/1993 |
| EP | 0556889 | 8/1993 |
| EP | 0565488 | 10/1993 |
| EP | 0604800 | 7/1994 |
| EP | 0667343 | 8/1995 |
| EP | 0801059 | 10/1997 |
| EP | 0857483 | 8/1998 |
| EP | 0940387 | 9/1999 |
| EP | 1074549 | 2/2001 |
| EP | 1097709 | 5/2001 |
| EP | 1287133 | 3/2003 |
| EP | 1040831 | 5/2003 |
| EP | 1338651 | 8/2003 |
| EP | 1340749 | 9/2003 |
| EP | 1475094 | 11/2004 |
| EP | 1902730 | 3/2008 |
| FR | 1551400 | 12/1968 |
| GB | 935595 | 8/1963 |
| GB | 1250624 | 10/1971 |
| GB | 1311956 | 3/1973 |
| GB | 1393993 | 5/1975 |
| GB | 1493380 | 11/1977 |
| GB | 1495665 | 12/1977 |
| JP | 55-17382 | 2/1980 |
| JP | 61-057587 | 3/1986 |
| JP | 05-33359 | 12/1993 |
| JP | 07-53546 | 2/1995 |
| JP | 11-193277 | 7/1999 |
| JP | 2000-038350 | 2/2000 |
| JP | 2001-089452 | 4/2001 |
| JP | 200467575 A | 3/2004 |
| JP | 2004-269468 | 9/2004 |
| JP | 2004-269469 | 9/2004 |

(56) References Cited

FOREIGN PATENT DOCUMENTS

| | | |
|---|---|---|
| NL | 6614961 | 4/1967 |
| NL | 6814810 | 4/1969 |
| RU | 2067978 | 10/1996 |
| RU | 2119917 | 10/1998 |
| RU | 2153495 | 7/2000 |
| RU | 2158258 | 10/2000 |
| RU | 2198879 | 2/2003 |
| RU | 2200734 | 3/2003 |
| SU | 938 559 | 11/1993 |
| WO | WO 81/03174 | 11/1981 |
| WO | WO 92/01697 | 2/1992 |
| WO | WO 92/12976 | 8/1992 |
| WO | WO 94/07858 | 4/1994 |
| WO | WO 1994/13677 | 6/1994 |
| WO | WO 1995/33750 | 12/1995 |
| WO | WO 1996/28427 | 9/1996 |
| WO | WO 96/33980 | 10/1996 |
| WO | WO 1996/32383 | 10/1996 |
| WO | WO 1996/33994 | 10/1996 |
| WO | WO 96/35689 | 11/1996 |
| WO | WO 1996/36613 | 11/1996 |
| WO | WO 1997/08152 | 3/1997 |
| WO | WO 1997/26252 | 7/1997 |
| WO | WO 97/28137 | 8/1997 |
| WO | WO 1997/29109 | 8/1997 |
| WO | WO 1997/40832 | 11/1997 |
| WO | WO 97/48696 | 12/1997 |
| WO | WO 1997/49706 | 12/1997 |
| WO | WO 1998/04528 | 2/1998 |
| WO | WO 1998/08846 | 3/1998 |
| WO | WO 1998/08847 | 3/1998 |
| WO | WO 1998/11094 | 3/1998 |
| WO | WO 98/13354 | 4/1998 |
| WO | WO 1998/19998 | 5/1998 |
| WO | WO 98/27081 | 6/1998 |
| WO | WO 98/35967 | 8/1998 |
| WO | WO 1998/47874 | 10/1998 |
| WO | WO 1998/47903 | 10/1998 |
| WO | WO 1999/09026 | 2/1999 |
| WO | WO 1999/51599 | 10/1999 |
| WO | WO 2000/11003 | 3/2000 |
| WO | WO 2000/27825 | 5/2000 |
| WO | WO 2000/31068 | 6/2000 |
| WO | WO 2000/31258 | 6/2000 |
| WO | WO 2000/34241 | 6/2000 |
| WO | WO 2000/35875 | 6/2000 |
| WO | WO 2000/35886 | 6/2000 |
| WO | WO 2000/55153 | 9/2000 |
| WO | WO 2001/60807 | 2/2001 |
| WO | WO 2001/22938 | 4/2001 |
| WO | WO 2001/23387 | 4/2001 |
| WO | WO 2001/23388 | 4/2001 |
| WO | WO 2001/25210 | 4/2001 |
| WO | WO 2001/27107 | 4/2001 |
| WO | WO 2001/037831 | 5/2001 |
| WO | WO 2001/046204 | 6/2001 |
| WO | WO 2001/47887 | 7/2001 |
| WO | WO 2001/49677 | 7/2001 |
| WO | WO 2001/53263 | 7/2001 |
| WO | WO 2001/58900 | 8/2001 |
| WO | WO 2001/60870 | 8/2001 |
| WO | WO 2001/62233 | 8/2001 |
| WO | WO 2001/76573 | 10/2001 |
| WO | WO 2001/85699 | 11/2001 |
| WO | WO 2001/87829 | 11/2001 |
| WO | WO 2001/87892 | 11/2001 |
| WO | WO 2001/90082 | 11/2001 |
| WO | WO 2002/02539 | 1/2002 |
| WO | WO 2002/002549 | 1/2002 |
| WO | WO 2002/06237 | 1/2002 |
| WO | WO 2002/006237 | 1/2002 |
| WO | WO 2002/006274 | 1/2002 |
| WO | WO 2002/08188 | 1/2002 |
| WO | WO 2002/45652 | 2/2002 |
| WO | WO 2002/019975 | 3/2002 |
| WO | WO 2002/24169 | 3/2002 |
| WO | WO 2002/032408 | 4/2002 |
| WO | WO 2002/032893 | 4/2002 |
| WO | WO 2002/040451 | 5/2002 |
| WO | WO 2002/040456 | 5/2002 |
| WO | WO 2002/040458 | 5/2002 |
| WO | WO 2002/40480 | 5/2002 |
| WO | WO 2002/040480 | 5/2002 |
| WO | WO 2002/044362 | 6/2002 |
| WO | WO 2002/045652 | 6/2002 |
| WO | WO 2002/050071 | 6/2002 |
| WO | WO 2002/059083 | 8/2002 |
| WO | WO 2002/060388 | 8/2002 |
| WO | WO 2002/064094 | 8/2002 |
| WO | WO 2002/070485 | 9/2002 |
| WO | WO 2002/072101 | 9/2002 |
| WO | WO 2002/081454 | 10/2002 |
| WO | WO 2002/85892 | 10/2002 |
| WO | WO 2002/098864 | 12/2002 |
| WO | WO 2002/098878 | 12/2002 |
| WO | WO 2002/102313 | 12/2002 |
| WO | WO 2003/000666 | 1/2003 |
| WO | WO 2003/002544 | 1/2003 |
| WO | WO 2003/004498 | 1/2003 |
| WO | WO 2003/018556 | 3/2003 |
| WO | WO 2003/026661 | 4/2003 |
| WO | WO 2003/032989 | 4/2003 |
| WO | WO 2003/050117 | 6/2003 |
| WO | WO 2003/051822 | 6/2003 |
| WO | WO 2003/057689 | 7/2003 |
| WO | WO 2003/059378 | 7/2003 |
| WO | WO 2003/061663 | 7/2003 |
| WO | WO 2003/076418 | 9/2003 |
| WO | WO 2003/077656 | 9/2003 |
| WO | WO 2003/080070 | 10/2003 |
| WO | WO 2003/087064 | 10/2003 |
| WO | WO 2003/088962 | 10/2003 |
| WO | WO 2003/093269 | 11/2003 |
| WO | WO 2003/094845 | 11/2003 |
| WO | WO 2003/103632 | 12/2003 |
| WO | WO 2003/103633 | 12/2003 |
| WO | WO 2003/103640 | 12/2003 |
| WO | WO 2003/104208 | 12/2003 |
| WO | WO 2003/105763 | 12/2003 |
| WO | WO 2003/106450 | 12/2003 |
| WO | WO 2004/000762 | 12/2003 |
| WO | WO 2004/000819 | 12/2003 |
| WO | WO 2004/000843 | 12/2003 |
| WO | WO 2004/002495 | 1/2004 |
| WO | WO 2004/004777 | 1/2004 |
| WO | WO 2004/004778 | 1/2004 |
| WO | WO 2004/009596 | 1/2004 |
| WO | WO 2004/009597 | 1/2004 |
| WO | WO 2004/009602 | 1/2004 |
| WO | WO 2004/010936 | 2/2004 |
| WO | WO 2004/010992 | 2/2004 |
| WO | WO 2004/013633 | 2/2004 |
| WO | WO 2004/014871 | 2/2004 |
| WO | WO 2004/017896 | 3/2004 |
| WO | WO 2004/019869 | 3/2004 |
| WO | WO 2004/020408 | 3/2004 |
| WO | WO 2004/020409 | 3/2004 |
| WO | WO 2004/024943 | 3/2004 |
| WO | WO 2004/029204 | 4/2004 |
| WO | WO 2004/031189 | 4/2004 |
| WO | WO 2004/033431 | 4/2004 |
| WO | WO 2004/033710 | 4/2004 |
| WO | WO 2004/035588 | 4/2004 |
| WO | WO 2004/037823 | 5/2004 |
| WO | WO 2004/041164 | 5/2004 |
| WO | WO 2004/056748 | 7/2004 |
| WO | WO 2004/056825 | 7/2004 |
| WO | WO 2004/056829 | 7/2004 |
| WO | WO 2004/058174 | 7/2004 |
| WO | WO 2004/058727 | 7/2004 |
| WO | WO 2004/062665 | 7/2004 |
| WO | WO 2004/065380 | 8/2004 |
| WO | WO 2004/066963 | 8/2004 |
| WO | WO 2004/074218 | 9/2004 |

(56) References Cited

FOREIGN PATENT DOCUMENTS

| | | |
|---|---|---|
| WO | WO 2004/076413 | 9/2004 |
| WO | WO 2004/085401 | 10/2004 |
| WO | WO 2004/098583 | 11/2004 |
| WO | WO 2004/099144 | 11/2004 |
| WO | WO 2004/103997 | 12/2004 |
| WO | WO 2004/110368 | 12/2004 |
| WO | WO 2004/111000 | 12/2004 |
| WO | WO 2005/007647 | 1/2005 |
| WO | WO 2005/007658 | 1/2005 |
| WO | WO 2005/016894 | 2/2005 |
| WO | WO 2005/020920 | 3/2005 |
| WO | WO 2005/025554 | 3/2005 |
| WO | WO 2005/026148 | 3/2005 |
| WO | WO 2005/030127 | 4/2005 |
| WO | WO 2005/030129 | 4/2005 |
| WO | WO 2005/030751 | 4/2005 |
| WO | WO 2005/033099 | 4/2005 |
| WO | WO 2005/035525 | 4/2005 |
| WO | WO 2005/037215 | 4/2005 |
| WO | WO 2005/023762 | 5/2005 |
| WO | WO 2005/040095 | 5/2005 |
| WO | WO 2005/042488 | 5/2005 |
| WO | WO 2005/046603 | 5/2005 |
| WO | WO 2005/047297 | 5/2005 |
| WO | WO 2005/049033 | 6/2005 |
| WO | WO 2005/058315 | 6/2005 |
| WO | WO 2005/058849 | 6/2005 |
| WO | WO 2005/061489 | 7/2005 |
| WO | WO 2005/063750 | 7/2005 |
| WO | WO 2005/072530 | 8/2005 |
| WO | WO 2005/075426 | 8/2005 |
| WO | WO 2005/080330 | 9/2005 |
| WO | WO 2005/090348 | 9/2005 |
| WO | WO 2005/100365 | 10/2005 |
| WO | WO 2005/117909 | 12/2005 |
| WO | WO 2005/121121 | 12/2005 |
| WO | WO 2006/034446 | 3/2006 |
| WO | WO 2006/039325 | 4/2006 |
| WO | WO 2006/040966 | 4/2006 |
| WO | WO 2006/043490 | 4/2006 |
| WO | WO 2006/047516 | 5/2006 |
| WO | WO 2006/050946 | 5/2006 |
| WO | WO 2006/052566 | 5/2006 |
| WO | WO 2006/067531 | 6/2006 |
| WO | WO 2006/067532 | 6/2006 |
| WO | WO 2006/070208 | 7/2006 |
| WO | WO 2006/076231 | 7/2006 |
| WO | WO 2006/076243 | 7/2006 |
| WO | WO 2006/076455 | 7/2006 |
| WO | WO 2006/078992 | 7/2006 |
| WO | WO 2006/083491 | 8/2006 |
| WO | WO 2007/003964 | 1/2007 |
| WO | WO 2007/005673 | 1/2007 |
| WO | WO 2007/035355 | 3/2007 |
| WO | WO 2007/039470 | 4/2007 |
| WO | WO 2007/089335 | 8/2007 |
| WO | WO 2007/120689 | 10/2007 |
| WO | WO 2007/120702 | 10/2007 |
| WO | WO 2008/005569 | 1/2008 |
| WO | WO 2008/005576 | 1/2008 |
| WO | WO 2008/008895 | 1/2008 |
| WO | WO 2008/025798 | 3/2008 |
| WO | WO 2008/070692 | 6/2008 |
| WO | WO 2008/076243 | 6/2008 |
| WO | WO 2008/128832 | 10/2008 |
| WO | WO 2008/137435 | 11/2008 |
| WO | WO 2009/038974 | 3/2009 |
| WO | WO 2009/125434 | 10/2009 |
| WO | WO 2009/126245 | 10/2009 |
| WO | WO 2009/126535 | 10/2009 |
| WO | WO 2010/074271 | 7/2010 |
| WO | WO 2010/075271 | 7/2010 |
| WO | WO 2010/075273 | 7/2010 |
| WO | WO2010084944 A1 | 7/2010 |
| WO | WO 2011/005929 | 1/2011 |
| WO | WO 2011/008663 | 1/2011 |
| WO | WO 2011/030139 | 3/2011 |
| WO | WO 2011/127051 | 10/2011 |
| WO | WO 2012/040279 | 3/2012 |
| WO | WO 2012/135570 | 10/2012 |
| WO | WO 2012/145361 | 10/2012 |
| WO | WO 2012/145603 | 10/2012 |
| WO | WO 2012/145604 | 10/2012 |
| WO | WO 2012/170702 | 12/2012 |
| WO | WO 2013/055910 | 4/2013 |

OTHER PUBLICATIONS

Abe et al., "First Synthesis and Determination of the Absolute Configuration of Sulphostin, a Novel Inhibitor of Dipeptidyl Peptidase IV," *J. Nat. Prod.*, 2004, 67, 999-1004.

Abramovitch et al., "Solution and flash vacuum pyrolysis of some 2.6-disubstituted B-phenethylsulfonyl azides and of (B-styrenesulfonyl azide," *J. Org. Chem.*, 1985, 50, 2066-2073.

Abstract #107, p. 56, *Toward Understanding Islet Biology*, Jan. 21, 2003-Jan. 26, 2003, Keystone, Colorado, 2 pp.

Abstract #112, p. 42, Diabetes Mellitus: Molecular Mechanisms, Genetics and New Therapies, Jan. 27, 2005-Feb. 2, 2005, Keystone, Colorado, 2 pp.

Abstract #117 & Poster, Diabetes: Molecular Genetics, Signaling Pathways and Integrated Physiology, Jan. 14, 2007-Jan. 19, 2007, Keystone, Colorado, 3 pp.

Abstract #228, p. 54, Diabetes Mellitus: Molecular Mechanisms, Genetics and New Therapies, Jan. 27, 2005-Feb. 2, 2005, Keystone, Colorado, 2 pp.

Abstract #230 & Poster, Diabetes: Molecular Genetics, Signaling Pathways and Integrated Physiology, Jan. 14, 2007-Jan. 19, 2007, Keystone, Colorado, 6 pp.

Accession No. 2003, 2415108 CHEMCATS, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1, 1 page.

Accession No. 2003, 2415906 CHEMCATS, Interbioscreen Compound Library, Chemical Name: 1H-Pyrazolo[3,4-d]pyrimidine-4-amine, N-cyclohexyl-1-1-(4-methylphenyl)-, XP-002311325, 2003, CAS Registry No. 393844-89-8, 1 page.

Accession No. 2003, 2416398 CHEMCATS, Interbioscreen Compound Library, Chemical Name: 1H-Pyrazolo[3,4-d]pyrimidine-4-amine, N-cyclohexyl-1-1-(2,4-dimethylphenyl)-N-methyl-, XP-002311324, 2003, CAS Registry No. 393844-91-2, 1 page.

Accession No. 2003, 2417080 CHEMCATS, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6, 1 page.

Adrian et al., "Human Distribution and Release of a Putative New Gut Hormone, Peptide YY," *Gastroenterol.*, 1985, 89(5), 1070-1077.

Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," *Endocrinol.*, 2005, 146, 2055-2059.

Ahren et al., "Inhibition of Dipeptidyl Peptidase-4 Reduces Glycemia, Sustains Insulin Levels, and Reduces Glucagon Levels in Type 2 Diabetes," *J. Clin. Endocrinol. Metab.*, 2004, 89, 2078-2084.

Ahren et al., "Inhibition of Dipeptidyl Peptidase IV Improves Metabolic Control Over a 4-week Study Period in Type 2 Diabetes," *Diabetes Care*, 2002, 25, 869-875.

American Diabetes Association, "Hyperglycemia (High blood glucose)," downloaded from http://www.diabetes.org/living-with-diabetes/treatment-and-care/blood-glucose-control/hyperglycemia.html?print=t on Jan. 28, 2011, 2 pp.

Appukkuttan et al., "Translation-Metal-Free Sonogashira-Type Coupling Reactions in Water," *Eur. J. Org. Chem.*, 2003, 24, 4713-4716.

Arehart et al., "Acceleration of Cardiovascular Disease by a Dysfunctional Prostacyclin Receptor Mutation—Potential Implications for Cyclooxygenase-2 Inhibition," *Circ. Res.*, 2008, 102, 986-993.

(56) References Cited

OTHER PUBLICATIONS

Arvanitis et al., "CRF Ligands via Suzuki and Negishi couplings of 3-pyridyl boronic acids or halides with 2-benzyloxy-4-chloro-3-nitropyridione," *Bioorg. Med. Chem. Lett.*, 2003, 13(2), 289-291.
Arvanitis et al., "Imidazo[4,5-b]pyridines as corticotropin releasing factor receptor ligands," *Bioorg. Med. Chem. Lett.*, 2003, 12(1), 125-128.
Arvanitis et al., "Non-peptide corticotropin-releasing hormone antagonists; syntheses and structure-activity relationships of 2-anilinopyrimidines and triazines," *J. Med. Chem.*, 1999, 42(5), 805-18.
Arvanitis et al., Supporting Information for Arvantis et al., "Non-peptide corticotropin-releasing hormone antagonists; syntheses and structure-activity relationships of 2-anilinopyrimidines and triazines," *J. Med. Chem.*, 1999, 42(5), 805-18 (10 pp.).
Arvela et al., "Rapid cyanation of aryl iodides in water using microwave promotion," *Org. Biomol. Chem.*, 2003, 1, 1119-1121.
Arvela et al., "Rapid, Easy Cyanation of Aryl Bromides and Chlorides Using Nickel Salts in Conjunction with Microwave Promotion," *J. Org. Chem.*, 2003, 68, 9122-9125.
Baindur et al., "Solution-Phase Synthesis of a Library of 3,5,7-Trisubstituted 3H-[1,2,3]triazolo[4,5-Id]pyrimidines," *J. Comb. Chem.*, 2003, 5, 653-659.
Bakkestuen et al., "Regioselective N-9 arylation of purines employing arylboronic acids in presence of Cu(III)," *Tetrahedron Lett.*, 2003, 44, 3359-3362.
Balasubramaniam et al., "Neuropeptide Y (NPY) Y2 receptor-selective agonist inhibits food intake and promotes fat metabolism in mice: Combined anorectic effects of Y2 and Y4 receptor-selective agonists," *Peptides*, 2007, 28, 235-240.
Balasubramaniam et al., "Structure-Activity Studies Including a (CH—NH) Scan of Peptide YY (PYY) Active Site, PYY(22-36), for Interaction with Rat Intestinal PYY Receptors: Development of Analogues with Potent in Vivo Activity in the Intestine," *J. Med. Chem.*, 2000, 43, 3420-3427.
Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions," *Tetrahedron*, 2002, 58, 7607-7611.
Barta et al., "Synthesis and activity of selective MMP inhibitors with an aryl backbone," *Bioorg. Med. Chem. Lett.*, 2000, 10(24), 2815-2817.
Baskin et al., "A mild, convenient synthesis of sulfinic acid salts and sulfonamides from alkyl and acyl halides," *Tetrahedron Lett.*, 2002, 43, 8479-8483.
Baskin et al., "An Efficient Copper Catalyst for the Formation of Sulfones from Sulfuric Acid Salts and Aryl Iodides," *Org. Lett.*, 2002, 4(25) 4423-4425, Supporting Material #1.
Baskin et al., "An Efficient Copper Catalyst for the Formation of Sulfones from Sulfuric Acid Salts and Aryl Iodides," *Org. Lett.*, 2002, 4(25) 4423-4425, Supporting Material #2.
Baskin et al., "An Efficient Copper Catalyst for the Formation of Sulfones from Sulfuric Acid Salts and Aryl Iodides," *Org. Lett.*, 2002, 4(25) 4423-4425.
Batterham et al., "Gut hormone PYY3-36 physiologically inhibits food intake," *Nature*, 2002, 418, 650-654.
Bedford et al., "Nonquaternary cholinesterase reactivators. 3.3(5)-Substituted 1,2,4-oxadiazol-5(3)-aldoximes and 1,2,4-oxadiazole-5(3)-thiocarbohydroximates as reactivators of organophsphonate-inhibited eel and hunan acetylcholinesterase in vitro," *J. Med. Chem.*, 1986, 29(11), 2174-2183.
Behre, "Adiponectin, obesity and atherosclerosis," *Scand. J. Clin. Lab. Invest.*, 2007, 67, 449-458.
Beller et al., Based-catalyzed amination of olefins; an example of an environmentally friendly synthesis of amines, *Chemosphere*, 2001, 43(1), 21-26.
Berge et al., "Pharmaceutical Salts," *J. Pharm. Sci.*, 1977, 66(1), 1-19.
Betti, et al., "Novel 3-Aralkyl-7 (amino-substituted)-1,2,3-triazole[4,5-d]primidines with High Affinity toward A1 Adenosine Receptors," *J. Med. Chem.*, 1998, 41, 668-673.
Biagi et al., "5,5,6-trisubstituted 2-phenylpyrimidines and their affinity towards A1 adenosine receptors," *Farmaco*, 1997, 52(1), 61-65.
Bilchik et al., "Peptide YY is a Physiological Regulator of Water and Electrolyte Absorption in the Canine Small Bowel in Vivo," *Gastroenterol.*, 1993, 105, 1441-1448.
Boey et al., "Peptide YY ablation in mice leads to the development of hyperinsulinaemia and obesity," *Diabetologia*, 2006, 49, 1360-1370.
Boey et al., "PYY transgenic mice are protected against diet-induced and genetic obesity," *Neuropeptides*, 2008, 42, 19-30.
Boldt et al., "Synthesis of 2,4-diaminopyridines," *Angew. Chem. Int. Ed.*, 1970, 9(5), 377.
Bollag et al., "Glucose-dependent insulinotropic peptide is an integrative hormone with osteotropic effects," *Mol. Cell. Endocrinol.*, 2001, 177, 35-41.
Bollag et al., "Osteoblast-Derived Cells Express Functional Glucose-Dependent Insulinotropic Peptide Receptors," *Endocrinol.*, 2000, 141, 1228-1235.
Bomika et al., Translation of "Certain reactions of nucleophilic substitution in the 2-chloro-3-cyanopyridine series," *Khimiya Geterotsiklicheskikh Soedinenii*, 1976, (8) 1085-1088 (Translated pp. 896-899).
Boschelli et al., "1,3,4-Oxadiazole, 134-thiadiazole, and 1,2,4-triazole analogs of the fenamates: in vitro inhibition of cyclooxygenase activities," *J. Med. Chem.*, 1953, 36, 1802-1810.
Boswell et al., "Synthesis of Some N-carboxylic acid derivatives of phenoxypyrrolidines, 4-phenoxypiperidines, and 3-phpenoxynortropanes with muscle relaxant and anticonvulsant activities," *J. Med. Chem.*, 1974, 17(9), 100-1008.
Bradley, "TNF-mediated inflammatory disease," *J. Pathol.*, 2008, 214, 149-160.
Brancati et al., "Body Weight Patterns from 20 to 49 Years of Age and Subsequent Risk for Diabetes Mellitus: The Johns Hopkins Precursors Study," *Arch. Intern. Med.*, 1999, 159, 957-963.
Bromidge et al., "Design of [R-(Z)-]-(+)-alpha-(methoxylmino)-1azabicyclo[2.2.2]octane-3-acetonitri le (SB 202026), a functionally selective azabicyclic muscarinic M1 against incorporating the N-methoxy imidoyl nitrile group as a novel ester bioisostere," *J. Med. Chem.*, 1997, 40(26), 4265-4280.
Buehler et al., "Physiologically active compounds. VI. Cyclic amino thiolesters of substituted chloracetic, benzilic and glycolic acids," *J. Med. Chem.*, 1965, 8, 643-647.
Bulger et al., "An investigation into the alkylation of 1,2,4-triazole," *Tetrahedron Lett.*, 2000, 41, 1297-1301.
Caldwell et al., "Fluoropyrrolidine amides as dipeptidyl peptidase IV inhibitors," *Bioorg. Med.*, 2004, 14, 1265-1268.
Chan et al., "Isoquinoline-6-Carboxamides as Potent and Selective Anti-Human Cytomegalovirus (HCMV)Inhibitors," *Bioorg. Med. Chem. Lett.*, 1999, 9, 2583-2586.
Chaudhri et al., "Gastrointestinal Satiety Signals," *Ann. Rev. Physiol.*, 2008, 70, 239-255.
Chen et al., "Design and Synthesis of a Series of Non-Peptide High Affinity Human Corticotropin-Releasing Factor 1 Receptor Antagonists," *J. Med. Chem.*, 1996, 39, 4358-4360.
Chen et al., "Free Radical Method for the Synthesis of Spiro-Piperidinyl Heterocycles," *Tetrahedron Lett.*, 1996, 37(3), 5233-5234.
Chen et al., "Optimization of 3-phyenylprazolo[1,5-alpha]pyrimidines as potent corticotrophin-releasing factor-I antagonists with adequate lipophilicity and water solubility," *Bioorg. Med. Chem. Lett.*, 2004, 14, 3669-3673.
Chorvat et al., "Synthesis, Corticotropin-Releasing Factor Receptor Binding Affinity, and Pharmacokinetic Properties of Triazolo-, Imidazo-, and Pyrrolopyrimidines and -pyridines," *J. Med. Chem.*, 1999, 42, 833-848.
Chu et al., "A Role for Intestinal Endocrine Cell-expressed GPR119 in Glycemic Control by Enhancing GLP-1 and GIP Release," *Endocrinol.*, 2008, 149(5), 2038-2047.

(56) References Cited

OTHER PUBLICATIONS

Chu et al., "A role for β-cell-expressed G protein-coupled receptor 119 in glycemic control by enhancing glucose-dependent insulin release," *Endocrinol.*, 2007, 148, 2601-2609.

Clark et al., "Synthesis and Analgesic Activity of 1,3-Dihydro-3-(Substituted phenyl)imidazo(4,5-b]pyridine-2-ones and 3-(Substituted phenyl)-1,2,3-triazolo(4,5bpyridines," *J. Med. Chem.*, 1978, 21(9), 965-978.

Cocco et al., "Transformation of 6-Methylthiopyrimidines," *J. Het. Chem.*, 2000, 37(4), 707-710.

Cocuzza et al., "Use of the Suzuki Reaction for the Synthesis of Aryl-Substituted Heterocycles as Corticotropin-Releasing Hormone (CRH) Antagonists," *Bioorg. Med. Chem. Lett.*, 1999, 9, 1063-1066.

Cohen et al., "The Preparation and Properties of 6-Halomethylpurines," *J. Org. Chem.*, 1962, 27, 3545-3549.

Colandrea et al., "Synthesis and regioselective alkylation of 1,6- and 1,7-naphythridines," *Tetrahedron Lett.*, 2000, 41, 8053-8057.

Collier et al., "Radiosynthesis and in-vivo evaluation of the pseudopeptide 8-opioid antagonist [$^{125}$I] ITIPP(Ψ)," *J. Labeled Comp. Radiopharm.*, 1999, 42(Suppl. 1), S264-S266.

Cossey et al., "Amide-acid chloride adducts. VI. Pyridines and pyridinium salts from cyanoacetamides," *Aus. J. Chem.*, 1976, 29(5), 1039-1050.

Cover Sheet and 23 Compounds, ChemCats file, 11 pp., (2006).

Cover Sheet and 1185 Compounds, CAS Registry and ChemCats files (various dates—Jan. 12, 2005-Nov. 10, 2006), 402 pp.

Cover Sheet and 18 Compounds, CAS Registry, 9 pp., (various dates—Aug. 1, 2004-Jan. 13, 2005).

Cover Sheet and 2534 Compounds, CAS Registry and ChemCats files, 817 pp., (various dates—Feb. 7, 2006-Nov. 6, 2006).

Cox, "Peptide YY: A neuroendocrine neighbor of note," *Peptides*, 2007, 28, 345-351.

Cruze et al., "The Y2 receptor mediates increases in collateral-dependent blood flow in a model of peripheral arterial insufficiency," *Peptides*, 2007, 28, 269-280.

Cryan et al., "Behavioral characterization of the novel GABAB receptor-positive modulator GS539783 (N,N'-dicyclopentyl-2-methylsulfanyl-5nitropyrmidine-4,6 diamine): Anxiolytic-like activity without side effects associated with baclofen or benzodiazepines," *J. Pharmacol. Exp. Ther.*, 2004, 310(3), 952-963.

Dai et al., "The first general method for palladium-catalyzed Negishi cross-coupling of aryl and vinyl chlorides: use of commercially available Pd(P(i-Bu)$_3$)$_2$ as a catalyst," *J. Med. Chem. Soc.*, 2001, 123(12), 2179-2724.

Deacon et al., "Degradation of Endogenous and Exogenous Gastric Inhibitory Polypeptide in Healthy and in Type 2 Diabetic Subjects as Revealed Using a New Assay for the Intact Peptide," *J. Clin. Endocrinol. Metab.*, 2000, 85, 3575-3581.

Deacon, "What do we know about the secretion and degradation of incretin hormones?" *Reg. Pept.*, 2005, 128, 117-124.

Demuth et al., "Type 2 diabetes-therapy with dipeptidyl peptidase IV inhibitors," *Biochim. Biophys. Acta*, 2005, 1751, 33-44.

Desimoni et al., "Polynuclear Isoxazole Types-I-Isoxazolo[4,5-d]Pyrimidines," *Tetrahedron*, 1967, 23, 675-680.

Devita et al., "Identification and initial structure-activity relationships of a novel non-peptide quinolone GnRH receptor antagonist," *Bioorg. Med. Chem. Lett.*, 1999, 9(17), 2615-2620.

Di Braccio et al., "Synthesis and preliminary pharmacological examination of 2,4-disubstituted N,N-dialky1-1,8-napthyridine-3-carboxamides," *Farmaco*, 1989, 44(9), 865-881.

Dorwald, "Side Reactions in Organic Synthesis: A Guide to Successful Synthesis Design," 2005, Wiley: VCH, Weinheim, p. IX of Preface. (table of contents).

Drucker, "The biology of incretin hormones," *Cell Metab.*, 2006, 3, 153-165.

Dzierba et al., "Synthesis, Structure-Activity Relationships, and in Vivo Properties of 3,4-Dihydo-1H-pyrido[2,3$_b$]pyrazin-2-ones as Corticotropin-Releasing Factor-1 Receptor Antagonists," *J. Med. Chem.*, 2004, 47(23), 5783-5790.

Eberlein et al., "A New Molecular Form of PYY: Structural Characterization of Human PYY (3-36) and PYY(1-36)," *Peptides*, 1989, 10, 797-803.

Edmondson et al., "Potent and selective proline derived dipeptidyl peptidase IV inhibitors," *Bioorg. Med. Chem. Lett.*, 2004, 14, 5151-5155.

Eicher et al., "Reaction of trialfulvenes with isonitriles. A simple synthesis of diphenyl-substituted functionalized cyclobutene derivatives and related products," *Synthesis*, 1987, 7, 619-626.

Ekblad et al., "Distribution of pancreatic polypeptide and peptide YY," *Peptides*, 2002, 23, 251-261.

Ekstrand et al., "Deletion of neuropeptide Y (NPY) 2 receptor in mice results in blockage of NPY-induced angiogenesis and delayed wound healing," *Proc. Nat. Acad. Sci. USA*, 2003, 100, 6033-6038.

El Bahh et al., "The anti-epileptic actions of neuropeptide Y in the hippocampus are mediated by Y2 and not Y5 receptors," *Eur. J. Neurosci.*, 2005, 22, 1417-1430.

emedicinehealth.com, "High Blood Sugar", http://www.emedicinehealth.com/high_blood_sugar_hyperglycemia/page9_em.htm, accessed Jul. 1, 2011, 3 pp.

Escher et al., "Cyclopentylamine Substituted Triazolo[4,5-d]Pyrimidine: Implications for Binding to the Adenosine Receptor," *Tetrahedron Lett.*, 1991, 32(29), 3583-3584.

Fyfe et al. "GPR119 agonists as potential new oral agents for the treatment of type 2 diabetes and obesity," *Exp. Opin. Drug Discov.*, 2008, 3(4), 403-413, 11 pp.

Fyfe et al., "GPR119 Agonists are Potential Novel Oral Agents for the Treatment of Diabesity," *Diabetes*, 2007, 56(Suppl. 1), A142 (Abstract #532-P).

Gangloff et al., "Synthesis of 3,5-disubstituted-1,2,4-oxadiazoles using tetrabutylammonium fluoride a mild and efficient catalyst," *Tetrahedron Lett.*, 2001, 42, 1441-1443.

Gilligan et al., "Corticotropin-releasing factor antagonists: Recent advances and exciting prospects for the treatment of human diseases," *Current Opin Drug Discovery & Develop.*, 2004, 7(4), 487-497.

Gilligan, et al., "Corticotropin Releasing Factor (CRF) Receptor Modulators Progress and Opportunities for New Therapeutic Agents," *J. Med. Chem.*, 2000, 43(9), 1641-1660.

Giner-Sorolla et al., "The Synthesis and Properties of 6-Mercaptomethylpurine and Derivatives," *J. Med. Chem.*, 1965, 8, 667-672.

Goldner et al., "Die Darstellung 2,9-; 2,6,9- and 6,9-substituierter Purine," *J. Prakt. Chem. (Leipzig)*, 1961, 12, 242-252.

Gomez et al., "Intestinal peptide YY: ontogeny of gene expression in rat bowel and trophic actions on rat and mouse bowel," *Am. J Physiol.*, 1995, 268, G71-G81.

Gomtsyan et al., "Design, synthesis, and structure-activity relationship of 6-alkynylpyrimidines as potent adenosine kinase inhibitors," *J. Med. Chem.*, 2002, 45(17), 3639-3648.

Gonon et al., "Adiponectin protects against myocardial ischaemia-reperfusion injury via AMP-activated protein kinase, Akt, and nitric oxide," *Cardiovasc. Res.*, 2008, 78, 116-122.

Gottlieb et al., "NMR Chemical Shifts of Common Laboratory Solvents as Trace Impurities" *J. Org. Chem.*, 1997, 62,7512-7515.

Grandt et al., "Two molecular forms of Peptide YY (PYY) are abundant in human blood: characterization of a radioimmunoassay recognizing PYY 1-36 and PYY 3-36," *Regul. Pept.*, 1994, 51,151-159.

Greig et al., "New Therapeutic Strategies and Drug Candidates for Neurodegenerative Diseases," *Ann. NY Acad. Sci.*, 2004, 1035, 290-315.

Grise et al., "Peptide YY Inhibits Growth of Human Breast Cancer in Vitro and in Vivo," *J. Surg. Res.*, 1999, 82, 151-155.

Groger "Moderne methoden der Suzuki-kreuzkupplung: die langerwarteten universellen synthesevarianten mit arylchloriden," *J. Prakt. Chem.*, 2000, 342(4), 334-339.

Guerre-Millo, "Adiponectin: An Update," *Diabetes & Metabolism*, 2008, 34, 12-18.

Hamda et al., "An improved synthesis of arylsulfonyl chlorides from arylhalides," *Synthesis*, 1986, 852-854.

(56) References Cited

OTHER PUBLICATIONS

Hansmann et al., "Pulmonary Arterial Hypertension is Linked to Insulin Resistance and Reversed by Peroxisome Proliferator-Activated Receptor-γ Activation," *Circulation*, 2007, 115, 1275-1284.
Hara et al., "Measurement of the High-Molecular Weight Form a Adiponectin in Plasma is Useful for the Prediction of Insulin Resistance and Metabolic Syndrome," *Diabetes Care*, 2006, 29, 1357-1362.
Hay et al., "Inflammatory Bowel Disease: Costs-of-Illness," *J. Clin. Gastroenterol*, 1992, 14, 309-317.
He et al., "4-(1,3-Dimethozyprop-2-ylamino)-2,7-dimethyl-8-(2,4-diehlorophenyl)-pyrazolo[1,5-al-1,3,5-triazine: A Potent, Orally Bioavailable CRF1 Receptor Antagonist," *J. Med. Chem*., 2000, 43, 449-456.
Hecht et al., "On the 'activation' of cytokines", *J. Biol. Chem*., 1975, 250(18), 7343-7351.
Hersperger et al., "Palladium-Catalyzed Cross-Coupling Reactions for the Synthesis of 6,8-Disubstituted 1,7-Naphthyridines: A Novel Class of Potent and Selective Phosphodiesterase Type 4D Inhibitors," *J. Med. Chem*., 2000, 43, 675-682.
Hill and Peters, "Environmental Contributions to the Obesity Epidemic," *Science*, 1998, 280, 1371-1374.
Hocek et al., "An Efficient Synthesis of 2-Substituted 6-Methylpurine Bases and Nucleosides by Fe- or Pd-Catalyzed Cross-Coupling Reactions of 2,6-Dichloropurines," *J. Org. Chem*., 2003, 68, 5773-5776.
Huang et al., "Synthesis and Antiplatelet Activity of Phenyl Quinolones," *Bioorg. Med. Chem*., 1998, 6, 1657-1662.
Jia et al., "Design, Synthesis and Biological Activity of Novel Non-Amidine Factor Xa Inhibitors. Part 1: P1 Structure-Activity Relationships of the Substituted 1-(2-Naphtyl)-1H-pyrazole-5-carboxylamides," *Bioorg. Med. Chem. Lett*., 2002, 12, 1651-1655.
Jogie et al., "Unusual protein-binding specificity and capacity of aza-arenophilic gels," *J. Mol. Recog*., 1998, 11, 261-262.
Jones and Leonard, "The Emergence of GPR119 Agonists as Anti-Diabetic Agents," *Ann. Rep. Med. Chem*., 2009, 44, 149-170.
Kawase et al., "α-Trifluoromethylated acyloins induce apoptosis in human oral tumor cell lines," *Bioorg. Med. Chem. Lett*., 1999, 9(21), 3113-3118.
Keighley et al. "Inflammatory bowel disease," *Aliment. Pharmacol. Ther*., 2003, 18, 66-70.
Keire et al., "Primary structures of PYY, [Pro34]PYY, and PYY-(3-36) confer different conformations and receptor selectivity," *Am. J. Physiol. Gastrointest. Liver Physiol*., 2000, 279, G126-G131.
Kelley et al., "Benzodiazepine receptor binding activity of 8-substituted-9-(3-substituted-benzyl)-6 dimethylamino)-9H-purines," *Med. Chem*., 1990, 33(1), 196-202.
Kelly et al., "A Synthesis of Aaptamine," *Tetrahedron*, 1985, 41(15), 3033-3066.
Kempson et al., "Fused pyrimidine based inhibitors of phosphodiesterase 7 (PDE7): synthesis and initial structure-activity relationships," *Bioorg. Med. Chem. Lett*., 2005, 15, 1829-1833.
Khattab et al., "Quinolines with heteroatom substituents in position 2 and 4. Nucleophilic substitution of 2,4-dichloro-3-phenylquinolines," *ACH—Models in Chem*., 1994, 131(3-4), 521-527.
Klotzer et al., "Chlorierende formylierungsreaktionen an pyrimidinen," *Monat. Chem*., 1965, 96(5), 1567-1572.
Kotian et al., "Synthesis, ligand binding, and quantitative structure-activity relationship study of 3β-(4'-substituted phenyl)-2β-heterocyclic tropanes: evidence for an electrostatic interaction at the 2β-position," *J. Med. Chem*., 1996, 39(14), 2753-2763.
Krauze et al., "Derivatives of 3-cyano-6-phenyl-4-(3'-pyridyl)-pyridine-2(1H)-thione and their neurotropic activity," *Eur. J. Med. Chem*., 1999, 34(4), 301-310.
Krauze et al., "Synthesis of 3-oxoisothiazolo[5,4-b]pyridines," *Khimiya Geterotsiklicheskikh Soedinenii*, 1982, (4), 508-512.
Kreisberg et al., "Hyperlipidemia (High Blood Fat)", *J. Clin. Endocrinol. Metabol*., 2005, 90, 0, 2 pp.

Kubota et al., "Disruption of Adiponectin Causes Insulin Resistance and Neointimal Formation," *J. Biol. Chem*., 2002, 277, 25863-25866.
Kumegai et al., "Synthesis, SAR and biological activities of CRH1 Receptor: Novel 3- or 4-carbamoyl-1,2,5,6-tetrahydropyridinopyrrolopyrimidine derivative," 4th ACS National Meeting, Aug. 18-22, 2002, Boston, MA. Poster #259.
Lai et al., "A one-pot method for the efficient conversion of aryl-and acyl-substituted methyl alcohols into chlorides," *Synthetic Commun*., 2003, 33(10), 1727-1732.
Lamb et al., "Novel Selective Neuropeptide Y2 Receptor PEGylated Peptide Agonists Reduce Food Intake and Body Weight in Mice," *J. Med. Chem*., 2007, 50, 2264-2268.
Lan, "GPR119 is Required for Physiological Regulation of Glucagon-like Peptide-1 Secretion but not for Metabolic Homeostasis," *J. Endocrinol*., 2009, 201, 219-230.
Lanier et al., "Small molecule corticotrophin-releasing factor antagonists," *Expert Opin. Ther. Patents*, 2002, 12(11), 1619-1630.
Le Bas et al., "Radioiodinated analogs of EP 00652218 for the exploration of the tachykinin NK1 receptor by spect," *J. Labeled Compd. Radiopharm*., 2001, 44, S280-S282.
Le Stunff et al., "Early Changes in Postprandial Insulin Secretion, Not in Insulin Sensitivity, Characterize Juvenile Obesity," *Diabetes*, 1994, 43, 696-702.
Leadbeater et al., "First Examples of Transition-Metal Free Sonogashira-Type Couplings," *Org. Lett*., 2003, 5(21), 3919-3922.
Leadbeater et al., Supplemental Information for Leadbeater et al., First Examples of Transition-Metal Free Sonogashira-Type Couplings, *Org. Lett*., 2003, 5(21), 3919-3922.
Lee et al., "Neuropeptide Y induces ischemia angiogenesis and restores function of ischemic skeletal muscles," *J. Clin. Invest*., 2003, 111, 1853-1862.
Lee et al., "Impaired angiogenesis in neuropeptide Y (NPY)-Y2 receptor knockout mice," *Peptides*, 2003, 24, 99-106.
Lee et al., "Synthesis and biological evaluation of clitocine analogues as adenosine kinase inhibitors," *Bioorg. Med. Chem. Lett*., 2001, 11(18), 2419-2422.
Leese et al., "Potential antipurines. H. Synthesis of 6- and 9-substituted purines and 8-azapurines," *J. Chem. Soc*., 1958, 4107-4110.
Lin et al., "Synthesis and Antitumor Activity of Halogen-Substituted 4-(3,3-Dimethyl-1-triazeno)quinolones," *J. Med. Chem*., 1978, 21(3), 268-272.
Litvak et al., "Polynucleotides and Their Components in the Processes of Aromatic Nucleophilic Substitution: 11.1 Nucleophilic Modification of 3',5'-Bis-O-(a,(β,a',(β-tetrafluoropyrid-y-yl)thymidine," *Russian J. Bioorg. Chem*., 2004, 30(4), 337-343.
Litvinov et at., "Naphthyridines. Structure, physicochemical properties and general methods of synthesis," *Russian Chem. Rev*., 2000, 69(3), 201-220.
Liu et al., "Human Pancreatic Cancer Growth is inhibited by Peptide YY and BIM-43004-1," *J. Surg. Res*., 1995, 58, 707-712.
Liu et al., "Pancreatic Peptide YY mRNA Levels Increase during Adaptation after Small Intestinal Resection," *J. Surg. Res*., 1995, 58, 6-11.
Liu et al., "Peptide YY: A Potential Proabsorptive Hormone for the Treatment of Malabsorptive Disorders," *Am Surg*., 1996, 62, 232-236.
Liu et al., "Y2 receptors decrease human pancreatic cancer growth and intracellular cyclic adenosine monophosphate levels," *Surgery*, 1995, 118, 229-236.
Loupy et al., "Easy and efficient $S_NAr$ Reactions on halopyridines in solvent free conditions," *Heterocycles*, 1991, 32(10), 1947-1952.
Lundberg et al., "Localization of peptide YY (PYY) in gastrointestinal endocrine cells and effects on intestinal blood flow and motility," *Proc. Nat. Acad. Sci. USA*, 1982, 79, 4471-4475.
Luo et al., "Microwave-assisted synthesis of aminopyrimidines," *Tetrahedron Lett*., 2002, 43, 5739-5742.
Ma et al. "Mild Method for Ullmann Coupling Reaction of Amines and Aryl Halides," *Org. Lett*., 2003, 5(14), 2453-2455.
Maccia et al., "New N-n-propyl-substituted 3-aryl- and 3-cyclohexylpiperidines as partial agonists at the D4 dopamine receptor," *J. Med. Chem*., 2003, 46(1), 161-168.

(56) References Cited

OTHER PUBLICATIONS

Madman et al., "2-(2-Hydroxy-3-alkoxyphenyl)-IH-benzimidazole-5-carboxamidine derivatives as potent and selective urokinase-type plasminogen activator inhibitors," *Bioorg. Med. Chem. Lett.*, 2002, 12(15), 2019-2022.
Maeda et al., "Diet-induced insulin resistance in mice lacking adiponectin/ACRP30," *Nat. Med.*, 2002, 8, 731-737.
Majeed, et al., "Stannylation Reactions and Cross-Couplings in Pyrimidines," *Tetrahedron*, 1989, 45(4), 993-1006.
Marso et al., "Low Adiponectin Levels are Associated with Atherogenic Dyslipidemia and Lipid-Rich Plaque in Nondiabetic Coronary Arteries," *Diabetes Care*, 2008, 31, 989-944.
Matsuda et al., "Role of Adiponectin in Preventing Vascular Stenosis," *J. Biol. Chem.*, 2002, 277, 37487-37491.
Matsui et al., "Highly potent inhibitors of TNF-a production. Part II: metabolic stabilization of a newly found chemical lead and conformational analysis of an active diastereoisomer," *Bioorg. Med. Chem.*, 2002, 10(12), 3787-805.
Matsuno et al., "Potent and selective inhibitors of platelet-derived growth factor receptor phosphorylation 3. Replacement of quinazoline moiety and improvement of metabolic polymorphism of 4-[-N-substituted (thio) caramoyl]-1-piperazinyl]-6,7-diamethoxyquinazoline derivatives," *J. Med. Chem.*, 2003, 46(23), 4910-4925.
MayoClinic.com "Obesity: Prevention", http://www.mayoclinic.com/health/obesity/ds00314/dsection-prevention, accessed Dec. 19, 2012, 2 pp.
MayoClinic.com "Obesity: Prevention", http://www.mayoclinic.com/health/obesity/ds00314/dsection-prevention, accessed May 19, 2010, 4 pp.
MayoClinic.com "Type 2 diabetes," downloaded from http, //www.mayoclinic.com/health/type-2-diabetes/DS00585/METHOD=print on Jan. 28, 2011, 14 pp.
McFadden et al., "Peptide YY inhibits the growth of Barrett's esophageal adenocarcinoma in vitro," *Am. J. Surg.*, 2004, 188, 516-519.
McIntosh et al., "Dipeptidyl peptidase IV inhibitors: How do they work as new antidiabetic agents," *Regul. Pept.*, 2005, 128, 159-165.
Mentlein, "Therapeutic assessment of glucagon-like peptide-1 agonists compared with dipeptidyl peptidase IV inhibitors as potential antidiabetic drugs," *Expert Opin. Investig. Drugs*, 2005, 14, 57-64.
Mesguiche et al., "4-Alkoxy-2,6-diaminopyrimidine derivatives: inhibitors of cyclin dependent kinases 1 and 2," *Bioorg. Med. Chem. Lett.*, 2003, 13(2), 217-222.
Metzger et al., "Einstufensynthese von 2,4-Bis(sec-alkylamino-6-halogen-3-pyridincarbonitrilen," *Liebigs Ann. Chem.*, 1980, (6), 946-953.
Mittelbach et al., "Syntheses with nitriles. 60. Preparation of 4-amino-5-cyano-6-phenylpyrimidines from 2-amino-1,1-dicyano-2-phenylethene," *J. Heterocyclic Chem.*, 1980, 17(7), 1385-1387.
Miyashita et al., "Preparation of Heterarenecarbonitriles by Reaction of Haloheteroarenes with Potassium Cyanide Catalyzed by Sodium p-Toluenesulfinate;" *Heterocycles*, 1994, 39(1), 345-350.
Mohan et al., "Solid-phase synthesis of N-substituted amidinophenoxy pyridines as factor Xa inhibitors," *Bioorg. Med. Chem. Lett.*, 1998, 8(14), 1877-1882.
Mombereau et al., "Genetic and Pharmacological Evidence of a Role for GABAB Receptors in the Modulation of Anxiety- and Antidepressant-Like Behavior," *Neuropsychopharmacol.*, 2004, 29(6), 1050-1062.
Mongin.
Mongin et al., "Advances in the directed metallation of azines and diazines (pyridines, pyrimidines, pyrazines, pyridazines, quinolones, benzodiazines and carbolines). Part 1: Metallation of pyridines, quinolones and carbolines," *Tetrahedron*, 2001, 57(19), 4059-4090.
Montgomery et al., "Isonucleosides. I. Preparation of methyl 2-deoxy-2-(purin-9-yl)arabinofuranosides and methyl 3-deoxy-3-(purin-9-yl) arabinofuranosides and methyl 3-deoxy-3-(purin-9-yl)xylofuranosides," *J. Org. Chem.*, 1975, 40(13), 1923-1927.

Morimoto et al., "Potent and selective ET-A antagonists. 1. Syntheses and structure-activity relationships of N-(6-(2-(aryloxy)ethoxy)-4-pyrimidinyl)sulfonamide derivatives," *J. Med. Chem.*, 2001, 44 (21), 3355-3368.
Morissette et al., "High-throughput crystallization: polymorphs, salts, co-crystals and solvates of pharmaceutical solids," *Adv. Drug Delivery Rev.*, 2004, 56, 275-300.
Moschitskii et al., Translation of "Reaction of 2,3,5,6-tetrachloro-4-pyridyl-vinyl sulfone with nucleophilic agents," *Khimiya Geterotsiklicheskikh Soedinenii*, 1972, 1634-1637, (Translated pp. 1482-1485).
Muci et al. "Practical Palladium Catalysts for C—N and C—O Bond Formation," *Top. Curr. Chem.*, 2002, 219, 131-209.
Muller et al., "7-Deaza-2-phenyladenines: Structure-Activity Relationships of Potent A1 Selective adenosine Receptor Antagonists," *J. Med. Chem.*, 1990, 33, 2822-2828.
Nakazato et al., "Design, synthesis and structure-affinity relationships of 4-methylidenepiperidine and 4-aryl-1,2,3,6-tetrahydropyridine derivatives as corticotropin-releasing factors receptor antagonists," *Bioorg. Med. Chem.*, 2000, 8(5), 1183-1193.
Nakazato et al., "Synthesis, SAR and biological activities of CRH1 Receptor: Novel 3- or 4-carbamoyl-1,2,5,6-tetrahydropyridinoquinoline derivative," 24th ACS National Meeting, Aug. 18-22, 2002, Boston, MA. Poster #258.
National Diabetes Information Clearinghouse, "Insulin resistance and Pre-Diabetes," http://diabetes.niddk.nih.gov/dm/pubs/insulinresistance/, accessed Jul. 1, 2011, 6 pp.
Nauck et al., "Gastric Inhibitory Polypeptide and Glucagon-Like Peptide-1 in the Pathogenesis of Type 2 Diabetes," *Diabetes*, 2004, 53(Suppl. 3), S190-196.
Nauck et al., "Incretins and Their Analogues as New Antidiabetic Drugs," *Drug News Perspect.*, 2003, 16, 413-422.
ndep.nih.gov, "Diabetes Prevention" (May 26, 2009) http://ndep.nih.gov/diabetes/prev/prevention.htm, accessed Jul. 1, 2011, 7 pp.
Nesi et al., "New Difunctionalized 4-Nitroisoxazoles from Alpha-Nitroacetophenone Oxime," *Heterocycles*, 1985, 23(6), 1465-1469.
Nicewonger et al., "Microwave-assisted acylation of 7-amino-5-aryl-6-cyanopyrido[2,3-dipynmidines," *Molecular Diversity*, 2003, 7(2-4), 247-252.
Nightingale et al., "Gastrointestinal hormones in short bowel syndrome. Peptide YY may be the "colonic brake" to gastric emptying," *Gut*, 1996, 39, 267-272.
Nishimura et al., "Adiponectin Prevents Cerebral Ischemic Injury Through Endothelial Nitric Oxide Synthase-Dependent Mechanisms," *Circulation*, 2008, 117, 216-223.
Norman et al., "Structure-activity relationships of a series of pyrrolo(3,2-d) pyrimidine derivatives and related compounds as neuropeptide Y5 receptor antagonists" *J. Med. Chem.*, 2000, 43(22), 4288-4312.
Norman et al., "Structure-activity relationships of a series of pyrrolo(3,2-d) pyrimidine derivatives and related compounds as neuropeptideY5 receptor antagonists" *J. Med. Chem.*, 2000, 43(22), 4288-4312, JM000269T, Supplemental Material, pp. 1-11.
Oku et al., "Adiponectin deficiency suppresses ABCA1 expression and ApoA-I synthesis in the liver," *FEBS Letters*, 2007, 581, 5029-5033.
Olesen et al., "The use of bioisosteric groups in lead optimization," *Curr. Opin. Drug Discovery Develop.*, 2001, 4(4), 471-478.
Ortiz et al., "A Novel Long-Acting Selective Neuropeptide Y2 Receptor Polyethylene Glycol-Conjugated Peptide Agonist Reduces Food Intake and Body Weight and Improves Glucose Metabolism in Rodents," *J. Pharmacol. Exp. Ther.*, 2007, 323, 692-700.
Ouchi et al., "Adiponectin as an anti-inflammatory factor," *Clin. Chim. Acta*, 2007, 380, 24-30.
Ouchi et al., "Novel Modulator for Endothelial Adhesion Molecules: Adipocyte-Derived Plasma Protein Adiponectin," *Circulation*, 1999, 100, 2473-2476.
Overton et al., "Deorphanization of a G protein-coupled receptor for oleoylethanolamide and its use in the discovery of small-molecule hypophagic agents," *Cell Metab.*, 2006, 3, 167-175.
Parker and Balasubramaniam, "Neuropeptide Y Y2 receptor in health and disease," *Brit. J. Pharmacol.*, 2008, 153, 420-431.

(56) References Cited

OTHER PUBLICATIONS

Parlow et al., "Design, synthesis, and crystal structure of selective 2-pyridone tissue factor VIIa inhibitors," *J. Med. Chem.*, 2003, 46(22), 4696-4701.
Paulsen et al., "Darstellung von Bausteinen zur Synthese carbocyclischer furanose-analoga," *Chem. Ber.*, 1981, 114(1), 346-358.
Pearson, "Inflammatory bowel disease," *Nursing Times*, 2004, 100, 86-90.
Pederson, "The Impact of Obesity on the Pathogenesis of Non-Insulin-Dependent Diabetes Mellitus: A Review of Current Hypotheses," *Diab. Metab. Rev.*, 1989, 5(6), 495-509.
Perry et al., "Prospective study of risk factors for development of non-insulin dependent diabetes in middle aged British men," *Brit. Med. J.*, 1995, 310, 560-564.
Peters et al., "Aminomethylpyrimidines as novel DPP-IV inhibitors: A $10^5$-fold activity increase by . optimization of aromatic substituents," *Bioorg. Med. Chem. Lett.*, 2004, 14, 1491-1493.
Phillips et al., "Discovery of N-[245-[Amino(imino)methyl]-2-hydroxyphenoxyl]-3,5-difluoro-6-[3-(4'5-dihydro-1-methyl-1H-imidazol-2-yl)phenoxy]pyridine-4-yl)-N-methylglycine(ZK-807834): A Potent, Selective, and Orally Active Inhibitor of the Blood Coagulation Enzyme Factor Xa," *J. Med. Chem.*, 1998, 41(19), 3557-3562.
Pittner et al., "Effects of PYY[3-36] in rodent models of diabetes and obesity," *Int. J. Obes. Relat. Metab. Disord.*, 2004, 28, 963-971.
Pomorski "Synthesis of Acids, Derivatives of 4-Hydroxy-1,5-Naphthyridine," *Roczniki Chemii Ann. Soc. Chim. Polonorum*, 1974, 48, 321-325.
Potenza et al., "A rapid quantitative bioassay for evaluating the effects of ligands upon receptors that modulate cAMP levels in a melanophore cell line," *Pigment Cell Res.*, 1992, 5(6), 372-8.
Prasad et al., "Convenient Methods for the Reduction of Amides, Nitriles, Carboxylic Esters, Acids and Hydroboration of Alkenes Using NaBH+/$I_2$System," *Tetrahedron*, 1992, 48(22), 4623-4628.
Press et al., "Synthesis and SAR of 6-Substituted Purine Derivatives as Novel Selective Positive Inotropes," *J. Med. Chem.*, 1992, 35(24), 4509-4515.
Quesada et al., 2-Amino-5-nitro-4,6-dipperidionpyrimidinium hydrogensulfate monohydrate, *Acta Cryst.*, 2003, C59, 102-104 (Abstract; 1 page).
Quintela et al., "6-Dimethylamino 1H-Pyrazolo[3,4-d]pyrimidine Derivatives as New Inhibitors of Inflammatory Mediators in Intact Cells," *Bioorg. Med. Chem.*, 2003, 11, 863-868.
Quintela et al., "Pyrazolopyrimidines: synthesis, effect on histamine release from rat peritoneal mast cells and cytotoxic activity," *Eur. J. Med. Chem.*, 2001, 36, 321-332.
Raffel et al., "Diabetes Mellitus," Principles and Practice of Medical Genetics, 3b Ed. 1, 1401-1440 (1996).
Raisz, "Pathogenesis of osteoporosis: concepts, conflicts, and prospects," *J. Clin. Invest.*, 2005, 115, 3318-3325.
Ram et al., "Chemotherapeutic agents. Part XXII. Synthesis of n-deficient pyrimidines as leishmanicides," *Ind. J. Chem. B*, 1991, 30B(10), 962-965.
Rao et al., "Impaired Glucose Tolerance and Impaired Fasting Glucose," *Am. Fam. Physician*, 2004, 69(8), 1961-1968.
Raysam et al., "Fatty Acid Receptors as New Therapeutic Targets for Diabetes," *Exp. Opin. Ther. Targets*, 2007, 11(5), 661-671.
Reed et al., "In-vivo and in-vitro models of type 2 diabetes in pharmaceutical drug discovery," *Diabetes Obes Metab*, 1999, 1(2), 75-86.
Rehwald et al., "Syntheses of thieno[2,3-d)pyrimidines and aminopyrimidines from 2-alkoxy-5-cyano-4-thioxopyrimidine intermediates," *Heterocycles*, 1998, 48(6), 1157-1167.
Remington's Pharmaceutical Sciences, $17^{th}$ Ed., (1985), Mack Publishing Company, Easton, PA, pp. 1418-1419.
Renshaw et al., "Peptide YY: A Potential Therapy for Obesity," *Current Drug Targets*, 2005, 6, 171-179.
Rewcastle et al., "Tyrosine Kinase Inhibitors. 10. Isomeric 4-[(3-Bromophenyl)amino]pyrido[d]pyrimidines are Potent ATP Binding Site Inhibitors of the Tyrosine Kinase Function of the Epidermal Growth Factor Receptor," *J. Med. Chem.*, 1996, 39, 1823-1835.
Roberts et al., "Peroxy-acid oxidation of N,N-disubstituted aminotetrafluoro-, amino-3-chlorotrifluoro-, and amino-3,5-dichlorodifluoro-pyridines," *J. Chem. Soc. C*, 1969, 11, 1485-1491.
Roberts et al., "Polychloroaromatic compounds. L Oxidation of pentachloropyridine and its N,N-disubstituted amino derivatives with peroxyacids," *J. Chem. Soc. C*, 1968, 12, 1537-1541.
Robev et al., "4-Cyclopropylamino- and 4-cyclobutylamino derivatives of some aryl-substituted 5-cyanopyrimidines," *Doktady Bolgarskoi Akademii Nauk*, 1981, 34(12), 1677-1680.
Robins et al., "Potential Purine Antagonists. W. Synthesis of Some 9-Methyl-6-substituted purines," *J. Am. Chem. Soc.*, 1957, 79, 490-494.
Rodriquez-Spong et al., "General Principles of Pharmaceutical Solid state Polymorphism: A Supramolecular Perspective," *Adv. Drug Delivery Rev.*, 2004, 56, 241-274.
Rotwein et al., "Polymorphism in the 5' flanking region of the human insulin gene: a genetic marker for non-insulin-dependent diabetes," *N. Engl. J. Med.*, 1983, 308, 65-71.
Ruggeri, "Platelets in atherothrombosis," *Nat. Med.*, 2002, 8, 1227-1234.
Schwartz and Holst, "An Enteroendocrine Full Package Solution," *Cell Metab.*, 2010, 11, 445-447.
Shah et al., "GPR119 Agonists for the Potential Treatment of Type 2 Diabetes and Related Metabolic Disorders," *Vitamins and Hormones*, 2010, 84, 415-448.
Shah, "GPR119 agonists: A promising new approach for the treatment of type 2 diabetes and related metabolic disorders," *Current Opin Drug Discov Develop.*, 2009, 12, 519-532.
Shibata et al., "Adiponectin protects against myocardial ischemia-reperfusion injury through AMPK- and COX-2-dependent mechanisms," *Nat. Med.*, 2005, 11, 1096-1103.
Shibata et al., "Adiponectin Stimulates Angiogenesis in Response to Tissue Ischemia through Stimulation of AMP-activated Protein Kinase Signaling," *J. Biol. Chem.*, 2004, 279, 28670-28674.
Shibata et al., "Adiponection protects against the development of systolic dysfunction following myocardial infarction," *J. Mol. Cell Cardiol.*, 2007, 42, 1065-1074.
Shore et al., "Adiponectin attenuates allergen-induced airway inflammation and hyperresponsiveness in mice," *J. Allergy Clin. Immunol.*, 2006, 118, 389-395.
Showell et al., "Tetrahydropyridyloxadiazoles: semirigid muscarinic ligands," *J. Med. Chem.*, 1991, 34(3), 1086-1094.
Sigma-Aldrich, catalog entry for 2-amino-6-chloro-4-pyrimidinol hydrate (catalog No. 07460); 1 page; retrieval date Mar. 16, 2010.
Sigma-Aldrich, catalog entry for 2-amino-6-hydroxy-2-mercaptopyrimidine monohydrate (catalog No. A57406); 1 page; retrieval date Mar. 16, 2010.
Sigma-Aldrich, catalog entry for 4,5-diamino-6-hydroxy-2-mercaptopyrimidine hemisulfate salt hydrate (392464); 1 page; retrieval date Mar. 16, 2010.
Sigma-Aldrich, catalog entry for 4,6-diamino-2-mercaptopyrimidine hydrate (catalog No. 125830); 1 page; retrieval date Mar. 16, 2010.
Silhar et al., "Facile and Efficient Synthesis of 6-(Hydroxymethyl)purines," *Org. Lett.*, 2004, 6(19), 3225-3228.
Silvestri et al., "Novel indolyl aryl sulfones active against HIV-1 carrying NNRTI resistance mutations: synthesis and SAR studies," *J. Med. Chem.*, 2003, 46(12), 2482-2493.
Smith et al., "Effects of positive allosteric modulators of the GABAB receptor on cocaine self-administration in rats," *Psychopharmacol.*, 2004, 173(1-2), 105-111.
Soga et al., "Lysophosphatidylcholine enhances glucose-dependent insulin secretion via an orphan G-protein-coupled receptor," *Biochem. Biophys. Res. Commun.*, 2005, 326, 744-751.
Steensma et al., "A novel method for the synthesis of aryl sulfones," *Tetrahedron Lett.*, 2001, 42, 2281-2283.
Sternfeld et al., "Synthesis and serotonergic activity of 3[2-(pyrrolidin-l-yl)ethyl]indoles: potent agonists for the h5-HT1D receptor with high selectivity over the h5-HTIB receptor," *J. Med. Chem.*, 1999, 42(4), 677-690.

(56) References Cited

OTHER PUBLICATIONS

Strupczewski et al., "Synthesis and neuroleptic activity of 3-(1-substituted-4-piperidinyl)-1,2-benzisoxazoles," *J. Med. Chem.*, 1985, 28(6), 761-769.

Suami et al., "Nucleoside analogs. I. Synthesis of 1,3-dihydroxy-2-(6-substituted-9-purinyl)cyclohexane," *J. Het. Chem.*, 1969, 6(5), 663-665.

Sugimoto et al., "Lithiation of 1H-Pyrazolo[3,4-d]pyrimidine Derivative Using Lithium Alkanetellurolate," *Tetrahedron Lett.*, 1999, 40, 2139-2140.

Sugimoto et al., "Preparation of Nitrogen-Containing π-Deficient Heteroaromatic Grignard Reagents: Oxidative Magnesiation of Nitrogen-Containing π-Deficient Halogen Heteroaromatics Using Active Magnesium," *J. Org. Chem.*, 2003, 68, 2054-2057.

Summer et al., "Alveolar macrophage activation and an emphysema-like phenotype in adiponectin-deficient mice," *Am J. Physiol. Lung Cell Mol. Physiol*, 2008, 294, L1035-L1042.

Tao et al., "Adiponectin Cardioprotection After Myocardial Ischemia/Reperfusion Involves the Reduction of Oxidative/Nitrative Stress," *Circulation*, 2007, 115, 1408-1416.

Tatemoto et al., "Isolation of two novel candidate hormones using a chemical method for finding naturally occurring polypeptides," *Nature*, 1980, 285, 417-418.

Terashima et al., "Inhibition of human 06-alkylguanine-DNA alkyltransferase and potentiation of the cytotoxicity of chloroethylnitrosourea by 4(6)-(benzyloxy)-2,6(4)-diamino-5-(nitro or nitroso)pyrimidine derivatives and analogues," *J. Med. Chem.*, 1998, 41(4), 503-508.

Thompson et al., "$N_6$,9-Disubstituted Adenines: Potent, Selective Antagonists at the A1 Adenosine Receptor," *J. Med. Chem.*, 1991, 34, 2877-2882.

Thompson et al., "Synthesis and evaluation of 6-(dibromomethyl)-5-nitropyrimidines as potential antitumor agents," *J. Med. Chem.*, 1997, 40(5), 766-770.

Tilg et al., "Adipocytokines: mediators linking adipose tissue, inflammation and immunity," *Nat. Rev. Immunol.*, 2006, 6, 772-783.

Tseng and Liu, "Peptide YY and cancer: current findings and potential clinical applications," *Peptides*, 2002, 23, 389-395.

Tsukiyama et al., "Gastric Inhibitory Polypeptide as an Endogenous Factor Promoting New Bone Formation after Food Ingestion," *Mol. Endocrinol.*, 2006, 20, 1644-1651.

Turck et al., "Advances in the directed metallation of azines and diazines (pyridines, pyrimidines, pyrazines, pyridazines, uinolones, benzodiazines and carbolines). Part 2: Metallation of pyrimidines, pyrazines, pyridazines and benzodiazines," *Tetrahedron*, 2001, 57(21), 4489-4505.

Ueno et al., "The role of PYY in feeding regulation," *Regul. Pept.*, 2008, 145, 12-16.

University of Maryland Medical Center, "Familial hypercholesterolemia", http://www.umm.edu/ency/article/000392prv.htm, accessed Jul. 1, 2011, 4 pp.

Urgaonkar et al., "$Pd/P(i-BuNCH_2CH_2)_3N$: an efficient catalyst for Suzuki cross-coupling of aryl bromides and chlorides with arylboronic adds," *Tetrahedron Lett.*, 2002, 43(49), 8921-8924.

Urwyler et al., "N,N'-Dicydopentyl-2-methylsulfanyl-5-nitro-pyrimidine-4,6-diamine (GS39783) and structurally related compounds: Novel allosteric enhancers of γ-aminobutyric adds receptor function," *J. Pharm. Exp. Ther.*, 2003, 307(1), 322-330.

Vascular Web, "Hyperlipidemia," downloaded from https://www.vascularweb.org./vascularhealth/Pp./Hyperlipidemia.aspx on Jan. 28, 2011, 4 pp.

Vaughan et al., "The Reformatsky Reaction. I. Zinc and Ethyl Alpha-Bromoisobutyrate," *J. Org. Chem.*, 1965, 30(6), 1790-1795.

Vice et al., "Concise Formation of 4-Benzyl Piperidines and Related Derivatives Using a Suzuki Protocol," *J. Org. Chem.*, 2001, 66, 2487-2492.

Vice et al., "Concise Formation of 4-Benzyl Piperidines and Related Derivatives Using a Suzuki Protocol," *J. Org. Chem.*, 2001, 66, 2487-2492, Supporting Information, pp. S1-S32.

Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties," *J. Med. Chem.*, 2003, 46, 2774-2789.

Villhauer et al., "1-[2-[(5-Cyanopyridin-2-yl)amino]-ethylamino]acetyl-2-(S)-pyrrolidine-carbonitrile: A Potent, Selective, and Orally Bioavailable Dipeptidyl Peptidase IV Inhibitor with Antihyperglycemic Properties," *J. Med. Chem.*, 2002, 45, 2362-2365.

Vippagunta et al., "Crystalline Solids," *Adv. Drug Delivery Rev.*, 2001, 28, 3-26.

Vona-Davis et al., "PYY and the pancreas: Inhibition of tumor growth and inflammation," *Peptides*, 2007, 28, 334-338.

Wang et al., "Improving the oral efficacy of CNS drug candidates: discovery of highly orally efficacious piperidinyl piperidine M2 muscarinic receptor antagonists," *J. Med. Chem.*, 2002, 45(25), 5415-5418.

Weber et al., "Microbic Superinfection in Relapse of Inflammatory Bowel Disease," *J. Clin. Gastroenterol.*, 1992, 14(4), 302-308.

Webmd.com, "Type I Diabetes Prevention," http://diabetes.webmd.com/tc/type-1-diabetes-prevention, accessed May 26, 2009, 3 pp.

Wei et al., "Association between Obesity and Hyperlipidemia Among Children," *Yale J. Biol. Med.*, 2001, 74, 205-210.

Wells et al., Regioselective nucleophilic substitutions of fluorobenzene derivatives, *Tetrahedron Lett.*, 1996, 37(36), 6439-6442.

Werbel et al., "Synthesis and antimalarial effects of 5,6-dichloro-2-[(4-[[ [4-(diethylamino)1-methylbutyl]amino [[-6-methyl-2-pyrimidinyl)amino] benzimidazole and related benzimidazoles and I,H-Imidazo[4,5-b] pyridines," *J. Het. Chem.*, 1973, 10, 363-382.

Wilson et al., "Microwave-assisted synthesis of 2-aminoquinolines," *Tetrahedron Lett.*, 2002, 43(4), 581-583.

Woldbye et al., "Differential suppression of seizures via Y2 and Y5 neuropeptide Y receptors," *Neurobiol. Disease*, 2005, 20, 760-772.

Wolfe et al., "Scope and limitations of the Pd/BINAP-catalyzed amination of aryl bromides," *J. Org. Chem.*, 2000, 65(4), 1144-1157.

Wolfe et al., "Simple, efficient catalyst system for the palladium-catalyzed amination of aryl chlorides, bromides, and Inflates," *J. Org. Chem.*, 2000, 65(4), 1158-1174.

Wolter et al., "Copper-Catalyzed Coupling of Aryl Iodides with Aliphatic Alcohols," *Org. Lett.*, 2002, 4(6), 973-976.

Wolter et al., "Copper-Catalyzed Coupling of Aryl Iodides with Aliphatic Alcohols," *Org. Lett.*, 2002, 4(6), 973-976, Supporting Information, pp. S1-S16.

World Health Organization Technical Report Series 921, "Prevention and Management of Osteoporosis," 2003, 206 pp.

Wortley et al., "Peptide YY Regulates Bone Turnover in Rodents," *Gastroenterol.*, 2007, 133, 1534-1543.

Wu et al., "One-Pot Two-Step Microwave-Assisted Reaction in Constructing 4,5-Disubstituted Pyrazolopyrimidines," *Org. Lett.*, 2003, 5(20), 3587-3590.

Xia et al., "Discovery of a nortropanol derivative as a potent and orally active GPR119 agonist for type 2 diabetes," *Bioorg. Med. Chem. Lett.*, 2011, 21, 3290-3296.

Xie et al., "Glucose-dependent insulinotropic polypeptide receptor knockout mice have altered bone turnover," *Bone*, 2005, 37, 759-769.

Yamamoto et al., "Correlation of the adipocyte-derived protein adiponectin with insulin resistance index and serum high-density lipoprotein-cholesterol, independent of body mass index, in the Japanese population," *Clin. Sci.*, 2002, 103, 137-142.

Yarovenko et al., "New method for the preparation of 5-amino-1,2,4-oxadiazoles," *Bull. Acad. Sci., USSR Div. Chem. Sci.*, 1991, 40, 1924.

Yokota et al., "Adiponectin, a new member of the family of soluble defense collagens, negatively regulates the growth of myelomonocytic progenitors and the functions of macrophages," *Blood*, 2000, 96, 1723-1732.

Yoon et al., "Reaction of Diisobutylaluminum Hydride with Selected Organic Compounds Containing Representative Functional Groups," *J. Org. Chem.*, 1985, 50, 2443-2450.

Zamponi et al., "Unique structure-activity relationship for 4-isoxazolyl-1,4-dihydropyridines," *J. Med. Chem.*, 2003, 46, 87-96.

(56) References Cited

OTHER PUBLICATIONS

Zamponi et al., Supporting Information for "Unique structure-activity relationship for 4-isoxazolyl-1,4-dihydropyridines," *J. Med. Chem.*, 2003, 46, 87-96 (31 pp.).
Zander et al., "Effect of 6-week course of glucagon-like peptide 1 on glycaemic control, insulin sensitivity, and β-cell function in type 2 diabetes: a parallel-group study," *Lancet*, 2002, 359, 824-830.
Zhang, et al., "Preparation of 1-(Tri-n-Butylstannyl) Furanoid Glycals and Their Use in Palladium-Mediated Coupling Reactions," *Tetrahedron Lett.*, 1993, 34(10), 1571-1574.
Zhu et al., "Synthesis and mode of action of (125)1- and (3)H-labeled thieno[2,3-c]pyridine antagonists of cell adhesion molecule expression," *J. Org. Chem.*, 2002, 67(3), 943-8.
"Dyslipidemia Prevalent in Type 2 Diabetes," American Diabetes Association, Jul. 2010, http://docnews.diabetesjournals.org/content/3/3/19.1.full, retrieved on Sep. 24, 2014, 2 pages.
"Metabolic Syndrome," Cleveland Clinic, http://my.clevelandclinic.org/disorders/metabolic_syndrome/hic_metabolic_syndrome.aspx, Dec. 2009, retrieved on Sep. 24, 2014, 2 pages.
"Syndrome X," The Diabetes mall, Feb. 2002, http://www.diabetesnet.com/diabetes_types/syndrome_x.php, retrieved on Sep. 24, 2014, 1 page.
Accession No. 2003:2246299 Chemicals, IH-Pyrazolo [3,4-d] pyrimidin-4-amine, N-cyclohexyl-N-methyl-1-(3 -methyphenyl)—(2003).
Accession No. 2003:2246300 Chemicals, 1H-Pyrazolo [3,4-d] pyrimidin-4-amine, N-cyclohexyl-1-(2,4-dimethlphenyl)-N-methyl—(2003).
Aidsinfo.nih.gov, "Dyslipidemia", updated Nov. 1, 2012, retrieved Jan. 22, 2014, http://aidsinfo.nih.gov/guidelines/html/2/pediatric-arv-guidelines/91/dyslipidemia, 4 pages.
American Diabetes Association, "Hyperglycemia (High blood sugar)," accessed Jul. 1, 2011, http://www.diabetes.org/living-with-diabetes/treatment-and-care/blood-glucose-control/hyperglycemia.html, 1 page.
American Heart Association, Metabolic Syndrome, http://www.americanheart.org/pre-senter.jhtml?identifier=4756, posted on or before Nov. 2001, retrieved on Sep. 24, 2014, 3 pages.
Atik et al., "Burden of Osteoporosis," Clin Orthop Relat Res, 2006, 443:19-24.
Augustyns, et al., "Inhibitors of proline-specific dipeptidyl peptidases: DPP IV inhibitors as a novel approach for the treatment of type 2 diabetes," Expert Opin. Ther. Patents, 2005, 15:1387-1407.
Bayes et al., "Apolipoprotein E alleles, Dyslipemia, and Kidney Transplantation", *Transplantation Proceedings*, 2002, 34(1):373.
Becalski et al., "Synthesis of carbolines by the Graebe-Ullmann method," *Acta Pol Pharm.*, 1977, 41:601-606.
Bhatt and Thakkar, "Preparation and study of a nickel(II) ion selective electrode," Indian J. Chem, May 1994, 33A:436-437.
Bol'but, et al., "A new synthetic approach to fused pyrimidin-4-ones", Institute of Organic Chemistry, National Academy of Sciences of Ukraine, 2003, accessed Mar. 30, 2008, http://conf.iflab.kiev.ua/eng/reports/show/?id=348, 2 pages (Abstract).
Bol'v, et al., "A new synthetic approach to fused pyrimidin-4-ones", Institute of Organic Chemistry, National Academy of Sciences of Ukraine, 2003, accessed Mar. 30, 2008,http://conf.iflab.kiev.ua/eng/reports/show/?id=348, 2 pages (Abstract).
Breuer, "Hypertriglyceridemia: A Review of Clinical Relevance and Treatment Options: Focus on Cerivastatin," *Current Medical Research and Opinion*, 2001, 17(1):60-73.
Brewer, "Benefit-Risk Assessment of Rosuvastatin 10 to 40 Milligrams," *American Journal of Cardiology*, 2003, 92(4B):23K-29K.
Brinkmann et al., "Fingolimod (FYU720): discovery and development of an oral drug to treat multiple sclerosis," Nature Reveiws, Nov. 2010, 9:883-897.
Bromidge et al., "Design of [R-(Z)-]-(+)-α-(methoxylmino)-1azabicyclo[2.2.2]octane-3-acetonitri le (SB 202026), a functionally selective azabicyclic muscarinic M1 against incorporating the N-methoxy imidoyl nitrile group as a novel ester bioisostere," *J Med Chem*, 1997, 40(26):4265-4280.
Caldwell et al., "Fluoropyrrolidine amides as dipeptidyl peptidase IV inhibitors," *Bioorg. Med.Chem. Lett.*, 2004, 14:1265-1268.

Capuzzi et al., "Beneficial Effects of Rosuvastatin Alone and in Combination with a Extended-Release Niacin in Patients with a Combined Hyperlipidemia and Low High-Density Lipoprotein Cholesterol Levels," *American Journal of Cardiology*, 2003, 91(11):1304-1310.
Capuzzi et al., "Rosuvastatin Alone or With Extended-Release Niacin: A New Therapeutic Option for Patients with Combined Hyperlipidemia," *Preventive Cardiology*, Fall 2004, 7(4):176-181.
Carswell et al., "Rosuvastatin," *Drugs*, 2002, 62(14):2075-2085.
Chapman et al., "Non-High-Density Lipoprotein Cholesterol as a Risk Factor: Addressing Risk Associated with Apolipoprotein B-Containing Lipoproteins," *European Heart Journal Supplements*, 2004, 6(Suppl. A):A43-A48.
Chapoulaud et al., "Synthesis of 4,8-Diarylcinnolines and Quinazolines with Potential Applications in Nonlinear Optics. Diazines. Part 28," *Tetrahedron* (2000) 56:5499-5507.
Chen et al., "Inhibitory Effect of Candesartan and Rosuvastatin on CD40 and MMPs Expression in Apo-E Knockout Mice: Novel Insights into the Role of RAS and Dyslipidemia in Atherogenesis," Journal of Cardiovascular Pharmacology, 2004, 44(4):446-452.
Chen et al., "Synthesis and Oral Efficacy of a 4-(Bulylethylamino)pyrrolo[2,3-d]pyrimidine: A Centrally Active Corticotropin-Releasing Factor: Receptor Antagonist," *J. Med. Chem.*, 1997, 40:1749-1754.
Cheng and Robins, "Potential purin antagonists. VI. Synthesis of 1-alkyl and 1-aryl-4-substituted pyrazolo[3,4-d]pyrimidines," J. Org Chem, 1956, 21:1240-1256.
Cheng, "Rosuvastatin in the Management of Hyperlipidemia," Clinical Therapeutics, 2004, 26(9):1368-1387.
Cheng-Lai, "Cerivastatin," Heart Disease, 2000, (2):93-99.
Cheng-Lai, Rosuvastatin: A New HMG-CoA Reductase Inhibitor for the Treatment of Hypercholesterolemia; Heart Disease, 5(1), 72-78 (2003).
Chu, "Section 1: Drug Development," Cancer: Principles and Ptractice of Oncology, 2005, Lippincott Williams & Wilkins, 27 pages.
Citkowitz, "Hypertriglyceridemia," eMedicine Endorinology, Jul. 2008, http://emedicine.medscape.com/article/126568-print, retrieved on Sep. 24, 2014, 18 pages.
Cover Sheet and 54 Compounds, CAS Registry and ChemCats files, 23 pp., (various dates—Jan. 15, 1998-Jun. 16, 2004).
Crouse, et al., "Measuring Effects on Intima Media Thickness: An Evaluation of Rosuvastatin in Subclinical Atherosclerosis—The Rationale and Methodology of the Meteor Study," Cardiovascular Drugs and Therapy, 2004, 18(3):231-238.
Davidson, "Rosuvastatin: A Highly Efficacious Statin for the Treatment of Dyslipidemia," Expert Opinion on Investigational Drugs, 2002, 11(3):455.
De Denus et al., "Dyslipidemias and HMG-CoA Reductase Inhibitor Prescription in Heart Transplant Recipients," Annals of Pharmacotherapy, 2004, 28 (7/8):1136-1141.
Deacon, "Therapeutic Strategies Based on Glucagon-Like Peptide 1," Diabetes, Sep. 2004, 53:2181-2189.
Deighan, et al., "Comparative Effects of Cerivastatin and Fenofibrate on the Atherogenic Lipoprotein Phenotype in Proteinuric Renal Disease," Journal of the American Society of Nephrology, 2001, 12(2):341-348.
Delmas and Meunier, "The Management of Paget's Disease of Bone," The New England Journal of Medicine, Feb. 1997, 336:558-566.
Dubau-Assibat et al., "Lawesson's Reagent: An Efficient 1,3-Dipole Trapping Agent", J. Org. Chem., 1995, 60(12):3904-3906.
Dugue et al., "Detection and Incidence of Muscular Adverse Drug Reactions: A prospective Analysis from Laboratory Signals," European Journal of Clinical Pharmacology, 2004, 60(4):285-292.
During et al., "Glucagon-like peptide-1 receptor is involved in learning and neuroprotection," Nat. Med., 2003, 9:1173-1179.
Fellstrom, et al, "Why Do We Need a Statin Trial in Hemodialysis Patients?" Kidney International Supplement, 2003 63(84):S204-S206.
Flock et al., "GPR119 Regulates Murine Glucose Homeostasis Through Incretin Receptor-Dependent and Independent Mechanisms," Endocrinology, Feb. 2011, 152(2):374-383.

(56) References Cited

OTHER PUBLICATIONS

Garcia, et al., "Effects of Cerivastatin in Dyslipemia and Other Cardiovascular Risk Factors after Renal Transplantation," Transplantation Proceedings, 2002, 34(1),:401-402.
Gewald and Bellmann, "Synthese and Raektionen von 4-aminosothizolen," Leibigs Ann. Chim, 1979, 10:1534-1546.
Girouard and Iadecola, "Neurovascular coupling in the normal brain and in hypertension, stroke and Alzheimer disease," J. Appl. Physiol., 2006, 100:328-335.
Guilherme et al., "Adipocyte dysfunctions linking obesity to insulin resistance and type 2 diabetes," Molecular Cell Biology, May 2008, 9:367-377.
Guillory, "Generation of Polymorphs, Hydrates, Solvates, and Amorphous Solids," Polymorphism in Pharmaceutical Solids, ed. Harry G. Britain, Marcel Dekker, Inc., New York, 1999, 95:202-209.
Gundersen "Synthesis of purinecarbonitriles by Pd(0)-catalysed coupling of halopurines with zinc cyanide," Acia Chemica Scandinavia (1996) 50:58-63.
Hafenbradl et al., "In vitro Characterization of Small-Molecule Kinase Inhibitors," Protein Kinase as Drug Targets, 2011 (B. Kiebl et al. eds) 185 pages.
Higuchi and Stella, "Pro-drugs as Novel Delivery Systems," vol. 14 of the A.C.S. Symposium Series, 1975, 129 pages. too voluminous to provide.
Holdgate et al., "Molecular Mechanism for Inhibition of 3-hydroxy-3-methyglutaryl CoA (HMG-CoA) Reductase by Rosuvastatin," Biochemical Society Transactions, 2003, 31(3):528-531.
Irwin et al., "Therapeutic potential of the original incretin hormone glucose-dependent insulinotropic polypeptide: diabetes, obesity, osteoporosis and Alzheimer's disease," Expert Opinion Investi. Drugs, 2010, 19(9):1039-1048.
Ismail et al., "Number and Type of Vertebral Deformities: Epidemiological Characteristics and Relation to Back Pain and Height Loss," Osteoporosis International, 1999, 9:206-213.
Jones et al., "GPR119 agonists for the treatment of type 2 diabetes," Expert Opin. Ther. Patents, 2009, 19(10): 1339-1359.
Joshi et al., "Endogenous PYY and GLP-1 mediate L-glutamine responses in intestinal mucosa," . British Journal of Pharmacology, 2013, 170:1092-1101.
Judge and Bever, "Potassium channel blockers in multiple sclerosis: Neuronal $K_v$ channels and effects of symptomatic treatment," Pharmacology & Therapeutics, 2006, 111:224-259.
Kametani et al. "Benzeyne Reaction. IX. Benzeyne Reaction of o-halobenzenes with acetonitrile or phenylacetonitrile in organic solvents," J. Org. Chem., 1972, 36(2):327-330.
Kanstrup et al., "Quality of Lipid-Lowering Therapy in Patients with Ischaemic Heart disease: A Register-Based Study in 3477 Patients," Journal of Internal Medicine, 2004, 255(3):367-372.
Kawakita et al., CAPLUS Abstract 115:136096, 1991, 3 pages.
Keane et al., "The CHORUS (Cerivastatin in Heart Outcomes in Renal Disease: Understanding Survival) Protocol: A Double-Blind, Placebo-Controlled Trial in Patients with ESRD," American Journal of Kidney Diseases, 2001, 37(1, Suppl. 2):548-553.
Kim and Egan, "The Role of Incretins in Glucose Homeostasis and Diabetes Treatment," Pharmacological Reviews, 2008, 60(4):470-512.
Kolosov et al., "The interaction between 4-[phenyl-5-acetyl-6-methyl-3,4-dihydropyrimidine-2-one and 4-brombenzaldehyde", Institute of Organic Chemistry, Kharkiv, retrieved on Mar. 30, 2008, http://conf.iflab.kiev.ua/eng/reports/show/?id=926, 2 pages (Abstract Only).
Koumbourlis, "Scoliosis and the respiratory system," Paediatric Respiratory Reviews, 2006. 7:152-160.
Lechleitner, "Dyslipidaemia and Renal Disease—Pathophysiology and Lipid Lowering Therapy in Patients with Impaired Renal Function," Journal of Clinical and Basic Cardiology, 2000, 3(1):3-6.
LeWitt, "Levodopa for the Treatment of Parkinson's Disease," The New England Journal of Medicine, Dec. 2008, 359(23):2468-2476.
Lindvall and Kokaia, "Stem cells for the treatment of neurological disorders," Nature, 2006, 44:1094-1096.

Markwalder, et al., "Synthesis and biological evaluation of 1-aryl-4,5-dihydro-1H-pyrazolo[3,4-d]pyrimidin-4-one inhibitors of cyclin-dependent kinases", J. Med. Chem., (2004), 47:5894-5911.
Martin et al., "A Double-Blind, Randomized, Incomplete Crossover Trial to Assess the Dose Proportionality of Rosuvastatin in Healthy Volunteers," Clinical Therapeutics, 2003, 25(8):2215-2224.
Martin et al., "Absolute Oral Bioavailability of Rosuvastatin in Healthy White Adult Male Volunteers," Clinical Therapeutics, 2003, 25(10):2553-2563.
Martin et al., "An Open-Label, Randomized, Three-Way Crossover Trial of the Effects of Coadministration of Rosuvastatin and Fenofibrate on the Pharmacokinetic Properties of Rosuvastatin and Fenofibric Acid in Healthy Male Volunteers," Clinical Therapeutics, 2003, 25(2):459-471.
Martin et al., "Metabolism, Excretion, and Pharmacokinetics of Rosuvastatin in Healthy Adult Male Volunteers," Clinical Therapeutics, 2003, 25(11):2822-2835.
Mayo Clinic, "Metabolic syndrome", accessed 18 Jul. 18, 2013, http://www.mayoclinic.com/health/metabolic%20syndrome/DSOO522, 2 pages.
Mitchell and Borasio, "Amyotrophic lateral sclerosis," The Lancet, Jun. 2007, 369: 2031-2041.
Mitsunobu, "The Use of Diethyl Azodicarboxylate and Triphenylphosphine in Synthesis and Transformation of Natural Products", Synthesis, 1981, 1-28.
Mosti et al., "4-Substituted 1-Phenyl-1H-Indazoles With Analgesic, Antiinflammatory, Antipyretic and Local Anesthetic Activities," IL Farmaco, 1990, 45(4):415-429.
Mosti et al., "Synthesis and Preliminary biological Evaluation of Novel N-Substited 1-Amino-3-[1-methyl(phenyl)-1H-indazol-4-yloxy]-propan-2-ols Interesting as Potential Antiarrhythmic, Local Anaesthetic and Anagesic Agents," Arzneim-Forsch Drug Res, 2000, 50(11):963-972.
Muck et al., "Lack of Pharmacokinetic Drug-Drug Interaction between Orlistat and Cerivastatin," Clinical Drug Investigation, 2000, 19(1):71-73.
Nakamura et al., "Effect of Cerivastatin on Endothelial Dysfunction and Aortic CD36 Expression in Diabetic Hyperlipidemic Rats," Hypertens Res, 2004, 27(8):589-598.
ndep.nih.gov, "Diabetes Prevention" (May 26, 2009) http://ndep.nih.gov/diabetes/prev/prevention.htm, accessed Jul. 1, 2011, 7 pages.
Nezasa et al., "Uptake of rosuvastatin by isolated rat hepatocytes: comparison with pravastatin," Xenobiotica, 2003, 33(4):379-388.
Niementowski, J. Praktika Chem., [2] "Synthesen von Chinazolinverbindugen" (1895), 51, 564-572.
Novinson et al., "Novel Heterocyclic Nitrofurfural Hydrazones. In vivo Antitrypanosomal Activity," J Med Chem, 1976, 19(4):512-516.
O'Brien et al., "Vascular cognitive impairment," The Lancet Neurology, Feb. 2003, 2:89-98.
Olsson et al., "Rosuvastatin: A Highly Effective New HMG-CoA Reductase Inhibitor," Cardiovascular Drug Reviews, 2002, 20(4): 303-328.
Olsson, "Statins: how far have we come? A review of rosuvastatin," International Journal of Clinical Practice, 2003, Supplement 137:15-25.
Organic Chemistry of Sulfur; Oae S., Ed.; Plenum Press: New York (1977) too voluminous to provide.
Overton et al., "GPR119 a Novel G Protein-coupled Receptor Target for the Treatment of Type 2 Diabetes and Obesity," Brit. J. Pharmacol., 2008, 153:576-581.
Ozeki el al., "Studies on Antiallergy Agent. 1. Synthesis of1,4-Dihydro-4-oxo-3-quinolmecarboxylic Acids" Yakugaku Zasshi, 1987, 107(2):123-134.
Peat et al., "Novel pyrazolopyrimidine derivatives as GSK-3 inhibitors", Bioorganic & Medicinal Chemistry Letters, 2004, 14:2121-2125.
Pei et al., "Discovery and Structure-Activity Relationships of Piperidinone- and Piperidine-Constrained Phenethylamines as Novel, Potent, and Selective Dipeptidyl Peptidase IV Inhibitors," J Med Chem, 2007, 50:1983-1987.

(56) References Cited

OTHER PUBLICATIONS

Pelat et al., "Rosuvastatin Decreases Caveolin-1 and Improves Nitric Oxide-Dependent Heart Rate and Blood Pressure Variability in Apolipoprotein E-/- Mice in Vivo," Circulation, 2003, 107(19): 2480-2486.
Poupaert, "Drug Design: Basic Principles and Applications," Encyclopedia of Pharmaceutical Technology, 2007, 1362-1369 (James Swarbrick 3rd ed.).
Prasad et al., "Convenient Methods for the Reduction of Amides, Nitriles, Carboxylic Esters, Acids and Hydroboration of Alkenes Using NaBH4/I2 System," Tetrahedron, 1992, 48(22):4623-4628.
Rehwald and Gewald, "Syntheses of Thieno[2,3-d)Pyrimidines and Aminopyrimidines from 2-Alkoxy-5-Cyano-4-Thioxopyrimidine Intermediates," Heterocycles, 1998, 48(6):1157-1167.
Rimoin et al., "Emery and Rimoin's Principles and Practice of Medical Genetics", 1996, 3:1401-1402.
Roberts, "Two More Drugs for Dyslipidemia", American Journal of Cardiology, 2004 93:809-811.
Roche, Bioreversible Carriers in Drug Design, ed., American Pharmaceutical Association and Pergamon Press (1987) too voluminous to provide.
Rondinone, "Diabetes: the latest developments in inhibitors, insulin sensitisers, new drug targets and novel approaches" Expert Opin, 2005, 9(2):415-418.
Rosenson, "Rosuvastatin: a new inhibitor of HMG-CoA reductase for the treatment of dyslipidemia", Expert Review of Cardiovascular Therapy, 2003, 1(4):495-505.
Sage, Document regarding search, Feb. 2003, 1 page.
Schafer et al., "Zur synthese von 4-aminochinolinen durch intramolekulare Friedel-Cfafts-Reaktion," Montash fur Chemie (1978) 109:527-535 (English Abstract).
Schuster, "Rosuvastatin—A Highly Effective New 3-hydroxy-3-methylglutaryl Coenzyme A Reductase Inhibitor: Review of clinical Trial Data at 10-40 mg doses in Dyslipidemic Patients" Cardiology, 99(3):126-139 (2003).
Scott et al., "Rosuvastatin: A Review of Its Use in the Management of Dyslipidemia," American Journal of Cardiovascular Drugs, 4(2), 117-138 (2004).
Semple et al., "Discovery of a second generation of the orphan G-protein coupled receptor GPR119 with an improved profile," Biooganic & Medicinal Chemistry Letters, 2012, 22:1750-1755.
Shah et al., "Current Approaches in the treatment of Alzheimer's disease," Biomedicine &Phamacotherapy, 2008, 62:199-207.
Shepherd et al., "Safety of Rosuvastatin," American Journal of Cardiology, 94(7):882-888 (2004).
Spruce, Lyle W., Document regarding search, 2004, 1 page.
Starosotnikov et al., "Synthesis of 3-substituted 1-aryl-4,6-dinitro-1H-indazoles based on picrylacetaldehyde and their behavior in nucleophilic substitution reactions," Russian Chemical Bulletin 2003, 52(8), 1782-1709.
Stein, "Management of Dyslipidemia in the High-Risk Patient," American Heart Journal, 144(6):S43-S50 (2002).

Takei et al., "A New Synthetic Method for Some Pyrazolo [4,3-]pyrimidines1)," Bulletin of the Chemical Society of Japan, Aug. 23, 2005, 52(1):208-211.
Trejo et al., "Design and Synthesis of 4-Azaindoles as Inhibitors of p38 MAP Kinase," J. Med. Chem., (2003) 46:4702-4713.
Tuomilehto et al., "A Review of the Efficacy of Rosuvastatin in Patients with Type 2 Diabetes," International Journal of Clinical Practice, Supplement, 143, 30-40 (2004).
Ulrich, "Crystallization," Kirk-Othmer Encyclopedia of the Chemical Technology, 2002, Chapter 4, 8:95-147.
Ural et al., "Treatment with Cervistatin in Primary Mixed Hyperlipidemia Induces Changes in Platelet Aggregation and Coagulation System Components," International Journal of Hematology, 76(3):279-283 (2002).
Urwyler et al., "N,N' -Dicydopentyl-2-methylsulfanyl-5-nitropyrimidine-4,6-diamine (GS39783) and structurally related compounds: Novel allosteric enhancers of y-aminobutyric acidB receptor function," Journal of Pharmacology and Experimental Therapeutics (2003) 307(1):322-330.
Vascular Web, "Hyperlipidemia," downloaded from https://www.vascularweb.org/vascularhealth/pages/Hyperlipidemia.aspx on Jan. 28, 2011, 4 pgs.
Vinogradov et al., "Synthesis and reactions of 1-aryl-3-formyl-4,6-dinitro-1H-indazoles," Mendeleev Communications, 2002, (5), 198-200.
Wang et al., "Amino-Substituted Heterocycles as Isosteres of Trans-Cinnamides: Design and Synthesis of Heterocyclic Biaryl Sulfides as Potent Antagonists of LFA-1/ICAM-1 Binding," Bioorganic & Medicinal Chemistry Letters, 15(1), 195-201 (2005).
West, Solid State Chemistry and its application, New York, 1988, pp. 358 & 365.
Winkelmann et al., "Haplotypes of the Cholesteryl Ester Transfer Protein Gene Predict Lipid-Modifying Response to Statin Therapy," Germany Pharmacogenomics Journal, 3(5): 284-296 (2003).
Wuts, Protective Groups in Organic Synthesis, 3rd edition. John Wiley & Sons, New York (1999) too voluminous to provide.
Yoshida et al., "AS1907417, a novel GPR119 agonist, as an insulinotropic and β-cell preservative agent for the treatment of type 2 diabetes," Biochemical and Biophysical Research Communicaitons, 2010, 400:745-751.
Yuan et al., "3-Aryl pyrazolo[4,3-d]pyrimidine derivatives nonpeptide CRF-1 antagonists," Bioorganic Medicinal Chemistry Lett. (2002) 2133-2136.
Zhong et al., "Effects of glucose-dependent insulinotropic peptide on osteoclast function," Am J Physiol Endocrinol Metab, 2007, 292:E543-E548.
Zhu et al., Synthesis and mode of action of (125)1- and (3)H-labeled thieno[2,3-c]pyridine antagonists of cell adhesion molecule expression, J Org Chem. (2002) 67(3):943-948.
Zon and Peterson, "In vivo Drug Discovery in the Zebrafish," Nature Reviews, Jan. 2005, 4:35-44.
Oxford Online Dictionary, Definition of Prescription, 2017, 4pp.
Drucker et al., "The incretin system: glucagon-linke peptide-1 receptor agonists and dipeptidyl peptidase-4 inhibitors in type 2 diabetes," Lancet, 2006, 368:1696-1705.

\* cited by examiner

*IN VIVO* EFFECTS OF COMPOUND 1 ON INCRETIN HORMONE GIP RELEASE

MODULATORS OF THE GPR119 RECEPTOR AND THE TREATMENT OF DISORDERS RELATED THERETO

CROSS-REFERENCE TO RELATED APPLICATIONS

This application is a national phase entry under 35 U.S.C. § 371 of PCT International Application No. PCT/US2011/052478, filed Sep. 21, 2011, which claims the benefit of priority of U.S. Provisional Application No. 61/385,410, filed Sep. 22, 2010 and U.S. Provisional Application No. 61/478,262, filed Apr. 22, 2011.

FIELD OF THE INVENTION

The present invention relates to the GPR119 receptor agonists: 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide; 3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide; and 3-fluoro-4-(5-fluoro-6-(4-(3-(2-fluoropropan-2-yl)-1,2,4-oxadiazol-5-yl)piperidin-1-yl)pyrimidin-4-ylamino)benzamide, and pharmaceutically acceptable salts, solvates, and hydrates thereof, that are useful as a single pharmaceutical agent or in combination with one or more additional pharmaceutical agents, such as, a DPP-IV inhibitor, a biguanide, an alpha-glucosidase inhibitor, an insulin analogue, a sulfonylurea, an SGLT2 inhibitor, a meglitinide, a thiazolidinedione, or an anti-diabetic peptide analogue, in the treatment of, for example, a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; type 2 diabetes; obesity; and complications related thereto.

BACKGROUND OF THE INVENTION

A. Diabetes Mellitus

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are type 1 (also referred to as insulin-dependent diabetes mellitus or IDDM) and type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or can not efficiently use the insulin they produce; therefore, they can not move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

About 5% to 10% of the people who have diabetes have IDDM. These individuals do not produce insulin and therefore must inject insulin to keep their blood glucose levels normal. IDDM is characterized by low or undetectable levels of endogenous insulin production caused by destruction of the insulin-producing beta cells of the pancreas, the characteristic that most readily distinguishes IDDM from NIDDM. IDDM, once termed juvenile-onset diabetes, strikes young and older adults alike.

Approximately 90% to 95% of people with diabetes have NIDDM (type 2). NIDDM subjects produce insulin, but the cells in their bodies are insulin resistant: the cells do not respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. *N. Engl. J. Med.* 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically inapparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. *Emery and Rimoin's Principles and Practice of Medical Genetics* 3$^{rd}$ Ed. 1:1401-1402 (1996)).

Many people with NIDDM have sedentary lifestyles and are obese: they weigh approximately 20% more than the recommended weight for their height and build. Furthermore, obesity is characterized by hyperinsulinemia and insulin resistance, a feature shared with NIDDM, hypertension and atherosclerosis.

The patient with diabetes faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions (Perry, I. J., et al., *BMJ* 310, 560-564 (1995)).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

B. Obesity

Obesity and diabetes are among the most common human health problems in industrialized societies. In industrialized countries a third of the population is at least 20% overweight. In the United States, the percentage of obese people has increased from 25% at the end of the 1970's, to 33% at the beginning the 1990's. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff, et al. *Diabetes* 43, 696-702 (1989)). However, after several decades, β cell function deteriorates and non-insulin-dependent diabetes develops in about 20% of the obese population (Pederson, P. *Diab. Metab. Rev.* 5, 505-509 (1989)) and (Brancati, F. L., et al., *Arch. Intern. Med.* 159, 957-963 (1999)). Given its high prevalence in modern societies, obesity has thus become the leading risk factor for NIDDM (Hill, J. O., et al., *Science* 280, 1371-1374 (1998)). However, the factors which predispose a fraction of patients to alteration of insulin secretion in response to fat accumulation remain unknown.

Whether someone is classified as overweight or obese can be determined by a number of different methods, such as, on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25-30 $kg/m^2$, and obesity as a BMI greater than 30 $kg/m^2$ (see table below). There are problems with this definition, such as, it does not take into account the proportion of body mass that is muscle in relation to fat (adipose tissue). To account for this, alternatively, obesity can be defined on the basis of body fat content: greater than 25% and 30% in males and females, respectively.

CLASSIFICATION OF WEIGHT BY BODY MASS INDEX (BMI)

| BMI | CLASSIFICATION |
| --- | --- |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases associated with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight.

C. Atherosclerosis

Atherosclerosis is a complex disease characterized by inflammation, lipid accumulation, cell death and fibrosis. Atherosclerosis is characterized by cholesterol deposition and monocyte infiltration into the subendothelial space, resulting in foam cell formation. Thrombosis subsequent to atherosclerosis leads to myocardial infarction and stroke. Atherosclerosis is the leading cause of mortality in many countries, including the United States. (See, e.g., Ruggeri, Nat Med (2002) 8:1227-1234; Arehart et al., Circ Res, Circ. Res. (2008) 102:986-993.)

D. Osteoporosis

Osteoporosis is a disabling disease characterized by the loss of bone mass and microarchitectural deterioration of skeletal structure leading to compromised bone strength, which predisposes a patient to increased risk of fragility fractures. Osteoporosis affects more than 75 million people in Europe, Japan and the United States, and causes more than 2.3 million fractures in Europe and the United States alone. In the United States, osteoporosis affects at least 25% of all post-menopausal white women, and the proportion rises to 70% in women older than 80 years. One in three women older than 50 years will have an osteoporotic fracture that causes a considerable social and financial burden on society. The disease is not limited to women; older men also can be affected. By 2050, the worldwide incidence of hip fracture projected to increase by 310% in men and 240% in women. The combined lifetime risk for hip, forearm, and vertebral fractures presenting clinically is around 40%, equivalent to the risk for cardiovascular disease. Osteoporotic fractures therefore cause substantial mortality, morbidity, and economic cost. With an ageing population, the number of osteoporotic fractures and their costs will at least double in the next 50 years unless effective preventive strategies are developed. (See, e.g., Atik et al., Clin. Orthop. Relat. Res. (2006) 443:19-24; Raisz, J. Clin. Invest. (2005) 115:3318-3325; and World Health Organization Technical Report Series 921 (2003), Prevention and Management of Osteoporosis).

E. Inflammatory Bowel Disease (IBD)

Inflammatory bowel disease (IBD) is the general name for diseases that cause inflammation in the intestines and includes, e.g. Crohn's disease, ulcerative colitis, and ulcerative proctitis. U.S. medical costs of inflammatory bowel disease for 1990 have been estimated to be $1.4 to $1.8 billion. Lost productivity has been estimated to have added an additional $0.4 to $0.8 billion, making the estimated cost of inflammatory bowel disease $1.8 to $2.6 billion. (See, e.g., Pearson, Nursing Times (2004) 100:86-90; Hay et al., J. Clin. Gastroenterol. (1992) 14:309-317; Keighley et al., Ailment Pharmacol. Ther. (2003) 18:66-70).

Enteritis refers to inflammation of the intestine, especially the small intestine, a general condition that can have any of numerous different causes. Enterocolitis refers to inflammation of the small intestine and colon.

Crohn's disease (CD) is an inflammatory process that can affect any portion of the digestive tract, but is most commonly seen in the last part of the small intestine otherwise called the (terminal) ileum and cecum. Altogether this area is also known as the ileocecal region. Other cases may affect one or more of: the colon only, the small bowel only (duodenum, jejunum and/or ileum), the anus, stomach or esophagus. In contrast with ulcerative colitis, CD usually does not affect the rectum, but frequently affects the anus instead. The inflammation extends deep into the lining of the affected organ. The inflammation can cause pain and can make the intestines empty frequently, resulting in diarrhea. CD may also be called enteritis. Granulomatous colitis is another name for CD that affects the colon. Ileitis is CD of the ileum which is the third part of the small intestine. Crohn's colitis is CD affecting all or part of the colon.

Ulcerative colitis (UC) is an inflammatory disease of the large intestine, commonly called the colon. UC causes inflammation and ulceration of the inner lining of the colon and rectum. The inflammation of UC is usually most severe in the rectal area with severity diminishing (at a rate that varies from patient to patient) toward the cecum, where the large and small intestines join together. Inflammation of the rectum is called proctitis. Inflammation of the sigmoid colon (located just above the rectum) is called sigmoiditis. Inflammation involving the entire colon is termed pancolitis. The inflammation causes the colon to empty frequently resulting in diarrhea. As the lining of the colon is destroyed ulcers form releasing mucus, pus and blood. Ulcerative proctitis is a form of UC that affects only the rectum.

F. GPR119

GPR119 is a G protein-coupled receptor (GPR119; e.g., human GPR119, GenBank® Accession No. AAP72125 and alleles thereof; e.g., mouse GPR119, GenBank® Accession No. AY288423 and alleles thereof) and is selectively expressed on pancreatic beta cells. GPR119 activation leads to elevation of a level of intracellular cAMP, consistent with GPR119 being coupled to Gs. Agonists to GPR119 stimulate glucose-dependent insulin secretion in vitro and lower an elevated blood glucose level in vivo; see, e.g., International Applications WO 04/065380 and WO 04/076413, and EP 1338651. In the literature, GPR119 has also been referred to as RUP3 (see, International Application WO 00/31258) and as Glucose-Dependent Insulinotropic Receptor GDIR (see, Jones, et. al. *Expert Opin. Ther. Patents* (2009), 19(10): 1339-1359).

GPR119 agonists also stimulate the release of Glucose-dependent Insulinotropic Polypeptide (GIP), Glucagon-Like Peptide-1 (GLP-1), and at least one other L-cell peptide, Peptide YY (PYY) (Jones, et. al. *Expert Opin. Ther. Patents* (2009), 19(10): 1339-1359); for specific references related to GPR119 agonists and the release of:

GIP, see Shah, *Current Opinion in Drug Discovery & Development*, (2009) 12:519-532; Jones, et al., *Ann. Rep. Med. Chem.*, (2009) 44:149-170; WO 2007/120689; and WO 2007/120702;

GLP-1, see Shah, *Current Opinion in Drug Discovery & Development*, (2009) 12:519-532; Jones, et al., *Ann. Rep. Med. Chem.*, (2009) 44:149-170; Schwartz et. al., *Cell Metabolism*, 2010, 11:445-447; and WO 2006/076231; and PYY, see Schwartz et. al., *Cell Metabolism*, 2010, 11:445-447; and WO 2009/126245.

As mentioned above, GPR119 agonists enhance incretin release and therefore can be used in treatment of disorders related to the incretins, such as, GIP, GLP-1, and PYY. However, a number of the incretins, such as, GIP and GLP-1, are substrates for the enzyme dipeptidyl peptidase-4 (DPP-IV). Jones and co-workers (Jones, et al., *Ann. Rep. Med. Chem.*, (2009) 44:149-170) have demonstrated that a combined administration of a GPR119 agonist, (2-Fluoro-4-methanesulfonyl-phenyl)-{6-[4-(3-isopropyl-[1,2,4]oxa-diazol-5-yl)-piperidin-1-yl]-5-nitro-pyrimidin-4-yl}-amine (see, Compound B111 in WO 2004/065380), and a DPP-IV inhibitor acutely increased plasma GLP-1 levels and improved glucose tolerance to a significantly greater degree than either agent alone.

G. Glucose-Dependent Insulinotropic Polypeptide (GIP)

Glucose-dependent insulinotropic polypeptide (GIP, also known as gastric inhibitory polypeptide) is a peptide incretin hormone of 42 amino acids that is released from duodenal endocrine K cells after meal ingestion. The amount of GIP released is largely dependent on the amount of glucose consumed. GIP has been shown to stimulate glucose-dependent insulin secretion in pancreatic beta cells. GIP mediates its actions through a specific G protein-coupled receptor, namely GIPR.

As GIP contains an alanine at position 2, it is an excellent substrate for DPP-IV, an enzyme regulating the degradation of GIP. Full-length GIP(1-42) is rapidly converted to bioinactive GIP(3-42) within minutes of secretion from the endocrine K cell. Inhibition of DPP-IV has been shown to augment GIP bioactivity. (See, e.g., Drucker, *Cell Metab* (2006) 3:153-165; McIntosh et al., *Regul Pept* (2005) 128: 159-165; Deacon, *Regul Pept* (2005) 128:117-124; and Ahren et al., *Endocrinology* (2005) 146:2055-2059.). Analysis of full length bioactive GIP, for example in blood, can be carried out using N-terminal-specific assays (see, e.g., Deacon et al., *J Clin Endocrinol Metab* (2000) 85:3575-3581).

Recently, GIP has been shown to promote bone formation. GIP has been shown to activate osteoblastic receptors, resulting in increases in collagen type I synthesis and alkaline phosphatase activity, both associated with bone formation. GIP has been shown to inhibit osteoclast activity and differentiation in vitro. GIP administration has been shown to prevent the bone loss due to ovariectomy. GIP receptor (GIPR) knockout mice evidence a decreased bone size, lower bone mass, altered bone microarchitecture and biochemical properties, and altered parameters for bone turnover, especially in bone formation. (See, e.g., Thong et al., *Am J Physiol Endocrinol Metab* (2007) 292:E543-E548; Bollag et al., Endocrinology (2000) 141:1228-1235; Bollag et al., *Mol Cell Endocrinol* (2001) 177:35-41; Xie et al., Bone (2005) 37:759-769; and Tsukiyama et al., *Mol Endocrinol* (2006) 20:1644-1651.)

The usefulness of GIP for maintaining or increasing bone density or formation has been acknowledged by the United States Patent and Trademark Office by issuance of U.S. Pat. No. 6,410,508 for the treatment of reduced bone mineralization by administration of GIP peptide. However, current GIP peptide agonists suffer from a lack of oral bioavailability, negatively impacting patient compliance. An attractive alternative approach is to develop an orally active composition for increasing an endogenous level of GIP activity.

GPR119 agonists have been shown to stimulate the release of GIP; see Shah, *Current Opinion in Drug Discovery & Development*, (2009) 12:519-532; Jones, et al., *Ann. Rep. Med. Chem.*, (2009) 44:149-170; WO 2007/120689; and WO 2007/120702.

H. Glucagon-Like Peptide-1 (GLP-1)

Glucagon-like peptide-1 (GLP-1) is an incretin hormone derived from the posttranslational modification of proglucagon and secreted by gut endocrine cells. GLP-1 mediates its actions through a specific G protein-coupled receptor (GPCR), namely GLP-1R. GLP-1 is best characterized as a hormone that regulates glucose homeostasis. GLP-1 has been shown to stimulate glucose-dependent insulin secretion and to increase pancreatic beta cell mass. GLP-1 has also been shown to reduce the rate of gastric emptying and to promote satiety. The efficacy of GLP-1 peptide agonists in controlling blood glucose in type 2 diabetics has been demonstrated in several clinical studies [see, e.g., Nauck et al., *Drug News Perspect* (2003) 16:413-422], as has its efficacy in reducing body mass [Zander et al., *Lancet* (2002) 359:824-830].

GLP-1 receptor agonists are additionally useful in protecting against myocardial infarction and against cognitive and neurodegenerative disorders. GLP-1 has been shown to be cardioprotective in a rat model of myocardial infarction [Bose et al., *Diabetes* (2005) 54:146-151], and GLP-1R has been shown in rodent models to be involved in learning and neuroprotection [During et al., *Nat. Med.* (2003) 9:1173-1179; and Greig et al., *Ann N Y Acad Sci* (2004) 1035:290-315].

Certain disorders such as type 2 diabetes are characterized by a deficiency in GLP-1 [see, e.g., Nauck et al., *Diabetes* (2004) 53 Suppl 3:S190-196].

Current GLP-1 peptide agonists suffer from a lack of oral bioavailability, negatively impacting efficacy. Efforts to develop orally bioavailable non-peptidergic, small-molecule agonists of GLP-1R have so far been unsuccessful (Mentlein, Expert Opin Investig Drugs (2005) 14:57-64). An attractive alternative approach is to develop an orally active composition for increasing an endogenous level of GLP-1 in the blood.

GPR119 agonists have been shown to stimulate the release of GLP-1, see Shah, *Current Opinion in Drug Discovery & Development*, (2009) 12:519-532; Jones, et al., *Ann. Rep. Med. Chem.*, (2009) 44:149-170; Schwartz et. al., *Cell Metabolism*, 2010, 11:445-447; and WO 2006/076231.

I. Peptide YY (PYY)

Peptide YY (PYY) is a 36 amino acid peptide originally isolated in 1980 from porcine intestine (Tatemoto et al., Nature (1980) 285:417-418). PYY is secreted from enteroendocrine L-cells within both the large and small intestine. It has been shown that in rat and human gut concentrations of immunoreactive PYY are low in duodenum and jejunum, high in ileum and colon, and highest in rectum (Lundberg et al., PNAS USA (1982) 79:4471-4475; Adrian et al., *Gastroenterol.* (1985) 89:1070-1077; Ekblad et al., *Peptides* (2002) 23:251-261; Ueno et al., Regul Pept (2008) 145:12-16). PYY expression in rat has also been reported to extend to alpha cells of the islets of Langerhans and to cells in the medulla oblongata (Ekblad et al., Peptides (2002) 23:251-261); PYY is released into the circulation as $PYY_{1-36}$ and $PYY_{3-36}$ (Eberlein et al., *Peptides* (1989) 10:797-803). $PYY_{3-36}$ is generated from $PYY_{1-36}$ by cleavage of the N-terminal Tyr and Pro residues by DPP-IV. $PYY_{3-36}$ is the predominant form of PYY in human postprandial plasma (Grandt et al., *Regul. Pept.* (1994) 51:151-159). $PYY_{1-36}$ and $PYY_{3-36}$ have been reported to have comparable agonist activity at NPY Y2 receptor (Y2R), a G protein-coupled receptor (Parker et al., *Br. J. Pharmacol.* (2008) 153:420-431); however, $PYY_{3-36}$ has been reported to be a high-affinity Y2R selective agonist (Keire et al., *Am. J. Physiol. Gastrointest. Liver Physiol.* (2000) 279:G126-G131). PYY was subsequently reported to reduce high-fat food intake in rats after peripheral administration (Okada et al., Endocrinology Supplement (1993) 180) and to cause weight loss in mice after peripheral administration (Morley et al., *Life Sciences* (1987) 41:2157-2165).

Peripheral administration of $PYY_{3-36}$ has been reported to markedly reduce food intake and weight gain in rats, to decrease appetite and food intake in humans, and to decrease food intake in mice, but not in Y2R-null mice, which was said to suggest that the food intake effect requires the Y2R. In human studies, infusion of $PYY_{3-36}$ was found to significantly decrease appetite and reduce food intake by 33% over 24 hours. Infusion of $PYY_{3-36}$ to reach the normal postprandial circulatory concentrations of the peptide led to peak serum levels of $PYY_{3-36}$ within 15 minutes, followed by a rapid decline to basal levels within 30 minutes. It was reported that there was significant inhibition of food intake in the 12-hour period following the $PYY_{3-36}$ infusion, but that there was essentially no effect on food intake in the 12-hour to 24-hour period. In a rat study, repeated administration of $PYY_{3-36}$ intraperitoneally (injections twice daily for 7 days) reduced cumulative food intake (Batterham et al., Nature (2002) 418:650-654; Renshaw et al., *Current Drug Targets* (2005) 6:171-179).

Peripheral administration of $PYY_{3-36}$ has been reported to reduce food intake, body weight gain and glycemic indices in diverse rodent models of metabolic diseases of both sexes (Pittner et al., *Int. J. Obes. Relat. Metab. Disord.* (2004) 28:963-971). It has been reported that blockade of Y2R with the specific antagonist BIIE-246 attenuates the effect of peripherally administered endogenous and exogenous $PYY_{3-36}$ for reducing food intake (Abbott et al., *Brain Res* (2005) 1043:139-144). It has been reported that peripheral administration of a novel long-acting selective Y2R polyethylene glycol-conjugated peptide agonist reduces food intake and improves glucose metabolism (glucose disposal, plasma insulin and plasma glucose) in rodents (Ortiz et al., *JPET* (2007) 323:692-700; Lamb et al., *J. Med. Chem.* (2007) 50:2264-2268). It has been reported that PYY ablation in mice leads to the development of hyperinsulinemia and obesity (Boey et al., *Diabetologia* (2006) 49:1360-1370). It has been reported that peripheral administration of a long-acting, potent and highly selective Y2R agonist inhibits food intake and promotes fat metabolism in mice (Balasubramaniam et al., *Peptides* (2007) 28:235-240).

There is evidence that agents which stimulate PYY synthesis in vivo can confer protection against diet-induced and genetic obesity and can improve glucose tolerance (Boey et al., *Neuropeptides* (2008) 42:19-30).

It has been reported that Y2R agonists such as $PYY_{1-36}$ and $PYY_{3-36}$ can confer protection against epileptic seizures, such as against kainate seizures (El Bahh et al., *Eur. J. Neurosci.* (2005) 22:1417-1430; Woldbye et al., *Neurobiology of Disease* (2005) 20:760-772).

It has been reported that Y2R agonists such as $PYY_{1-36}$ and $PYY_{3-36}$ act as proabsorbtive (or anti-secretory) hormones, increasing upon intravenous administration the absorption of both water and sodium in various parts of the bowel (Bilchik et al., *Gastroenterol.* (1993) 105:1441-1448; Liu et al., *J. Surg. Res.* (1995) 58:6-11; Nightingale et al., Gut (1996) 39:267-272; Liu et al., *Am Surg* (1996) 62:232-236; Balasubramaniam et al., *J. Med. Chem.* (2000) 43:3420-3427). It has been reported that Y2R agonists such as PYY analogues inhibit secretion and promote absorption and growth in the intestinal epithelium (Balasubramaniam et al., *J. Med. Chem.* (2000) 43:3420-3427). It has been reported that PYY promotes intestinal growth in normal rats (Gomez et al., *Am. J. Physiol.* (1995) 268:G71-G81). It has been reported that Y2R agonists such as $PYY_{1-36}$ and $PYY_{3-36}$ inhibit bowel motility and work to prevent diarrhea (EP1902730; also see Cox, *Peptides* (2007) 28:345-351).

It has been reported that Y2R agonists such as $PYY_{1-36}$ and $PYY_{3-36}$ can confer protection against inflammatory bowel disease such as ulcerative colitis and Crohn's disease (WO 03/105763). It has been reported that PYY-deficient mice exhibit an osteopenic phenotype, i.e. that PYY can increase bone mass and/or can confer protection against loss of bone mass (e.g., decreases loss of bone mass) (Wortley et al., *Gastroenterol.* (2007) 133:1534-1543). It has been reported that $PYY_{3-36}$ can confer protection in rodent models of pancreatitis (Vona-Davis et al., *Peptides* (2007) 28:334-338).

It has been reported that angiogenesis is impaired in Y2R-deficient mice (Lee et al., Peptides (2003) 24:99-106), i.e. that agonists of Y2R such as $PYY_{1-36}$ and $PYY_{3-36}$ promote angiogenesis. It has been reported that wound healing is impaired in Y2R-deficient mice (Ekstrand et al., *PNAS USA* (2003) 100:6033-6038), i.e. that agonists of Y2R such as $PYY_{1-36}$ and $PYY_{3-36}$ promote wound healing. It has been reported that ischemic angiogenesis is impaired in Y2R-deficient mice (Lee et al., *J. Clin. Invest.* (2003) 111:1853-1862), i.e. that agonists of Y2R such as $PYY_{1-36}$ and $PYY_{3-36}$ promotes revascularization and restoration of function of ischemic tissue. It has been reported that agonists of Y2R such as $PYY_{1-36}$ and $PYY_{3-36}$ mediate increases in collateral-dependent blood flow in a rat model of peripheral arterial disease (Cruze et al., *Peptides* (2007) 28:269-280).

It has been reported that PYY and Y2R agonists such as $PYY_{3-36}$ can suppress tumor growth in the cases of, e.g., pancreatic cancer such as pancreatic ductal adenocarcinoma, breast cancer such as breast infiltrative ductal adenocarcinoma, colon cancer such as colon adenocarcinoma and Barrett's adenocarcinoma (Liu et al., *Surgery* (1995) 118: 229-236; Liu et al., *J. Surg. Res.* (1995) 58:707-712; Grise et al., *J. Surg. Res.* (1999) 82:151-155; Tseng et al., *Peptides* (2002) 23:389-395; McFadden et al., *Am. J. Surg.* (2004) 188:516-519).

It has been reported that stimulation of Y2R such as by $PYY_{3-36}$ leads to an increase in plasma adiponectin (Ortiz et al., *JPET* (2007) 323:692-700). Adiponectin is an adipokine with potent anti-inflammatory properties (Ouchi et al., Clin Chim Acta (2007) 380:24-30; Tilg et al., *Nat. Rev. Immunol.* (2006) 6:772-783). Adiponectin exerts anti-atherogenic effects by targeting vascular endothelial cells and macrophages and insulin-sensitizing effects, predominantly in muscle and liver (Kubota et al., *J. Biol. Chem.* (2002) 277:25863-25866; Maeda et al., *Nat. Med.* (2002) 8:731-737). Low adiponectin levels have been reported to be associated with atherogenic lipoproteins in dyslipidemia (elevated triglycerides, small dense LDL cholesterol, and low HDL cholesterol) (Marso et al., *Diabetes Care* (2008) 31:989-994). Adiponectin has been implicated in high density lipoprotein (HDL) assembly (Oku et al., *FEBS Letters* (2007) 581:5029-5033). Adiponectin has been found to ameliorate the abnormalities of metabolic syndrome, including insulin resistance, hyperglycemia, and dyslipidemia, in a mouse model of obesity-linked metabolic syndrome associated with decreased adiponectin levels (Hara et al., *Diabetes Care* (2006) 29:1357-1362). Adiponectin has been reported to stimulate angiogenesis in response to tissue ischemia (Shibata et al., *J. Biol. Chem.* (2004) 279:28670-28674). Adiponectin has been reported to prevent cerebral ischemic injury through endothelial nitric oxide synthase-dependent mechanisms (Nishimura et al., *Circulation* (2008) 117:216-223). Adiponectin has been reported to confer protection against myocardial ischemia-reperfusion injury (Shibata et al., *Nat Med* (2005) 11:1096-1103; Tao et al., *Circulation* (2007) 115:1408-1416). Adiponectin has been reported to confer protection against myocardial ischemia-reperfusion injury via AMP-activated protein kinase, Akt, and nitric oxide (Gonon et al., *Cardiovasc Res.* (2008) 78:116-122). Adiponectin has been reported to confer protection against the development of systolic dysfunction following myocardial infarction, through its abilities to suppress cardiac hypertrophy and interstitial fibrosis, and protect against myocyte and capillary loss (Shibata et al., *J. Mol. Cell. Cardiol.* (2007) 42:1065-1074). Adiponectin has been reported to confer protection against inflammatory lung disease; adiponectin-deficient mice exhibit an emphysema-like phenotype (Summer et al., *Am J. Physiol. Lung Cell Mol. Physiol.* (Mar. 7, 2008)). Adiponectin has been reported to confer protection against allergic airway inflammation and airway hyperresponsiveness such as may be associated with asthma (Shore et al., *J. Allergy Clin. Immunol* (2006) 118:389-395). Adiponectin has been suggested to confer protection against pulmonary arterial hypertension by virtue of its insulin-sensitizing effects (Hansmann et al., *Circulation* (2007) 115:1275-1284). Adiponectin has been reported to ameliorate obesity-related hypertension, with said amelioration of hypertension being associated in part with upregulated prostacyclin expression (Ohashi et al., Hypertension (2006) 47:1108-1116). Adiponectin has been reported to decrease tumor necrosis factor (TNF)-α-induced expression of the adhesion molecules VCAM-1, E-selectin and ICAM-1 in human aortic endothelial cells (HAECs) (Ouchi et al., *Circulation* (1999) 100:2473-2476) and to inhibit production of TNF-α in macrophages (Yokota et al., *Blood* (2000) 96:1723-1732). Adiponectin has been reported to confer protection against restenosis after vascular intervention (Matsuda et al., *J Biol Chem* (2002) 277:37487-37491). The central role of TNF-α in inflammation has been demonstrated by the ability of agents that block the action of TNF-α to treat a range of inflammatory conditions. TNF-α-mediated inflammatory conditions encompass rheumatoid arthritis, inflammatory bowel disease such as Crohn's disease, ankylosing spondylitis, psoriasis, ischemic brain injury, cardiac allograft rejection, asthma, and the like (Bradley, *J Pathol* (2008) 214:149-160). See, e.g., Yamamoto et al., *Clinical Science* (2002) 103:137-142; Behre, *Scand J Clin Lab Invest* (2007) 67:449-458; Guerre-Millo, *Diabetes & Metabolism* (2008) 34:12-18; Parker et al., *Br. J. Pharmacol.* (2008) 153:420-431.

GPR119 agonists have been shown to stimulate the release of PYY; see Schwartz et. al., *Cell Metabolism*, 2010, 11:445-447; and WO 2009/126245.

SUMMARY OF THE INVENTION

The present invention is drawn to 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Formula (Ia), Compound 1) and pharmaceutically acceptable salts, solvates, and hydrates thereof,

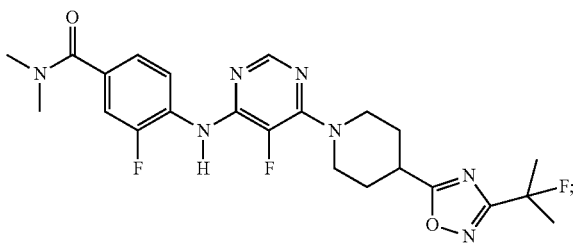

(Ia)

3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide (Formula (Ib), Compound 2) and pharmaceutically acceptable salts, solvates, and hydrates thereof,

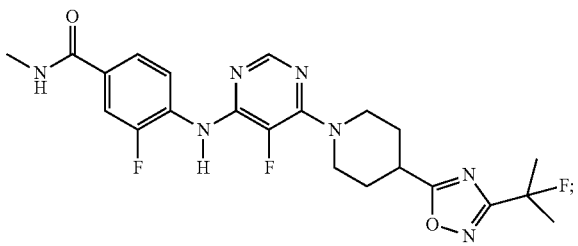

(Ib)

and
3-fluoro-4-(5-fluoro-6-(4-(3-(2-fluoropropan-2-yl)-1,2,4-oxadiazol-5-yl)piperidin-1-yl)pyrimidin-4-ylamino)benzamide (Formula (Ic), Compound 3) and pharmaceutically acceptable salts, solvates, and hydrates thereof,

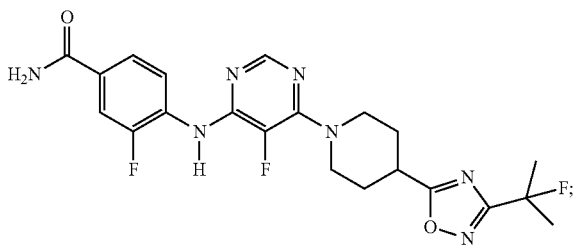

(Ic)

which bind to and modulate the activity of a GPCR, referred to herein as GPR119, and uses thereof.

One aspect of the present invention pertains to compounds selected from 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Formula (Ia), Compound 1) and pharmaceutically acceptable salts, solvates, and hydrates thereof.

One aspect of the present invention pertains to compositions comprising a compound of the present invention.

One aspect of the present invention pertains to compositions comprising a compound of the present invention and a pharmaceutically acceptable carrier.

One aspect of the present invention pertains to methods for preparing a composition comprising the step of admixing a compound of the present invention and a pharmaceutically acceptable carrier.

One aspect of the present invention pertains to pharmaceutical products selected from: a pharmaceutical composition, a formulation, a dosage form, a combined preparation, a twin pack, and a kit; comprising a compound of the present invention.

One aspect of the present invention pertains to compositions comprising a compound of the present invention and a second pharmaceutical agent.

One aspect of the present invention pertains to methods for preparing a composition comprising the step of admixing a compound of the present invention and a second pharmaceutical agent.

One aspect of the present invention pertains to compositions comprising a compound of the present invention, a second pharmaceutical agent, and a pharmaceutically acceptable carrier.

One aspect of the present invention pertains to methods for preparing a composition comprising the step of admixing a compound of the present invention, a second pharmaceutical agent, and a pharmaceutically acceptable carrier.

One aspect of the present invention pertains to compositions obtained by a method of the present invention.

One aspect of the present invention pertains to a pharmaceutical products selected from: a pharmaceutical composition, a formulation, a dosage form, a combined preparation, a twin pack, and a kit; comprising a compound of the present invention and a second pharmaceutical agent.

One aspect of the present invention pertains to methods for modulating the activity of a GPR119 receptor, comprising administering to an individual in need thereof: a therapeutically effective amount of a compound of the present invention; a composition of the present invention; or a pharmaceutical product of the present invention.

One aspect of the present invention pertains to methods for modulating the activity of a GPR119 receptor, comprising prescribing to an individual in need thereof: a therapeutically effective amount of a compound of the present invention; a composition of the present invention; or a pharmaceutical product of the present invention.

One aspect of the present invention pertains to the use of a compound of the present invention; or a composition of the present invention; in the manufacture of a medicament for modulating the activity of a GPR119 receptor in an individual.

One aspect of the present invention pertains to a compound of the present invention; a composition of the present invention; or a pharmaceutical product of the present invention; for use in a method of treatment of the human or animal body by therapy.

One aspect of the present invention pertains to a compound of the present invention; a composition of the present invention; or a pharmaceutical product of the present invention; for use in a method of modulating the activity of a GPR119 receptor in an individual.

One aspect of the present invention pertains to a pharmaceutical product selected from: a pharmaceutical composition, a formulation, a dosage form, a combined preparation, a twin pack, and a kit; comprising a compound of the present invention; for use in a method of treatment of the human or animal body by therapy.

One aspect of the present invention pertains to a pharmaceutical product selected from: a pharmaceutical composition, a formulation, a dosage form, a combined preparation, a twin pack, and a kit; comprising a compound of the present invention; for use in a method of modulating the activity of a GPR119 receptor in an individual.

One aspect of the present invention pertains to compounds, methods, compositions, uses of compounds, and pharmaceutical products, each as described herein, in combination with a second pharmaceutical agent. For example, one aspect of the present invention pertains to methods for modulating the activity of a GPR119 receptor, comprising administering to an individual in need thereof, a therapeutically effective amount of a compound of the present invention in combination with a therapeutically effective amount of a second pharmaceutical agent.

One aspect of the present invention pertains to compositions, methods, pharmaceutical products, uses, and compounds, each as described herein, in combination with a second pharmaceutical agent, wherein the second pharmaceutical agent is selected from: a DPP-IV inhibitor, a biguanide, an alpha-glucosidase inhibitor, an insulin analogue, a sulfonylurea, an SGLT2 inhibitor, a meglitinide, a thiazolidinedione, and an anti-diabetic peptide analogue.

One aspect of the present invention pertains to compounds, methods, compositions, uses of compounds, and pharmaceutical products, each as described herein, wherein modulating the activity of a GPR119 receptor in an individual is agonizing the GPR119 receptor.

One aspect of the present invention pertains to compounds, methods, compositions, uses of compounds, and pharmaceutical products, each as described herein, wherein modulating the activity of a GPR119 receptor in an individual is increasing the secretion of an incretin.

One aspect of the present invention pertains to compounds, methods, compositions, uses of compounds, and pharmaceutical products, each as described herein, wherein modulating the activity of a GPR119 receptor in an individual is increasing a blood incretin level.

One aspect of the present invention pertains to compounds, methods, compositions, uses of compounds, and pharmaceutical products, each as described herein, wherein modulating the activity of a GPR119 receptor in an individual is treating a disorder, wherein the disorder is selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

One aspect of the present invention pertains to compounds, methods, compositions, uses of compounds, and pharmaceutical products, each as described herein, wherein the metabolic-related disorder is type 2 diabetes.

These and other aspects of the invention disclosed herein will be set forth in greater detail as the patent disclosure proceeds.

DETAILED DESCRIPTION OF THE INVENTION

Figure 1:
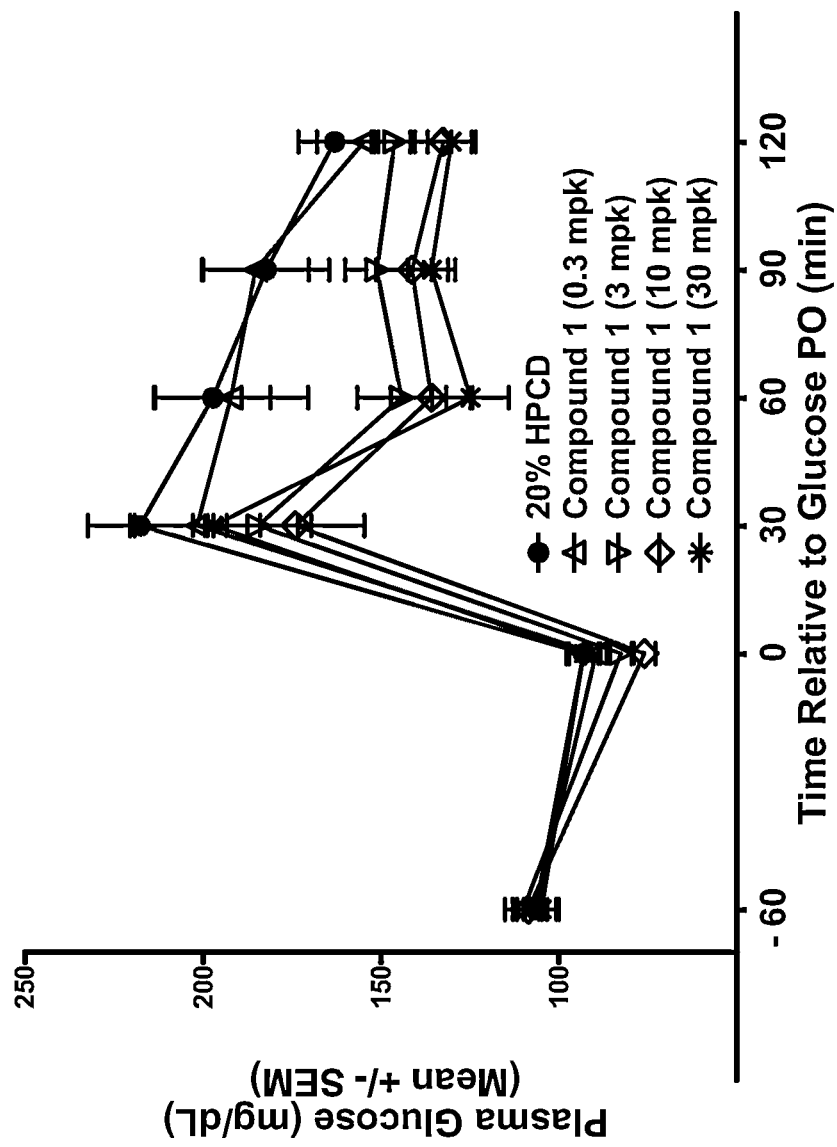
FIG. 1 shows the effects of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide on glucose homeostasis in male diabetic ZDF rats (oral glucose tolerance test (oGTT)).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Accordingly, all combinations of uses and medical indications described herein specifically embraced by the present invention just as if each and every subcombination of uses and medical indications was individually and explicitly recited herein.

Definitions

For clarity and consistency, the following definitions will be used throughout this patent document.

The term "agonist" as used herein refers to a moiety that interacts with and activates a G-protein-coupled receptor, for instance a GPR119-receptor, and can thereby initiate a physiological or pharmacological response characteristic of that receptor. For example, an agonist may activate an intracellular response upon binding to a receptor, or enhance GTP binding to a membrane. An agonist can be a full agonist or a partial agonist.

The term "antagonist" as used herein refers to a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

The term "GPR119" as used herein includes the human amino acid sequences found in GenBank accession number AY288416, and naturally-occurring allelic variants thereof, and mammalian orthologs thereof. A preferred human GPR119 for use in screening and testing of the compounds of the invention is provided in the nucleotide sequence of Seq. ID.No:1 and the corresponding amino acid sequence in Seq. ID.No:2 found in PCT Application No. WO2005/007647.

The term "in need of treatment" and the term "in need thereof" when referring to treatment are used interchangeably and refer to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" refers to any animal, including mammals, preferably mice, rats, other rodents, rabbits, dogs, cats, swine, cattle, sheep, horses, or primates, and most preferably humans.

The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. Preferably, the baseline intracellular response is inhibited in the presence of the inverse agonist by at least 30%, more preferably by at least 50% and most preferably by at least 75%, as compared with the baseline response in the absence of the inverse agonist.

The term "modulate or modulating" refers to an increase or decrease in the amount, quality, response or effect of a particular activity, function or molecule.

The term "composition" refers to a compound, including but not limited to, a compound of the present invention and salts, solvates, and hydrates thereof, in combination with at least one additional component.

The term "pharmaceutical composition" refers to a composition comprising at least one active ingredient, such as a compound of the present invention; including but not limited to, a compound of the present invention and salts, solvates, and hydrates thereof, whereby the composition is amenable for treating and/or investigating a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) preventing the disease, for example, preventing a disease, condition or disorder in an individual that may be predisposed to the disease, condition or disorder but does not yet experience or display the pathology or symptomatology of the disease;

(2) inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) ameliorating the disease, for example, ameliorating a disease, condition or disorder in an individual that is experiencing or displaying the pathology or symptomatology of the disease, condition or disorder (i.e., reversing the pathology and/or symptomatology).

The term "weight management" as used herein means controlling body weight and in the context of the present invention is directed toward weight loss and the maintenance of weight loss (also called weight maintenance herein). In addition to controlling body weight, weight management includes controlling parameters related to body weight, for example, BMI, percent body fat, and waist circumference. For example, weight management for an individual who is overweight or obese can refer to losing weight with the goal of keeping weight in a healthier range. Also, for example, weight management for an individual who is overweight or obese can include losing body fat or waist circumference with or without the loss of body weight.

The term "maintenance of weight loss" or "weight maintenance" as used herein includes preventing, reducing, or controlling weight gain after weight loss. It is well known that weight gain often occurs after weight loss. Weight loss can occur, for example, from dieting, exercising, illness, drug treatment, surgery, or any combination of these methods, but often an individual that has lost weight will regain some or all of the lost weight. Therefore, weight maintenance in an individual who has lost weight can include preventing weight gain after weight loss, reducing the amount of weight gained after weight loss, controlling weight gain after weight loss, or slowing the rate of weight gain after weight loss.

COMPOUNDS OF THE INVENTION

One aspect of the present invention provides, inter alia, compounds selected from the following compounds and pharmaceutically acceptable salts, solvates, and hydrates thereof:

3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide;

3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide; and 3-fluoro-4-(5-fluoro-6-(4-(3-(2-fluoropropan-2-yl)-1,2,4-oxadiazol-5-yl)piperidin-1-yl)pyrimidin-4-ylamino)benzamide.

One aspect of the present invention provides compounds selected from 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Formula (Ia), Compound 1) and pharmaceutically acceptable salts, solvates, and hydrates thereof.

Compounds of the invention can also include tautomeric forms, such as keto-enol tautomers and the like. It is understood that the various tautomeric forms are within the scope of the compounds of the present invention.

The compounds of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

Crystalline Forms of Compound 1

One aspect of the present invention relates to crystalline forms of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Formula (Ia), Compound 1).

Crystalline forms of Compound 1 can be identified by their unique solid state signature with respect to, for example, differential scanning calorimetry (DSC), powder X-ray diffraction (PXRD), and other solid state methods.

Further characterization with respect to water or solvent content of crystalline forms can be gauged by any of the following methods for example, thermogravimetric analysis (TGA), DSC and the like.

For DSC, it is known that the temperatures observed will depend upon sample purity, the rate of temperature change, as well as sample preparation technique and the particular instrument employed. Thus, the values reported herein relating to DSC thermograms can vary by plus or minus about 4° C. The values reported herein relating to DSC thermograms can also vary by plus or minus about 20 joules per gram.

For PXRD, the relative intensities of the peaks can vary, depending upon the sample preparation technique, the sample mounting procedure and the particular instrument employed. Moreover, instrument variation and other factors can often affect the °2θ values. Therefore, the peak assignments of diffraction patterns can vary by plus or minus 0.2 °2θ.

For TGA, the features reported herein can vary by plus or minus about 10° C. For TGA, the features reported herein can also vary by plus or minus about 2% weight change due to, for example, sample variation.

Further characterization with respect to hygroscopicity of the crystalline forms can be gauged by, for example, dynamic moisture sorption (DMS). The DMS features reported herein can vary by plus or minus about 5% relative humidity. The DMS features reported herein can also vary by plus or minus about 5% weight change.

Compound 1 (Anhydrous Form)

One aspect of the present invention relates to an anhydrous form of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1). The physical properties of the crystalline form of Compound 1 anhydrous form are summarized in the following table.

Figure 6:
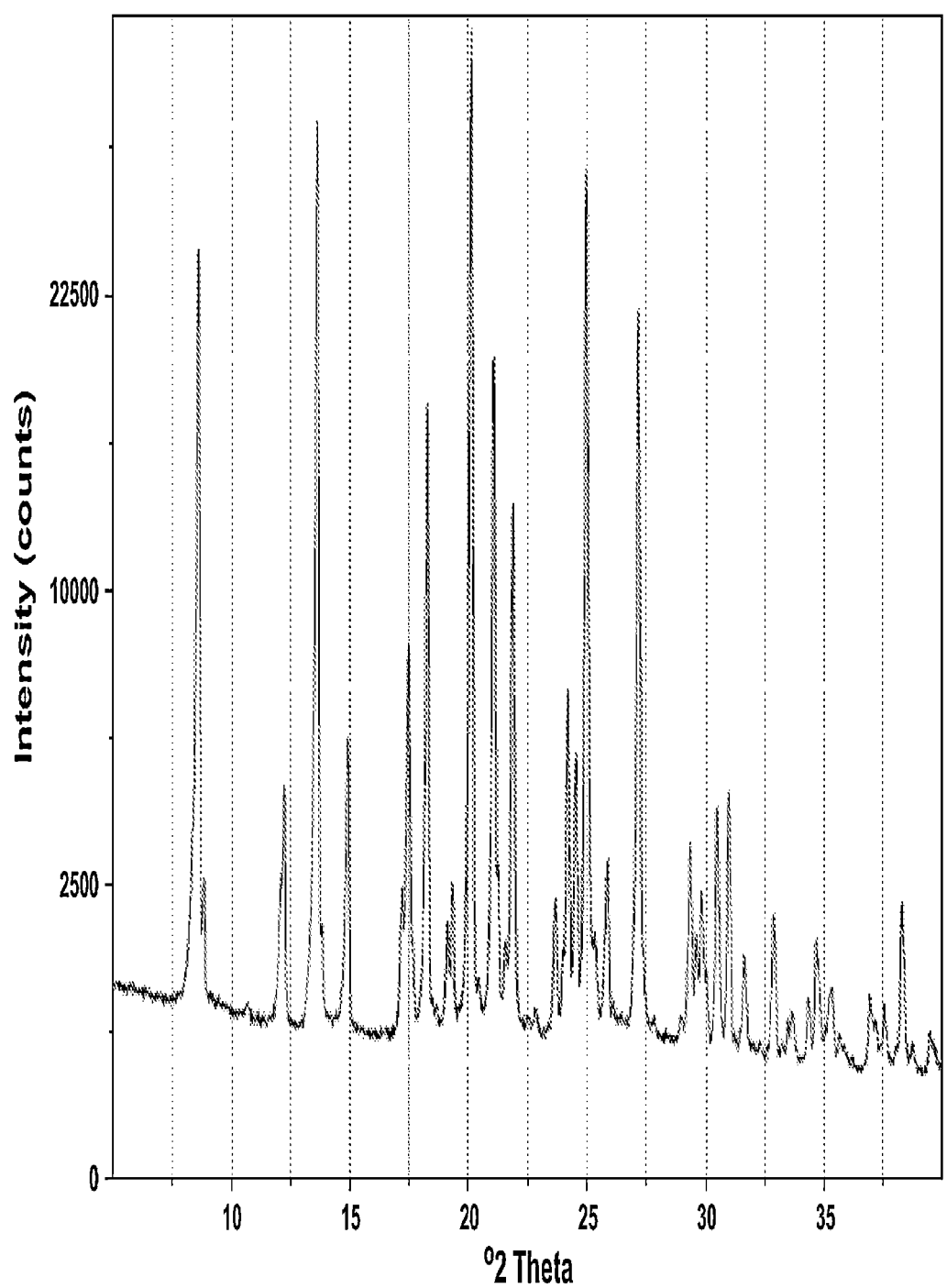
FIG. 6 shows the PXRD for the anhydrous form of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide.

| | Compound 1 (Anhydrous Form) |
|---|---|
| PXRD | FIG. 6: Peaks of about ≥9.5% relative intensity at 8.6, 12.2, 13.6, 14.9, 17.5, 18.3, 20.1, 21.1, 21.9, 24.2, 24.5, 25.0, 27.2, 30.5, and 31.0 °2θ |
| TGA | FIG. 7: Negligible Decrease in weight. |
| DSC | FIG. 7: Extrapolated onset temperature: about 148.9° C., and an enthalpy of fusion of 99.5 joules per gram. |
| DMS | FIG. 8: Less than about 0.35% weight gain at about 90% RH and 25° C. |

One aspect of the present invention relates to an anhydrous crystalline form of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1), wherein the anhydrous crystalline form has a powder X-ray diffraction pattern comprising every combination of one or more peaks, in terms of 2θ, selected from the peaks found in the following table:

| Pos. [°2θ] | d-spacing [Å] | Rel. Int. [%] |
|---|---|---|
| 8.6 | 10.3 | 64.4 |
| 8.8 | 10.0 | 4.8 |
| 12.1 | 7.3 | 5.5 |
| 12.2 | 7.2 | 10.1 |
| 13.6 | 6.5 | 85.8 |
| 14.9 | 5.9 | 13.8 |
| 17.2 | 5.2 | 5.1 |
| 17.5 | 5.1 | 20.7 |
| 18.3 | 4.9 | 44.5 |
| 19.3 | 4.6 | 5.3 |
| 20.1 | 4.4 | 100.0 |
| 21.1 | 4.2 | 51.0 |
| 21.3 | 4.2 | 5.8 |
| 21.9 | 4.1 | 34.1 |
| 23.7 | 3.8 | 4.6 |
| 24.2 | 3.7 | 17.1 |
| 24.5 | 3.6 | 12.2 |
| 25.0 | 3.6 | 76.9 |
| 25.9 | 3.4 | 6.3 |
| 27.2 | 3.3 | 57.2 |
| 29.4 | 3.0 | 7.3 |
| 29.8 | 3.0 | 5.2 |
| 30.5 | 2.9 | 9.5 |
| 31.0 | 2.9 | 10.5 |
| 32.9 | 2.7 | 4.4 |
| 38.3 | 2.3 | 5.0 |

One aspect of the present invention relates to an anhydrous crystalline form of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide, wherein the anhydrous crystalline form has a powder X-ray diffraction pattern comprising a peak, in terms of 2θ, at 20.1°±0.2°. In some embodiments, the anhydrous crystalline form has a powder X-ray diffraction pattern comprising peaks, in terms of 2θ, at 13.6°±0.2°, and 20.1°±0.2°. In some embodiments, the anhydrous crystalline form has a powder X-ray diffraction pattern comprising peaks, in terms of 2θ, at 13.6°±0.2°, 20.1°±0.2°, and 25.0°±0.2°. In some embodiments, the anhydrous crystalline form has a powder X-ray diffraction pattern comprising peaks, in terms of 2θ, at 8.6°±0.2°, 13.6°±0.2°, 20.1°±0.2°, 25.0°±0.2°, and 27.2°±0.2°. In some embodiments, the anhydrous crystalline form has a powder X-ray diffraction pattern comprising peaks, in terms of 2θ, at 8.6°±0.2°, 13.6°±0.2°, 18.3°±0.2°, 20.1°±0.2°, 21.1°±0.2°, 25.0°±0.2°, and 27.2°±0.2°. In some embodiments, the anhydrous crystalline form has a powder X-ray diffraction pattern comprising peaks, in terms of 2θ, at 8.6°±0.2°, 13.6°±0.2°, 17.5°±0.2°, 18.3°±0.2°, 20.1°±0.2°, 21.1°±0.2°, 21.9°±0.2°, 25.0°±0.2°, and 27.2°±0.2°. In some embodiments, the anhydrous crystalline form has a powder X-ray diffraction pattern comprising peaks, in terms of 2θ, at 8.6°±0.2°, 13.6°±0.2°, 14.9°±0.2°, 17.5°±0.2°, 18.3°±0.2°, 20.1°±0.2°, 21.1°±0.2°, 21.9°±0.2°, 24.2°±0.2°, 24.5°±0.2°, 25.0°±0.2°, and 27.2°±0.2°. In some embodiments, the anhydrous crystalline form has a powder X-ray diffraction pattern substantially as shown in FIG. 6, wherein by "substantially" is meant that the reported peaks can vary by about ±0.2 °2θ.

Figure 7:
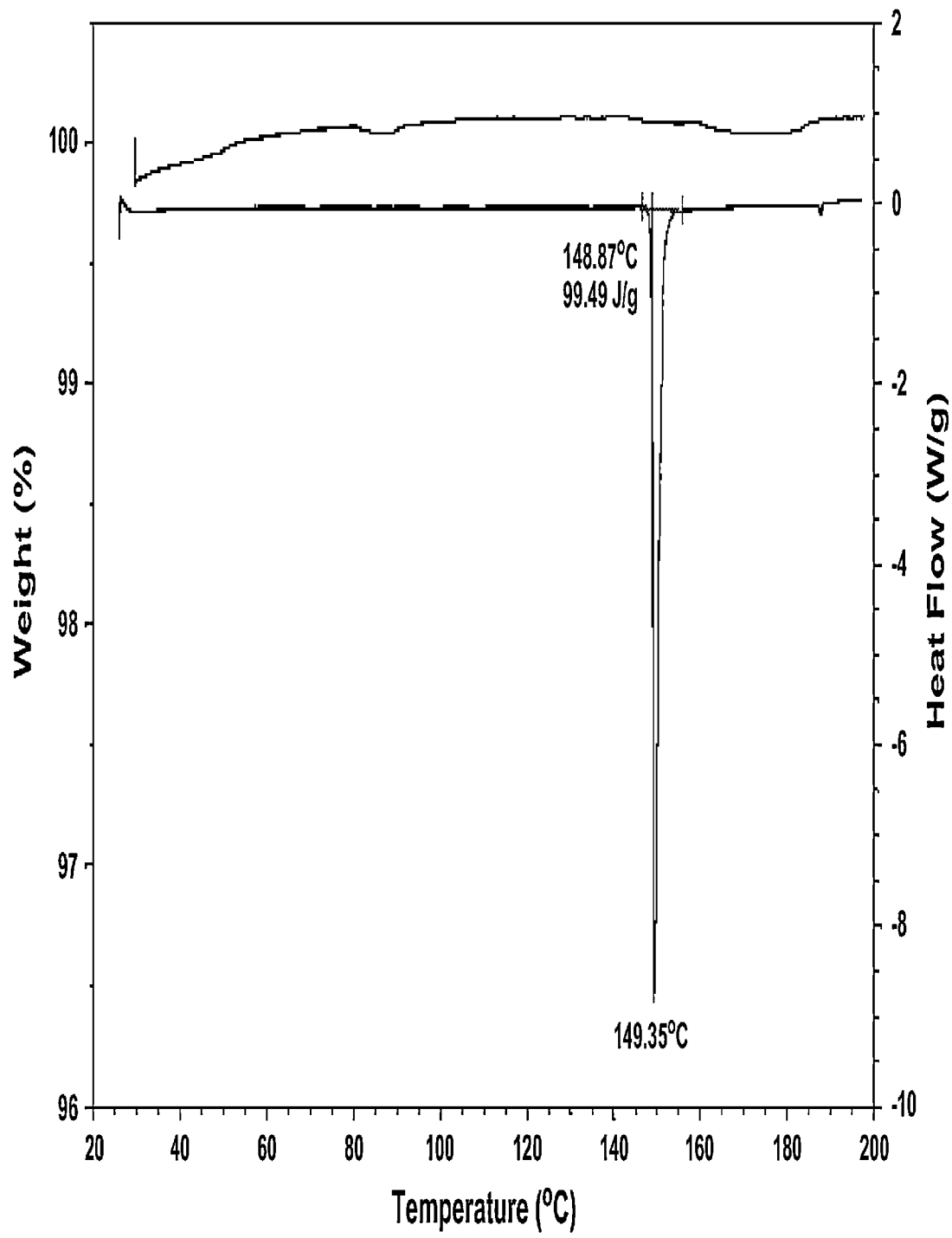
FIG. 7 shows the DSC and TGA for the anhydrous form of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide.

In some embodiments, the anhydrous crystalline form has a differential scanning calorimetry thermogram comprising an endotherm with an extrapolated onset temperature between about 143.9° C. and about 153.9° C. In some embodiments, the anhydrous crystalline form has a differential scanning calorimetry thermogram comprising an endotherm with an extrapolated onset temperature between 145.9° C. and about 151.9° C. In some embodiments, the anhydrous crystalline form has a differential scanning calorimetry thermogram comprising an endotherm with an extrapolated onset temperature between about 146.9° C. and about 150.9° C. In some embodiments, the anhydrous crystalline form has having a differential scanning calorimetry thermogram comprising an endotherm with an extrapolated onset temperature between about 147.9° C. and about 149.9° C. In some embodiments, the anhydrous crystalline form has a differential scanning calorimetry thermogram comprising an endotherm with an extrapolated onset temperature at about 148.9° C. In some embodiments, the anhydrous crystalline form has a differential scanning calorimetry thermogram substantially as shown in FIG. 7, wherein by "substantially" is meant that the reported DSC features can vary by about ±4° C. and that the reported DSC features can vary by about ±20 joules per gram.

In some embodiments, the anhydrous crystalline form has a thermogravimetric analysis profile showing ≤1.0% weight loss up to about 120° C. In some embodiments, the anhydrous crystalline form has a thermogravimetric analysis profile showing ≤0.5% weight loss up to about 120° C. In some embodiments, the anhydrous crystalline form has a thermogravimetric analysis profile showing ≤0.25% weight loss up to about 120° C. In some embodiments, the anhydrous crystalline form has a thermogravimetric analysis profile showing ≤0.05% weight loss up to about 120° C. In some embodiments, the anhydrous crystalline form has a thermogravimetric analysis profile substantially as shown in FIG. 7, wherein by "substantially" is meant that the reported TGA features can vary by about ±10° C., and that that the reported TGA features can vary by about ±2% weight change.

Figure 8:
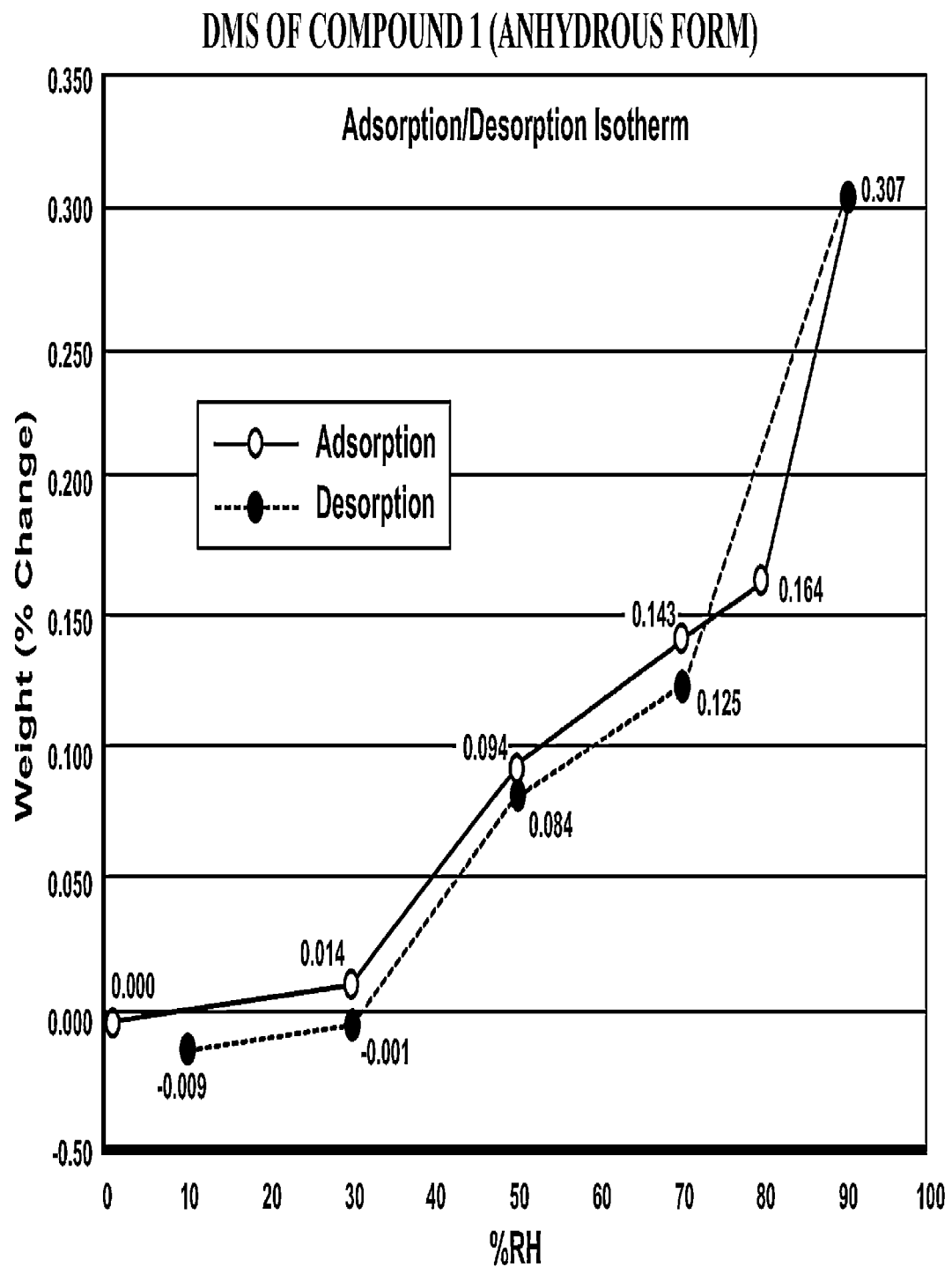
FIG. 8 shows the DMS for the anhydrous form of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide.

In some embodiments, the anhydrous crystalline form has a dynamic moisture sorption analysis profile of less than about 0.35% weight gain out to about 90% RH at about 25° C. In some embodiments, the anhydrous crystalline form has a dynamic moisture sorption analysis profile substantially as shown in FIG. 8, wherein by "substantially" is meant that the reported DMS features can vary by plus or minus about 5% weight change.

One aspect of the present invention relates to the anhydrous crystalline form having:
1) a powder X-ray diffraction pattern comprising peaks, in terms of 2θ, at 13.6°±0.2°, and 20.1°±0.2°;
2) a differential scanning calorimetry thermogram comprising an endotherm with an extrapolated onset temperature between about 143.9° C. and about 153.9° C.; and/or
3) a thermogravimetric analysis profile showing ≤0.5% weight loss up to about 120° C.

One aspect of the present invention relates to the anhydrous crystalline form having:
1) a powder X-ray diffraction pattern comprising peaks, in terms of 2θ, at 13.6°±0.2°, 20.1°±0.2°, and 25.0°±0.2°;
2) a differential scanning calorimetry thermogram comprising an endotherm with an extrapolated onset temperature between about 145.9° C. and about 151.9° C.; and/or
3) a thermogravimetric analysis profile showing ≤0.25% weight loss up to about 120° C.

One aspect of the present invention relates to the anhydrous crystalline form having:
1) a powder X-ray diffraction pattern comprising peaks, in terms of 2θ, at 8.6°±0.2°, 13.6°±0.2°, 20.1°±0.2°, 25.0°±0.2°, and 27.2°±0.2°; 2) a differential scanning calorimetry thermogram comprising an endotherm with an extrapolated onset temperature between about 146.9° C. and about 150.9° C.; and/or
3) a thermogravimetric analysis profile showing ≤0.05% weight loss up to about 120° C.

One aspect of the present invention relates to the anhydrous crystalline form having:
1) a powder X-ray diffraction pattern comprising peaks, in terms of 2θ, at 8.6°±0.2°, 13.6°±0.2°, 18.3°±0.2°, 20.1°±0.2°, 21.1°±0.2°, 25.0°±0.2°, and 27.2°±0.2°;
2) a differential scanning calorimetry thermogram comprising an endotherm with an extrapolated onset temperature between about 147.9° C. and about 149.9° C.; and/or
3) a thermogravimetric analysis profile showing ≤0.05% weight loss up to about 120° C.

One aspect of the present invention relates to the anhydrous crystalline form having:
1) a powder X-ray diffraction pattern comprising peaks, in terms of 2θ, at 8.6°±0.2°, 13.6°±0.2°, 17.5°±0.2°, 18.3°±0.2°, 20.1°±0.2°, 21.1°±0.2°, 21.9°±0.2°, 25.0°±0.2°, and 27.2°±0.2°;
2) a differential scanning calorimetry thermogram comprising an endotherm with an extrapolated onset temperature at about 147.9° C. and about 149.9° C.; and/or
3) a thermogravimetric analysis profile showing ≤0.05% weight loss up to about 120° C.

One aspect of the present invention relates to the anhydrous crystalline form having:
1) a powder X-ray diffraction pattern comprising peaks, in terms of 2θ, at 8.6°±0.2°, 13.6°±0.2°, 14.9°±0.2°, 17.5°±0.2°, 18.3°±0.2°, 20.1°±0.2°, 21.1°±0.2°, 21.9°±0.2°, 24.2°±0.2°, 24.5°±0.2°, 25.0°±0.2°, and 27.2°±0.2°;
2) a differential scanning calorimetry thermogram comprising an endotherm with an extrapolated onset temperature at about 148.9° C.; and/or
3) a thermogravimetric analysis profile showing ≤0.05% weight loss up to about 120° C.

One aspect of the present invention relates to the anhydrous crystalline form having:
1) a powder X-ray diffraction pattern substantially as shown in FIG. 6;
2) a differential scanning calorimetry thermogram substantially as shown in FIG. 7;
3) a thermogravimetric analysis profile substantially as shown in FIG. 7; and/or
4) a dynamic moisture sorption analysis profile substantially as shown in FIG. 8.

CERTAIN EMBODIMENTS

Compositions, Methods, Indications, Pharmaceutical Products, Combinations, and Uses of Compounds of the Present Invention In addition to the foregoing, without limitation, certain other embodiments are described and provided below.
Certain Compositions of the Present Invention:
One aspect of the present invention pertains to compositions comprising a compound of the present invention.
The term "composition" refers to at least one compound of the invention in combination with at least one other component. It is understood, that the amount of a compound of the present invention in a composition can be any amount ranging from less than 100.00% to greater than 0.00%. Examples of compositions include, but are not limited to, a reference standard comprising a compound of the present invention (e.g., for use in method development, in-process testing, and the like); bulk API (i.e., Active Pharmaceutical Ingredient) of a compound of the present invention (e.g., for use in formulating a pharmaceutical composition); a combined preparation (i.e., a compound of the present invention in combination with a pharmaceutical/therapeutic agent or agents); a biological sample comprising a compound of the present invention (e.g., for use in or obtained from a patient, an animal, a pharmacokinetic study, ADME study, LADME study, and the like); a reaction mixture comprising a compound of the present invention, such as, a reaction mixture as described in any of the Examples herein; a manufacturing reaction mixture comprising a compound of the present invention in combination with one or more components such as solvents, reactants, side-products, etc.; and the like. It is understood that pharmaceutical compositions are a specific subset of compositions.

One aspect of the present invention pertains to compositions comprising a compound of the present invention and a pharmaceutically acceptable carrier.

One aspect of the present invention pertains to methods for preparing a composition comprising the step of admixing a compound of the present invention and a pharmaceutically acceptable carrier.

One aspect of the present invention pertains to pharmaceutical products selected from: a pharmaceutical composition, a formulation, a dosage form, a combined preparation, a twin pack, and a kit; comprising a compound of the present invention.

One aspect of the present invention pertains to compositions comprising a compound of the present invention and a second pharmaceutical agent.

In any of the embodiments that recites the terms "a pharmaceutical agent" and/or "a second pharmaceutical agent", it is appreciated that these terms in some aspects be further limited to a pharmaceutical agent or a second pharmaceutical agent that is not a Compound of Formula (Ia). It is understood that the terms "a pharmaceutical agent" and "a second pharmaceutical agent" may refer to a pharmaceutical agent or a second pharmaceutical agent that is not detectable or has an $EC_{50}$ that is greater than a value selected from: 50 µM, 10 µM, 1 µM, and 0.1 µM in a GPR119 receptor activity assay as described in Example 5.

One aspect of the present invention pertains to methods for preparing a composition comprising the step of admixing a compound of the present invention and a second pharmaceutical agent.

One aspect of the present invention pertains to compositions comprising a compound of the present invention, a second pharmaceutical agent, and a pharmaceutically acceptable carrier.

One aspect of the present invention pertains to methods for preparing a composition comprising the step of admixing a compound of the present invention, a second pharmaceutical agent, and a pharmaceutically acceptable carrier.

The present invention further provides pharmaceutical compositions. Accordingly, one aspect of the present invention pertains to pharmaceutical compositions comprising a compound of the present invention and a pharmaceutically acceptable carrier. One aspect of the present invention pertains to methods for preparing a composition comprising the step of admixing a compound of the present invention and a pharmaceutically acceptable carrier. One aspect of the present invention pertains to pharmaceutical compositions comprising a compound of the present invention, a second pharmaceutical agent, and a pharmaceutically acceptable carrier. One aspect of the present invention pertains to methods for preparing a composition comprising the step of admixing a compound of the present invention, a second pharmaceutical agent, and a pharmaceutically acceptable carrier.

One aspect of the present invention pertains to a pharmaceutical product selected from: a pharmaceutical composition, a formulation, a dosage form, a combined preparation, a twin pack, and a kit; comprising a compound of the present invention and a second pharmaceutical agent.

One aspect of the present invention pertains to compositions obtained by the methods of the present invention as described herein.

Certain Methods, Pharmaceutical Products, Combinations, and Uses of the Present Invention One aspect of the present invention pertains to methods for modulating the activity of a GPR119 receptor, comprising administering to an individual in need thereof: a therapeutically effective amount of a compound of the present invention; a composition of the present invention; or a pharmaceutical product of the present invention.

One aspect of the present invention pertains to methods for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; comprising administering to the individual in need thereof: a therapeutically effective amount of a compound of the present invention; a composition of the present invention; or a pharmaceutical product of the present invention.

One aspect of the present invention pertains to methods for increasing the secretion of an incretin in an individual or increasing a blood incretin level in an individual, comprising administering to the individual in need thereof: a therapeutically effective amount of a compound of the present invention; a composition of the present invention; or a pharmaceutical product of the present invention.

One aspect of the present invention pertains to methods for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; comprising prescribing to the individual in need thereof: a therapeutically effective amount of a compound of the present invention; a composition of the present invention; or a pharmaceutical product of the present invention.

Example 6 shows that Compound 1 is metabolized to Compound 2 and Compound 3. Accordingly, one aspect of the present invention pertains to methods for increasing the secretion of an incretin in an individual or increasing a blood incretin level in an individual, comprising administering to the individual in need thereof, a therapeutically effective amount of a compound of the present invention, wherein the compound is generated as a result of a metabolic chemical reaction of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1), or a pharmaceutically acceptable salt thereof. Another aspect of the present invention pertains to methods for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; comprising administering to the individual in need thereof, a therapeutically effective amount of a compound of the present invention, wherein the compound is generated as a result of a metabolic chemical reaction of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1), or a pharmaceutically acceptable salt thereof. In some embodiments, the compound is 3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide (Compound 2), or a pharmaceutically acceptable salt thereof. In some embodiments, the compound is 3-fluoro-4-(5-fluoro-6-(4-(3-(2-fluoropropan-2-yl)-1,2,4-oxadiazol-5-yl)piperidin-1-yl)pyrimidin-4-ylamino)benzamide (Compound 3), or a pharmaceutically acceptable salt thereof.

One aspect of the present invention pertains to the use of a compound of the present invention; or a composition of the present invention; in the manufacture of a medicament for modulating the activity of a GPR119 receptor in an individual.

One aspect of the present invention pertains to the use of a compound of the present invention; or a composition of the present invention; in the manufacture of a medicament for increasing the secretion of an incretin in an individual or increasing a blood incretin level in an individual.

One aspect of the present invention pertains to the use of a compound of the present invention; or a composition of the present invention; in the manufacture of a medicament for the treating a disorder in an individual, wherein the disorder is selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

One aspect of the present invention pertains to a compound of the present invention; a composition of the present invention; or a pharmaceutical product of the present invention; for use in a method of treatment of the human or animal body by therapy.

One aspect of the present invention pertains to a compound of the present invention; a composition of the present invention; or a pharmaceutical product of the present invention; for use in a method of modulating the activity of a GPR119 receptor in an individual.

One aspect of the present invention pertains to a compound of the present invention; a composition of the present invention; or a pharmaceutical product of the present invention; for use in a method of increasing the secretion of an incretin in an individual or increasing a blood incretin level in an individual.

One aspect of the present invention pertains to a compound of the present invention; a composition of the present invention; or a pharmaceutical product of the present invention; for use in a method of treating a disorder in an individual, wherein the disorder is selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

One aspect of the present invention pertains to a compound of the present invention for use in a method of treatment of the human or animal body by therapy, wherein the compound is generated as a result of a metabolic chemical reaction of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide, or a pharmaceutically acceptable salt thereof.

One aspect of the present invention pertains to a compound of the present invention for use in a method of increasing the secretion of an incretin in an individual or increasing a blood incretin level in an individual, wherein the compound is generated as a result of a metabolic chemical reaction of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide, or a pharmaceutically acceptable salt thereof.

One aspect of the present invention pertains to a compound of the present invention for use in a method of treating a disorder in an individual, wherein the compound is generated as a result of a metabolic chemical reaction of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide, or a pharmaceutically acceptable salt thereof, and the disorder is selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

One aspect of the present invention pertains to a pharmaceutical product selected from: a pharmaceutical composition, a formulation, a dosage form, a combined preparation, a twin pack, and a kit; comprising a compound of the present invention; for use in a method of treatment of the human or animal body by therapy.

One aspect of the present invention pertains to a pharmaceutical product selected from: a pharmaceutical composition, a formulation, a dosage form, a combined preparation, a twin pack, and a kit; comprising a compound of the present invention; for use in a method of modulating the activity of a GPR119 receptor in an individual.

One aspect of the present invention pertains to a pharmaceutical product selected from: a pharmaceutical composition, a formulation, a dosage form, a combined preparation, a twin pack, and a kit; comprising a compound according to claim 1; for use in a method of increasing the secretion of an incretin in an individual or increasing a blood incretin level in an individual.

One aspect of the present invention pertains to a pharmaceutical product selected from: a pharmaceutical composition, a formulation, a dosage form, a combined preparation, a twin pack, and a kit; comprising a compound of the present invention for use in a method of treating a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual.

One aspect of the present invention pertains to methods for modulating the activity of a GPR119 receptor, comprising administering to an individual in need thereof, a compound of the present invention in combination with a second pharmaceutical agent.

One aspect of the present invention pertains to methods for agonizing a GPR119 receptor, comprising administering to an individual in need thereof, a compound of the present invention in combination with a second pharmaceutical agent.

One aspect of the present invention pertains to methods for increasing the secretion of an incretin in an individual or increasing a blood incretin level in an individual, comprising administering to the individual in need thereof, a compound of the present invention in combination with a second pharmaceutical agent.

One aspect of the present invention pertains to methods for increasing the secretion of an incretin in an individual or increasing a blood incretin level in an individual, comprising prescribing to the individual in need thereof, a compound of the present invention in combination with a second pharmaceutical agent.

One aspect of the present invention pertains to methods for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; comprising administering to the individual in need thereof, a compound of the present invention in combination with a second pharmaceutical agent.

One aspect of the present invention pertains to methods for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; comprising prescribing to the individual in need thereof, a compound of the present invention in combination with a second pharmaceutical agent.

One aspect of the present invention pertains to the use of a compound of the present invention in combination with a second pharmaceutical agent in the manufacture of a medicament for modulating the activity of a GPR119 receptor in an individual.

One aspect of the present invention pertains to the use of a compound of the present invention in combination with a second pharmaceutical agent in the manufacture of a medicament for agonizing a GPR119 receptor in an individual.

One aspect of the present invention pertains to the use of a compound of the present invention in combination with a second pharmaceutical agent in the manufacture of a medicament for increasing the secretion of an incretin in an individual or increasing a blood incretin level in an individual.

One aspect of the present invention pertains to the use of a compound of the present invention in combination with a second pharmaceutical agent, in the manufacture of a medicament for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

One aspect of the present invention pertains to the use of a pharmaceutical agent in combination with a compound of the present invention, in the manufacture of a medicament for modulating the activity of a GPR119 receptor in an individual.

One aspect of the present invention pertains to the use of a pharmaceutical agent in combination with a compound of the present invention, in the manufacture of a medicament for agonizing a GPR119 receptor in an individual.

One aspect of the present invention pertains to the use of a pharmaceutical agent in combination with a compound of the present invention, in the manufacture of a medicament for increasing the secretion of an incretin in an individual or increasing a blood incretin level in an individual.

One aspect of the present invention pertains to the use of a pharmaceutical agent in combination with a compound of the present invention, in the manufacture of a medicament for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

One aspect of the present invention pertains to a compound of the present invention for use in combination with a second pharmaceutical agent in a method of treatment of the human or animal body by therapy.

One aspect of the present invention pertains to a compound of the present invention for use in combination with a second pharmaceutical agent in a method of modulating the activity of a GPR119 receptor in an individual.

One aspect of the present invention pertains to a compound of the present invention for use in combination with a second pharmaceutical agent in a method of agonizing a GPR119 receptor in an individual.

One aspect of the present invention pertains to a compound of the present invention for use in combination with a second pharmaceutical agent for increasing the secretion of an incretin in an individual or increasing a blood incretin level in an individual.

One aspect of the present invention pertains to a compound of the present invention for use in combination with a second pharmaceutical agent in a method of treating a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual.

One aspect of the present invention pertains to a pharmaceutical agent for use in combination with a compound of the present invention, in a method of treatment of the human or animal body by therapy.

One aspect of the present invention pertains to a pharmaceutical agent for use in combination with a compound of the present invention, in modulating the activity of a GPR119 receptor in an individual.

One aspect of the present invention pertains to a pharmaceutical agent for use in combination with a compound of the present invention, in a method of agonizing a GPR119 receptor in an individual.

One aspect of the present invention pertains to a pharmaceutical agent in combination with a compound of the present invention, for increasing the secretion of an incretin in an individual or increasing a blood incretin level in an individual.

One aspect of the present invention pertains to a pharmaceutical agent for use in combination with a compound of the present invention, in a method of treating a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual.

One aspect of the present invention pertains to a pharmaceutical product selected from: a pharmaceutical composition, a formulation, a dosage form, a combined preparation, a twin pack, and a kit; comprising a compound of the present invention and a second pharmaceutical agent; for use in a method of treatment of the human or animal body by therapy.

One aspect of the present invention pertains to a pharmaceutical product selected from: a pharmaceutical composition, a formulation, a dosage form, a combined preparation, a twin pack, and a kit; comprising a compound of the present invention and a second pharmaceutical agent; for use in a method of modulating the activity of a GPR119 receptor in an individual.

One aspect of the present invention pertains to a pharmaceutical product selected from: a pharmaceutical composition, a formulation, a dosage form, a combined preparation, a twin pack, and a kit; comprising a compound of the present invention and a second pharmaceutical agent; for use in a method of agonizing a GPR119 receptor in an individual.

One aspect of the present invention pertains to a pharmaceutical product selected from: a pharmaceutical composition, a formulation, a dosage form, a combined preparation, a twin pack, and a kit; comprising a compound of the present invention and a second pharmaceutical agent; for use in a method of increasing the secretion of an incretin in an individual or increasing a blood incretin level in an individual.

One aspect of the present invention pertains to a pharmaceutical product selected from: a pharmaceutical composition, a formulation, a dosage form, a combined preparation, a twin pack, and a kit; comprising a compound of the present invention and a second pharmaceutical agent for use in a method of treating a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual.

One aspect of the present invention pertains to compounds, methods, compositions, uses of compounds, pharmaceutical agents, and pharmaceutical products, each as described herein, wherein modulating the activity of a GPR119 receptor is agonizing the GPR119 receptor in an individual.

One aspect of the present invention pertains to compounds, methods, compositions, uses of compounds, pharmaceutical agents, and pharmaceutical products, each as described herein, wherein modulating the activity of a GPR119 receptor is increasing the secretion of an incretin in an individual.

One aspect of the present invention pertains to compounds, methods, compositions, uses of compounds, pharmaceutical agents, and pharmaceutical products, each as described herein, wherein modulating the activity of a GPR119 receptor is increasing a blood incretin level in an individual.

One aspect of the present invention pertains to compounds, methods, compositions, uses of compounds, pharmaceutical agents, and pharmaceutical products, each as described herein, wherein modulating the activity of a GPR119 receptor treating a disorder, wherein the disorder is selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity.

In some embodiments, the pharmaceutical agent or the second pharmaceutical agent is selected from: a DPP-IV inhibitor, a biguanide, an alpha-glucosidase inhibitor, a sulfonylurea, an SGLT2 inhibitor, and a meglitinide. In some embodiments, the pharmaceutical agent or the second pharmaceutical agent is selected from: sitagliptin, vildagliptin, saxagliptin, alogliptin, linagliptin, phenformin, metformin, buformin, acarbose, miglitol, voglibose, tolbutamide, acetohexamide, tolazamide, chlorpropamide, glipizide, glibenclamide, glimepiride, gliclazide, dapagliflozin, remogliflozin, and sergliflozin.

In some embodiments, the disorder is type 2 diabetes. In some embodiments, the disorder is hyperglycemia. In some embodiments, the disorder is hyperlipidemia. In some embodiments, the disorder is hypertriglyceridemia. In some embodiments, the disorder is type 1 diabetes. In some embodiments, the disorder is dyslipidemia. In some embodiments, the disorder is syndrome X. In some embodiments, the disorder is obesity.

In some embodiments, the pharmaceutical product comprises a pharmaceutical composition. In some embodiments, the pharmaceutical product comprises a formulation. In some embodiments, the pharmaceutical product comprises a dosage form. In some embodiments, the pharmaceutical product comprises a combined preparation. In some embodiments, the pharmaceutical product comprises a twin pack. In some embodiments, the pharmaceutical product comprises a kit.

In some embodiments, the compound and the second pharmaceutical agent are administered simultaneously, separately, or sequentially. In some embodiments, the compound and the pharmaceutical agent or second pharmaceutical agent are administered simultaneously. In some embodiments, the compound and the pharmaceutical agent or second pharmaceutical agent are administered separately. In some embodiments, the compound and the pharmaceutical agent or second pharmaceutical agent are administered sequentially.

In some embodiments, the incretin is GLP-1. In some embodiments, the incretin is GIP. In some embodiments, the incretin is PYY.

One aspect of the present invention pertains to compounds, methods, compositions, uses of compounds, pharmaceutical agents, and pharmaceutical products wherein the amount of the compound of the present invention and the amount of the second pharmaceutical agent when administered alone are substantially therapeutically ineffective (i.e., a sub-therapeutic amount); however the amount of the compound of the present invention and the amount of the second pharmaceutical agent when administered simultaneously, separately, or sequentially, are sufficient to be therapeutically effective at treating the disorder.

In some embodiments, the compound and the pharmaceutical agent or the second pharmaceutical agent are provided in amounts which give a synergistic effect in treating the disorder. In some embodiments, the amount of the compound alone is substantially therapeutically ineffective at treating the disorder. In some embodiments, the amount of the pharmaceutical agent alone or the second pharmaceutical agent alone is substantially therapeutically ineffective at treating the disorder.

One aspect of the present invention pertains to methods for preparing a pharmaceutical product, as described herein, comprising: mixing the compound of the present invention with a first pharmaceutically acceptable carrier to prepare a compound dosage form, mixing the second pharmaceutical agent with a second pharmaceutically acceptable carrier to prepare a second pharmaceutical agent dosage form, and providing the compound dosage form and the second pharmaceutical agent dosage form in a combined dosage form for simultaneous, separate, or sequential use.

In some embodiments, the first pharmaceutically acceptable carrier and the second pharmaceutically acceptable carrier are different. In some embodiments, the different pharmaceutically acceptable carriers are suitable for administration by the same route or different routes. In some embodiments, the first pharmaceutically acceptable carrier and the second pharmaceutically acceptable carrier are substantially the same. In some embodiments, the substantially the same pharmaceutically acceptable carriers are suitable for administration by the same route. In some embodiments, the substantially the same pharmaceutically acceptable carriers are suitable for oral administration.

In some embodiments, the pharmaceutical agent or the second pharmaceutical agent is selected from: a DPP-IV inhibitor, a biguanide, an alpha-glucosidase inhibitor, an insulin analogue, a sulfonylurea, an SGLT2 inhibitor, a meglitinide, a thiazolidinedione, and an anti-diabetic peptide analogue. In some embodiments, the pharmaceutical agent or the second pharmaceutical agent is selected from: a DPP-IV inhibitor, a biguanide, an alpha-glucosidase inhibitor, a sulfonylurea, an SGLT2 inhibitor, and a meglitinide. In some embodiments, the pharmaceutical agent or the second pharmaceutical agent is selected from: a DPP-IV inhibitor, a biguanide, and an alpha-glucosidase inhibitor. In some embodiments, the pharmaceutical agent or the second pharmaceutical agent is a DPP-IV inhibitor. In some embodiments, the pharmaceutical agent or the second pharmaceutical agent is a biguanide. In some embodiments, the pharmaceutical agent or the second pharmaceutical agent is an alpha-glucosidase inhibitor. In some embodiments, the pharmaceutical agent or the second pharmaceutical agent is a sulfonylurea. In some embodiments, the pharmaceutical agent or the second pharmaceutical agent is an SGLT2 inhibitor. In some embodiments, the pharmaceutical agent or the second pharmaceutical agent is a meglitinide. In some embodiments, the pharmaceutical agent or the second pharmaceutical agent is a biguanide selected from the following compounds and pharmaceutically acceptable salts, solvates, and hydrates thereof: metformin, phenformin, buformin, and proguanil. In some embodiments, the pharmaceutical agent or the second pharmaceutical agent is an alpha-glucosidase inhibitor selected from the following compounds and pharmaceutically acceptable salts, solvates, and hydrates thereof: acarbose, miglitol, and voglibose.

One aspect of the present invention pertains to methods for weight management, comprising administering to an individual in need thereof, a compound of the present invention in combination with a second pharmaceutical agent, such as any agent described herein.

In some embodiments, the weight management comprises weight loss. In some embodiments, the weight management comprises maintenance of weight loss. In some embodiments, the weight management further comprises a reduced-calorie diet. In some embodiments, the weight management further comprises a program of regular exercise. In some embodiments, the weight management further comprises both a reduced-calorie diet and a program of regular exercise.

In some embodiments, the individual in need of weight management is a patient with an initial body mass of index $\geq 40$ kg/m$^2$; $\geq 39$ kg/m$^2$; $\geq 38$ kg/m$^2$; $\geq 37$ kg/m$^2$; $\geq 36$ kg/m$^2$; $\geq 35$ kg/m$^2$; $\geq 34$ kg/m$^2$; $\geq 33$ kg/m$^2$; $\geq 32$ kg/m$^2$; $\geq 31$ kg/m$^2$; $\geq 30$ kg/m$^2$; $\geq 29$ kg/m$^2$; $\geq 28$ kg/m$^2$; $\geq 27$ kg/m$^2$; $\geq 26$ kg/m$^2$; $\geq 25$ kg/m$^2$; $\geq 24$ kg/m$^2$; $\geq 23$ kg/m$^2$; $\geq 22$ kg/m$^2$; $\geq 21$ kg/m$^2$; or $\geq 20$ kg/m$^2$; and the patient optionally has at least one or at least two weight related comorbid condition(s).

In some embodiments, the comorbid condition(s) when present are selected from: hypertension, dyslipidemia, cardiovascular disease, glucose intolerance, and sleep apnea.

Certain Indications of the Present Invention

In the context of the present invention, a compound as described herein or a pharmaceutical composition thereof can be utilized for modulating the activity of GPR119-receptor-related diseases, conditions and/or disorders as described herein.

In some embodiments, modulating the activity of the GPR119 receptor includes the treatment of a GPR119-receptor-related disorder. In some embodiments, the GPR119-receptor-related disorder is a condition ameliorated by increasing secretion of an incretin. In some embodiments, the GPR119-receptor-related disorder is a condition ameliorated by increasing a blood incretin level. In some embodiments, the incretin is GLP-1. In some embodiments, the incretin is GIP. In some embodiments, the incretin is PYY.

In some embodiments, the GPR119-receptor-related disorder is a condition characterized by low bone mass. In some embodiments, the GPR119-receptor-related disorder is a neurological disorder. In some embodiments, the GPR119-receptor-related disorder is a metabolic-related disorder. In some embodiments, the GPR119-receptor-related disorder is type 2 diabetes. In some embodiments, the GPR119-receptor-related disorder is obesity Some embodiments of the present invention include every combination of one or more conditions characterized by low bone mass selected from: osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

In some embodiments, the neurological disorder selected from: stroke and Parkinson's disease.

Some embodiments of the present invention include every combination of one or more metabolic-related disorders selected from: type 1 diabetes, type 2 diabetes mellitus, and conditions associated therewith, such as, but not limited to, coronary heart disease, ischemic stroke, restenosis after angioplasty, peripheral vascular disease, intermittent claudication, myocardial infarction (e.g. necrosis and apoptosis), dyslipidemia, postprandial lipemia, conditions of impaired glucose tolerance (IGT), conditions of impaired fasting plasma glucose, metabolic acidosis, ketosis, arthritis, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertriglyceridemia, insulin resistance, impaired glucose metabolism, erectile dysfunction, skin and connective tissue disorders, foot ulcerations and ulcerative colitis, endothelial dysfunction and impaired vascular compliance.

Some embodiments of the present invention include every combination of one or more metabolic-related disorders selected from: diabetes, type 1 diabetes, type 2 diabetes, inadequate glucose tolerance, impaired glucose tolerance, insulin resistance, hyperglycemia, hyperlipidemia, hypertriglyceridemia, hypercholesterolemia, dyslipidemia, atherosclerosis, stroke, syndrome X, hypertension, pancreatic beta-cell insufficiency, enteroendocrine cell insufficiency, glycosuria, metabolic acidosis, a cataract, diabetic nephropathy, diabetic neuropathy, peripheral neuropathy, diabetic coronary artery disease, diabetic cerebrovascular disease, diabetic peripheral vascular disease, diabetic retinopathy, metabolic syndrome, a condition related to diabetes, myocardial infarction, learning impairment, memory impairment, a neurodegenerative disorder, a condition ameliorated by increasing a blood GLP-1 level in an individual with a neurodegenerative disorder, excitotoxic brain damage caused by severe epileptic seizures, Alzheimer's disease, Parkinson's disease, Huntington's disease, prion-associated disease, stroke, motor-neuron disease, traumatic brain injury, spinal cord injury, and obesity.

In some embodiments, the disorder is type 2 diabetes. In some embodiments, the disorder is hyperglycemia. In some embodiments, the disorder is hyperlipidemia. In some embodiments, the disorder is hypertriglyceridemia. In some embodiments, the disorder is type 1 diabetes. In some embodiments, the disorder is dyslipidemia. In some embodiments, the disorder is syndrome X. In some embodiments, the disorder is obesity. In some embodiments, the disorder is metabolic syndrome.

The term "metabolic syndrome" as used herein, refers to a set of risk factors that make a patient more susceptible to cardiovascular disease and/or type 2 diabetes. An individual is referred to having metabolic syndrome if the individual simultaneously has three or more of the following five risk factors as set forth by the American Heart Association and the National Heart, Lung, and Blood Institute: (1) Elevated waist circumference: Men—≥40 inches (102 cm), Women—≥35 inches (88 cm); (2) Elevated triglycerides: ≥150 mg/dL; (3) Reduced HDL ("good") cholesterol: Men—<40 mg/dL, Women—<50 mg/dL; (4) Elevated blood pressure: ≥130/85 mm Hg; and (5) Elevated fasting glucose: ≥100 mg/dL.

Formulations and Compositions

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.).

While it is possible that, for use in the prophylaxis or treatment, a compound of the invention may, in an alternative use, be administered as a raw or pure chemical, however, it is preferable to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as GPR119 receptor modulators. The term "active ingredient", defined in the context of a "pharmaceutical composition", refers to a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to about 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate, or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size. The powders and tablets may contain varying percentage amounts of the active compound. A representative amount in a powder or tablet may contain from 0.5% to about 90% of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" refers to the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminum, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1, 2-diamine), chloroprocaine (2-(diethylamino)ethyl 4-(chloroamino)benzoate), choline, diethanolamine, ethylenediamine, meglumine ((2R,3R,4R,5S)-6-(methylamino) hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention may also be administered via a rapid dissolving or a slow release composition, wherein the composition includes a biodegradable rapid dissolving or slow release carrier (such as a polymer carrier and the like) and a compound of the invention. Rapid dissolving or slow release carriers are well known in the art and are used to form complexes that capture therein an active compound(s) and either rapidly or slowly degrade/dissolve in a suitable environment (e.g., aqueous, acidic, basic, etc). Such particles are useful because they degrade/dissolve in body fluids and release the active compound(s) therein. The particle size of a compound of the present invention, carrier or any excipient used in such a composition may be optimally adjusted using techniques known to those of ordinary skill in the art.

Particle size can play an important role in formulation. Reducing the size of the particles can be used to modify the physical characteristics. Particle size reduction increases both the number of particles and the amount of surface area per unit of volume. The increased surface area can improve the rate of solvation and therefore solubility. In addition, particle size reduction can improve gastrointestinal absorption for less soluble compounds. Particle size reduction can be obtained by any of the methods know in the art, for example, precipitation/crystallization, comminution (size reduction by a mechanical process), and the like, see for example Remington, *The Science and Practice of Pharmacy*, 20$^{th}$ Edition, 2000, Lippincott Williams & Wilkins, (Editors: Gennaro et al.).

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the GPR119 receptor modulators are utilized as active ingredients in pharmaceutical compositions, these are not intended for use in humans only, but in non-human mammals as well. Recent advances in the area of animal health-care mandate that consideration be given for the use of active agents, such as GPR119 receptor modulators, for the treatment of a GPR119 receptor-associated disease or disorder in companionship animals (e.g., cats, dogs, etc.) and in livestock animals (e.g., horses, cows, etc.). Those of ordinary skill in the art are readily credited with understanding the utility of such compounds in such settings.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to salts described herein, it embraces pharmaceutically acceptable solvates and/or hydrates of such salts.

It will be apparent to those skilled in the art that the dosage forms described herein may comprise, as the active component, either a compound described herein or a pharmaceutically acceptable salt or as a pharmaceutically acceptable solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present invention pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Polymorphs and Pseudopolymorphs

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily. By way of example, Stahly recently published a polymorph screen of 245 compounds consisting of a "wide variety of structural types" that revealed about 90% of the compounds exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026.)

Combination Therapy

A compound of the invention can be administered as the sole active pharmaceutical agent (i.e., mono-therapy), or it can be used in combination with one or more pharmaceutical agents (i.e., combination-therapy), such as pharmaceutical agents, such as, known anti-diabetic agents, either administered together or separately for the treatment of the diseases, conditions, and disorders described herein. Therefore, another aspect of the present invention includes methods of treatment of a metabolic related disorder, including a weight-related disorder, such as obesity, comprising administering to an individual in need thereof a Compound of Formula (Ia) or a pharmaceutically acceptable salt, solvate, or hydrate thereof, in combination with one or more pharmaceutical agents, such as anti-diabetic agents, as described herein.

In accordance with the present invention, the combination can be used by mixing the respective active components, a Compound of Formula (Ia) and a pharmaceutical agent, either together or independently optionally with a physiologically acceptable carrier, excipient, binder, diluent, etc., as described herein, and administering the mixture or mixtures either orally or non-orally as a pharmaceutical composition(s). When a Compound of Formula (Ia) is administered as a combination therapy with another active compound the Compound of Formula (Ia) and the pharmaceutical agent can be formulated as separate pharmaceutical compositions given at the same time or at different times; or the Compound of Formula (Ia) and the pharmaceutical agent can be formulated together as a single unit dosage.

Suitable pharmaceutical agents that can be used in combination with the compounds of the present invention include anti-obesity agents such as apolipoprotein-B secretion/microsomal triglyceride transfer protein (apo-B/MTP) inhibitors; MCR-4 agonists, cholecystokinin-A (CCK-A) agonists; serotonin and norepinephrine reuptake inhibitors (for example, sibutramine); sympathomimetic agents; β3 adrenergic receptor agonists; dopamine agonists (for example, bromocriptine); melanocyte-stimulating hormone receptor analogues; cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide]; melanin concentrating hormone antagonists; leptin (the OB protein); leptin analogues; leptin receptor agonists; galanin antagonists; lipase inhibitors (such as tetrahydrolipstatin, i.e., orlistat); anorectic agents (such as a bombesin agonist); neuropeptide-Y antagonists; thyromimetic agents; dehydroepiandrosterone or an analogue thereof; glucocorticoid receptor agonists or antagonists; orexin receptor antagonists; urocortin binding protein antagonists; glucagon-like peptide-1 (GLP-1) receptor agonists; ciliary neurotrophic factors (such as Axokine™ available from Regeneron Pharmaceuticals, Inc., Tarrytown, N.Y. and Procter & Gamble Company, Cincinnati, Ohio); human agouti-related proteins (AGRP); ghrelin receptor antagonists; histamine 3 receptor (H3R) antagonists or inverse agonists; neuromedin U receptor agonists; noradrenergic anorectic agents (for example, phentermine, mazindol and the like); appetite suppressants (for example, bupropion); and 5-HT$_{2c}$ agonists (for example, lorcaserin).

Other anti-obesity agents, including the agents set forth infra, are well known, or will be readily apparent in light of the instant disclosure, to one of ordinary skill in the art. In some embodiments, the anti-obesity agents are selected from the group consisting of orlistat, sibutramine, bromocriptine, ephedrine, leptin, pseudoephedrine, and lorcaserin. In a further embodiment, compounds of the present invention and combination therapies are administered in conjunction with exercise and/or a calorie-controlled diet.

It is understood that the scope of combination-therapy of the compounds of the present invention with anti-obesity agents, anorectic agents, appetite suppressant and related agents is not limited to those listed above, but includes in principle any combination with any pharmaceutical agent or pharmaceutical composition useful for the treatment of overweight and obese individuals.

It is understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic related disorders.

Some embodiments of the present invention include methods of treatment of a disease, disorder, condition or complication thereof as described herein, comprising administering to an individual in need of such treatment a therapeutically effective amount or dose of a Compound of Formula (Ia) in combination with at least one pharmaceutical agent selected from the group consisting of: sulfonylureas (for example, tolbutamide (Orinase); acetohexamide (Dymelor); tolazamide (Tolinase); chlorpropamide (Diabinese); glipizide (Glucotrol); glyburide (Diabeta, Micronase, Glynase); glimepiride (Amaryl); gliclazide (Diamicron); and sulfonylureas known in the art); meglitinides (for example, repaglinide (Prandin), nateglinide (Starlix), mitiglinide, and other meglitinides known in the art); biguanides (for example, phenformin, metformin, buformin, and biguanides known in the art); α-glucosidase inhibitors (for example, acarbose, miglitol, and alpha-glucosidase inhibitors known in the art); thiazolidinediones-peroxisome proliferators-activated receptor-γ (i.e., PPAR-γ) agonists (for example, rosiglitazone (Avandia), pioglitazone (Actos), troglitazone (Rezulin), rivoglitazone, ciglitazone, and thiazolidinediones known in the art); insulin and insulin analogues; anti-diabetic peptide analogues (for example, exenatide, liraglutide, taspoglutide, and anti-diabetic peptides analogues know in the art); HMG-CoA reductase inhibitors (for example, rosuvastatin, pravastatin and its sodium salt, simvastatin, lovastatin, atorvastatin, fluvastatin, cerivastatin, rosuvastatin, pitavastatin, pravastatin, and other HMG-CoA reductase inhibitors known in the art); cholesterol-lowering drugs (for example, fibrates that include: bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and other fibrates known in the art; bile acid sequestrants which include: cholestyramine, colestipol and the like; and niacin); antiplatelet agents (for example, aspirin and adenosine diphosphate receptor antagonists that include: clopidogrel, ticlopidine and the like); angiotensin-converting enzyme inhibitors (for example, captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and other angiotensin converting enzyme inhibitors known in the art); angiotensin II receptor antagonists [for example, losartan (and the potassium salt form), and other angiotensin II receptor antagonists known in the art; adiponectin; squalene synthesis inhibitors {for example, (S)-α-[bis[2,2-dimethyl-1-oxopropoxy)methoxy]phosphinyl]-3-phenoxybenzenebutanesulfonic acid, mono potassium salt (BMS-188494) and other squalene synthesis inhibitors known in the art}; and the like. In some embodiments, compounds of the present invention and the pharmaceutical agents are administered separately. In further embodiments, compounds of the present invention and the pharmaceutical agents are administered simultaneously.

Suitable pharmaceutical agents that can be used in conjunction with compounds of the present invention include, but are not limited to: amylin agonists (for example, pramlintide); insulin secretagogues (for example, GLP-1 agonists, exendin-4, and insulinotropin (NN2211)); acyl CoA cholesterol acetyltransferase inhibitors (for example, ezetimibe, eflucimibe, and other acyl CoA cholesterol acetyltransferase inhibitors known in the art); cholesterol absorption inhibitors (for example, ezetimibe, pamaqueside and other cholesterol absorption inhibitors known in the art); cholesterol ester transfer protein inhibitors (for example, CP-529414, JTT-705, CETi-1, and other cholesterol ester transfer protein inhibitors known in the art); microsomal triglyceride transfer protein inhibitors (for example, implitapide, and other microsomal triglyceride transfer protein inhibitors known in the art); cholesterol modulators (for example, NO-1886, and other cholesterol modulators known in the art); bile acid modulators (for example, GT103-279 and other bile acid modulators known in the art); insulin signaling pathway modulators; inhibitors of protein tyrosine phosphatases (PTPases); non-small molecule mimetics and inhibitors of glutamine-fructose-6-phosphate amidotransferase (GFAT); compounds influencing a dysregulated hepatic glucose production; inhibitors of glucose-6-phosphatase (G6Pase); inhibitors of fructose-1,6-bisphosphatase (F-1,6-BPase); inhibitors of glycogen phosphorylase (GP); glucagon receptor antagonists; inhibitors of phosphoenolpyruvate carboxykinase (PEPCK); pyruvate dehydrogenase kinase (PDHK) inhibitors; insulin sensitivity enhancers; insulin secretion enhancers; inhibitors of gastric emptying; $\alpha_2$-adrenergic antagonists; retinoid X receptor (RXR) agonists; and dipeptidyl peptidase-4 (DPP-IV) inhibitors; and the like.

Tripartite Combinations

Some aspects of the present invention include compounds of Formula (Ia) that can be employed in any of the methods, pharmaceutical products, uses, compounds, and pharmaceutical agents, as described herein, in combination with two distinct pharmaceutical agents.

In some embodiments, the two distinct pharmaceutical agents are selected from any of the pharmaceutical agents, or classes of pharmaceutical agents described herein. In some embodiments, the two distinct pharmaceutical agents are selected from: a DPP-IV inhibitor, a biguanide, an alpha-glucosidase inhibitor, an insulin analogue, a sulfonylurea, an SGLT2 inhibitor, a meglitinide, a thiazolidinedione, and an anti-diabetic peptide analogue. In some embodiments, the two distinct pharmaceutical agents include every combination selected from pharmaceutical agents of the following group: a DPP-IV inhibitor, a biguanide, an alpha-glucosidase inhibitor, a sulfonylurea, and an SGLT2 inhibitor.

Some embodiments of the present invention include every combination of one or more compounds selected from compounds of the following group and pharmaceutically acceptable salts, solvates, and hydrates thereof: a DPP-IV inhibitor selected from: 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one; 1-[2-(3-hydroxyadamant-1-ylamino)acetyl]pyrrolidine-2(S)-carbonitrile; (1S,3S,5S)-2-[2(S)-amino-2-(3-hydroxyadamantan-1-yl)acetyl]-2-azabicyclo[3.1.0]hexane-3-carbonitrile; 2-[6-[3(R)-aminopiperidin-1-yl]-3-methyl-2,4-dioxo-1,2,3,4-tetrahydropyrimidin-1-ylmethyl]benzonitrile; 8-[3(R)-aminopiperidin-1-yl]-7-(2-butynyl)-3-methyl-1-(4-methylquinazolin-2-ylmethyl) xanthine; 1-[N-[3(R)-pyrrolidinyl]glycyl]pyrrolidin-2(R)-yl boronic acid; 4(S)-fluoro-1-[2-[(1R,3S)-3-(1H-1,2,4-triazol-1-ylmethyl)cyclopentylamino]acetyl]pyrrolidine-2(S)-carbonitrile; 1-[(2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one; (2S,4S)-2-cyano-4-fluoro-1-[(2-hydroxy-1,1-dimethyl) ethylamino]acetylpyrrolidine; 8-(cis-hexahydro-pyrrolo[3,2-b]pyrrol-1-yl)-3-methyl-7-(3-methyl-but-2-enyl)-1-(2-oxo-2-phenylethyl)-3,7-dihydro-purine-2,6-dione; 1-((3S,4S)-4-amino-1-(4-(3,3-difluoropyrrolidin-1-yl)-1,3,5-triazin-2-yl)pyrrolidin-3-yl)-5,5-difluoropiperidin-2-one; (R)-2-((6-(3-aminopiperidin-1-yl)-3-methyl-2,4-dioxo-3,4-dihydropyrimidin-1 (2H)-yl)methyl)-4-fluorobenzonitrile; 5-{(S)-2-[2-((S)-2-cyano-pyrrolidin-1-yl)-2-oxo-ethylamino]-propyl}-5-(1H-tetrazol-5-yl)10,11-dihydro-5H-dibenzo[a,d]cycloheptene-2,8-dicarboxylic acid bis-dimethylamide; ((2S,4S)-4-(4-(3-methyl-1-phenyl-1H-pyrazol-5-yl)piperazin-1-yl)pyrrolidin-2-yl)(thiazolidin-3-yl)methanone; (2S,4S)-1-[2-[(4-ethoxycarbonylbicyclo[2.2.2]oct-1-yl)amino]acetyl]-4-fluoropyrrolidine-2-carbonitrile; 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione; 2-({6-[(3R)-3-amino-3-methyl- piperidin-1-yl]-1,3-dimethyl-2,4-dioxo-1,2,3,4-tetrahydro-5H-pyrrolo[3,2-d]pyrimidin-5-yl}methyl)-4-fluorobenzonitrile; (2S)-1-{[2-(5-methyl-2-phenyl-oxazol-4-yl)-ethyl-amino]-acetyl}-pyrrolidine-2-carbonitrile; (2S)-1-{[1,1-dimethyl-3-(4-pyridin-3-yl-imidazol-1-yl)-propylamino]-acetyl}-pyrrolidine-2-carbonitrile; (3,3-difluoropyrrolidin-1-yl)-((2S,4S)-4-(4-(pyrimidin-2-yl)piperazin-1-yl)pyrrolidin-2-yl)methanone; (2S,4S)-1-[(2S)-2-amino-3,3-bis(4-fluorophenyl)propanoyl]-4-fluoropyrrolidine-2-carbonitrile; (2S,5R)-5-ethynyl-1-{N-(4-methyl-1-(4-carboxy-pyridin-2-yl)piperidin-4-yl)glycyl}pyrrolidine-2-carbonitrile; and (1S,6R)-3-{[3-(trifluoromethyl)-5,6-dihydro[1,2,4]triazolo[4,3-a]pyrazin-7(8H)-yl]carbonyl}-6-(2,4,5-trifluorophenyl) cyclohex-3-en-1-amine; a biguanide selected from: phenformin ((phenylethyl)biguanide); metformin (dimethylbiguanide); buformin (butylbiguanide); and proguanil (1-(p-chlorophenyl)-5-isopropylbiguanide); an alpha-glucosidase inhibitor selected from: acarbose ((2R,3R,4R,5R)-4-((2R,3R,4R,5S,6R)-5-((2R,3R,4S,5S,6R)-3,4-dihydroxy-6-methyl-5-(1S,4R,5S,6S)-4,5,6-trihydroxy-3-(hydroxymethyl)cyclohex-2-enylamino)tetrahydro-2H-pyran-2-yloxy)-3,4-dihydroxy-6-(hydroxymethyl)tetrahydro-2H-pyran-2-yloxy)-2,3,5,6-tetrahydroxyhexanal); miglitol ((2R,3R,4R,5S)-1-(2-hydroxyethyl)-2-(hydroxymethyl)piperidine-3,4,5-triol); and voglibose ((1S,2S,3R,4S,5S)-5-(1,3-dihydroxypropan-2-ylamino)-1-(hydroxymethyl)cyclohexane-1,2,3,4-tetraol); an insulin analogue selected from: NPH insulin (also known as Humulin N, Novolin N, NPH Lletin II, and insulin isophane); insulin lispro (28B-L-lysine-29B-L-proline-insulin, wherein insulin is human insulin); insulin aspart (28B-L-aspartic acid-insulin, wherein insulin is human insulin); and insulin glulisine (3B-L-lysine-29B-L-glutamic acid-insulin, wherein insulin is human insulin); a sulfonylurea selected from: tolbutamide (Orinase, N-(butylcarbamoyl)-4-methylbenzenesulfonamide); acetohexamide (Dymelor, 4-acetyl-N-(cyclohexylcarbamoyl)benzenesulfonamide); tolazamide (Tolinase, N-(azepan-1-ylcarbamoyl)-4-methylbenzenesulfonamide); chlorpropamide (Diabinese, 4-chloro-N-(propylcarbamoyl)benzenesulfonamide); glipizide (Glucotrol, N-(4-(N-(cyclohexylcarbamoyl)sulfamoyl)phenethyl)-5-methylpyrazine-2-carboxamide); glibenclamide, also known as glyburide (Diabeta, Micronase, Glynase, 5-chloro-N-(4-(N-(cyclohexylcarbamoyl)sulfamoyl)phenethyl)-2-methoxybenzamide); glimepiride (Amaryl, 3-ethyl-4-methyl-N-(4-(N-((1r,4r)-4-methylcyclohexylcarbamoyl)sulfamoyl)phenethyl)-2-oxo-2,5-dihydro-1H-pyrrole-1-carboxamide); and gliclazide (Diamicron, N-(hexahydrocyclopenta[c]pyrrol-2(1H)-ylcarbamoyl)-4-methylbenzenesulfonamide); an SGLT2 inhibitor selected from: dapagliflozin ((2S,3R,4R,5S,6R)-2-(4-chloro-3-(4-ethoxybenzyl)phenyl)-6-(hydroxymethyl)tetrahydro-2H-pyran-3,4,5-triol); remogliflozin (ethyl ((2R,3S,4S,5R,6S)-3,4,5-trihydroxy-6-(4-(4-isopropoxybenzyl)-1-isopropyl-5-methyl-1H-pyrazol-3-yloxy)tetrahydro-2H-pyran-2-yl) methyl carbonate); ASP1941, canagliflozin ((2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol); ISIS 388626; sergliflozin (ethyl ((2R,3S,4S,5R,6S)-3,4,5-trihydroxy-6-(2-(4-methoxybenzyl)phenoxy) tetrahydro-2H-pyran-2-yl)methyl carbonate), AVE2268 ((2R,3S,4S,5R,6S)-2-(hydroxymethyl)-6-(2-(4-methoxybenzyl)thiophen-3-yloxy)tetrahydro-2H-pyran-3,4,5-triol), BI10773, CSG453; and LX4211; a meglitinide selected from: repaglinide (Prandin, (S)-2-ethoxy-4-(2-(3-methyl-1-(2-(piperidin-1-yl)phenyl)butylamino)-2-oxoethyl)benzoic acid); nateglinide (Starlix, (R)-2-((1r,4R)-4-isopropylcyclohexanecarboxamido)-3-phenylpropanoic acid); and mitiglinide ((S)-2-benzyl-4-(3aR,7aS)-1H-isoindol-2(3H,3aH,4H,5H,6H,7H,7aH)-yl)-4-oxobutanoic acid); a thiazolidinedione selected from: rosiglitazone (Avandia, 5-(4-(2-(methyl(pyridin-2-yl)amino)ethoxy)benzyl)thiazolidine-2,4-dione); pioglitazone (Actos, 5-(4-(2-(5-ethylpyridin-2-yl)ethoxy)benzyl)thiazolidine-2,4-dione); troglitazone (Rezulin, 5-(4-((6-hydroxy-2,5,7,8-tetramethylchroman-2-yl)methoxy)benzyl)thiazolidine-2,4-dione); rivoglitazone (5-(4-((6-methoxy-1-methyl-1H-benzo[d]imidazol-2-yl) methoxy)benzyl)thiazolidine-2,4-dione); and ciglitazone (5-(4-(1-methylcyclohexyl)methoxy)benzyl)thiazolidine-2,4-dione); and an anti-diabetic peptide analogue selected from: exenatide; liraglutide; and taspoglutide.

In some embodiments, the two distinct pharmaceutical agents include every combination selected from pharmaceutical agents of the following group: sitagliptin, vildagliptin, saxagliptin, alogliptin, linagliptin, phenformin, metformin, buformin, acarbose, miglitol, voglibose, tolbutamide, acetohexamide, tolazamide, chlorpropamide, glipizide, glibenclamide, glimepiride, gliclazide, dapagliflozin, remogliflozin, and sergliflozin.

Dipeptidyl Peptidase IV Inhibitors

Dipeptidyl peptidase IV (DPP-IV, EC 3.4.14.5) exhibits catalytic activity against a broad range of peptide substrates that includes peptide hormones, neuropeptides, and chemokines. The incretins glucagon-like peptide 1 (GLP-1), and glucose-dependent insulinotropic polypeptide (GIP), which stimulate glucose-dependent insulin secretion and otherwise promote blood glucose homeostasis, are rapidly cleaved by DPP-IV at the position-2 alanine leading to inactivation of their biological activity. Peptide YY (PYY) is a gut peptide that has been implicated in modulating satiety (Chaudhri et al., Annu Rev Physiol (2008) 70:239-255). PYY is released into the circulation as $PYY_{1-36}$ and $PYY_{3-36}$ (Eberlein et al., Peptides (1989) 10:797-803). $PYY_{3-36}$ is generated from $PYY_{1-36}$ by cleavage of the N-terminal Tyr and Pro residues by DPP-IV. Both pharmacological and genetic attenuation of DPP-IV activity is associated with enhanced incretin action, increased insulin, and lower blood glucose in vivo. Genetic attenuation of DPP-IV activity has been shown to provide resistance to obesity and to improve insulin sensitivity. DPP-IV inhibitors have shown to be useful as therapeutics, for example, oral administration of vildagliptin (1-[2-(3-hydroxyadamant-1-ylamino)acetyl]pyrrolidine-2(S)-carbonitrile) or sitagliptin (3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one) to human patients suffering with type 2 diabetes has been found to reduce fasting glucose and postprandial glucose excursion in association with significantly reduced $HbA_{1c}$ levels. For reviews on the application of DPP-IV inhibitors for the treatment of type 2 diabetes, reference is made to the following publications: (1) H.-U. Demuth, et al., "Type 2 diabetes-therapy with DPP-IV inhibitors," Biochim. Biophys. Acta, 1751: 33-44 (2005), and (2) K. Augustyns, et al., "Inhibitors of proline-specific dipeptidyl peptidases: DPP-IV inhibitors as a novel approach for the treatment of type 2 diabetes", Expert Opin. Ther. Patents, 15: 1387-1407 (2005).

Accordingly, suitable pharmaceutical agents include DPP-IV inhibitors that can be used in conjunction with compounds of the present invention either dosed separately or together. DPP-IV inhibitors are well-known in the art or can be readily identified and their in vitro biological activity determined using any number of methods available, for example, O'Brien, M., Daily, B., Schurria, M., "Assay for DPPIV activity using a homogeneous, luminescent method," Cell Notes, Issue 11, 2005; see also the DPPIV-Glo™ Protease Assay Technical Bulletin #TB339.

Examples of DPP-IV inhibitors are described in Villhauer et al., J. Med. Chem. (2003) 46:2774-2789, for LAF237; Ahren et al., J. Clin. Endocrinol. Metab. (2004) 89:2078-2084; Villhauer et al., J. Med. Chem. (2002) 45:2362-2365 for NVP-DPP728; Ahren et al., Diabetes Care (2002) 25:869-875 for NVP-DPP728; Peters et al., Bioorg. Med. Chem. Lett. (2004) 14:1491-1493; Caldwell et al., Bioorg. Med. Chem. Lett. (2004) 14:1265-1268; Edmondson et al., Bioorg. Med. Chem. Lett. (2004) 14:5151-5155; and Abe et al., J. Na.t Prod. (2004) 67:999-1004.

Specific examples of DPP-IV inhibitors include, but are not limited to, dipeptide derivatives or dipeptide mimetics such as alanine-pyrrolidide, isoleucine-thiazolidide, and the pseudosubstrate N-valyl prolyl, O-benzoyl hydroxylamine, as described, for example, in U.S. Pat. No. 6,303,661.

Some embodiments of the present invention include every combination of one or more DPP-IV inhibitors selected from the DPP-IV inhibitors found in U.S. Pat. Nos. 6,869,947, 6,867,205, 6,861,440, 6,849,622, 6,812,350, 6,803,357, 6,800,650, 6,727,261, 6,716,843, 6,710,040, 6,706,742, 6,645,995, 6,617,340, 6,599,871, 6,573,287, 6,432,969, 6,395,767, 6,380,398, 6,303,661, 6,242,422, 6,166,063, 6,100,234, and 6,040,145.

Some embodiments of the present invention include every combination of one or more DPP-IV inhibitors selected from the DPP-IV inhibitors found in U.S. Patent Nos. 2005059724, 2005059716, 2005043292, 2005038020, 2005032804, 2005004205, 2004259903, 2004259902, 2004259883, 2004254226, 2004242898, 2004229926, 2004180925, 2004176406, 2004138214, 2004116328, 2004110817, 2004106656, 2004097510, 2004087587, 2004082570, 2004077645, 2004072892, 2004063935, 2004034014, 2003232788, 2003225102, 2003216450, 2003216382, 2003199528, 2003195188, 2003162820, 2003149071, 2003134802, 2003130281, 2003130199, 2003125304, 2003119750, 2003119738, 2003105077, 2003100563, 2003087950, 2003078247, 2002198205, 2002183367, 2002103384, 2002049164, and 2002006899.

Some embodiments of the present invention include every combination of one or more DPP-IV inhibitors selected from the DPP-IV inhibitors found in International Patent Application Publication Nos. WO 2005/087235, WO 2005/082348, WO 2005/082849, WO 2005/079795, WO 2005/075426, WO 2005/072530, WO 2005/063750, WO 2005/058849, WO 2005/049022, WO 2005/047297, WO 2005/044195, WO 2005/042488, WO 2005/040095, WO 2005/037828, WO 2005/037779, WO 2005/034940, WO 2005/033099, WO 2005/032590, WO 2005/030751, WO 2005/030127, WO 2005/026148, WO 2005/025554, WO 2005/023762, WO 2005/020920, WO 05/19168, WO 05/12312, WO 05/12308, WO 05/12249, WO 05/11581, WO 05/09956, WO 05/03135, WO 05/00848, WO 05/00846, WO 04/112701, WO 04/111051, WO 04/111041, WO 04/110436, WO 04/110375, WO 04/108730, WO 04/104216, WO 04/104215, WO 04/103993, WO 04/103276, WO 04/99134, WO 04/96806, WO 04/92128, WO 04/87650, WO 04/87053, WO 04/85661, WO 04/85378, WO 04/76434, WO 04/76433, WO 04/71454, WO 04/69162, WO 04/67509, WO 04/64778, WO 04/58266, WO 04/52362, WO 04/52850, WO 04/50022, WO 04/50658, WO 04/48379, WO 04/46106, WO 04/43940, WO 04/41820, WO 04/41795, WO 04/37169, WO 04/37181, WO 04/33455, WO 04/32836, WO 04/20407, WO 04/18469, WO 04/18468, WO 04/18467, WO 04/14860, WO 04/09544, WO 04/07468, WO 04/07446, WO 04/04661, WO 04/00327, WO 03/106456, WO 03/104229, WO 03/101958, WO 03/101448, WO 03/99279, WO 03/95425, WO 03/84940, WO 03/82817, WO 03/80633, WO 03/74500, WO 03/72556, WO 03/72528, WO 03/68757, WO 03/68748, WO 03/57666, WO 03/57144, WO 03/55881, WO 03/45228, WO 03/40174, WO 03/38123, WO 03/37327, WO 03/35067, WO 03/35057, WO 03/24965, WO 03/24942, WO 03/22871, WO 03/15775, WO 03/04498, WO 03/04496, WO 03/02530, WO 03/02596, WO 03/02595, WO 03/02593, WO 03/02553, WO 03/02531, WO 03/00181, WO 03/00180, WO 03/00250, WO 02/83109, WO 02/83128, WO 02/76450, WO 02/68420, WO 02/62764, WO 02/55088, WO 02/51836, WO 02/38541, WO 02/34900, WO 02/30891, WO 02/30890, WO 02/14271, WO 02/02560, WO 01/97808, WO 01/96295, WO 01/81337, WO 01/81304, WO 01/68603, WO 01/55105, WO 01/52825, WO 01/34594, WO 00/71135, WO 00/69868, WO 00/56297, WO 00/56296, WO 00/34241, WO 00/23421, WO 00/10549, WO 99/67278, WO 99/62914, WO 99/61431, WO 99/56753, WO 99/25719, WO 99/16864, WO 98/50066, WO 98/50046, WO 98/19998, WO 98/18763, WO 97/40832, WO 95/29691, WO 95/15309, WO 93/10127, WO 93/08259, and WO 91/16339.

Some embodiments of the present invention include every combination of one or more DPP-IV inhibitors selected from the DPP-IV inhibitors found in Patent Publication Nos. EP 1517907, EP 1513808, EP 1492777, EP 1490335, EP 1489088, EP 1480961, EP 1476435, EP 1476429, EP 1469873, EP 1465891, EP 1463727, EP 1461337, EP 1450794, EP 1446116, EP 1442049, EP 1441719, EP 1426366, EP 1412357, EP1406873, EP 1406872, EP 1406622, EP 1404675, EP 1399420, EP 1399471, EP 1399470, EP 1399469, EP 1399433, EP 1399154, EP 1385508, EP 1377288, EP 1355886, EP 1354882, EP 1338592, EP 1333025, EP 1304327, EP 1301187, EP 1296974, EP 1280797, EP 1282600, EP 1261586, EP 1258476, EP 1254113, EP 1248604, EP 1245568, EP 1215207, EP 1228061, EP 1137635, EP 1123272, EP 1104293, EP 1082314, EP 1050540, EP 1043328, EP 0995440, EP 0980249, EP 0975359, EP 0731789, EP 0641347, EP 0610317, EP 0528858, CA 2466870, CA 2433090, CA 2339537, CA 2289125, CA 2289124, CA 2123128, DD 296075, DE 19834591, DE 19828113, DE 19823831, DE 19616486, DE 10333935, DE 10327439, DE 10256264, DE 10251927, DE 10238477, DE 10238470, DE 10238243, DE 10143840, FR 2824825, FR 2822826, JP2005507261, JP 2005505531, JP 2005502624, JP 2005500321, JP 2005500308, JP2005023038, JP 2004536115, JP 2004535445, JP 2004535433, JP 2004534836, JP 2004534815, JP 2004532220, JP 2004530729, JP 2004525929, JP 2004525179, JP 2004522786, JP 2004521149, JP 2004503531, JP 2004315496, JP 2004244412, JP 2004043429, JP 2004035574, JP 2004026820, JP 2004026678, JP 2004002368, JP 2004002367, JP 2003535898, JP 2003535034, JP 2003531204, JP 2003531191, JP 2003531118, JP 2003524591, JP 2003520849, JP 2003327532, JP 2003300977, JP 2003238566, JP 2002531547, JP 2002527504, JP 2002517401, JP 2002516318, JP 2002363157, JP 2002356472, JP 2002356471, JP 2002265439, JP 2001510442, JP 2000511559, JP 2000327689, JP 2000191616, JP 1998182613, JP 1998081666, JP 1997509921, JP 1995501078, and JP 1993508624.

In some embodiments, the DPP-IV inhibitor has an $IC_{50}$ of less than about 10 μM, less than about 1 μM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM, in any one of the DPP-IV inhibitor assays known in the art, including the assays in the references disclosed herein. In some embodiments, the DPP-IV inhibitor has an $IC_{50}$ of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM, in any one of the DPP-IV inhibitor assays known in the art, including the assays in the references disclosed herein.

In some embodiments, the DPP-IV inhibitor is a selective DPP-IV inhibitor, wherein the selective DPP-IV inhibitor has a selectivity for human plasma DPP-IV over one or more of PPCE, DPP-II, DPP-8 and DPP-9 of at least about 10-fold. In some embodiments, the DPP-IV inhibitor is a selective DPP-IV inhibitor, wherein the selective DPP-IV inhibitor has a selectivity for human plasma DPP-IV over one or more of PPCE, DPP-II, DPP-8 and DPP-9 of at least about 100-fold. In some embodiments, the DPP-IV inhibitor is a selective DPP-IV inhibitor, wherein the selective DPP-IV inhibitor has a selectivity for human plasma DPP-IV over one or more of PPCE, DPP-II, DPP-8 and DPP-9 of at least about 10-fold. In some embodiments, the DPP-IV inhibitor is a selective DPP-IV inhibitor, wherein the selective DPP-IV inhibitor has a selectivity for human plasma DPP-IV over one or more of PPCE, DPP-II, DPP-8 and DPP-9 of at least about 1000-fold.

In some embodiments, the DPP-IV inhibitor is orally active.

In some embodiments, the DPP-IV inhibitor is an inhibitor of human DPP-IV.

Some embodiments of the present invention include every combination of one or more DPP-IV inhibitors selected from DPP-IV inhibitors of the following group and pharmaceutically acceptable salts, solvates, and hydrates thereof: 3(R)- amino-1-[3-(trifluoromethyl)-5,6,7,8-tetrahydro[1,2,4]triazolo[4,3-a]pyrazin-7-yl]-4-(2,4,5-trifluorophenyl)butan-1-one; 1-[2-(3-hydroxyadamant-1-ylamino)acetyl]pyrrolidine-2(S)-carbonitrile; (1S,3S,5S)-2-[2[(S)-amino-2-(3-hydroxyadamantan-1-yl)acetyl]-2-azabicyclo[3.1.0]hexane-3-carbonitrile; 2-[6-[3(R)-aminopiperidin-1-yl]-3-methyl-2,4-dioxo-1,2,3,4-tetrahydropyrimidin-1-ylmethyl]benzonitrile; 8-[3(R)-aminopiperidin-1-yl]-7-(2-butynyl)-3-methyl-1-(4-methylquinazolin-2-ylmethyl)xanthine; 1-[N-[3(R)-pyrrolidinyl]glycyl]pyrrolidin-2(R)-yl boronic acid; 4(S)-fluoro-1-[2-[(1R,3S)-3-(1H-1,2,4-triazol-1-ylmethyl)cyclopentylamino]acetyl]pyrrolidine-2(S)-carbonitrile; 1-[(2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one; (2S,4S)-2-cyano-4-fluoro-1-[(2-hydroxy-1,1-dimethyl)ethylamino]acetylpyrrolidine; 8-(cis-hexahydropyrrolo[3,2-b]pyrrol-1-yl)-3-methyl-7-(3-methyl-but-2-enyl)-1-(2-oxo-2-phenylethyl)-3,7-dihydro-purine-2,6-dione; 1-((3S,4S)-4-amino-1-(4-(3,3-difluoropyrrolidin-1-yl)-1,3,5-triazin-2-yl)pyrrolidin-3-yl)-5,5-difluoropiperidin-2-one; (R)-2-((6-(3-aminopiperidin-1-yl)-3-methyl-2,4-dioxo-3,4-dihydropyrimidin-1 (2H)-yl)methyl)-4-fluorobenzonitrile; 5-{(S)-2-[2-((S)-2-cyano-pyrrolidin-1-yl)-2-oxoethylamino]-propyl}-5-(1H-tetrazol-5-yl)10,11-dihydro-5H-dibenzo[a,d]cycloheptene-2,8-dicarboxylic acid bis-dimethylamide; ((2S,4S)-4-(4-(3-methyl-1-phenyl-1H-pyrazol-5-yl)piperazin-1-yl)pyrrolidin-2-yl)(thiazolidin-3-yl) methanone; (2S,4S)-1-[2-[(4-ethoxycarbonylbicyclo[2.2.2]oct-1-yl)amino]acetyl]-4-fluoropyrrolidine-2-carbonitrile; 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione; 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile; (2S)-1-{[2-(5-methyl-2-phenyl-oxazol-4-yl)-ethylamino]-acetyl}-pyrrolidine-2-carbonitrile; (2S)-1-{[1,1-dimethyl-3-(4-pyridin-3-yl-imidazol-1-yl)-propylamino]-acetyl}-pyrrolidine-2-carbonitrile; (3,3-difluoropyrrolidin-1-yl)-((2S,4S)-4-(4-(pyrimidin-2-yl)piperazin-1-yl)pyrrolidin-2-yl)methanone; (2S,4S)-1-[(2S)-2-amino-3,3-bis(4-fluorophenyl)propanoyl]-4-fluoropyrrolidine-2-carbonitrile; (2S,5R)-5-ethynyl-1-{N-(4-methyl-1-(4-carboxy-pyridin-2-yl)piperidin-4-yl)glycyl}pyrrolidine-2-carbonitrile; and (1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine.

Sitagliptin phosphate (Januvia®, MK-0431, dihydrogenphosphate salt of 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one) is marketed by Merck & Co. for once-daily oral treatment of type 2 diabetes. Januvia was first launched in Mexico followed by commercialization in the U.S. In 2007, the product was approved by the European Medicines Evaluation Agency (EMEA) and is currently available in the U.K., Germany and Spain. In 2009, Januvia was approved and launched in Japan. In addition, Merck has also filed for approval of Januvia in the U.S. as an adjunct to diet and exercise and in combination with other therapies to improve glycemic control in the treatment of diabetes. The compound, 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one, and pharmaceutically acceptable salts thereof are disclosed in international patent publication WO2003/004498. Some embodiments of the present invention include every combination of one or more compounds selected from compounds disclosed in WO2003/004498 and pharmaceutically acceptable salts, solvates, and hydrates thereof. In some embodiments, the DPP-IV inhibitor is selected from 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one, and pharmaceutically acceptable salts, solvates, and hydrates thereof:

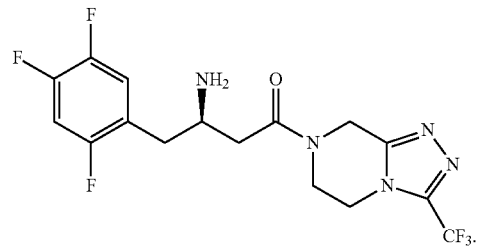

In some embodiments, the DPP-IV inhibitor is 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one phosphate:

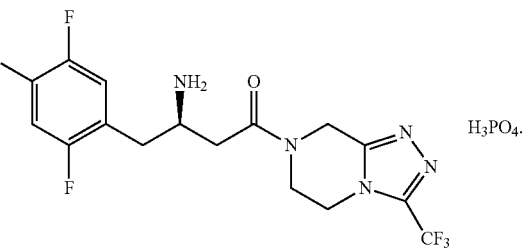

The crystalline form of 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one phosphate salt monohydrate is disclosed in international patent publication WO2005/003135. In some embodiments, the DPP-IV inhibitor is crystalline 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one phosphate monohydrate.

Vildagliptin (Galvus®, LAF-237, 1-[2-(3-hydroxyadamant-1-ylamino)acetyl]pyrrolidine-2(S)-carbonitrile) is another DPP-IV inhibitor and was first commercialized in Brazil and Mexico by Novartis for oral, once-daily treatment of type 2 diabetes. In 2008, a marketing authorization application (MAA) was approved in the E.U. for this indication and launch took place in the U.K. in March, 2008. An approvable letter has been received for the regulatory application filed in the U.S. Vildagliptin was approved in Japan in 2010. The compound, 1-[2-(3-hydroxyadamant-1-ylamino)acetyl]pyrrolidine-2(S)-carbonitrile, is disclosed in international patent publication WO2000/034241. Some embodiments of the present invention include every combination of one or more compounds selected from compounds disclosed in WO2000/034241 and pharmaceutically acceptable salts, solvates, and hydrates thereof. In some embodiments, the DPP-IV inhibitor is selected from 1-[2-(3-hydroxyadamant-1-ylamino)acetyl]pyrrolidine-2(S)-carbonitrile, and pharmaceutically acceptable salts, solvates, and hydrates thereof:

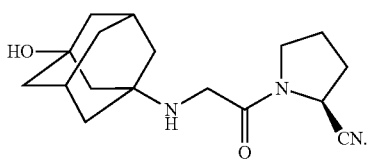 [SMILES: N#C[C@@H]1CCCN1C(=O)CNC12CC3CC(CC(O)(C3)C1)C2]

Certain salts of the compound, 1-[2-(3-hydroxyadamant-1-ylamino)acetyl]pyrrolidine-2(S)-carbonitrile, are disclosed in international patent publication WO2007/019255. In some embodiments, the DPP-IV inhibitor is 1-[2-(3-hydroxyadamant-1-ylamino)acetyl]pyrrolidine-2(S)-carbonitrile HCl:

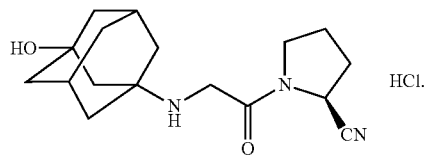

Saxagliptin (Onglyza™, BMS-477118, (1S,3S,5S)-2-[2(S)-amino-2-(3-hydroxyadamantan-1-yl)acetyl]-2-azabicyclo[3.1.0]hexane-3-carbonitrile) is another DPP-IV inhibitor, which was launched in 2009 by AstraZeneca and Bristol-Myers Squibb in the U.S. for the treatment of type 2 diabetes. In 2009, the product was approved in the E.U. for the treatment of type 2 diabetes independently or in combination with metformin. Phase 3 clinical studies are ongoing in Japan for the treatment of type 2 diabetes. The compound, (1S,3S,5S)-2-[2(S)-amino-2-(3-hydroxyadamantan-1-yl)acetyl]-2-azabicyclo[3.1.0]hexane-3-carbonitrile, is disclosed in international patent publication WO2001/068603. Some embodiments of the present invention include every combination of one or more compounds selected from compounds disclosed in WO2001/068603 and pharmaceutically acceptable salts, solvates, and hydrates thereof. In some embodiments, the DPP-IV inhibitor is selected from (1S,3S,5S)-2-[2(S)-amino-2-(3-hydroxyadamantan-1-yl)acetyl]-2-azabicyclo[3.1.0]hexane-3-carbonitrile, and pharmaceutically acceptable salts, solvates, and hydrates thereof:

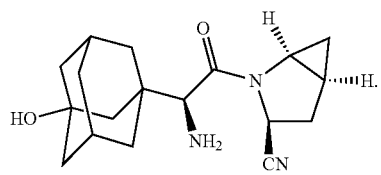

Takeda has filed for regulatory approval of the DPP-IV inhibitor, alogliptin (SYR-322, Nesina®, 2-[6-[3(R)-aminopiperidin-1-yl]-3-methyl-2,4-dioxo-1,2,3,4-tetrahydropyrimidin-1-ylmethyl]benzonitrile) in Japan and the U.S. for the once-daily, oral treatment of type 2 diabetes. The compound, 2-[6-[3(R)-aminopiperidin-1-yl]-3-methyl-2,4-dioxo-1,2,3,4-tetrahydropyrimidin-1-ylmethyl]benzonitrile, and pharmaceutically acceptable salts thereof are disclosed in international patent publication WO 2005/095381. Some embodiments of the present invention include every combination of one or more compounds selected from compounds disclosed in WO 2005/095381 and pharmaceutically acceptable salts, solvates, and hydrates thereof. In some embodiments, the DPP-IV inhibitor is selected from 2-[6-[3(R)-aminopiperidin-1-yl]-3-methyl-2,4-dioxo-1,2,3,4-tetrahydropyrimidin-1-ylmethyl]benzonitrile, and pharmaceutically acceptable salts, solvates, and hydrates thereof:

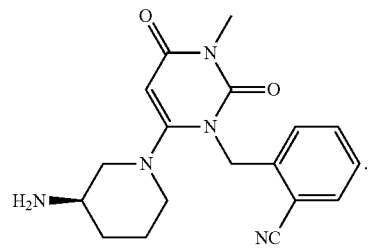

The crystalline form of 2-[6-[3(R)-aminopiperidin-1-yl]-3-methyl-2,4-dioxo-1,2,3,4-tetrahydropyrimidin-1-ylmethyl]benzonitrile is disclosed in international patent publication WO2007/035372. In some embodiments, the DPP-IV inhibitor is 2-[6-[3(R)-aminopiperidin-1-yl]-3-methyl-2,4-dioxo-1,2,3,4-tetrahydropyrimidin-1-ylmethyl]benzonitrile benzoate:

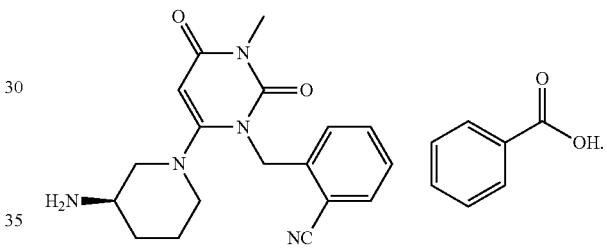

Linagliptin (BI-1356, Ondero®, Tradjenta™, 8-[3(R)-aminopiperidin-1-yl]-7-(2-butynyl)-3-methyl-1-(4-methylquinazolin-2-ylmethyl)xanthine) is a DPP-IV inhibitor in phase 3 clinical development at Boehringer Ingelheim to evaluate its potential as add-on therapy to metformin for the treatment of type 2 diabetes. The compound, 8-[3(R)-aminopiperidin-1-yl]-7-(2-butynyl)-3-methyl-1-(4-methylquinazolin-2-ylmethyl)xanthine, is disclosed in international patent publication WO2004/018468. Some embodiments of the present invention include every combination of one or more compounds selected from compounds disclosed in WO2004/018468 and pharmaceutically acceptable salts, solvates, and hydrates thereof. In some embodiments, the DPP-IV inhibitor is selected from 8-[3 (R)-aminopiperidin-1-yl]-7-(2-butynyl)-3-methyl-1-(4-methylquinazolin-2-ylmethyl)xanthine, and pharmaceutically acceptable salts, solvates, and hydrates thereof:

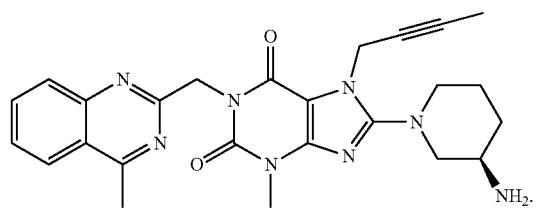 [SMILES: CC#CCn1c(N2CCC[C@@H](N)C2)nc2c1c(=O)n(Cc1nc(C)c3ccccc3n1)c(=O)n2C]

Certain polymorphs of the compound, 8-[3(R)-aminopiperidin-1-yl]-7-(2-butynyl)-3-methyl-1-(4-methylquinazolin-2- ylmethyl)xanthine, are disclosed in international patent publication WO 2007/128721. In some embodiments, the DPP-IV inhibitor is a crystalline form of 8-[3(R)-aminopiperidin-1-yl]-7-(2-butynyl)-3-methyl-1-(4-methylquinazolin-2-ylmethyl)xanthine.

Dutogliptin (PHX-1149, 1-[N-[3(R)-pyrrolidinyl]glycyl] pyrrolidin-2(R)-yl boronic acid) is a DPP-IV inhibitor in phase 3 clinical trials by Phenomix and Forest for the oral, once-daily treatment of type 2 diabetes. The compound, 1-[N-[3(R)-pyrrolidinyl]glycyl]pyrrolidin-2(R)-yl boronic acid, and pharmaceutically acceptable salts thereof are disclosed in international patent publication WO2005/047297. Some embodiments of the present invention include every combination of one or more compounds selected from compounds disclosed in WO2005/047297 and pharmaceutically acceptable salts, solvates, and hydrates thereof. In some embodiments, the DPP-IV inhibitor is selected from 1-[N-[3(R)-pyrrolidinyl]glycyl]pyrrolidin-2(R)-yl boronic acid, and pharmaceutically acceptable salts, solvates, and hydrates thereof:

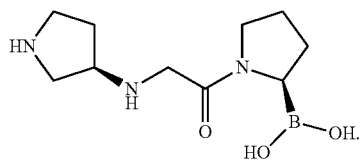 [SMILES: O=C(CN[C@@H]1CCNC1)N1CCC[C@H]1B(O)O]

The crystalline form of 1-[N-[3(R)-pyrrolidinyl]glycyl]pyrrolidin-2(R)-yl boronic acid tartrate is disclosed in international patent publication WO2008/027273. In some embodiments, the DPP-IV inhibitor is 1-[N-[3(R)-pyrrolidinyl]glycyl]pyrrolidin-2(R)-yl boronic acid tartrate:

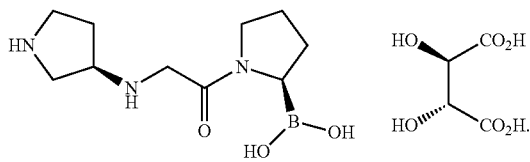 [SMILES: O=C(CN[C@@H]1CCNC1)N1CCC[C@H]1B(O)O ; O=C(O)[C@H](O)[C@@H](O)C(=O)O]

Melogliptin (GRC-8200, 4(S)-fluoro-1-[2-[(1R,3S)-3-(1H-1,2,4-triazol-1-ylmethyl)cyclopentylamino]acetyl]pyrrolidine-2(S)-carbonitrile) is a DPP-IV inhibitor currently undergoing phase 2 clinical trials by Glenmark Pharmaceuticals and Merck KGaA for the treatment of type 2 diabetes. The compound, 4(S)-fluoro-1-[2-[(1R,3S)-3-(1H-1,2,4-triazol-1-ylmethyl)cyclopentylamino]acetyl]pyrrolidine-2(S)-carbonitrile, is disclosed in international patent publication WO2006/040625. Some embodiments of the present invention include every combination of one or more compounds selected from compounds disclosed in WO2006/040625 and pharmaceutically acceptable salts, solvates, and hydrates thereof. In some embodiments, the DPP-IV inhibitor is selected from 4(S)-fluoro-1-[2-[(1R,3S)-3-(1H-1,2,4-triazol-1-ylmethyl)cyclopentylamino]acetyl]pyrrolidine-2(S)-carbonitrile, and pharmaceutically acceptable salts, solvates, and hydrates thereof:

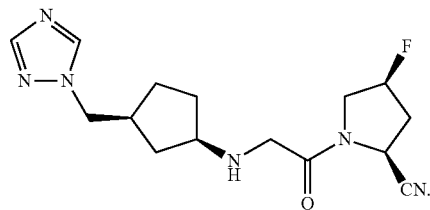 [SMILES: N#C[C@@H]1C[C@H](F)CN1C(=O)CN[C@@H]1CC[C@H](Cn2cncn2)C1]

Carmegliptin (R-1579, 1-[2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one) is a DPP-IV inhibitor. The compound, 1-[(2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one, is disclosed in international patent publication WO2005/000848. Some embodiments of the present invention include every combination of one or more compounds selected from compounds disclosed in WO2005/000848 and pharmaceutically acceptable salts, solvates, and hydrates thereof. In some embodiments, the DPP-IV inhibitor is selected from 1-[(2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one, and pharmaceutically acceptable salts, solvates, and hydrates thereof:

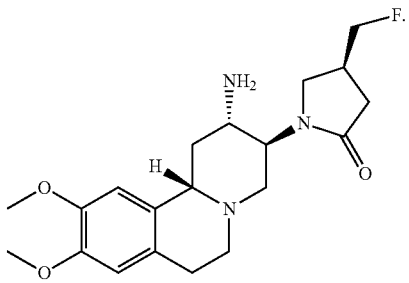 [SMILES: COc1cc2c(cc1OC)[C@@H]1C[C@H](N)[C@@H](N3C[C@@H](CF)CC3=O)CN1CC2]

Taisho disclosed (2S,4S)-2-cyano-4-fluoro-1-[(2-hydroxy-1,1-dimethyl) ethylamino]acetylpyrrolidine, a DPP-IV inhibitor in US patent publication US 2007/0112059. Some embodiments of the present invention include every combination of one or more compounds selected from compounds disclosed in US 2007/0112059 and pharmaceutically acceptable salts, solvates, and hydrates thereof. In some embodiments, the DPP-IV inhibitor is selected from (2S,4S)-2-cyano-4-fluoro-1-[(2-hydroxy-1,1-dimethyl)ethylamino]acetylpyrrolidine, and pharmaceutically acceptable salts, solvates, and hydrates thereof:

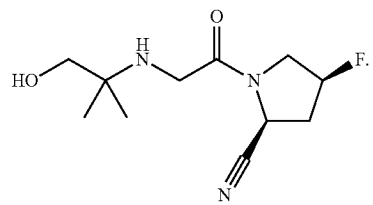 [SMILES: CC(C)(CO)NCC(=O)N1C[C@@H](F)C[C@H]1C#N]

Sanofi-Aventis disclosed a series of substituted bicyclic 8-pyrrolidineoxanthine derivatives as DPP-IV inhibitors in US publication US 2007/0167468. Some embodiments of the present invention include every combination of one or more compounds selected from compounds disclosed in US publication US 2007/0167468 and pharmaceutically acceptable salts, solvates, and hydrates thereof. In some embodiments, the DPP-IV inhibitor is selected from 8-(cis-hexahydro-pyrrolo[3,2-b]pyrrol-1-yl)-3-methyl-7-(3-methyl-but-2-enyl)-1-(2-oxo-2-phenylethyl)-3,7-dihydro-purine-2,6-dione, and pharmaceutically acceptable salts, solvates, and hydrates thereof:

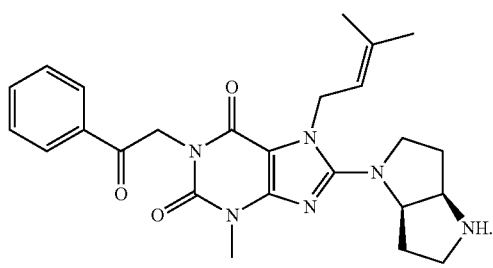 [SMILES: CC(C)=CCn1c(N2CC[C@H]3NCC[C@H]32)nc2c1c(=O)n(CC(=O)c1ccccc1)c(=O)n2C]

Pfizer disclosed a series of 3-amino-pyrrolidine-4-lactam derivatives as DPP-IV inhibitors in international patent publication WO2007/148185. Some embodiments of the present invention include every combination of one or more compounds selected from compounds disclosed in WO2007/148185 and pharmaceutically acceptable salts, solvates, and hydrates thereof. One such compound is 1-((3S,4S)-4-amino-1-(4-(3,3-difluoropyrrolidin-1-yl)-1,3,5-triazin-2-yl)pyrrolidin-3-yl)-5,5-difluoropiperidin-2-one. In some embodiments, the DPP-IV inhibitor is selected from 1-((3S,4S)-4-amino-1-(4-(3,3-difluoropyrrolidin-1-yl)-1,3,5-triazin-2-yl)pyrrolidin-3-yl)-5,5-difluoropiperidin-2-one, and pharmaceutically acceptable salts, solvates, and hydrates thereof:

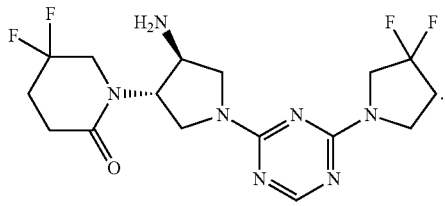 [SMILES: N[C@H]1CN(c2ncnc(N3CCC(F)(F)C3)n2)C[C@@H]1N1CC(F)(F)CCC1=O]

Syrrx disclosed a series of substituted pyrimidine-2,4(1H,3H)-dione derivatives as DPP-IV inhibitors in international patent publication WO2005/095381. Some embodiments of the present invention include every combination of one or more compounds selected from compounds disclosed in WO2005/095381 and pharmaceutically acceptable salts, solvates, and hydrates thereof. One such compound is (R)-2-(6-(3-aminopiperidin-1-yl)-3-methyl-2,4-dioxo-3,4-dihydropyrimidin-1(2H)-yl)methyl)-4-fluorobenzonitrile. In some embodiments, the DPP-IV inhibitor is selected from (R)-2-((6-(3-aminopiperidin-1-yl)-3-methyl-2,4-dioxo-3,4-dihydropyrimidin-1(2H)-yl)methyl)-4-fluorobenzonitrile, and pharmaceutically acceptable salts, solvates, and hydrates thereof:

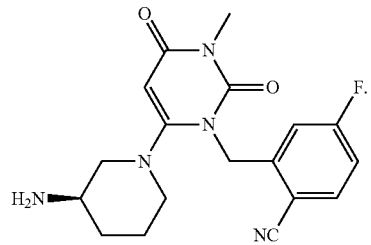 [SMILES: Cn1c(=O)cc(N2CCC[C@@H](N)C2)n(Cc2cc(F)ccc2C#N)c1=O]

Various crystalline forms of (R)-2-((6-(3-aminopiperidin-1-yl)-3-methyl-2,4-dioxo-3,4-dihydropyrimidin-1(2H)-yl) methyl)-4-fluorobenzonitrile succinic acid salt are disclosed in international patent publication WO2008/067465. One embodiment of the present invention pertains to any one or more crystalline forms of (R)-2-(6-(3-aminopiperidin-1-yl)-3-methyl-2,4-dioxo-3,4-dihydropyrimidin-1(2H)-yl) methyl)-4-fluorobenzonitrile succinic acid salt as described in international patent publication WO2008/067465. In some embodiments, the DPP-IV inhibitor is crystalline (R)-2-((6-(3-aminopiperidin-1-yl)-3-methyl-2,4-dioxo-3,4-dihydropyrimidin-1(2H)-yl)methyl)-4-fluorobenzonitrile succinic acid salt:

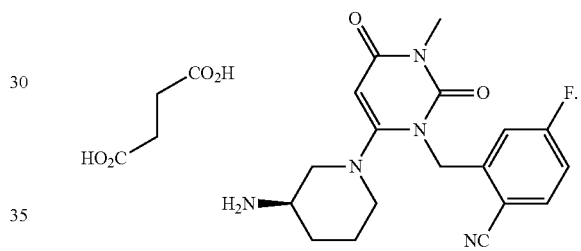

Alantos disclosed a series of substituted 2-cyano-pyrrolidine derivatives as DPP-IV inhibitors in international patent publication WO2006/116157. Some embodiments of the present invention include every combination of one or more compounds selected from compounds disclosed in WO2006/116157 and pharmaceutically acceptable salts, solvates, and hydrates thereof. One such compound is 5-{(S)-2-[2-((S)-2-cyano-pyrrolidin-1-yl)-2-oxo-ethylamino]-propyl}-5-(1H-tetrazol-5-yl)10,11-dihydro-5H-dibenzo[a,d] cycloheptene-2,8-dicarboxylic acid bis-dimethylamide. In some embodiments, the DPP-IV inhibitor is selected from 5-{(S)-2-[2-((S)-2-cyano-pyrrolidin-1-yl)-2-oxo-ethylamino]-propyl}-5-(1H-tetrazol-5-yl)10,11-dihydro-5H-dibenzo[a,d]cycloheptene-2,8-dicarboxylic acid bis-dimethylamide, and pharmaceutically acceptable salts, solvates, and hydrates thereof:

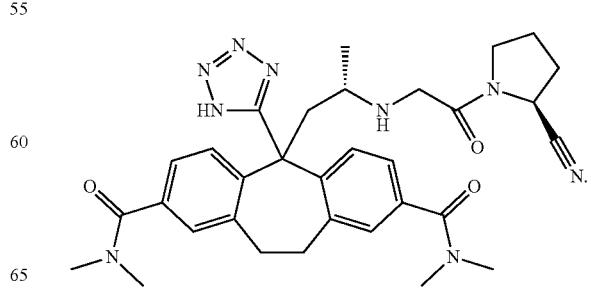

Mitsubishi disclosed a series of 2,4-disubstituted pyrrolidine derivatives as DPP-IV inhibitors in international patent publication WO2002/0014271. Some embodiments of the present invention include every combination of one or more compounds selected from compounds disclosed in WO2002/0014271 and pharmaceutically acceptable salts, solvates, and hydrates thereof. One such compound is ((2S,4S)-4-(4-(3-methyl-1-phenyl-1H-pyrazol-5-yl)piperazin-1-yl)pyrrolidin-2-yl)(thiazolidin-3-yl)methanone. In some embodiments, the DPP-IV inhibitor is selected from ((2S,4S)-4-(4-(3-methyl-1-phenyl-1H-pyrazol-5-yl)piperazin-1-yl)pyrrolidin-2-yl)(thiazolidin-3-yl)methanone, and pharmaceutically acceptable salts, solvates, and hydrates thereof:

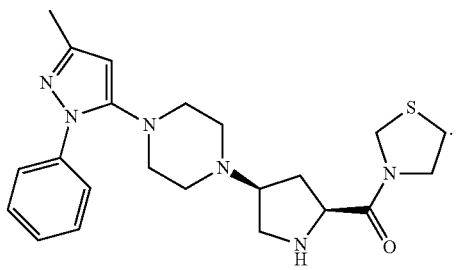 [SMILES: Cc1cc(N2CCN([C@@H]3CN[C@H](C(=O)N4CCSC4)C3)CC2)n(-c2ccccc2)n1]

Various crystalline forms of ((2S,4S)-4-(4-(3-methyl-1-phenyl-1H-pyrazol-5-yl)piperazin-1-yl)pyrrolidin-2-yl)(thiazolidin-3-yl)methanone salts are disclosed in international patent publication WO2006/088129 and US publication 2009/0216016. One embodiment of the present invention pertains to any one or more crystalline forms of ((2S,4S)-4-(4-(3-methyl-1-phenyl-1H-pyrazol-5-yl)piperazin-1-yl)pyrrolidin-2-yl)(thiazolidin-3-yl)methanone salt as described in international patent publication WO2006/088129 and US publication 2009/0216016. In some embodiments, the DPP-IV inhibitor is crystalline ((2S,4S)-4-(4-(3-methyl-1-phenyl-1H-pyrazol-5-yl)piperazin-1-yl)pyrrolidin-2-yl)(thiazolidin-3-yl)methanone 2.5 hydrobromide salt:

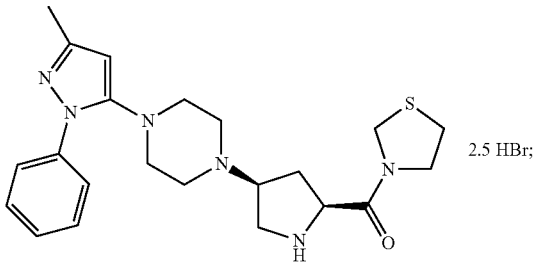 [SMILES: Cc1cc(N2CCN([C@@H]3CN[C@H](C(=O)N4CCSC4)C3)CC2)n(-c2ccccc2)n1]

or a mono or a dihydrate thereof. In some embodiments, the DPP-IV inhibitor is crystalline ((2S,4S)-4-(4-(3-methyl-1-phenyl-1H-pyrazol-5-yl)piperazin-1-yl)pyrrolidin-2-yl)(thiazolidin-3-yl)methanone di-hydrobromide salt.

Kyorin disclosed a series of pyrrolidinecarbonitrile derivatives as DPP-IV inhibitors in international patent publication WO2008/114857 and US publication US 2008/0146818. Some embodiments of the present invention include every combination of one or more compounds selected from compounds disclosed in WO2008/114857 and US publication US 2008/0146818, and pharmaceutically acceptable salts, solvates, and hydrates thereof. One such compound is (2S,4S)-1-[2-[(4-ethoxycarbonylbicyclo[2.2.2]oct-1-yl)amino]acetyl]-4-fluoropyrrolidine-2-carbonitrile. In some embodiments, the DPP-IV inhibitor is selected from (2S,4S)-1-[2[(4-ethoxycarbonylbicyclo[2.2.2]oct-1-yl)amino]acetyl]-4-fluoropyrrolidine-2-carbonitrile, and pharmaceutically acceptable salts, solvates, and hydrates thereof:

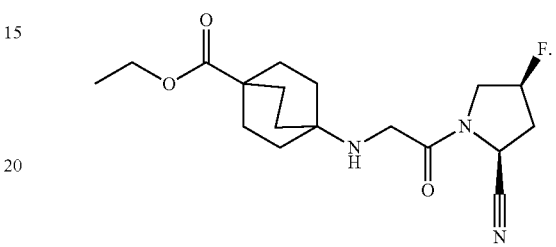

Dainippon Sumitomo disclosed a series of bicyclic pyrrole derivatives as DPP-IV inhibitors in international patent publication WO2006/068163 and US publication US 2009/0192129. Some embodiments of the present invention include every combination of one or more compounds selected from compounds disclosed in WO2006/068163 and US publication US 2009/0192129 and pharmaceutically acceptable salts, solvates, and hydrates thereof. One such compound is (6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione. In some embodiments, the DPP-IV inhibitor is selected from (6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione, and pharmaceutically acceptable salts, solvates, and hydrates thereof:

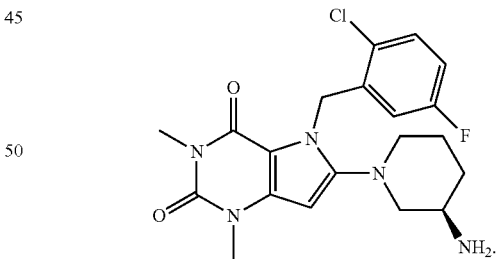

Dainippon Sumitomo disclosed 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile as a DPP-IV inhibitor in international patent publication WO2009/084497. In some embodiments, the DPP-IV inhibitor is selected from 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile, and pharmaceutically acceptable salts, solvates, and hydrates thereof:

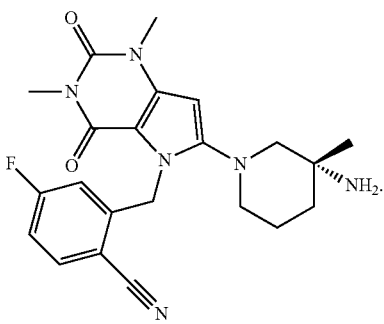 [SMILES: Cn1c(=O)c2c(cc(N3CCC[C@@](C)(N)C3)n2Cc2cc(F)ccc2C#N)n(C)c1=O]

Hoffmann-La Roche disclosed a series of N-substituted pyrrolidine derivatives as DPP-IV inhibitors in international patent publication WO 03/037327. Some embodiments of the present invention include every combination of one or more compounds selected from compounds disclosed in WO 03/037327 and pharmaceutically acceptable salts, solvates, and hydrates thereof. One such compound is (2S)-1-{[2-(5-methyl-2-phenyl-oxazol-4-yl)-ethylamino]-acetyl}-pyrrolidine-2-carbonitrile. In some embodiments, the DPP-IV inhibitor is selected from (2S)-1-{[2-(5-methyl-2-phenyl-oxazol-4-yl)-ethylamino]-acetyl}-pyrrolidine-2-carbonitrile, and pharmaceutically acceptable salts, solvates, and hydrates thereof:

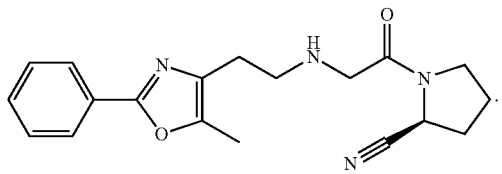 [SMILES: Cc1oc(-c2ccccc2)nc1CCNCC(=O)N1CCC[C@H]1C#N]

Various crystalline forms of (2S)-1-{[2-(5-methyl-2-phenyl-oxazol-4-yl)-ethylamino]-acetyl}-pyrrolidine-2-carbonitrile methanesulfonic acid salt are disclosed in international patent publication WO2006/100181. In some embodiments, the DPP-IV inhibitor is (2S)-1-{[2-(5-methyl-2-phenyl-oxazol-4-yl)-ethylamino]-acetyl}-pyrrolidine-2-carbonitrile methanesulfonic acid salt (i.e., mesylate):

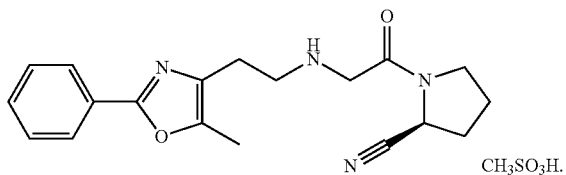 [SMILES: Cc1oc(-c2ccccc2)nc1CCNCC(=O)N1CCC[C@H]1C#N]

Other compounds disclosed by Hoffmann-La Roche in international patent publication WO 03/037327 include (2S)-1-{[1,1-dimethyl-3-(4-pyridin-3-yl-imidazol-1-yl)-propylamino]-acetyl}-pyrrolidine-2-carbonitrile, and pharmaceutically acceptable salts thereof, such as the methanesulfonic acid salt. In some embodiments, the DPP-IV inhibitor is selected from (2S)-1-{[1,1-dimethyl-3-(4-pyridin-3-yl-imidazol-1-yl)-propylamino]-acetyl}-pyrrolidine-2-carbonitrile, and pharmaceutically acceptable salts, solvates, and hydrates thereof:

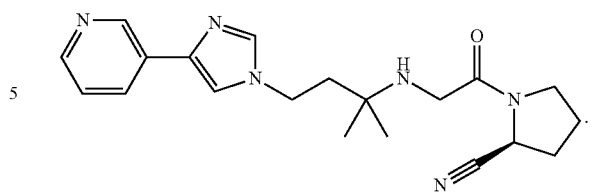

In some embodiments, the DPP-IV inhibitor is (2S)-1-{[1,1-dimethyl-3-(4-pyridin-3-yl-imidazol-1-yl)-propylamino]-acetyl}-pyrrolidine-2-carbonitrile methanesulfonic acid:

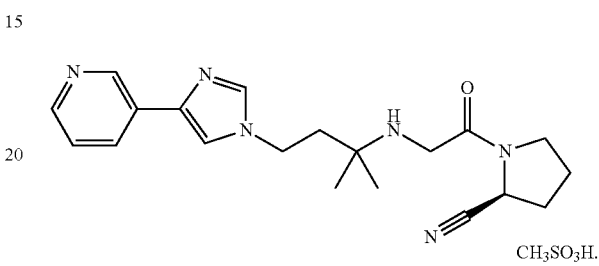

Various crystalline forms of (2S)-1-{[1,1-dimethyl-3-(4-pyridin-3-yl-imidazol-1-yl)-propylamino]-acetyl}-pyrrolidine-2-carbonitrile fumaric acid salt are disclosed in international patent publication WO2007/071576. In some embodiments, the DPP-IV inhibitor is (2S)-1-{[1,1-dimethyl-3-(4-pyridin-3-yl-imidazol-1-yl)-propylamino]-acetyl}-pyrrolidine-2-carbonitrile fumaric acid salt (i.e., fumarate):

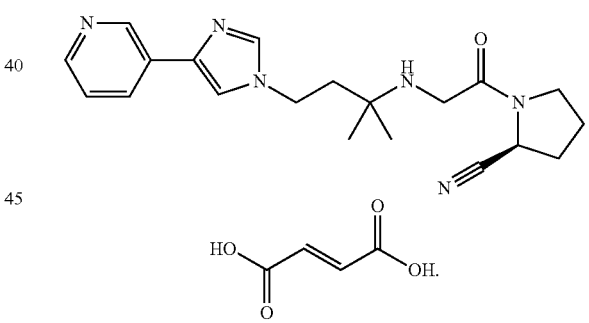

Pfizer disclosed a series of proline derivatives as DPP-IV inhibitors in international patent publication WO2005/116014. Some embodiments of the present invention include every combination of one or more compounds selected from compounds disclosed in WO2005/116014 and pharmaceutically acceptable salts, solvates, and hydrates thereof. One such compound is (3,3-difluoropyrrolidin-1-yl)-((2S,4S)-4-(4-(pyrimidin-2-yl)piperazin-1-yl)pyrrolidin-2-yl)methanone. In some embodiments, the DPP-IV inhibitor is selected from (3,3-difluoropyrrolidin-1-yl)-((2S,4S)-4-(4-(pyrimidin-2-yl)piperazin-1-yl)pyrrolidin-2-yl)methanone, and pharmaceutically acceptable salts, solvates, and hydrates thereof:

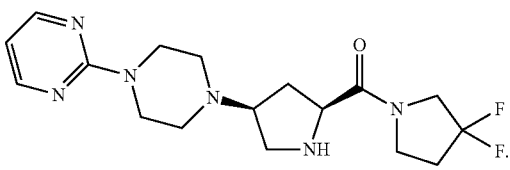 [SMILES: O=C([C@@H]1C[C@H](N2CCN(c3ncccn3)CC2)CN1)N1CCC(F)(F)C1]

GlaxoSmithKline disclosed a series of fluoropyrrolidine derivatives as DPP-IV inhibitors in international patent publication WO 03/002531. Some embodiments of the present invention include every combination of one or more compounds selected from the DPP-IV inhibitors disclosed in WO 03/037327 and pharmaceutically acceptable salts, solvates, and hydrates thereof. One such compound is (2S,4S)-1-[(2S)-2-amino-3,3-bis(4-fluorophenyl)propanoyl]-4-fluoropyrrolidine-2-carbonitrile (Denagliptin). In some embodiments, the DPP-IV inhibitor is selected from (2S,4S)-1-[(2S)-2-amino-3,3-bis(4-fluorophenyl)propanoyl]-4-fluoropyrrolidine-2-carbonitrile, and pharmaceutically acceptable salts, solvates, and hydrates thereof:

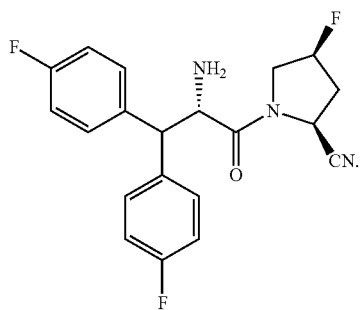 [SMILES: N#C[C@@H]1C[C@H](F)CN1C(=O)[C@@H](N)C(c1ccc(F)cc1)c1ccc(F)cc1]

Various crystalline forms of (2S,4S)-1-[(2S)-2-amino-3,3-bis(4-fluorophenyl)propanoyl]-4-fluoropyrrolidine-2-carbonitrile and salts have been disclosed in international patent publication WO 2005/009956. One salt disclosed is (2S,4S)-1-[(2S)-2-amino-3,3-bis(4-fluorophenyl)propanoyl]-4-fluoropyrrolidine-2-carbonitrile p-toluenesulfonic acid salt (also referred to as (2S,4S)-4-fluoro-1-[4-fluoro-β-(4-fluorophenyl)-L-phenylalanyl]-2-pyrrolidinecarbonitrile p-toluenesulfonic acid salt, or Denagliptin tosylate). In some embodiments, the DPP-IV inhibitor is (2S,4S)-1-[(2S)-2-amino-3,3-bis(4-fluorophenyl)propanoyl]-4-fluoropyrrolidine-2-carbonitrile p-toluenesulfonic acid salt:

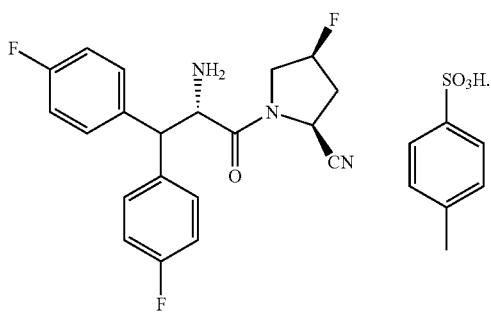 [SMILES: N#C[C@@H]1C[C@H](F)CN1C(=O)[C@@H](N)C(c1ccc(F)cc1)c1ccc(F)cc1 ; Cc1ccc(S(=O)(=O)O)cc1]

Abbott disclosed a series of substituted pyrrolidinyl derivatives as DPP-IV inhibitors in international patent publication WO 2004/026822. Some embodiments of the present invention include every combination of one or more compounds selected from the DPP-IV inhibitors disclosed in WO 2004/026822 and pharmaceutically acceptable salts, solvates, and hydrates thereof. One such compound is (2S,5R)-5-ethynyl-1-{N-(4-methyl-1-(4-carboxy-pyridin-2-yl)piperidin-4-yl)glycyl}pyrrolidine-2-carbonitrile. In some embodiments, the DPP-IV inhibitor is selected from (2S,5R)-5-ethynyl-1-{N-(4-methyl-1-(4-carboxy-pyridin-2-yl)piperidin-4-yl)glycyl}pyrrolidine-2-carbonitrile, and pharmaceutically acceptable salts, solvates, and hydrates thereof:

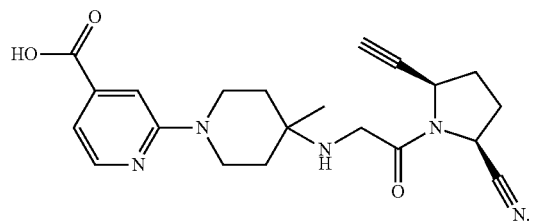 [SMILES: C#C[C@H]1CC[C@@H](C#N)N1C(=O)CNC1(C)CCN(c2cc(C(=O)O)ccn2)CC1]

Abbott has further disclosed a series of substituted cyclohexanyl/cyclohexenyl derivatives as DPP-IV inhibitors in international patent publication WO 2007/027651. Some embodiments of the present invention include every combination of one or more compounds selected from the DPP-IV inhibitors disclosed in WO 2007/027651 and pharmaceutically acceptable salts, solvates, and hydrates thereof. One such compound is (1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine. In some embodiments, the DPP-IV inhibitor is selected from (1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine, and pharmaceutically acceptable salts, solvates, and hydrates thereof:

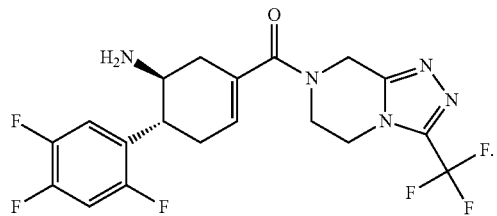 [SMILES: N[C@H]1CC(C(=O)N2CCn3c(nnc3C(F)(F)F)C2)=CC[C@@H]1c1cc(F)c(F)cc1F]

Biguanides

The biguanides are a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin ((phenylethyl)biguanide), metformin (dimethylbiguanide), buformin (butylbiguanide), proguanil (1-(p-chlorophenyl)-5-isopropylbiguanide), and biguanides known in the art.

In some embodiments, the pharmaceutical agent or the second pharmaceutical agent is a biguanide selected from the following biguanides and pharmaceutically acceptable salts, solvates, and hydrates thereof:

(phenylethyl)biguanide, dimethylbiguanide, butylbiguanide, 1-(p-chlorophenyl)-5-isopropylbiguanide.

In some embodiments, the pharmaceutical agent or the second pharmaceutical agent is a biguanide selected from (phenylethyl)biguanide (chemical structure shown below) and pharmaceutically acceptable salts, solvates, and hydrates thereof:

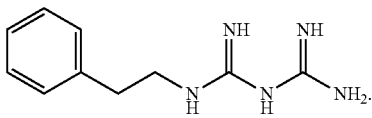 [SMILES: N=C(N)NC(=N)NCCc1ccccc1]

In some embodiments, the pharmaceutical agent or the second pharmaceutical agent is a biguanide selected from dimethylbiguanide (chemical structure shown below) and pharmaceutically acceptable salts, solvates, and hydrates thereof; the chemical structure is as follows:

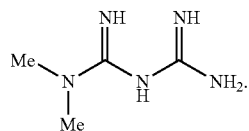

In some embodiments, the pharmaceutical agent or the second pharmaceutical agent is a biguanide selected from butylbiguanide (chemical structure shown below) and pharmaceutically acceptable salts, solvates, and hydrates thereof; the chemical structure is as follows:

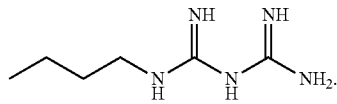

In some embodiments, the pharmaceutical agent or the second pharmaceutical agent is a biguanide selected from 1-(p-chlorophenyl)-5-isopropylbiguanide (chemical structure shown below) and pharmaceutically acceptable salts, solvates, and hydrates thereof; the chemical structure is as follows:

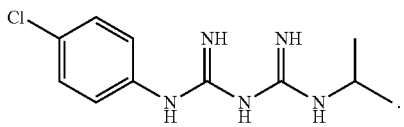 [SMILES: CC(C)NC(=N)NC(=N)Nc1ccc(Cl)cc1]

In some embodiments, the pharmaceutical agent or the second pharmaceutical agent is a biguanide selected from the following biguanides: metformin, phenformin, buformin, and proguanil. In some embodiments, the pharmaceutical agent or the second pharmaceutical agent is metformin. In some embodiments, the pharmaceutical agent or the second pharmaceutical agent is phenformin. In some embodiments, the pharmaceutical agent or the second pharmaceutical agent is buformin. In some embodiments, the pharmaceutical agent or the second pharmaceutical agent is proguanil.

Alpha-Glucosidase Inhibitors

Alpha-Glucosidase inhibitors belong to the class of drugs which competitively inhibit digestive enzymes such as alpha-amylase, maltase, alpha-dextrinase, sucrase, etc. in the pancreas and or small intestine. The reversible inhibition by alpha-glucosidase inhibitors retard, diminish or otherwise reduce blood glucose levels by delaying the digestion of starch and sugars. Some representative examples of alpha-glucosidase inhibitors include acarbose ((2R,3R,4R,5R)-4-((2R,3R,4R,5S,6R)-5-((2R,3R,4S,5S,6R)-3,4-dihydroxy-6-methyl-5-((1S,4R,5S,6S)-4,5,6-trihydroxy-3-(hydroxymethyl)cyclohex-2-enylamino)tetrahydro-2H-pyran-2-yloxy)-3,4-dihydroxy-6-(hydroxymethyl)tetrahydro-2H-pyran-2-yloxy)-2,3,5,6-tetrahydroxyhexanal), miglitol ((2R,3R,4R,5S)-1-(2-hydroxyethyl)-2-(hydroxymethyl)piperidine-3,4,5-triol), voglibose ((1S,2S,3R,4S,5S)-5-(1,3-dihydroxypropan-2-ylamino)-1-(hydroxymethyl)cyclohexane-1,2,3,4-tetraol), and alpha-glucosidase inhibitors known in the art.

In some embodiments, the pharmaceutical agent or the second pharmaceutical agent is a alpha-glucosidase inhibitor selected from the following alpha-glucosidase inhibitors and pharmaceutically acceptable salts, solvates, and hydrates thereof:

(2R,3R,4R,5R)-4-((2R,3R,4R,5S,6R)-5-((2R,3R,4S,5S,6R)-3,4-dihydroxy-6-methyl-5-((1S,4R,5S,6S)-4,5,6-trihydroxy-3-(hydroxymethyl)cyclohex-2-enylamino)tetrahydro-2H-pyran-2-yloxy)-3,4-dihydroxy-6-(hydroxymethyl)tetrahydro-2H-pyran-2-yloxy)-2,3,5,6-tetrahydroxyhexanal; (2R,3R,4R,5S)-1-(2-hydroxyethyl)-2-(hydroxymethyl)piperidine-3,4,5-triol; (1S,2S,3R,4S,5S)-5-(1,3-dihydroxypropan-2-ylamino)-1-(hydroxymethyl)cyclohexane-1,2,3,4-tetraol.

In some embodiments, the pharmaceutical agent or the second pharmaceutical agent is a alpha-glucosidase inhibitor selected from (2R,3R,4R,5R)-4-((2R,3R,4R,5S,6R)-5-((2R,3R,4S,5S,6R)-3,4-dihydroxy-6-methyl-5-((1S,4R,5S,6S)-4,5,6-trihydroxy-3-(hydroxymethyl)cyclohex-2-enylamino)tetrahydro-2H-pyran-2-yloxy)-3,4-dihydroxy-6-(hydroxymethyl)tetrahydro-2H-pyran-2-yloxy)-2,3,5,6-tetrahydroxyhexanal (chemical structure shown below) and pharmaceutically acceptable salts, solvates, and hydrates thereof:

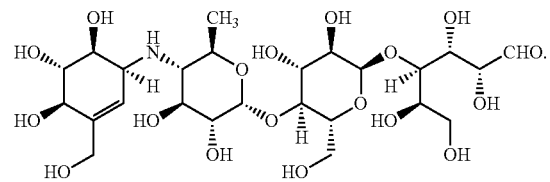 [SMILES: C[C@H]1O[C@H](O[C@H]2[C@H](O)[C@@H](O)[C@@H](O[C@@H]([C@H](O)[C@@H](O)C=O)[C@H](O)CO)O[C@@H]2CO)[C@H](O)[C@@H](O)[C@@H]1N[C@H]1C=C(CO)[C@@H](O)[C@H](O)[C@H]1O]

In some embodiments, the pharmaceutical agent or the second pharmaceutical agent is a alpha-glucosidase inhibitor selected from (2R,3R,4R,5S)-1-(2-hydroxyethyl)-2-(hydroxymethyl)piperidine-3,4,5-triol (chemical structure shown below) and pharmaceutically acceptable salts, solvates, and hydrates thereof:

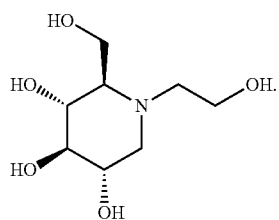 [SMILES: OCCN1C[C@H](O)[C@@H](O)[C@H](O)[C@H]1CO]

In some embodiments, the pharmaceutical agent or the second pharmaceutical agent is a alpha-glucosidase inhibitor selected from (1S,2S,3R,4S,5S)-5-(1,3-dihydroxypropan-2-ylamino)-1-(hydroxymethyl)cyclohexane-1,2,3,4-tetraol (chemical structure shown below) and pharmaceutically acceptable salts, solvates, and hydrates thereof:

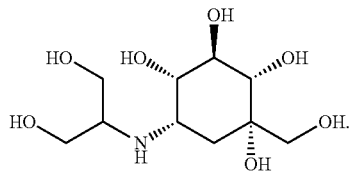 [SMILES: OCC(CO)N[C@H]1C[C@](O)(CO)[C@@H](O)[C@H](O)[C@H]1O]

In some embodiments, the pharmaceutical agent or the second pharmaceutical agent is an alpha-glucosidase inhibitor selected from: acarbose, miglitol, and voglibose. In some embodiments, the pharmaceutical agent or the second pharmaceutical agent is acarbose. In some embodiments, the pharmaceutical agent or the second pharmaceutical agent is miglitol. In some embodiments, the pharmaceutical agent or the second pharmaceutical agent is voglibose.

Insulin and Insulin Analogues

The term "insulin analogue" refers to the naturally occurring human hormone and insulin receptor ligands (i.e., synthetic insulin analogues). Insulin receptor ligands are structurally different from the natural human hormone, but have substantially the same activity as human insulin in terms of glycemic control. Examples of an insulin analogue include, NPH insulin (also known as Humulin N, Novolin N, NPH Lletin II, and insulin isophane), insulin lispro (28B-L-lysine-29B-L-proline-insulin, wherein insulin is human insulin), insulin aspart (28B-L-aspartic acid-insulin, wherein insulin is human insulin), insulin glulisine (3B-L-lysine-29B-L-glutamic acid-insulin, wherein insulin is human insulin), and insulin analogues known in the art.

NPH insulin is marketed by Eli Lilly and Company under the name Humulin N, and is considered as an intermediate-acting insulin analogue given to help control the blood sugar level of those with diabetes. Insulin lispro is marketed by Eli Lilly and Company under the name Humalog, and is considered a rapid acting insulin analogue. Insulin aspart is marketed by Novo Nordisk and sold as NovoRapid. Insulin aspart is considered a fast acting insulin analogue. Insulin glulisine was developed by Sanofi-Aventis and is sold under the trade name Apidra. Insulin glulisine is considered a rapid acting insulin analogue but shorter duration of action compared to human insulin.

In some embodiments, the pharmaceutical agent or the second pharmaceutical agent is an insulin analogue selected from NPH insulin and pharmaceutically acceptable salts, solvates, and hydrates thereof. In some embodiments, the pharmaceutical agent or the second pharmaceutical agent is an insulin analogue selected from insulin lispro and pharmaceutically acceptable salts, solvates, and hydrates thereof. In some embodiments, the pharmaceutical agent or the second pharmaceutical agent is an insulin analogue selected from insulin aspart and pharmaceutically acceptable salts, solvates, and hydrates thereof. In some embodiments, the pharmaceutical agent or the second pharmaceutical agent is an insulin analogue selected from insulin glulisine and pharmaceutically acceptable salts, solvates, and hydrates thereof.

Sulfonylureas

The sulfonylureas are drugs which promote secretion of insulin from pancreatic beta cells by transmitting signals of insulin secretion via receptors in the cell membranes. Examples of a sulfonylurea include tolbutamide (Orinase, N-(butylcarbamoyl)-4-methylbenzenesulfonamide); acetohexamide (Dymelor, 4-acetyl-N-(cyclohexylcarbamoyl)benzenesulfonamide); tolazamide (Tolinase, N-(azepan-1-ylcarbamoyl)-4-methylbenzenesulfonamide); chlorpropamide (Diabinese, 4-chloro-N-(propylcarbamoyl)benzenesulfonamide); glipizide (Glucotrol, N-(4-(N-(cyclohexylcarbamoyl)sulfamoyl)phenethyl)-5-methylpyrazine-2-carboxamide); glibenclamide, also known as glyburide (Diabeta, Micronase, Glynase, 5-chloro-N-(4-(N-(cyclohexylcarbamoyl)sulfamoyl)phenethyl)-2-methoxybenzamide); glimepiride (Amaryl, 3-ethyl-4-methyl-N-(4-(N-((1r,4r)-4-methylcyclohexylcarbamoyl)sulfamoyl)phenethyl)-2-oxo-2,5-dihydro-1H-pyrrole-1-carboxamide); gliclazide (Diamicron, N-(hexahydrocyclopenta[c]pyrrol-2(1H)-ylcarbamoyl)-4-methylbenzenesulfonamide); and sulfonylureas known in the art.

In some embodiments, the pharmaceutical agent or the second pharmaceutical agent is a sulfonylurea selected from sulfonylureas and pharmaceutically acceptable salts, solvates, and hydrates thereof:

N-(4-(N-(cyclohexylcarbamoyl)sulfamoyl)phenethyl)-5-methylpyrazine-2-carboxamide; 5-chloro-N-(4-(N-(cyclohexylcarbamoyl)sulfamoyl)phenethyl)-2-methoxybenzamide; 3-ethyl-4-methyl-N-(4-(N-((1r,4r)-4-methylcyclohexylcarbamoyl)sulfamoyl)phenethyl)-2-oxo-2,5-dihydro-1H-pyrrole-1-carboxamide.

In some embodiments, the pharmaceutical agent or the second pharmaceutical agent is a sulfonylurea selected from N-(butylcarbamoyl)-4-methylbenzenesulfonamide (chemical structure shown below) and pharmaceutically acceptable salts, solvates, and hydrates thereof:

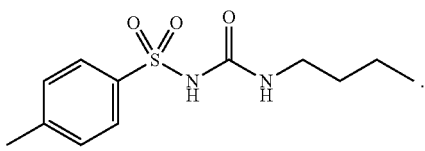 [SMILES: CCCCNC(=O)NS(=O)(=O)c1ccc(C)cc1]

In some embodiments, the pharmaceutical agent or the second pharmaceutical agent is a sulfonylurea selected from 4-acetyl-N-(cyclohexylcarbamoyl)benzenesulfonamide (chemical structure shown below) and pharmaceutically acceptable salts, solvates, and hydrates thereof:

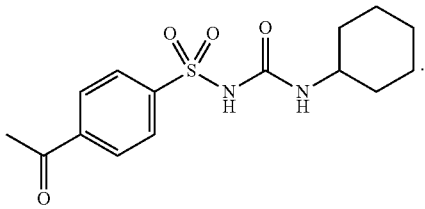 [SMILES: CC(=O)c1ccc(S(=O)(=O)NC(=O)NC2CCCCC2)cc1]

In some embodiments, the pharmaceutical agent or the second pharmaceutical agent is a sulfonylurea selected from N-(azepan-1-ylcarbamoyl)-4-methylbenzenesulfonamide (chemical structure shown below) and pharmaceutically acceptable salts, solvates, and hydrates thereof:

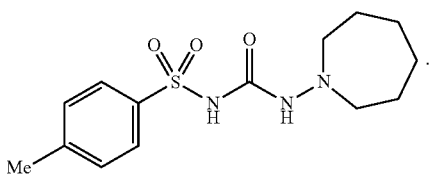

In some embodiments, the pharmaceutical agent or the second pharmaceutical agent is a sulfonylurea selected from 4-chloro-N-(propylcarbamoyl)benzenesulfonamide (chemical structure shown below) and pharmaceutically acceptable salts, solvates, and hydrates thereof:

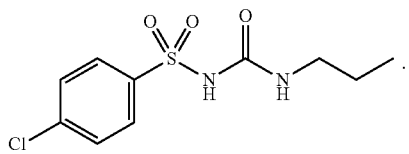 [SMILES: CCCNC(=O)NS(=O)(=O)c1ccc(Cl)cc1]

In some embodiments, the pharmaceutical agent or the second pharmaceutical agent is a sulfonylurea selected from N-(4-(N-(cyclohexylcarbamoyl)sulfamoyl)phenethyl)-5-methylpyrazine-2-carboxamide (chemical structure shown below) and pharmaceutically acceptable salts, solvates, and hydrates thereof:

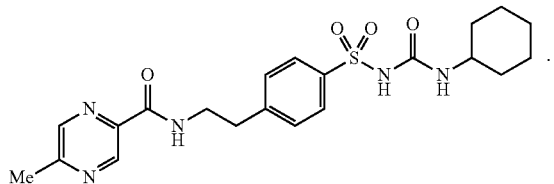 [SMILES: Cc1cnc(C(=O)NCCc2ccc(S(=O)(=O)NC(=O)NC3CCCCC3)cc2)cn1]

In some embodiments, the pharmaceutical agent or the second pharmaceutical agent is a sulfonylurea selected from 5-chloro-N-(4-(N-(cyclohexylcarbamoyl)sulfamoyl)phenethyl)-2-methoxybenzamide (chemical structure shown below) and pharmaceutically acceptable salts, solvates, and hydrates thereof:

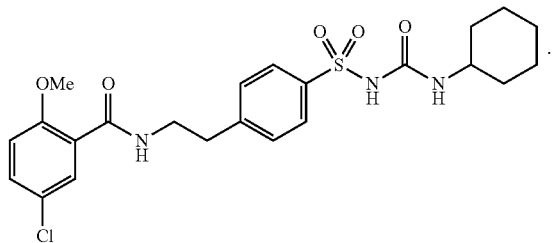 [SMILES: COc1ccc(Cl)cc1C(=O)NCCc1ccc(S(=O)(=O)NC(=O)NC2CCCCC2)cc1]

In some embodiments, the pharmaceutical agent or the second pharmaceutical agent is a sulfonylurea selected from 3-ethyl-4-methyl-N-(4-(N-((1r,4r)-4-methylcyclohexylcarbamoyl)sulfamoyl)phenethyl)-2-oxo-2,5-dihydro-1H-pyrrole-1-carboxamide (chemical structure shown below) and pharmaceutically acceptable salts, solvates, and hydrates thereof:

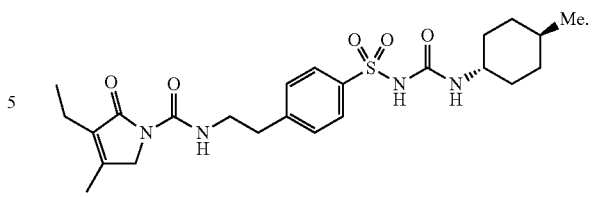

In some embodiments, the pharmaceutical agent or the second pharmaceutical agent is a sulfonylurea selected from N-(hexahydrocyclopenta[c]pyrrol-2(1H)-ylcarbamoyl)-4-methylbenzenesulfonamide (chemical structure shown below) and pharmaceutically acceptable salts, solvates, and hydrates thereof:

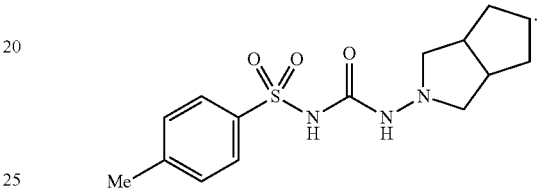

In some embodiments, the pharmaceutical agent or the second pharmaceutical agent is a sulfonylurea selected from the following sulfonylureas and pharmaceutically acceptable salts, solvates, and hydrates thereof: glipizide, glimepiride, and glibenclamide. In some embodiments, the pharmaceutical agent or the second pharmaceutical agent is tolbutamide. In some embodiments, the pharmaceutical agent or the second pharmaceutical agent is acetohexamide. In some embodiments, the pharmaceutical agent or the second pharmaceutical agent is tolazamide. In some embodiments, the pharmaceutical agent or the second pharmaceutical agent is chlorpropamide. In some embodiments, the pharmaceutical agent or the second pharmaceutical agent is glipizide. In some embodiments, the pharmaceutical agent or the second pharmaceutical agent is glyburide. In some embodiments, the pharmaceutical agent or the second pharmaceutical agent is glimepiride. In some embodiments, the pharmaceutical agent or the second pharmaceutical agent is gliclazide.

SGLT2 Inhibitors

Sodium-glucose transporter-2 (SGLT2) inhibitors belong to the class of drugs which inhibit the protein SGLT2 and the reabsorption of glucose in the kidney. The inhibition by SGLT2 inhibitors retard, diminish, or otherwise reduce the amount of glucose that is reabsorbed and therefore is eliminated in the urine. Some representative examples of SGLT2 inhibitors include dapagliflozin ((2S,3R,4R,5S,6R)-2-(4-chloro-3-(4-ethoxybenzyl)phenyl)-6-(hydroxymethyl)tetrahydro-2H-pyran-3,4,5-triol, Bristol-Myers Squibb and AstraZeneca), remogliflozin (ethyl ((2R,3S,4S,5R,6S)-3,4,5-trihydroxy-6-(4-(4-isopropoxybenzyl)-1-isopropyl-5-methyl-1H-pyrazol-3-yloxy)tetrahydro-2H-pyran-2-yl)methyl carbonate, GlaxoSmithKline), ASP1941 (Kotobuki/Astellas), canagliflozin ((2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol, Johnson & Johnson/Mitsubishi/Tanabe), ISIS 388626 (an antisense oligonucleotide, Isis Pharmaceuticals), sergliflozin (ethyl ((2R, 3S,4S,5R,6S)-3,4,5-trihydroxy-6-(2-(4-methoxybenzyl) phenoxy)tetrahydro-2H-pyran-2-yl)methyl carbonate, GlaxoSmithKline), AVE2268 ((2R,3S,4S,5R,6S)-2-(hydroxymethyl)-6-(2-(4-methoxybenzyl)thiophen-3-yloxy)tetrahydro-2H-pyran-3,4,5-triol, Sanofi-Aventis), BI10773 (Boehringer Ingelheim), CSG453 (Chugai/Roche), LX4211 (Lexicon), and SGLT2 inhibitors known in the art.

In some embodiments, the pharmaceutical agent or the second pharmaceutical agent is an SGLT2 inhibitor selected from the following SGLT2 inhibitors and pharmaceutically acceptable salts, solvates, and hydrates thereof:
(2S,3R,4R,5S,6R)-2-(4-chloro-3-(4-ethoxybenzyl)phenyl)-6-(hydroxymethyl)tetrahydro-2H-pyran-3,4,5-triol;
ethyl ((2R,3S,4S,5R,6S)-3,4,5-trihydroxy-6-(4-(4-isopropoxybenzyl)-1-isopropyl-5-methyl-1H-pyrazol-3-yloxy)tetrahydro-2H-pyran-2-yl)methyl carbonate; ethyl ((2R,3S,4S,5R,6S)-3,4,5-trihydroxy-6-(2-(4-methoxybenzyl)phenoxy)tetrahydro-2H-pyran-2-yl)methyl carbonate; (2R,3S,4S,5R,6S)-2-(hydroxymethyl)-6-(2-(4-methoxybenzyl)thiophen-3-yloxy)tetrahydro-2H-pyran-3,4,5-triol; (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol.

In some embodiments, the pharmaceutical agent or the second pharmaceutical agent is a sulfonylurea selected from (2S,3R,4R,5S,6R)-2-(4-chloro-3-(4-ethoxybenzyl)phenyl)-6-(hydroxymethyl)tetrahydro-2H-pyran-3,4,5-triol (chemical structure shown below) and pharmaceutically acceptable salts, solvates, and hydrates thereof:

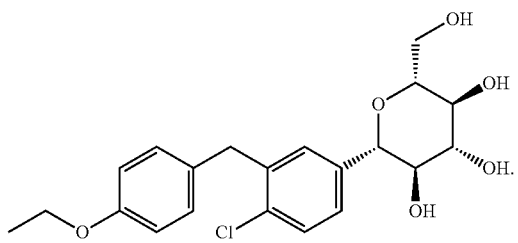 [SMILES: CCOc1ccc(Cc2cc([C@@H]3O[C@H](CO)[C@@H](O)[C@H](O)[C@H]3O)ccc2Cl)cc1]

In some embodiments, the pharmaceutical agent or the second pharmaceutical agent is a sulfonylurea selected from ethyl ((2R,3S,4S,5R,6S)-3,4,5-trihydroxy-6-(4-(4-isopropoxybenzyl)-1-isopropyl-5-methyl-1H-pyrazol-3-yloxy)tetrahydro-2H-pyran-2-yl)methyl carbonate (chemical structure shown below) and pharmaceutically acceptable salts, solvates, and hydrates thereof:

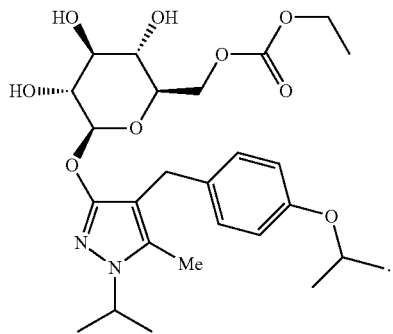 [SMILES: CCOC(=O)OC[C@H]1O[C@@H](Oc2nn(C(C)C)c(C)c2Cc2ccc(OC(C)C)cc2)[C@H](O)[C@@H](O)[C@@H]1O]

In some embodiments, the pharmaceutical agent or the second pharmaceutical agent is a sulfonylurea selected from ethyl ((2R,3S,4S,5R,6S)-3,4,5-trihydroxy-6-(2-(4-methoxybenzyl)phenoxy)tetrahydro-2H-pyran-2-yl)methyl carbonate (chemical structure shown below) and pharmaceutically acceptable salts, solvates, and hydrates thereof:

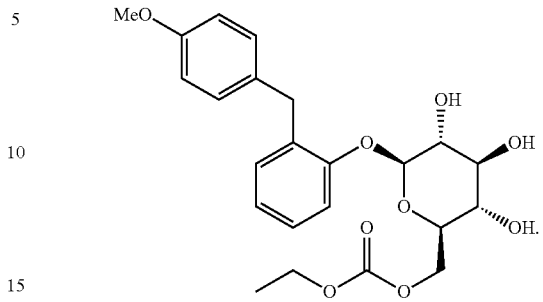

In some embodiments, the pharmaceutical agent or the second pharmaceutical agent is an SGLT2 inhibitor selected from: dapagliflozin, remogliflozin, and sergliflozin. In some embodiments, the pharmaceutical agent or the second pharmaceutical agent is dapagliflozin. In some embodiments, the pharmaceutical agent or the second pharmaceutical agent is remogliflozin. In some embodiments, the pharmaceutical agent or the second pharmaceutical agent is sergliflozin.

Astellas and Kotobuki disclosed a series of SGLT2 inhibitors in international patent publication WO2004/080990. Some embodiments of the present invention include every combination of one or more compounds selected from compounds disclosed in WO2004/080990 and pharmaceutically acceptable salts, solvates, and hydrates thereof.

Aventis disclosed a series of SGLT2 inhibitors in international patent publication WO2004/007517. Some embodiments of the present invention include every combination of one or more compounds selected from compounds disclosed in WO2004/007517 and pharmaceutically acceptable salts, solvates, and hydrates thereof. One such compound is (2R,3S,4S,5R,6S)-2-(hydroxymethyl)-6-(2-(4-methoxybenzyl)thiophen-3-yloxy)tetrahydro-2H-pyran-3,4,5-triol. In some embodiments, the SGLT2 inhibitor is selected from (2R,3S,4S,5R,6S)-2-(hydroxymethyl)-6-(2-(4-methoxybenzyl)thiophen-3-yloxy)tetrahydro-2H-pyran-3,4,5-triol, and pharmaceutically acceptable salts, solvates, and hydrates thereof:

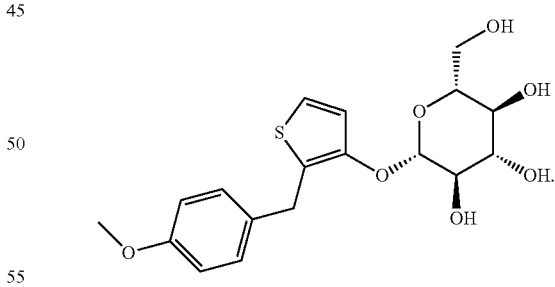

Tanabe disclosed a series of SGLT2 inhibitors in international patent publication WO2005/012326. Some embodiments of the present invention include every combination of one or more compounds selected from compounds disclosed in WO2005/012326 and pharmaceutically acceptable salts, solvates, and hydrates thereof. One such compound is (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol. In some embodiments, the SGLT2 inhibitor is selected from (2S,3R,4R,5S,6R)-2-(3-((5-(4-fluorophenyl)thiophen-2-yl)methyl)-4-methylphenyl)-6-

(hydroxymethyl)tetrahydro-2H-pyran-3,4,5-triol, and pharmaceutically acceptable salts, solvates, and hydrates thereof:

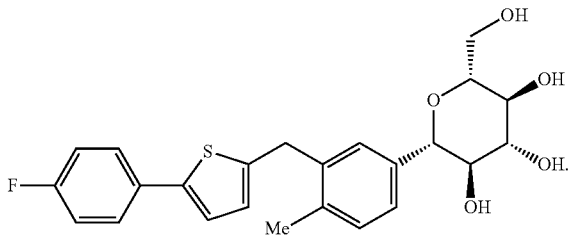 [SMILES: Cc1ccc([C@@H]2O[C@H](CO)[C@@H](O)[C@H](O)[C@H]2O)cc1Cc1ccc(-c2ccc(F)cc2)s1]

Boehringer Ingelheim disclosed a series of SGLT2 inhibitors in international patent publication WO2005/092877. Some embodiments of the present invention include every combination of one or more compounds selected from compounds disclosed in WO2005/092877 and pharmaceutically acceptable salts, solvates, and hydrates thereof.

Chugai disclosed a series of SGLT2 inhibitors in international patent publication WO2006/080421. Some embodiments of the present invention include every combination of one or more compounds selected from compounds disclosed in WO2006/080421 and pharmaceutically acceptable salts, solvates, and hydrates thereof.

Lexicon disclosed a series of SGLT2 inhibitors in international patent publication WO2008/109591. Some embodiments of the present invention include every combination of one or more compounds selected from compounds disclosed in WO2008/109591 and pharmaceutically acceptable salts, solvates, and hydrates thereof.

Meglitinides

The meglitinides promote secretion of insulin by binding to the pancreatic beta cells in a similar manner as sulfonylureas but at an alternative binding site. Examples of meglitinides include Novo Nordisk's repaglinide (Prandin, (S)-2-ethoxy-4-(2-(3-methyl-1-(2-(piperidin-1-yl)phenyl)butylamino)-2-oxoethyl)benzoic acid), nateglinide (Starlix, (R)-2-((1r,4R)-4-isopropylcyclohexanecarboxamido)-3-phenylpropanoic acid), mitiglinide ((S)-2-benzyl-4-((3aR,7aS)-1H-isoindol-2(3H,3aH,4H,5H,6H,7H,7aH)-yl)-4-oxobutanoic acid), and the like.

In some embodiments, the pharmaceutical agent or the second pharmaceutical agent is a meglitinide selected from the following meglitinides and pharmaceutically acceptable salts, solvates, and hydrates thereof:

(S)-2-ethoxy-4-(2-(3-methyl-1-(2-(piperidin-1-yl)phenyl)butylamino)-2-oxoethyl)benzoic acid; (R)-2-((1r,4R)-4-isopropylcyclohexanecarboxamido)-3-phenylpropanoic acid; (S)-2-benzyl-4-(3aR,7aS)-1H-isoindol-2(3H,3aH,4H,5H,6H,7H,7aH)-yl)-4-oxobutanoic acid.

In some embodiments, the pharmaceutical agent or the second pharmaceutical agent is (S)-2-ethoxy-4-(2-(3-methyl-1-(2-(piperidin-1-yl)phenyl)butylamino)-2-oxoethyl)benzoic acid (chemical structure shown below) and pharmaceutically acceptable salts, solvates, and hydrates thereof:

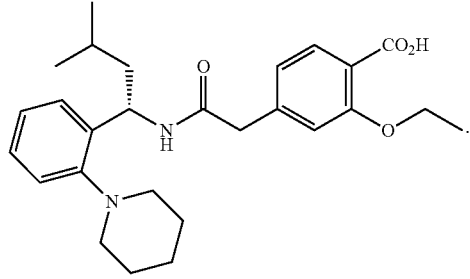 [SMILES: CCOc1cc(CC(=O)N[C@@H](CC(C)C)c2ccccc2N2CCCCC2)ccc1C(=O)O]

In some embodiments, the pharmaceutical agent or the second pharmaceutical agent is a sulfonylurea selected from (R)-2-((1r,4R)-4-isopropylcyclohexanecarboxamido)-3-phenylpropanoic acid (chemical structure shown below) and pharmaceutically acceptable salts, solvates, and hydrates thereof:

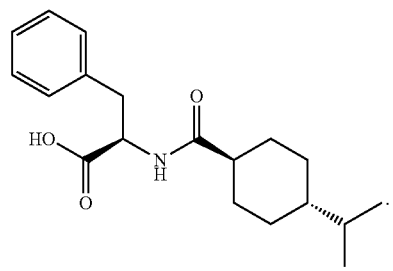 [SMILES: CC(C)[C@H]1CC[C@H](C(=O)N[C@H](Cc2ccccc2)C(=O)O)CC1]

In some embodiments, the pharmaceutical agent or the second pharmaceutical agent is a sulfonylurea selected from (S)-2-benzyl-4-(3aR,7aS)-1H-isoindol-2(3H,3aH,4H,5H,6H,7H,7aH)-yl)-4-oxobutanoic acid (chemical structure shown below) and pharmaceutically acceptable salts, solvates, and hydrates thereof:

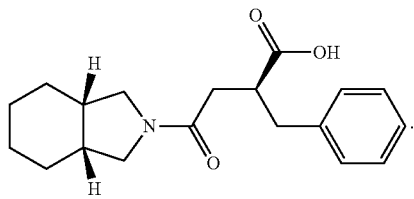 [SMILES: O=C(O)[C@H](CC(=O)N1C[C@H]2CCCC[C@H]2C1)Cc1ccccc1]

In some embodiments, the pharmaceutical agent or the second pharmaceutical agent is a meglitinide selected from the following meglitinides: repaglinide, nateglinide, mitiglinide, and pharmaceutically acceptable salts, solvates, and hydrates thereof. In some embodiments, the pharmaceutical agent or the second pharmaceutical agent is a meglitinide selected from repaglinide and pharmaceutically acceptable salts, solvates, and hydrates thereof. In some embodiments, the pharmaceutical agent or the second pharmaceutical agent is a meglitinide selected from nateglinide and pharmaceutically acceptable salts, solvates, and hydrates thereof. In some embodiments, the pharmaceutical agent or the second pharmaceutical agent is a meglitinide selected from mitiglinide and pharmaceutically acceptable salts, solvates, and hydrates thereof.

Thiazolidinediones

Thiazolidinediones belong to the class of drugs more commonly known as TZDs. These drugs act by binding to the nuclear receptor peroxisome proliferator-activated receptor gamma (PPARγ) activate transcription of a number of specific genes leading to a decrease in insulin resistance. Examples of thiazolidinediones include rosiglitazone (Avandia, 5-(4-(2-(methyl(pyridin-2-yl)amino)ethoxy)benzyl)thiazolidine-2,4-dione), pioglitazone (Actos, 5-(4-(2-(5-ethylpyridin-2-yl)ethoxy)benzyl)thiazolidine-2,4-dione), troglitazone (Rezulin, 5-(4-((6-hydroxy-2,5,7,8-tetramethylchroman-2-yl)methoxy)benzyl)thiazolidine-2,4-dione), rivoglitazone (5-(4-((6-methoxy-1-methyl-1H-benzo[d]imidazol-2-yl)methoxy)benzyl)thiazolidine-2,4-dione), ciglitazone(5-(4-((1-methylcyclohexyl)methoxy)benzyl)thiazolidine-2,4-dione), and thiazolidinediones known in the art.

In some embodiments, the pharmaceutical agent or the second pharmaceutical agent is a thiazolidinedione selected from the following thiazolidinediones and pharmaceutically acceptable salts, solvates, and hydrates thereof:

5-(4-(2-(methyl(pyridin-2-yl)amino)ethoxy)benzyl)thiazolidine-2,4-dione; 5-(4-(2-(5-ethylpyridin-2-yl)ethoxy)benzyl)thiazolidine-2,4-dione; 5-(4-((6-methoxy-1H-benzo[d]imidazol-2-yl)methoxy)benzyl)thiazolidine-2,4-dione; 5-(4-((1-methylcyclohexyl)methoxy)benzyl)thiazolidine-2,4-dione.

In some embodiments, the pharmaceutical agent or the second pharmaceutical agent is 5-(4-(2-(methyl(pyridin-2-yl)amino)ethoxy)benzyl)thiazolidine-2,4-dione (chemical structure shown below) and pharmaceutically acceptable salts, solvates, and hydrates thereof:

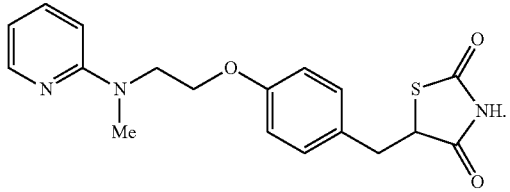 [SMILES: CN(CCOc1ccc(CC2SC(=O)NC2=O)cc1)c1ccccn1]

In some embodiments, the pharmaceutical agent or the second pharmaceutical agent is 5-(4-(2-(5-ethylpyridin-2-yl)ethoxy)benzyl)thiazolidine-2,4-dione (chemical structure shown below) and pharmaceutically acceptable salts, solvates, and hydrates thereof:

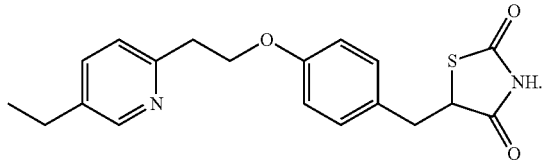 [SMILES: CCc1ccc(CCOc2ccc(CC3SC(=O)NC3=O)cc2)nc1]

In some embodiments, the pharmaceutical agent or the second pharmaceutical agent is 5-(4-((6-hydroxy-2,5,7,8-tetramethylchroman-2-yl)methoxy)benzyl)thiazolidine-2,4-dione (chemical structure shown below) and pharmaceutically acceptable salts, solvates, and hydrates thereof:

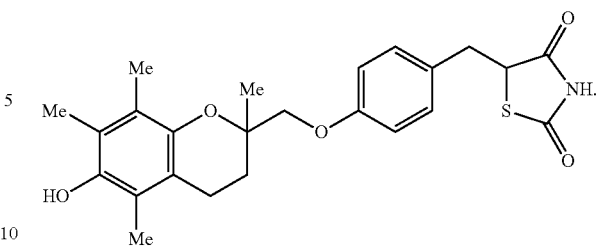

In some embodiments, the pharmaceutical agent or the second pharmaceutical agent is 5-(4-((6-methoxy-1-methyl-1H-benzo[d]imidazol-2-yl)methoxy)benzyl)thiazolidine-2,4-dione (chemical structure shown below) and pharmaceutically acceptable salts, solvates, and hydrates thereof:

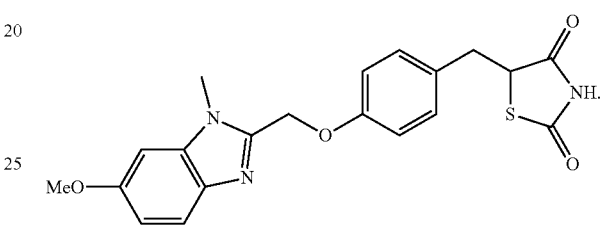

In some embodiments, the pharmaceutical agent or the second pharmaceutical agent is 5-(4-((1-methylcyclohexyl)methoxy)benzyl)thiazolidine-2,4-dione (chemical structure shown below) and pharmaceutically acceptable salts, solvates, and hydrates thereof:

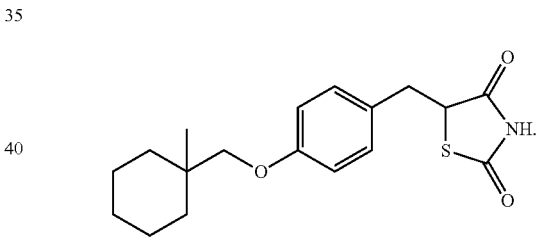

In some embodiments, the pharmaceutical agent or the second pharmaceutical agent is a thiazolidinedione selected from rosiglitazone and pharmaceutically acceptable salts, solvates, and hydrates thereof. In some embodiments, the pharmaceutical agent or the second pharmaceutical agent is a thiazolidinedione selected from pioglitazone and pharmaceutically acceptable salts, solvates, and hydrates thereof. In some embodiments, the pharmaceutical agent or the second pharmaceutical agent is a thiazolidinedione selected from troglitazone and pharmaceutically acceptable salts, solvates, and hydrates thereof. In some embodiments, the pharmaceutical agent or the second pharmaceutical agent is a thiazolidinedione selected from rivoglitazone and pharmaceutically acceptable salts, solvates, and hydrates thereof. In some embodiments, the pharmaceutical agent or the second pharmaceutical agent is a thiazolidinedione selected from ciglitazone and pharmaceutically acceptable salts, solvates, and hydrates thereof.

Anti-Diabetic Peptide Analogues

Anti-diabetic peptide analogues are peptides that promote secretion of insulin by acting as an incretin mimetic, such as, GLP-1 and GIP. Examples of an anti-diabetic peptide analog include, exenatide, liraglutide, taspoglutide, and anti-diabetic peptides analogues know in the art.

In some embodiments, the pharmaceutical agent or the second pharmaceutical agent is an anti-diabetic peptide analogue selected from: exenatide; liraglutide; and taspoglutide. In some embodiments, the pharmaceutical agent or the second pharmaceutical agent is exenatide. In some embodiments, the pharmaceutical agent or the second pharmaceutical agent is liraglutide. In some embodiments, the pharmaceutical agent or the second pharmaceutical agent is taspoglutide.

In some embodiments, the pharmaceutical agent or the second pharmaceutical agent is L-histidylglycyl-L-α-glutamylglycyl-L-threonyl-L-phenylalanyl-L-threonyl-L-seryl-L-α-aspartyl-L-leucyl-L-seryl-L-lysyl-L-glutaminyl-L-methionyl-L-α-glutamyl-L-α-glutamyl-L-α-glutamyl-L-alanyl-L-valyl-L-arginyl-L-leucyl-L-phenylalanyl-L-isoleucyl-L-α-glutamyl-L-tryptophyl-L-leucyl-L-lysyl-L- asparaginylglycylglycyl-L-prolyl-L-seryl-L-serylglycyl-L-alanyl-L-prolyl-L-prolyl-L-prolyl-L-serinamide (i.e., exenatide) and pharmaceutically acceptable salts, solvates, and hydrates thereof.

In some embodiments, the pharmaceutical agent or the second pharmaceutical agent is L-histidyl-L-alanyl-L-α-glutamylglycyl-L-threonyl-L-phenylalanyl-L-threonyl-L-seryl-L-α-aspartyl-L-valyl-L-seryl-L-seryl-L-tyrosyl-L-leucyl-L-α-glutamylglycyl-L-glutaminyl-L-alanyl-L-alanyl-N6-[N-(1-oxohexadecyl)-L-α-glutamyl]-L-lysyl-L-α-glutamyl-L-phenylalanyl-L-isoleucyl-L-alanyl-L-tryptophyl-L-leucyl-L-valyl-L-arginylglycyl-L-arginyl-glycine (liraglutide) and pharmaceutically acceptable salts, solvates, and hydrates thereof.

In some embodiments, the pharmaceutical agent or the second pharmaceutical agent is $H_2N$-His-2-methyl-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-2-methyl-Ala-Arg-$CONH_2$ (taspoglutide) and pharmaceutically acceptable salts, solvates, and hydrates thereof.

Other Utilities

Another object of the present invention relates to radiolabeled compounds of the present invention that would be useful not only in radio-imaging but also in assays, both in vitro and in vivo, for localizing and quantitating GPR119 receptors in tissue samples, including human and for identifying GPR119 receptor ligands by inhibition binding of a radiolabeled compound. It is a further object of this invention to develop novel GPR119 receptor assays of which comprise such radiolabeled compounds.

The present disclosure includes all isotopes of atoms occurring in the present compounds, intermediates, salts and crystalline forms thereof. Isotopes include those atoms having the same atomic number but different mass numbers. One aspect of the present invention includes every combination of one or more atoms in the present compounds, intermediates, salts, and crystalline forms thereof that is replaced with an atom having the same atomic number but a different mass number. One such example is the replacement of an atom that is the most naturally abundant isotope, such as $^1H$ or $^{12}C$, found in one the present compounds, intermediates, salts, and crystalline forms thereof, with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being an isotopically-labeled compound. Isotopic-labeling of the present compounds, intermediates, salts, and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}C$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, intermediates, salts, and crystalline forms thereof, wherein the naturally occurring distribution of the isotopes in the composition is perturbed. Another aspect of the present invention includes compositions and pharmaceutical compositions comprising compounds as described herein wherein the compound is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or a scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3H$]: This procedure is rather inexpensive and requires precursors containing reducible functional groups such as aldehydes, ketones, lactones, esters and the like.

C. Reduction with Lithium Aluminum Hydride [$^3H$]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A representative procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled GPR119 receptor Compound of Formula (Ia) can be used in a screening assay to identify/evaluate compounds. In general terms, a newly synthesized or identified compound (i.e., test compound) can be evaluated for its ability to reduce binding of the radiolabeled Compound of Formula (Ia) to a GPR119 receptor. Accordingly, the ability of a test compound to compete with the radiolabeled Compound of Formula (Ia) for the binding to a GPR119 receptor directly correlates to its binding affinity.

Certain labeled compounds of the present invention bind to certain GPR119 receptors. In one embodiment the labeled compound has an IC$_{50}$ less than about 500 μM. In one embodiment the labeled compound has an IC$_{50}$ less than about 100 μM. In one embodiment the labeled compound has an IC$_{50}$ less than about 10 μM. In one embodiment the labeled compound has an IC$_{50}$ less than about 1 μM. In one embodiment the labeled compound has an IC$_{50}$ less than about 0.1 μM. In one embodiment the labeled compound has an IC$_{50}$ less than about 0.01 μM. In one embodiment the labeled compound has an IC$_{50}$ less than about 0.005 μM.

Other uses of the disclosed receptors and methods will become apparent to those skilled in the art based upon, inter alia, a review of this disclosure.

EXAMPLES

The compounds of the invention and their syntheses are further illustrated by the following examples. The following examples are provided to further define the invention without, however, limiting the invention to the particulars of these examples. The compounds described herein, supra and infra, are named according to AutoNom version 2.2, AutoNom 2000, CS ChemDraw Ultra Version 7.0.1, or CS ChemDraw Ultra Version 9.0.7. In certain instances literature names and/or common names are used and it is understood that these names would be recognized by those skilled in the art.

Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, brs=broad singlet, brd=broad doublet, brt=broad triplet, brq=broad quartet.

Microwave irradiations were carried out using a Smith Synthesizer™ or an Emrys Optimizer™ (Biotage). Thin-layer chromatography (TLC) was performed on silica gel 60 F$_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1

Preparation of 5-Fluoropyrimidine-4,6-diol

Method A

To a three-neck round-bottom flask equipped with an overhead stirrer, nitrogen flow, and reflux condenser, was added 25 wt % sodium methoxide in methanol (950 mL, 4.15 mol) and formamide (357 mL, 8.98 mol). The mixture was heated to about 64° C. To the reaction mixture was added diethyl 2-fluoromalonate (177 mL, 1.12 mol) using an addition funnel over 1 h. The reaction temperature was maintained at 64° C. for 72 h. The reaction mixture was allowed to cool to room temperature and the solvent was removed under reduced pressure. The residue was cooled to 0° C. and slowly acidified with concentrated hydrochloric acid to pH 1-2 resulting in the precipitation of the product. The product was filtered and washed with an ice cold aqueous 1 N HCl solution. The off-white solid was suspended in acetonitrile, filtered and dried in a vacuum oven to give 5-fluoropyrimidine-4,6-diol (170 g, 1.31 mol) as a light brown-pinkish solid which was used without further purification. $^1$H NMR (400 MHz, DMSO-d$_6$) δ ppm 7.57 (s, 2H), 8.25 (s, 1H).

Method B

To a three neck 5 L round bottom flask equipped with magnetic stirrer, nitrogen flow and reflux condenser, was charged the following: sodium methoxide (25% NaOMe in Methanol) (1.425 L, 6.230 mol) and formamide (0.535 L, 13.5 mol) under nitrogen and heated to 64° C. To the reaction mixture diethyl 2-fluoromalonate (CAS #685-88-1, 0.266 L, 1.684 mol) was added slowly using an addition funnel (reaction exothermic). The reaction was heated at 64° C. for 72 h. The reaction was cooled down to room temperature and solvent was removed under reduced pressure. The residue was cooled to 0° C. by ice bath. The mixture was stirred and acidified slowly with 10 N HCl to pH-1-2. The product precipitated out and was filtered. The product was washed with ice cold 1N HCl. The off-white solid was suspended in ACN, filtered and dried (vacuum oven) at 30°

C. for 16 h to give 5-fluoropyrimidine-4,6-diol (349.4 g, 2.686 mol, 160% yield) as a light brown-pinkish solid. 5-Fluoropyrimidine-4,6-diol (CAS #106615-61-6, 600 g, 4.613 mol, 62% purity) was pulverized (sieved) and placed in a sintered glass funnel (4 L coarse). The material was suspended in an ice cold solution of 0.5 M HCl (aq) and the material was suspended (for 5 min) and then filtered. The filter cake was then washed with 1.2 L of ACN, EtOAc and finally hexanes. The solid was dried (vacuum oven) overnight to give 5-fluoropyrimidine-4,6-diol (276.459 g, 2.125 mol, 74% yield) as a purple-pinkish solid. $^1$H NMR (400 MHz, DMSO-$d_6$) δ ppm 7.9 (s, 1H), 12.3 (brs, 2H).

Example 1.2

Preparation of 4,6-Dichloro-5-fluoropyrimidine

Method A

To a 500 mL three-neck round-bottom flask containing phosphorus oxychloride (45.3 mL, 487 mmol) was slowly added 5-fluoropyrimidine-4,6-diol (20.0 g, 154 mmol) and the resulting reaction mixture was heated to 60° C. To the resulting slurry was slowly added N,N-dimethylaniline (42.2 mL, 331 mmol) over 4 h using a syringe pump and the reaction mixture was stirred at 60° C. for 16 h. The reaction mixture was cooled to room temperature and slowly added into a mixture of brine and ice (400 mL) with stirring. The aqueous layer was extracted with dichloromethane (2×250 mL). The combined organic layers (light amber) were washed with cold aqueous 6 N HCl solution (200 mL), dried over sodium sulfate, and filtered through a glass fiber paper by vacuum filtration and the solvent was removed under reduced pressure (no heat) to give 4,6-dichloro-5-fluoropyrimidine (13 g, 78 mmol, 50.6% yield) as an amber oil. $^1$H NMR (400 MHz, CDCl$_3$) δ ppm 8.62 (s, 1H).

Method B

To a 2 L three necked round bottom flask containing 5-fluoropyrimidine-4,6-diol (276.459 g, 2.125 mol) was added at room temperature slowly phosphoryl chloride (0.593 L, 6.376 mol) to form a slurry. To this slurry was added N,N-dimethylaniline (81 mL, 0.638 mol) very slowly using an addition funnel (exothermic) and the reaction was continued for 6 h at 110° C. After 6 h, the reaction mixture was cooled to room temperature and slowly added into brine and ice (2 L) with stirring. The aqueous layer (red) was extracted with DCM (2×2 L). The combined organic layers were washed with cold 6 N HCl (honey brown) (2×1 L) and washed with sat NaHCO$_3$ (1 L). The organic layer was dried (Na$_2$SO$_4$), filtered by vacuum filtration through a glass fiber paper and solvent was removed under reduced pressure (no heat) to give 4,6-dichloro-5-fluoropyrimidine (CAS #213265-83-9, 347.9 g, 2.084 mol, 98% yield) as an amber oil. NMR showed the oil contained traces of DCM. 4,6-Dichloro-5-fluoropyrimidine (420 g, 2.515 mol) was distilled by vacuum distillation to give 4,6-dichloro-5-fluoropyrimidine (332.574 g, 1.992 mol, 79% yield) as a colorless oil. The product solidified in the flask at −78° C. and melts when brought to room temperature. Conditions for distillation: Oil Bath: 100° C.; Product boiling temp: 35° C.; Pressure: 1 Torr. $^1$H NMR (400 MHz, DMSO-$d_6$) δ ppm 8.8 (s, 1H).

Example 1.3

Preparation of 2-Fluoro-2-methylpropanenitrile

Method A

To a 1 L three-neck round-bottom flask containing 2-hydroxy-2-methylpropanenitrile (120 mL, 1.31 mol) at 4° C. was slowly added (diethylamino)sulfur trifluoride (DAST) (172 mL, 1.31 mol) over 1 h via an additional funnel. The reaction mixture was allowed to warm to room temperature and stirred overnight. The mixture was directly purified by vacuum distillation (40-45° C./45 mmHg) to provide 2-fluoro-2-methylpropanenitrile (83.36 g, 0.957 mol, 73.0% yield) as a colorless oil containing methacrylonitrile (~10%). $^1$H NMR (400 MHz, CDCl$_3$) δ ppm 1.77 (d, J=20 Hz, 6H).

Method B

2-Hydroxy-2-methylpropanenitrile (CAS #75-86-5, 221 mL, 2.420 mol) was cooled down to −10° C. (ice/acetone/dry ice) in a 1 L three necked round bottomed flask and DAST (246 mL, 1.861 mol) was added slowly using an addition funnel over a period of 2 h. Once the addition was finished, the reaction was allowed to warm up to room temperature and stirred overnight. The product was distilled by vacuum distillation (30° C., 4 Torr) to give 2-fluoro-2-methylpropanenitrile (CAS #138999-34-5, 148.65 g, 1.707 mol, 92% yield) as colorless oil. The titled compound turned an amber color if not protected from light. Final product contained containing methacrylonitrile (NMR estimate-10%). $^1$H NMR (400 MHz, CDCl$_3$) δ ppm 1.8 (d, 6H).

Example 1.4

(Z)-2-Fluoro-N'-hydroxy-2-methylpropanimidamide

Method A

To a 1 L round-bottom flask was added 2-fluoro-2-methylpropanenitrile (80.7 g, 0.927 mol) and in ethanol (400 mL). To the resulting solution was slowly added a 50% aqueous solution of hydroxylamine (81.0 mL, 1.32 mol) via an additional funnel. The mixture was heated at 60° C. for 3 h. The mixture was allowed to cool to room temperature and ethanol was removed under reduced pressure. The residue was dissolved in dichloromethane (200 mL) and the organic layer was washed with water (2×200 mL) and brine solution (200 mL). The aqueous layer was back extracted with dichloromethane. The combined organics were dried over anhydrous sodium sulfate and filtered. The filtrate was concentrated under reduced pressure to provide (Z)-2-fluoro-N'-hydroxy-2-methylpropanimidamide (60.0 g, 0.499 mol, 53.9% yield) as an off-white solid. Exact mass calculated for C$_4$H$_9$FN$_2$O: 120.07, found: LCMS m/z=121.0 (M+H$^+$)(M+H)$^+$; $^1$H NMR (400 MHz, CDCl$_3$) δ ppm 1.58 (d, T=24 Hz, 6H), 4.64 (brs, 1H), 4.81 (brs, 2H).

Method B

2-Fluoro-2-methylpropanenitrile (148.65 g, 1.707 mol) was taken up in EtOH (700 mL) and hydroxylamine 50% water by weight (135 g, 2.048 mol) was added very slowly keeping the temperature at around 35° C. then the reaction mixture was heated to 80° C. for 16 h in a 1 L round bottomed flask. After 16 h the reaction mixture was cooled to room temp and solvent was removed under reduced pressure. The residue was taken up in DCM (500 mL) with slight heating and the solids that did not dissolve were decanted. The DCM was removed under reduced pressure to give (Z)-2-fluoro-N'-hydroxy-2-methylpropanimidamide 127 g, as a light yellow solid. The solid was sublimed at 100° C. and 3 Torr to give (Z)-2-fluoro-N'-hydroxy-2-methylpropanimidamide (74 g, 0.616 mol, 36.1% yield) as a white solid. The final product contained about 7% (NMR estimate) of the elimination side product (CAS #339075-08-0).

(Z)-2-fluoro-N'-hydroxy-2-methylpropanimidamide (120 g, 999 mmol) was purified by recrystallization from MTBE. The material was dissolved in MTBE, 5×-10× by volume. The solution was then cooled to −78° C. using dry ice and acetone. The resulting precipitate was collected by vacuum filtration and washed with cold MTBE to give (Z)-2-fluoro-N'-hydroxy-2-methylpropanimidamide (114.019 g, 949 mmol, 95% yield) as a white solid. The title compound contained about 1% by NMR of (Z)—N'-hydroxymethacrylimidamide. Mp: 101.9° C.; $^1$H NMR (400 MHz, CDCl$_3$) δ ppm 1.6 (d, 6H), 4.75 (brs, 2H), 7.55 (brs, 1H).

Example 1.5

Preparation of tert-Butyl 4-(3-(2-Fluoropropan-2-yl)-1,2,4-oxadiazol-5-yl)piperidine-1-carboxylate To a solution of 1-(tert-butoxycarbonyl)piperidine-4-carboxylic acid (85 g, 372 mmol) in acetonitrile (450 mL) was added di(1H-imidazol-1-yl)methanone (72.4 g, 447 mmol) at room temperature and the reaction mixture was heated at 45° C. for 1 h. The reaction was monitored by negative mode LC/MS. The reaction mixture was cooled down to room temperature and (Z)-2-fluoro-N'-hydroxy-2-methylpropanimidamide (44.7 g, 372 mmol) was added. The reaction mixture was stirred at room temperature for 1.5 h and the volatile organics were removed under vacuum. The residue was poured into a cold aqueous 1 M HCl solution (500 mL). The aqueous phase was extracted with ethyl acetate (3×250 mL). The organic layers were combined and rinsed with aqueous 1 M HCl solution (3×150 mL). The organic layers were combined and washed with saturated NaHCO$_3$ solution (2×100 mL) and brine. The organic phase was dried over sodium sulfate, filtered, and concentrated under reduced pressure to give (Z)-tert-butyl 4-(2-fluoro-1-(hydroxyimino)-2-methylpropylcarbamoyl)piperidine-1-carboxylate (114 g, 344 mmol, 92% yield) as a white solid.

A flask, containing (Z)-tert-butyl 4-(2-fluoro-1-(hydroxyimino)-2-methylpropylcarbamoyl)piperidine-1-carboxylate, was heated in a heating mantle at 115° C. for 16 h under reduced pressure. The reaction mixture was further dried at 50° C. under reduced pressure to give tert-butyl 4-(3-(2-fluoropropan-2-yl)-1,2,4-oxadiazol-5-yl)piperidine-1-carboxylate (94 g, 300 mmol, 81% yield) as a thick amber oil. Exact mass calculated for C$_{15}$H$_{24}$FN$_3$O$_3$: 313.37, found: LCMS m/z=314.2 [M+H]$^+$; $^1$H NMR (400 MHz, CDCl$_3$) δ ppm 1.46 (s, 9H), 1.75 (s, 3H), 1.77-1.90 (m, 5H), 2.02-2.11 (m, 2H), 2.89-3.01 (m, 2H), 3.06-3.16 (m, 1H), 4.04-4.14 (m, 2H).

Example 1.6

Preparation of tert-Butyl 4-(3-(2-Fluoropropan-2-yl)-1,2,4-oxadiazol-5-yl)piperidine-1-carboxylate Hydrochloride To a mixture of 4 M HCl solution in dioxane (244 mL, 975 mmol) cooled to 0° C. (external ice bath) was added tert-butyl 4-(3-(2-fluoropropan-2-yl)-1,2,4-oxadiazol-5-yl)piperidine-1-carboxylate (94 g, 300 mmol). The ice bath was removed and the reaction mixture was stirred at room temperature for 1 h. The reaction was monitored by LC/MS. The volatile organics were removed under reduced pressure to give a yellowish solid. The solids were triturated with tert-butyl methyl ether (MTBE) and collected by filtration to give 3-(2-fluoropropan-2-yl)-5-(piperidin-4-yl)-1,2,4-oxadiazole hydrochloride (70.1 g, 281 mmol, 94% yield) as a white solid. Exact mass calculated for C$_{10}$H$_{17}$ClFN$_3$O: 213.2, found: LCMS m/z=214.0 [M+H]$^+$; $^1$H NMR (400 MHz, DMSO-d$_6$) δ ppm 1.71-1.77 (d, T=20 Hz, 6H), 1.90-2.01 (m, 2H), 2.18-2.25 (m, 2H), 3.00-3.09 (m, 2H), 3.30-3.37 (m, 2H), 3.42-3.50 (m, 1H), 8.85 (brs, 1H), 9.02 (brs, 1H).

Example 1.7

Preparation of 5-(1-(6-Chloro-5-fluoropyrimidin-4-yl)piperidin-4-yl)-3-(2-fluoropropan-2-yl)-1,2,4-oxadiazoles To a suspension of 3-(2-fluoropropan-2-yl)-5-(piperidin-4-yl)-1,2,4-oxadiazole hydrochloride (45.0 g, 180 mmol) in acetonitrile was added diisopropylethylamine (94 mL, 541 mmol), followed by 4,6-dichloro-5-fluoropyrimidine (18.81 mL, 180 mmol). The reaction mixture was stirred at 40° C. for 1 h. The volatile organics were removed under vacuum to give a thick amber oil. The oil was poured into water and the product was extracted with ethyl acetate (2×250 mL). The organic layers were combined, dried over sodium sulfate, filtered, and concentrated under reduced vacuum to give a yellowish solid. This solid was purified by Biotage™ column chromatography (hexane:ethyl acetate gradient) to give 5-(1-(6-chloro-5-fluoropyrimidin-4-yl)piperidin-4-yl)-3-(2-fluoropropan-2-yl)-1,2,4-oxadiazole (40.4 g, 118 mmol, 65.2% yield) as a white solid. Exact mass calculated for C$_{14}$H$_{16}$ClF$_2$N$_5$O: 343.76, found: LCMS m/z=344.2 [M+H]$^+$; $^1$H NMR (400 MHz, CDCl$_3$) δ ppm 1.77-1.81 (d, J=20 Hz, 6H), 1.98-2.07 (m, 2H), 2.20-2.27 (m, 2H), 3.28-3.35 (m, 3H), 4.48-4.54 (m, 2H), 8.17 (s, 1H).

Example 1.8

Preparation of 4-Amino-3-fluoro-N,N-dimethylbenzamide

Method A

To a three-neck round-bottom flask, equipped with a mechanical stirrer, thermometer, and addition funnel, was added 4-amino-3-fluorobenzoic acid (40 g, 258 mmol), dimethylamine (520 mL, 1.04 mol), and dichloromethane (1 L). The reaction mixture was cooled in an ice-bath and 1-propanephosphonic acid cyclic anhydride (250 g, 393 mmol) was slowly added by addition funnel. After 1 h, the addition was complete and mixture was allowed to warm up to room temperature. After stirring overnight, the solution was concentrated under reduced pressure and the residue was extracted with dichloromethane and washed with an aqueous 2 M NaOH solution. The organic phases were dried over magnesium sulfate, filtered, and concentrated under reduced pressure. The residue was purified by Biotage™ column chromatography (hexane:ethyl acetate gradient) to give 4-amino-3-fluoro-N,N-dimethylbenzamide (31.9 g, 175 mmol, 67.9% yield) as a tan solid. Exact mass calculated for C$_9$H$_{11}$FN$_2$O 182.2, found: LCMS m/z=183.3 [M+H]$^+$; $^1$H NMR (400 MHz, CDCl$_3$) δ ppm 3.05 (s, 6H), 3.91 (brs, 2H), 6.76 (t, J=10 Hz, 1H), 7.07 (dt, J=8.15, 0.85 Hz, 1H), 7.13 (dd, J=11.43, 1.83 Hz, 1H).

Method B

4-Amino-3-fluorobenzoic acid (CAS #455-87-8, 221.85 g, 1.402 mol) was suspended in acetonitrile (1.80 L). To this suspension was added di(1H-imidazol-1-yl)methanone (250 g, 1.542 mol) at room temperature and the reaction bubbled and became a clear solution. The reaction mixture was cooled down to 0° C. then N-ethyl-N-isopropylpropan-2- amine (0.416 L, 2.383 mol) was added followed by dimethylamine hydrochloride (137 g, 1.682 mol). The reaction mixture was allowed to stir at room temp for 30 min. LCMS showed the reaction was complete. The solvent was removed under reduced pressure. The residue was taken up in DCM (2 L) and washed with 1 M HCl (2×2 L). The separation of the layers was difficult to observe due to the presence of some solids. The resulting mixture was filtered and the layers separated. The aqueous layer was back extracted with DCM (2×2 L). The organic layers were combined and dried ($Na_2SO_4$), filtered by vacuum filtration through a sintered glass funnel and solvent was removed under reduced pressure to give 270 g of a dark brown solid. To this solid was added a mixture of 2:1 toluene:hexane (2000 mL) and the mixture was heated to 45° C. to form a slurry. The resulting precipitate was collected by vacuum filtration and washed with 1:1 toluene:hexane (2 L) and with hexane (2 L). The resulting solid was dried (vacuum oven). The filtrate contained some of the product and the solvent was removed under reduced pressure and the slurry was repeated. The first batch was 196 g and the $2^{nd}$ batch contained 32.528 g. Both batches were the same by NMR and LC/MS and were combined to give 4-amino-3-fluoro-N,N-dimethylbenzamide (CAS #536748-06-8, 228.93 g, 1.257 mol, 90% yield) as a light brown solid. $^1$H NMR (400 MHz, DMSO-$d_6$) δ ppm 2.9 (s, 6H), 5.5 (s, 2H), 6.8 (t, 1H), 7.0 (dd, J=8.21, 1.9 Hz, 1H), 7.1 (dd, J=12.13, 1.8 Hz, 1H). Exact mass calculated for $C_9H_{11}FN_2O$ 182.2, found: LCMS m/z=183.2 [M+H]$^+$.

Example 1.9

Preparation of Ethyl 1-(6-Chloro-5-fluoropyrimidin-4-yl)piperidine-4-carboxylate To a three neck 5 L round bottom flask equipped with magnetic stirrer, and nitrogen flow, was charged the following: 4,6-dichloro-5-fluoropyrimidine (332.574 g, 1.992 mol) with the aid of Acetonitrile (2.6 L). The following were combined in an additional funnel: ethyl piperidine-4-carboxylate (CSA #1126-09-6, 0.316 L, 1.992 mol) and DIEA (0.522 L, 2.988 mol). The contents of the addition funnel were added slowly to the flask (exothermic). The addition funnel was rinsed with ACN. An LC/MS taken 30 min after completion of the addition and the reaction was determined to be complete. The solvent was removed under reduced pressure to obtain an oil residue. The residue was taken up in EtOAc (3.0 L) and washed with 1M HCl (2×2.0 L), washed with sat $NaHCO_3$ (1×2.0 L) and washed with sat NaCl (1 L). The organic layer was dried ($Na_2SO_4$), filtered by vacuum filtration through a glass fiber paper and solvent was removed under reduced pressure to give ethyl 1-(6-chloro-5-fluoropyrimidin-4-yl)piperidine-4-carboxylate (586.2 g, 2.037 mol, 102% yield) as a light yellow oil which was used without further purification. The title compound contained some EtOAc by NMR. Exact mass calculated for $C_{12}H_{15}ClFN_3O_2$ 287.08, found: LCMS m/z=288.4/290.2 [M+H]$^+$); $^1$H NMR (400 MHz, DMSO-$d_6$) δ ppm 1.2 (t, J=7.1 Hz, 3H), 1.6 (q, J=13.6, 3.8 Hz, 2H), 1.9 (dd, J=13.5, 3.7 Hz, 2H), 2.7-2.8 (m, 1H), 3.2-3.3 (m, 2H), 4.1 (q, J=7.2 Hz, 2H), 4.3 (d, 2H), 8.2 (d, J=1.5 Hz, 1H).

Example 1.10

Preparation of Ethyl 1-(6-(4-(Dimethylcarbamoyl)-2-fluorophenylamino)-5-fluoropyrimidin-4-yl)piperidine-4-carboxylate To a three neck 5 L round bottom flask equipped with overhead stirrer, nitrogen flow, and reflux condenser, was charged the following under $N_2$: ethyl 1-(6-chloro-5-fluoropyrimidin-4-yl)piperidine-4-carboxylate (362 g, 1.257 mol), 4-amino-3-fluoro-N,N-dimethylbenzamide (229 g, 1.257 mol), 1,1'-bis(di-t-butylphosphino)ferrocene (59.6 g, 126 mmol), cesium carbonate (491 g, 1.508 mol) and diacetoxypalladium (14.11 g, 62.8 mmol) with the aid of dioxane (2 L). The mixture was heated to 102° C. for 2 h. After 2 h the reaction was complete by LC/MS. The reaction mixture was allowed to cool down to room temperature. The mixture was diluted with EtOAc (2 L) and treated with a small amount of charcoal. This crude mixture was filtered through a pad of silica gel (12 cm height in 6 L filter funnel) and rinsed with additional EtOAc (6×2 L). The filtrate was concentrated under reduced pressure to dryness and dried under high vacuum to give ethyl 1-(6-(4-(dimethylcarbamoyl)-2-fluorophenylamino)-5-fluoropyrimidin-4-yl)piperidine-4-carboxylate (520.02 g, 1.2 mol, 95% yield) as a brown solid. Exact mass calculated for $C_{21}H_{25}F_2N_5O3$ 433.19, found: LCMS m/z=434.4 [M+H]$^+$). $^1$H NMR (400 MHz, DMSO-$d_6$) δ ppm 1.2 (t, J=7.2 Hz, 3H), 1.5-1.7 (m, 2H), 1.9 (dd, J=13.3, 3.4 Hz, 2H), 2.61-2.71 (m, 1H), 3.0 (s, 6H), 3.1 (t, J=11.2 Hz, 2H), 4.08 (q, J=7.07 Hz, 2H), 4.2 (d, J=13.4 Hz, 2H), 7.2 (dd, J=8.1, 1.5 Hz, 1H), 7.30 (dd, J=11.1, 1.8 Hz, 1H), 7.6 (t, J=8.1 Hz, 1H), 7.9 (d, J=1.8 Hz, 1H), 8.8 (s, 1H).

Example 1.11

Preparation of 1-(6-(4-(Dimethylcarbamoyl)-2-fluorophenylamino)-5-fluoropyrimidin-4-yl)piperidine-4-carboxylic acid To a three neck 5 L round bottom flask equipped with overhead stirrer and reflux condenser, was charged the following: ethyl 1-(6-(4-(dimethylcarbamoyl)-2-fluorophenylamino)-5-fluoropyrimidin-4-yl)piperidine-4-carboxylate (260 g, 0.6 mol) and triethylamine (251 mL, 1.8 mol) with the aid of MeCN (2 L) and water (40.8 mL). To this was added lithium bromide (521 g, 5.998 mol) portion wise (exothermic) maintaining the internal temperature under 50° C. The mixture was heated at 75° C. for 16 h. The mixture was filtered and the solid was washed with MeCN (2×1 L). The solid was dissolved in hot water (2 L) and the solution was cooled in an ice-bath. To the cold mixture was slowly added 10 N HCl (aqueous) by using dropping funnel to pH 1. The resulting precipitate was collected by vacuum filtration, washed with 1N HCl (aqueous) (1 L), and dried in an oven at 45° C. and under high vacuum to afford 1-(6-(4-(dimethylcarbamoyl)-2-fluorophenylamino)-5-fluoropyrimidin-4-yl)piperidine-4-carboxylic acid (231 g, 0.570 mol, 95% yield) as a light brown solid. Exact mass calculated for $C_{19}H_{21}F_2N_5O_3$ 405.16, found: LCMS m/z=406.4 [M+H]$^+$; $^1$H NMR (400 MHz, DMSO-$d_6$) δ ppm 1.5-1.7 (m, 2H), 1.9 (dd, J=13.4, 3.0 Hz, 2H), 2.5-2.6 (m, J=10.8, 10.8, 4.0, 3.9 Hz, 2H), 3.0 (s, 6H), 3.1 (t, J=11.2 Hz, 2H), 4.2 (d, J=13.39 Hz, 2H), 7.2 (dd, J=8.2, 1.6 Hz, 1H), 7.3 (dd, J=10.9, 1.8 Hz, 1H), 7.6 (t, J=8.1 Hz, 1H), 8.0 (d, J=1.3 Hz, 1H), 9.1 (brs, 1H), 11.3 (brs, 1H).

Example 1.12

Preparation of 3-Fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1)

Method A

To a suspension of 5-(1-(6-chloro-5-fluoropyrimidin-4-yl)piperidin-4-yl)-3-(2-fluoropropan-2-yl)-1,2,4-oxadiazole (1.0 g, 2.91 mmol) and 4-amino-3-fluoro-N,N-dimethylbenzamide (0.530 g, 2.91 mmol) in dioxane (9 mL) was added palladium(II) acetate (0.131 g, 0.582 mmol), 1,1'-bis(di-t-butylphosphino)ferrocene (0.552 g, 1.164 mmol), and cesium carbonate (3.32 g, 10.18 mmol) under nitrogen. The suspension was heated gradually to 95° C. in an oil bath and stirred at this temperature for 1 h. The reaction was quenched with water and the mixture was extracted with ethyl acetate. The organic layer was washed with water (2×50 mL), dried over magnesium sulfate, filtered, concentrated under reduced pressure, and purified by Biotage™ column chromatography (hexane:ethyl acetate gradient) to give 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (0.715 g, 1.461 mmol, 50.2% yield) as a light yellow solid. Exact mass calculated for $C_{23}H_{26}F_3N_7O_2$: 489.5, found: LCMS m/z=490.4 [M+H]$^+$; $^1$H NMR (400 MHz, CDCl$_3$) δ ppm 1.79 (d, J=20 Hz, 6H), 2.02 (dd, J=13.83, 3.85 Hz, 2H), 2.21 (dd, J=13.52, 3.66 Hz, 2H), 3.07 (brs, 6H), 3.19-3.40 (m, 3H), 4.36-4.56 (m, 2H), 6.86-7.02 (m, 1H), 7.18-7.32 (m, 2H), 8.14 (d, J=1.26 Hz, 1H), 8.55 (t, J=8.46 Hz, 1H).

Method B

To a three neck 5 L round bottom flask equipped with an overhead stirrer and nitrogen flow was charged the following: 1-(6-(4-(dimethylcarbamoyl)-2-fluorophenylamino)-5-fluoropyrimidin-4-yl)piperidine-4-carboxylic acid (340 g, 0.839 mol) and di(1H-imidazol-1-yl)methanone (143 g, 0.881 mol) with the aid of MeCN (2 L). After 5 min the reaction mixture became homogeneous. The reaction was allowed to continue for 30 min. LCMS at t=30 min (455.46 [M+H]$^+$) showed the activated acid reaction was complete. To the resulting mixture was added (Z)-2-fluoro-N'-hydroxy-2-methylpropanimidamide (106 g, 0.881 mol) and the reaction mixture was allowed to continue for 16 h. After 16 h the resulting precipitate was collected by vacuum filtration. The solid was washed with MeCN (2 L), followed by MTBE (2 L) and Hexane (2 L) and dried (vacuum oven) high vacuum and no heat to give (E)-1-(6-(4-(dimethylcarbamoyl)-2-fluorophenylamino)-5-fluoropyrimidin-4-yl)-N-(2-fluoro-1-(hydroxyimino)-2-methylpropyl)piperidine-4-carboxamide (330 g, 650 mmol, 78% yield) as an off-white solid. Exact mass calculated for $C_{23}H_{28}F_3N_7O_3$ 507.22, found: LCMS m/z=508.2 [M+H]$^+$); $^1$H NMR (400 MHz, DMSO-d$_6$) δ ppm 1.7 (s, 3H), 1.8 (s, 3H), 1.8-1.9 (m, 2H), 2.1 (dd, J=13.1, 2.8 Hz, 2H), 3.0 (s, 6H), 3.2-3.3 (m, 2H), 3.4-3.5 (m, J=11.0, 11.0, 4.0, 3.9 Hz, 1H), 4.3 (d, J=13.4 Hz, 2H), 7.2 (dd, J=8.2, 1.6 Hz, 1H), 7.3 (dd, J=11.0, 1.6 Hz, 1H), 7.6 (t, J=8.1 Hz, 1H), 7.9 (d, J=1.5 Hz, 1H), 8.8 (s, 1H).

The filtrate still contained some product by LC/MS. The solvent was removed under reduced pressure to give a black oil (250 g). The black oil was not combined with the solid but was instead heated to 90° C. under house vacuum for 16 h. After 16 h the reaction was complete and the solvent was removed under reduced pressure. The residue was diluted with EtOAc and passed through a silica plug using a 2 L coarse funnel with a 14 cm diameter and filled with 7 cm of silica. The product was eluted with 2 L of EtOAc to give 36 g of a pinkish solid. The solid was triturated with MTBE to give 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (19.2 g, 39.2 mmol, 4.68% yield) as a off-white solid, crop 2.

(E)-1-(6-(4-(dimethylcarbamoyl)-2-fluorophenylamino)-5-fluoropyrimidin-4-yl)-N-(2-fluoro-1-(hydroxyimino)-2-methylpropyl)piperidine-4-carboxamide (330 g, 650 mmol) was transferred to a 2 L round bottom flask and DMA (500 mL) was added. The reaction was heated to 110° C. for 4 h. The reaction was complete by LC/MS. The reaction was allowed to cool down to room temperature and diluted with MeCN. The resulting precipitate was collected by vacuum filtration to give 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (250 g, 511 mmol, 60.9% yield) as a white solid (crop 1). The filtrate still contained some product. The DMA and MeCN were removed under reduced pressure and the resulting precipitate was triturated with MTBE to give 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (96 g, 196 mmol, 23.38% yield) as a light brown solid (crop 3). All the crops of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide contained less then 6% of the starting material 1-(6-(4-(dimethylcarbamoyl)-2-fluorophenylamino)-5-fluoropyrimidin-4-yl)piperidine-4-carboxylic acid. To remove the starting material, each crop was dissolved (crop 2 and crop 3 were combined) in DMA (500 mL for crop 1, and 230 mL for combined crop 2,3) at 100° C. Once the solid was dissolved, aqueous saturated NaHCO$_3$ (500 mL for crop 1, and 230 mL for combined crop 2,3) was gently added to crash out the product. The mixture was diluted with DI water (1.250 L for crop 1, and 0.576 L for combined crop 2,3). The mixture was allowed to cool down to room temperature and the resulting precipitate was collected by vacuum filtration and washed with water to give 200 g as an off white solid (from crop 1) and 92.8 g as a light brown solid (from crop 2,3) for a total of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (292.8 g, 598 mmol, 71.3% yield).

3-Fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (281.8 g, 576 mmol) was taken up in DMA (600 mL) and heated to 100° C. in a 5 L three necked round bottomed flask attached to a mechanical stirrer. After all the solids went into solution, DI water (600 mL) was added gently. The reaction was then diluted with more DI water (1800 mL) to bring the total volume to 10× by weight. The resulting precipitate was collected by vacuum filtration and washed with water. The cake was allowed to dry under house vacuum on the fitted funnel. When the cake was mostly dried, it was dried further (vacuum oven) at 45° C. under high vacuum overnight to give 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (279.4 g, 571 mmol, 99% yield) as a tan solid.

Example 1.13

Preparation of 3-Fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide (Compound 2)

Step A: Preparation of Ethyl 3-Fluoro-4-(5-fluoro-6-(4-(3-(2-fluoropropan-2-yl)-1,2,4-oxadiazol-5-yl)piperidin-1-yl)pyrimidin-4-ylamino)benzoate A suspension of 5-(1-(6-chloro-5-fluoropyrimidin-4-yl)piperidin-4-yl)-3-(2-fluoropropan-2-yl)-1,2,4-oxadiazole (1.0 g, 2.91 mmol), ethyl 4-amino-3-fluorobenzoate (0.533 g, 2.91 mmol), diacetoxypalladium (0.098 g, 0.436 mmol), 1,1'-bis(di-t-butylphosphino)ferrocene (0.414 g, 0.873 mmol), and $Cs_2CO_3$ (2.464 g, 7.56 mmol) in dioxane (10 mL) was heated conventionally at 85° C. for 1 h. Reaction was quenched with water and extracted with AcOEt. The organic layer was concentrated to give a residue and the residue was purified by prep-HPLC. Fractions containing desired product were combined, basified with saturated $NaHCO_3$ (aq), partially concentrated under vacuum, and extracted with AcOEt. The organic layer was rinsed with brine, dried over sodium sulfate, filtered, and concentrated to give the title compound (1.0 g, 2.039 mmol, 70% yield). Exact mass calculated for $C_{23}H_{25}F_3N_6O_3$: 490.2, found: LCMS m/z=491.3 [M+H]$^+$; $^1$H NMR (400 MHz, CDCl$_3$) δ ppm 1.39 (t, J=7.07 Hz, 3H), 1.77 (s, 3H), 1.82 (s, 3H), 1.97-2.08 (m, 2H), 2.17-2.25 (m, 2H), 3.22-3.33 (m, 3H), 4.37 (q, J=7.07 Hz, 2H), 4.42-4.50 (m, 2H), 7.04-7.10 (m, 1H), 7.78 (dd, J=11.87, 1.89 Hz, 1H), 7.84-7.89 (m, 1H), 8.15-8.18 (m, 1H), 8.66 (t, J=8.46 Hz, 1H).

Step B: Preparation of 3-Fluoro-4-(5-fluoro-6-(4-(3-(2-fluoropropan-2-yl)-1,2,4-oxadiazol-5-yl)piperidin-1-yl)pyrimidin-4-ylamino)benzoic acid To a solution of ethyl 3-fluoro-4-(5-fluoro-6-(4-(3-(2-fluoropropan-2-yl)-1,2,4-oxadiazol-5-yl)piperidin-1-yl)pyrimidin-4-ylamino)benzoate (440 mg, 0.897 mmol) in a mixed solvent of MeOH (15 mL) and THF (5.0 mL) was added lithium hydroxide hydrate (188 mg, 4.49 mmol) and Water (5.0 mL). The mixture was stirred at room temperature overnight. The mixture was acidified with 1N HCl (aq) to pH 2-3 and concentrated in vacuo to remove the organic solvents. The solid was collected by vacuum filtration to give the title compound (394.3 mg, 0.853 mmol, 95% yield). Exact mass calculated for $C_{21}H_{21}F_3N_6O_3$: 462.2, found: LCMS m/z=463.4 [M+H]$^+$; $^1$H NMR (400 MHz, CDCl$_3$) δ ppm 1.77 (s, 3H), 1.82 (s, 3H), 1.98-2.07 (m, 2H), 2.19-2.23 (m, 2H), 3.23-3.34 (m, 3H), 4.43-4.51 (m, 2H), 7.16-7.20 (m, 1H), 7.83 (dd, J=11.87, 1.89 Hz, 1H), 7.90-7.94 (m, 1H), 8.17-8.19 (m, 1H), 8.71 (t, J=8.34 Hz, 1H), —OH was not observed.

Step C: Preparation of 3-Fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide (Compound 2)

To a solution of 3-fluoro-4-(5-fluoro-6-(4-(3-(2-fluoropropan-2-yl)-1,2,4-oxadiazol-5-yl)piperidin-1-yl)pyrimidin-4-ylamino)benzoic acid (73 mg, 0.158 mmol) and HATU (70 mg, 0.184 mmol) in DMF (2 mL), methanamine (315 µL, 0.630 mmol) was added. After stirring at room temperature for 1 h, mixture was purified by HPLC (5-95% $CH_3CN$). Fractions containing desired product were partly concentrated and residue was extracted with 1M NaOH and $CH_2Cl_2$. Organic phases were dried over $MgSO_4$, filtered, and concentrated to give the title compound (51.9 mg, 0.109 mmol, 69% yield). Exact mass calculated for $C_{22}H_{24}F_3N_7O_2$: 475.2, found: LCMS m/z=476.4 [M+H]$^+$; $^1$H NMR (400 MHz, CDCl$_3$) δ ppm 1.77 (s, 3H), 1.82 (s, 3H), 1.98-2.07 (m, 2H), 2.19-2.23 (m, 2H), 3.02 (d, J=4.80 Hz, 3H), 3.23-3.31 (m, 3H), 4.43-4.48 (m, 2H), 6.04-6.05 (m, 1H), 7.00-7.02 (m, 1H), 7.47-7.50 (m, 1H), 7.62 (dd, J=11.87, 1.89 Hz, 1H), 8.15 (d, J=1.39 Hz, 1H), 8.61 (t, J=8.34 Hz, 1H).

Example 1.14

Preparation of 3-Fluoro-4-(5-fluoro-6-(4-(3-(2-fluoropropan-2-yl)-1,2,4-oxadiazol-5-yl)piperidin-1-yl)pyrimidin-4-ylamino)benzamide (Compound 3)

To a suspension of 3-fluoro-4-(5-fluoro-6-(4-(3-(2-fluoropropan-2-yl)-1,2,4-oxadiazol-5-yl)piperidin-1-yl)pyrimidin-4-ylamino)benzoic acid (see Example 1.13, Step B, 50 mg, 0.108 mmol), ammonium chloride (17.35 mg, 0.324 mmol), and HATU (61.7 mg, 0.162 mmol) in DMF (2 mL) in a sealed tube was added N-ethyl-N-isopropylpropan-2-amine (0.094 mL, 0.541 mmol). The mixture was stirred at RT for 1 hr. The mixture was directly purified by prep HPLC. Pure fractions were combined, neutralized with saturated $NaHCO_3$ (aq), and evaporated MeCN to form a solid. The solid was collected by vacuum filtration to afford the title compound (22.5 mg, 0.049 mmol, 45.1% yield) as a white solid. Exact mass calculated for $C_{21}H_{22}F_3N_7O_2$: 461.2, found: LCMS m/z=462.4 (M+H$^+$); $^1$H NMR (400 MHz, CDCl$_3$) δ ppm 1.80 (d, J=21.5 Hz, 6H), 2.00-2.07 (m, 2H), 2.19-2.23 (m, 2H), 3.23-3.32 (m, 3H), 4.44-4.49 (m, 2H), 5.74 (bs, 2H), 7.06 (t, J=3.7 Hz, 1H), 7.55 (dd, J=8.6, 1.6 Hz, 1H), 7.66 (dd, J=11.9, 2.0 Hz, 1H), 8.16 (d, J=1.4 Hz, 1H), 8.66 (t, J=8.3 Hz, 1H).

Example 2

In Vivo Effects of 3-Fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1) on Glucose Homeostasis in Male Diabetic ZDF Rats (Oral Glucose Tolerance Test (oGTT))

Figure 2:
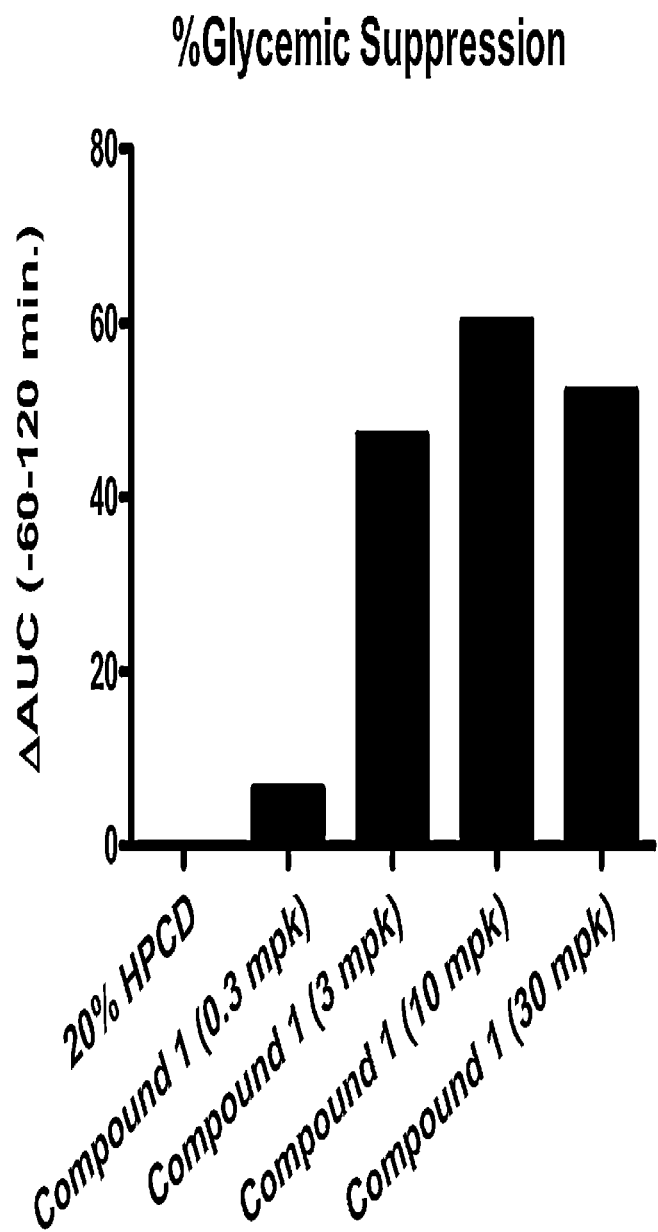
FIG. 2 shows the effects of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide on percent glycemic inhibition in male diabetic ZDF rats.

Male ZDF rats were fasted for 18 h and randomly grouped (n=6) to receive a GPR119 agonist, (Compound 1), at 0.3, 3, 10, or 30 mg/kg (mg compound per kg body weight). The compound was delivered orally via a gavage needle (p.o., volume 4 mL/kg) 60 min prior to glucose bolus (3 g/kg) (time=−60 min in FIG. 1), with a separate group receiving vehicle (20% hydroxypropyl-beta-cyclodextrin) as control. At time 0 min the glucose bolus was administered. Levels of blood glucose were assessed using a glucometer (One-Touch Ultra™ LifeScan) at time −60 minute (prior to compound administration), at 0 min (at time when glucose bolus was given), and at 30, 60, 90, and 120 min post glucose bolus. The plasma glucose concentration (mg/dL) at the different time points is shown in FIG. 1 and Table 1. Glucose excursion (AUC (area under the curve) reduction) in compound treated animals relative to vehicle control is shown in FIG. 2 and Table 2. These results demonstrated that the GPR119 agonist, 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1), lowered blood glucose after a challenge with glucose in diabetic ZDF rats.

TABLE 1

| | Plasma Glucose (mg/dL) | | | | | | | | | |
|---|---|---|---|---|---|---|---|---|---|---|
| | | | Compound 1 Dose (mg/kg) | | | | | | | |
| Time | 20% HPCD | | 0.3 | | 3.0 | | 10.0 | | 30.0 | |
| (min) | Mean | SEM | Mean | SEM | Mean | SEM | Mean | SEM | Mean | SEM |
| −60 | 106.7 | 3.2* | 106.3 | 5.7* | 110.0 | 5.2* | 108.7 | 3.1* | 104.8 | 4.8* |
| 0 | 93.2 | 4.8* | 89.7 | 3.0* | 82.7 | 3.0* | 76.0 | 3.0* | 93.0 | 4.1* |
| 30 | 217.7 | 14.7* | 201.7 | 17.7* | 184.5 | 15.0* | 174.0 | 19.3* | 197.0 | 23.6* |
| 60 | 197.3 | 16.2* | 192.2 | 21.7* | 144.2 | 12.5* | 135.8 | 11.5* | 124.8 | 10.8* |
| 90 | 182.3 | 17.7* | 185.3 | 15.0* | 151.2 | 8.9* | 141.3 | 10.2* | 135.8 | 6.7* |
| 120 | 163.0 | 10.3* | 154.8 | 13.2* | 146.2 | 4.6* | 132.5 | 7.9* | 130.2 | 6.7* |

*N = 6

TABLE 2

| Compound 1 Dose (mg/kg) | % Inhibition of Glucose Excursion |
|---|---|
| 0.3 | 6.5 |
| 3 | 47.0 |
| 10 | 60.1 |
| 30 | 52.1 |

Example 3

Figure 3:
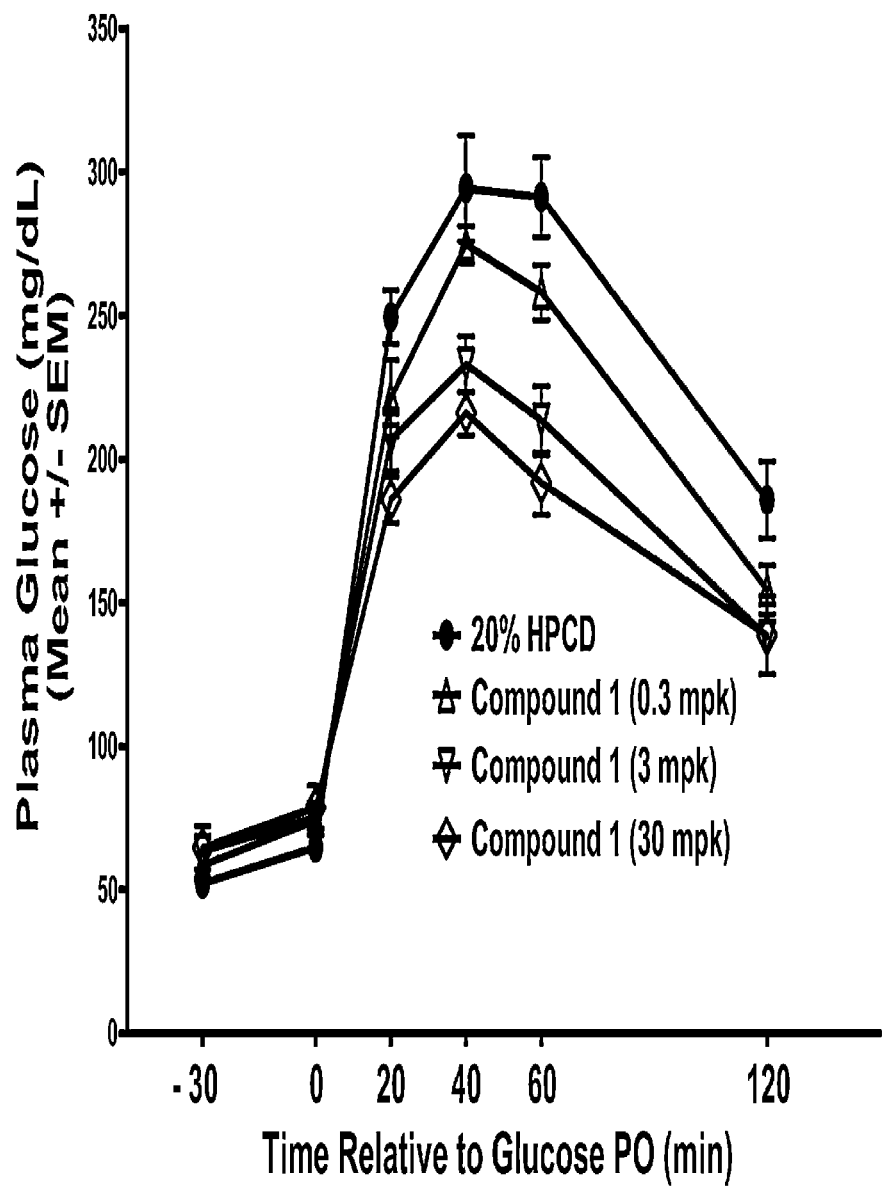
FIG. 3 shows the effects of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide on glucose homeostasis in male 129 SVE MICE (oGTT).
Figure 4:
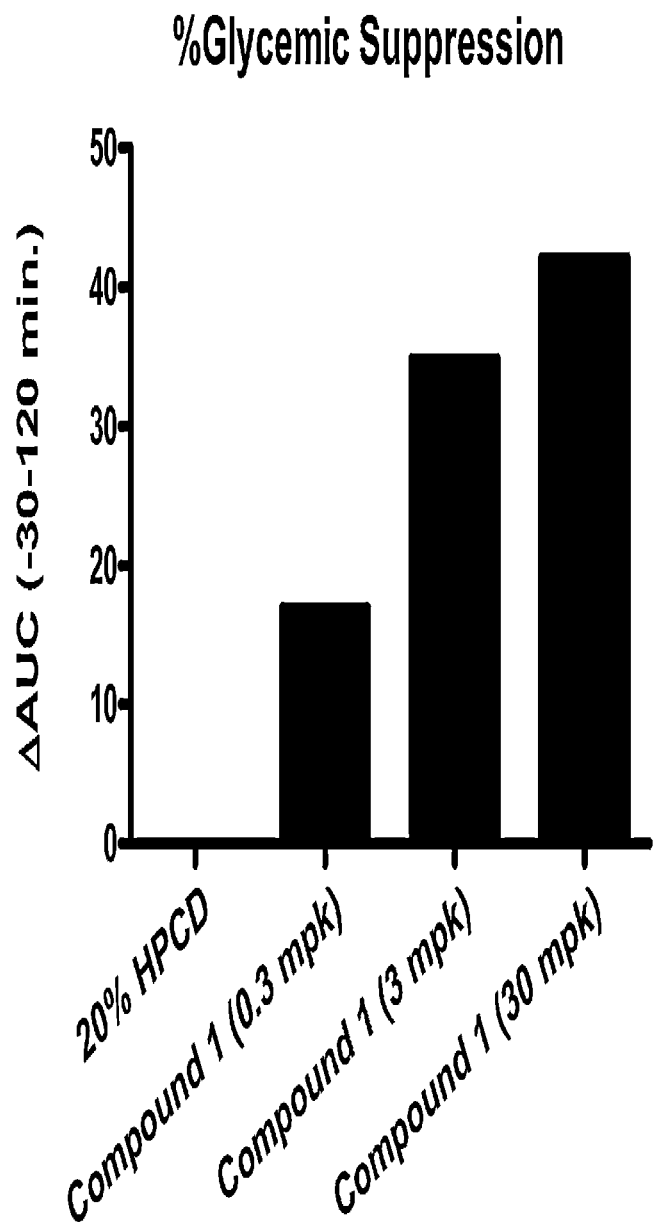
FIG. 4 shows the effects of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide on percent glycemic inhibition in male 129 SVE mice.

In Vivo Effects of 3-Fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1) on Glucose Homeostasis (Oral Glucose Tolerance Test (oGTT)) in Male 129SVE Mice Male 129SVE mice (approximately 8-week old) were fasted for 18 h and randomly grouped (n=6) to receive a GPR119 agonist, (Compound 1), at 0.3, 3, or 30 mg/kg (mg/kg body weight). The compound was delivered orally via a gavage needle (p.o., volume 4 mL/kg) 30 min prior to glucose bolus (3 g/kg) (time=−30 min in FIG. 3), with a separate group receiving vehicle (20% hydroxypropyl-beta-cyclodextrin) as control. At time 0 min. the glucose bolus was administered. Levels of blood glucose were assessed using a glucometer (One-Touch Ultra™, LifeScan) at time −30 minute (prior to compound administration), at 0 min (at time when glucose bolus was given), and at 20, 40, 60, 120 min post glucose bolus. The plasma glucose concentration (mg/dL) at the different time points is shown in FIG. 3 and Table 3. Glucose excursion (AUC (area under the curve) reduction) in compound treated animals relative to vehicle control is given in FIG. 4, and in Table 4. These results demonstrated that the GPR119 agonist, 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1), lowered blood glucose after a challenge with glucose in 129SVE mice.

TABLE 3

| | Plasma Glucose (mg/dL) | | | | | | | |
|---|---|---|---|---|---|---|---|---|
| | | | Compound 1 Dose (mg/kg) | | | | | |
| Time | 20% HPCD | | 0.3 | | 3.0 | | 30.0 | |
| (min) | Mean | SEM | Mean | SEM | Mean | SEM | Mean | SEM |
| −30 | 52.2 | 3.0* | 58.5 | 4.0* | 63.5 | 3.3* | 64.5 | 7.6* |
| 0 | 64.7 | 2.7* | 74.2 | 5.1* | 75.2 | 2.1* | 78.7 | 7.6* |
| 20 | 249.5 | 9.4* | 221.3 | 13.4* | 206.7 | 11.0* | 185.8 | 8.1* |
| 40 | 294.3 | 18.5* | 274.8 | 6.4* | 233.0 | 9.8* | 216.0 | 7.7* |
| 60 | 291.3 | 13.8* | 258.2 | 9.6* | 213.5 | 12.1* | 191.7 | 10.8* |
| 120 | 185.8 | 13.3* | 154.5 | 8.5* | 138.2 | 4.6* | 138.7 | 13.4* |

*N = 6

TABLE 4

| Compound 1 Dose (mg/kg) | % Inhibition of Glucose Excursion |
|---|---|
| 0.3 | 16.9 |
| 3 | 34.8 |
| 30 | 42.1 |

Example 4

Figure 5:
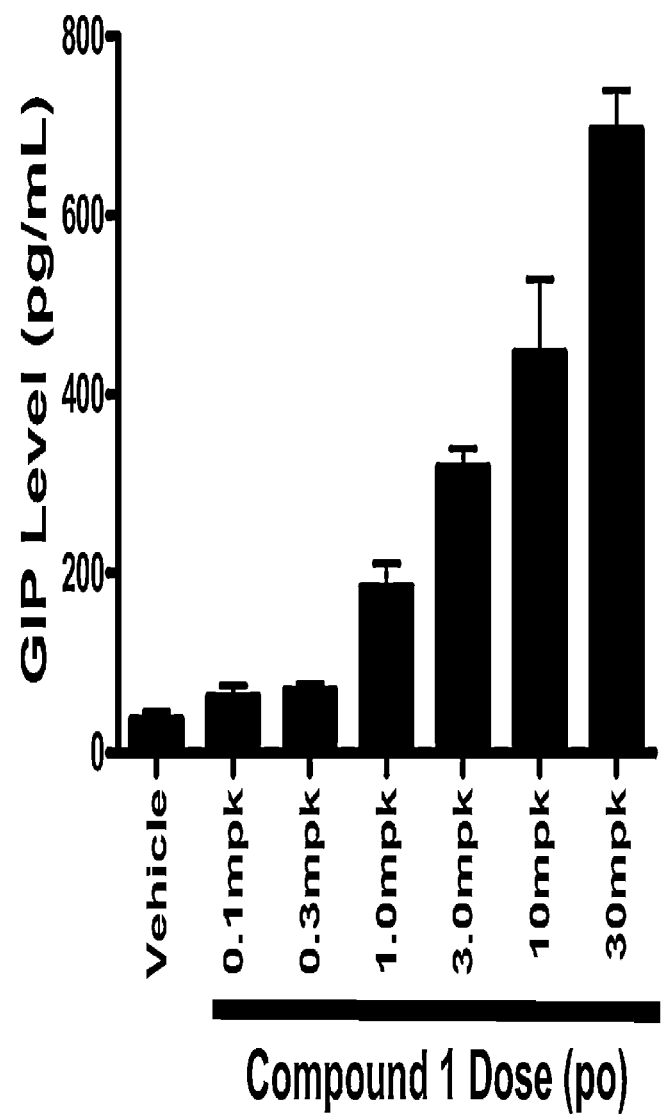
FIG. 5 shows the in vivo effects of 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide on incretin hormone GIP release.

In Vivo Effects of 3-Fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1) on Incretin Hormone GIP Release Male 129SVE mice (approximately 8-week old) were fasted for 18 h and randomly grouped (n=6) to receive a GPR119 agonist, (Compound 1), at an oral dose of 0.1, 0.3, 1, 3, 10, or 30 mpk (mg/kg body weight). Compounds were delivered orally via a gavage needle (p.o., volume 4 mL/kg), and after 45 min a blood sample was collected to determine plasma total GIP levels. A separate group received vehicle (PET: 80% PEG400, 10% ethanol, 10% Tween80) as control. Plasma GIP levels were determined using a Total GIP ELISA kit from Millipore. The results are shown in FIG. 5 and Table 5.

TABLE 5

| Compound 1 Dose (mg/kg) | Total Plasma GIP in Mice Total GIP, pg/mL |
|---|---|
| Vehicle | 36.01 |
| 0.1 | 60.92 |

TABLE 5-continued

| Compound 1 Dose (mg/kg) | Total Plasma GIP in Mice Total GIP, pg/mL |
|---|---|
| 0.3 | 68.21 |
| 1 | 183.8 |
| 3 | 318.5 |
| 10 | 444.8 |
| 30 | 695.0 |

Example 5

Homogeneous Time-Resolved Fluorescence (HTRF®) Assay for Direct cAMP Measurement The GPR119 agonist, Compound 1, was evaluated in an HTRF® cAMP detection assay according to the manufacturer's instructions (Cisbio, cAMP Dynamic 2 Assay Kit; #62AM4PEJ) using CHO-K1 cells stably expressing the GPR119 receptor. Briefly, CHO-K1 cells were transduced with a lentiviral vector encoding the nucleotide sequence of GPR119 (NCBI mRNA and protein reference sequences: NM_178471.2 & NP_848566, (GPR119 has also been referred to as Glucose-Dependent Insulinotropic Receptor (GDIR)). The N-terminus of the GPR119 nucleotide sequence was modified to replace the first, methionine-coding codon with a nucleotide sequence coding for a standard, nine amino acid, hemagglutinin tag. Following transduction, cells expressing the GPR119 receptor were isolated and a single clone was isolated following standard dilution-cloning procedures. On the day of the assay, cultured CHO-GPR119 cells were harvested, suspended in assay buffer and plated into 384-well assay plates (PerkinElmer Proxiplate #6008280) at a density of 2,000 cells per well. A cAMP standard curve was included on each plate. Test compounds were solubilized in DMSO, serially diluted in DMSO and then diluted in assay buffer before adding to the cells. Test compounds were evaluated in triplicate, using 10-point, 5-fold serial dilutions starting at 10 µM. The final DMSO concentration in the assay was 0.5%. Compounds and cells were incubated for 1 h at room temperature and then detection reagents were added to each well (cAMP-D2 in cell lysis buffer, followed by europium cryptate-labeled anti-cAMP antibody). Plates were then incubated at room temperature for 1 h prior to reading. Time-resolved fluorescence measurements were collected on PerkinElmer Envision™ or BMG Pherastar™ microplate readers. The compound N-(2-fluoro-4-(methylsulfonyl)phenyl)-6-(4-(3-isopropyl-1,2,4-oxadiazol-5-yl)piperidin-1-yl)-5-nitropyrimidin-4-amine was used as a positive control in each runset while assay buffer containing 0.5% DMSO was used as the negative control. Using the HTRF® assay, the $EC_{50}$ values for the following GPR119 agonists were observed:
3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1), 23.4 nM (n=32);
3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide (Compound 2), 27.0 nM (n=9); and
3-fluoro-4-(5-fluoro-6-(4-(3-(2-fluoropropan-2-yl)-1,2,4-oxadiazol-5-yl)piperidin-1-yl)pyrimidin-4-ylamino)benzamide (Compound 3), 28.2 nM (n=3).

Example 6

In Vivo and In Vitro Metabolism of 3-Fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide (Compound 1)

Example 6.1

In Vivo Metabolism of Compound 1

Metabolites of Compound 1 were identified in plasma samples collected from different pharmacokinetic studies in various species.

Four species, mouse, rat, dog and monkey were dosed with Compound 1, and plasma samples were collected at predetermined time points from each of the species according to specific study protocols. The samples were then processed and subjected to the LC/MS/MS analysis for the identification and quantification of the metabolites. Three metabolites, designated M1 (Compound 2), M2 (Compound 3), and M3 were identified in plasma samples from various species. The M1 metabolite was identified as a mono-N-demethylation of Compound 1, and the M2 metabolite was a di-N-demethylation product of Compound 1. The third metabolite M3 (i.e., 3-fluoro-4-(5-fluoro-6-(4-(3-(2-fluoropropan-2-yl)-1,2,4-oxadiazol-5-yl)piperidin-1-yl)pyrimidin-4-ylamino)benzoic acid, see below) was determined as a carboxylic acid of Compound 1.

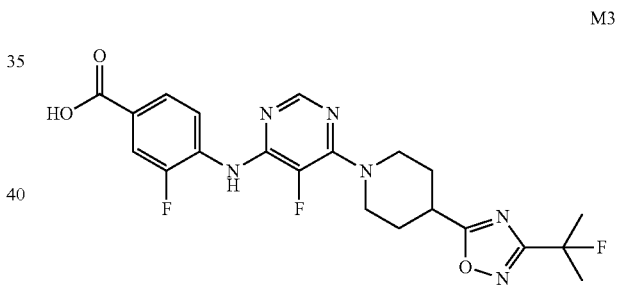

M3

Metabolites M1 and M2 were found to be pharmacologically active (see Example 5) whereas the M3 metabolite was shown to have substantially little activity ($EC_{50}$=100 µM, HTRF® assay). Quantification of these three metabolites showed that the order of formation was M3>M1>M2 in plasma samples. M3 was found to be the major circulating metabolite in all species. M2 was not observed in dog plasma samples under the analytical conditions used.

Example 6.2

In Vitro Metabolism of Compound 1 in Liver Microsomes from Various Species

Compound 1 was incubated with mouse, rat, dog, monkey and human liver microsomal protein (0.25 mg/mL final concentration) in 100 mM potassium phosphate buffer containing 3 mM $MgCl_2$ and 1 mM EDTA (pH 7.4) for over a period of time in the presence or absence of β-NADPH. The samples were then processed and the supernatant was analyzed by LC-MS/MS for the identification and quantification of the metabolites.

Figure 9:
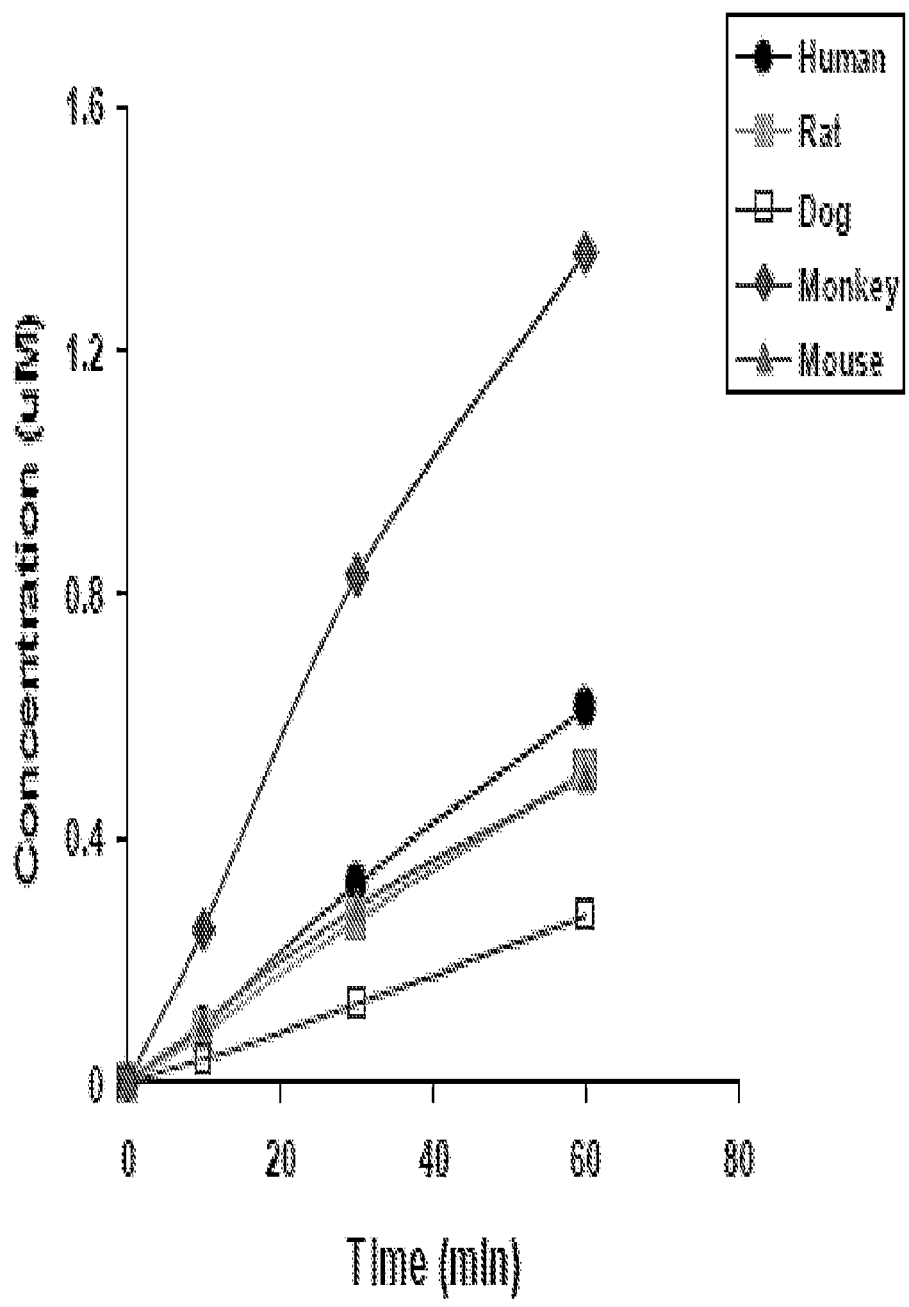
FIG. 9 shows M1 metabolite formation in liver microsomal incubation (mouse, monkey, dog, rat, and human).
Figure 10:
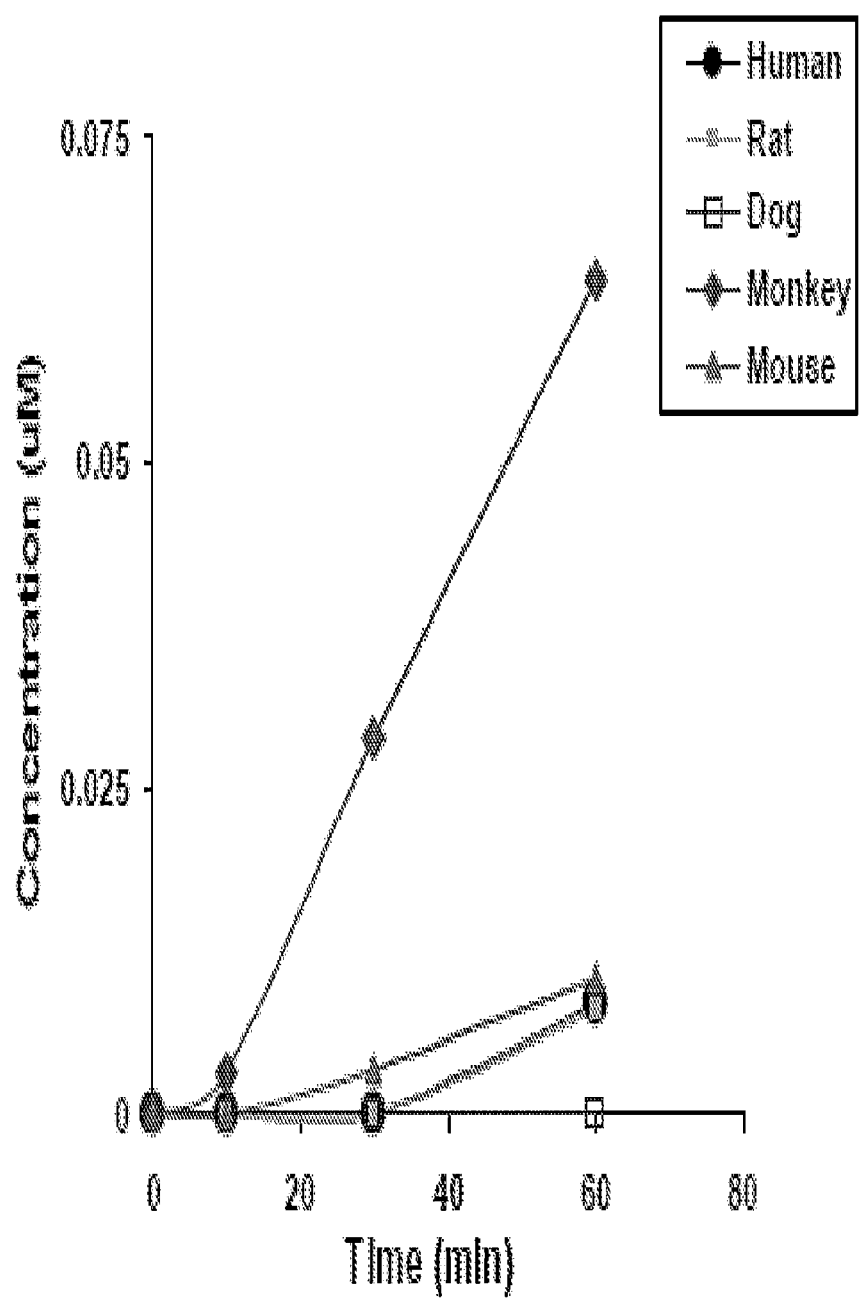
FIG. 10 shows M2 metabolite formation in liver microsomal incubation (mouse, monkey, dog, rat, and human).
Figure 11:
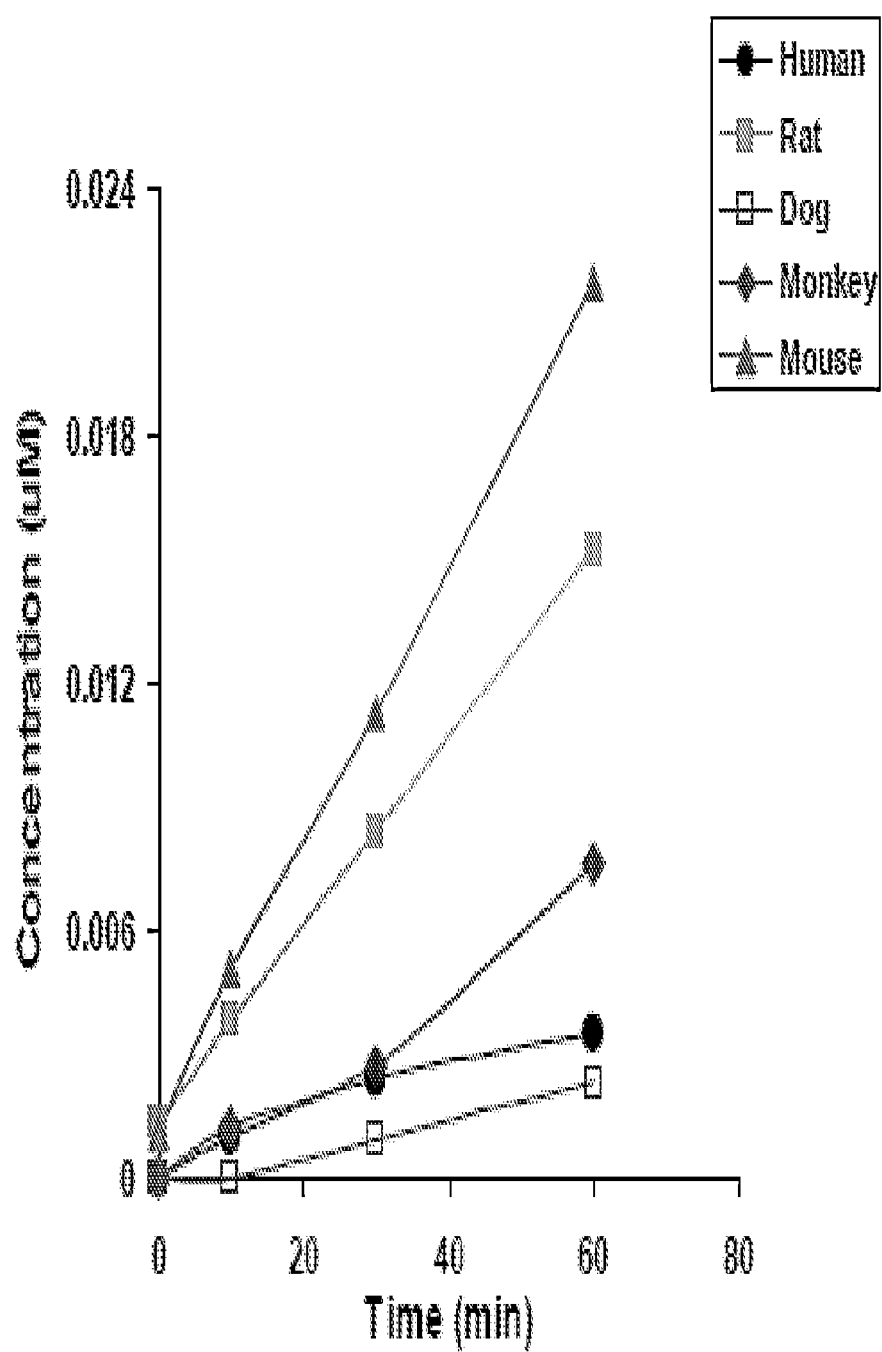
FIG. 11 shows M3 metabolite formation in liver microsomal incubation (mouse, monkey, dog, rat, and human).

Three metabolites, M1 (mono-N-demethylation), M2 (di-N-demethylation) and M3 (carboxylic acid), were identified in the microsomal incubation of all the species including human. Metabolites, M1, M2, and M3 were also quantified in liver microsomal incubations from all species. The rates of formation of these metabolites were varied across the species, however, the three metabolites observed in the liver microsomes of pre-clinical species were all found in human liver microsomes (FIGS. 9, 10, and 11). The rate of formation of M1 was highest followed by M2 and M3 under the in vitro experimental conditions used. M2 appeared to be a secondary metabolite of M1. Formation of M2 in dog liver microsomes was negligible.

Example 7

Powder X-Ray Diffraction

Powder X-ray Diffraction (PXRD) data were collected on an X'Pert PRO MPD powder diffractometer (PANalytical, Inc.) with a Cu source set at 45 kV and 40 mA, Cu(Kα) radiation and an X'Celerator detector. Samples were added to the sample holder and smoothed flat with a spatula and weigh paper. With the samples spinning, X-ray diffractogram was obtained by a 12-min scan over the range 5-40 °2θ. Diffraction data were viewed and analyzed with the X'Pert Data Viewer Software, version 1.0a and X'Pert HighScore Software, version 1.0b. The powder X-ray diffractogram for the anhydrous crystalline form of Compound 1 is shown in FIG. 6.

Example 8

Differential Scanning Calorimetry

Differential scanning calorimetry (DSC) studies were conducted using a TA Instruments, Q2000 at heating rate 10° C./min. The instruments were calibrated for temperature and energy using the melting point and enthalpy of fusion of an indium standard. Thermal events (desolvation, melting, etc.) were evaluated using Universal Analysis 2000 software, version 4.1D, Build 4.1.0.16. The DSC thermogram for the anhydrous crystalline form of Compound 1 is shown in FIG. 7.

Example 9

Thermal Gravimetric Analysis

Thermogravimetric analyses (TGA) were conducted using a TA Instruments TGA Q500 or Q5000 at heating rate 10° C./min. The instrument was calibrated using a standard weight for the balance, and Alumel and Nickel standards for the furnace (Curie point measurements). Thermal events such as weight-loss are calculated using the Universal Analysis 2000 software, version 4.1D, Build 4.1.0.16. The TGA thermogram for the anhydrous crystalline form of Compound 1 is shown in FIG. 7.

Example 10

Dynamic Moisture-Sorption Analysis

A dynamic moisture-sorption (DMS) study was conducted using a dynamic moisture-sorption analyzer, VTI Corporation, SGA-100. Samples were prepared for DMS analysis by placing 5 mg to 20 mg of a sample in a tared sample holder. The sample was placed on the hang-down wire of the VTI balance. A drying step was run, typically at 40° C. and 0.5-1% RH for 1 h. The isotherm temperature is 25° C. Defined % RH holds typically ranged from 10% RH to 90% RH, with intervals of 10 to 20% RH. A % weight change smaller than 0.010% over 10 min, or up to 2 h, whichever occurred first, was required before continuing to the next % RH hold. The water content of the sample equilibrated as described above was determined at each % RH hold. The dynamic moisture-sorption profile for the anhydrous crystalline form of Compound 1 is shown in FIG. 8.

Those skilled in the art will recognize that various modifications, additions, and substitutions to the illustrative examples set forth herein can be made without departing from the spirit of the invention and are, therefore, considered within the scope of the invention.

Citation of any reference throughout this application is not to be construed as an admission that such reference is prior art to the present application.

We claim:

1. A compound selected from the following compounds and pharmaceutically acceptable salts, solvates, and hydrates thereof:
   3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide;
   3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide; and
   3-fluoro-4-(5-fluoro-6-(4-(3-(2-fluoropropan-2-yl)-1,2,4-oxadiazol-5-yl)piperidin-1-yl)pyrimidin-4-ylamino)benzamide.

2. A compound according to claim 1 selected from 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide and pharmaceutically acceptable salts, solvates, and hydrates thereof.

3. A compound according to claim 1 selected from the following compounds and pharmaceutically acceptable salts, solvates, and hydrates thereof:
   3-fluoro-4-(5-fluoro-6-(4-(3-(2-fluoropropan-2-yl)-1,2,4-oxadiazol-5-yl)piperidin-1-yl)pyrimidin-4-ylamino)-N-methylbenzamide; and
   3-fluoro-4-(5-fluoro-6-(4-(3-(2-fluoropropan-2-yl)-1,2,4-oxadiazol-5-yl)piperidin-1-yl)pyrimidin-4-ylamino)benzamide.

4. A composition comprising a compound according to claim 2.

5. A composition comprising a compound according to claim 2 and a pharmaceutically acceptable carrier.

6. A method for preparing a composition comprising the step of admixing a compound according to claim 2 and a pharmaceutically acceptable carrier.

7. A composition comprising a compound according to claim 2 and a second pharmaceutical agent.

8. A method for preparing a composition comprising the step of admixing a compound according to claim 2 and a second pharmaceutical agent.

9. A pharmaceutical product selected from: a pharmaceutical composition, a formulation, a dosage form, a combined preparation, a twin pack, and a kit; wherein the product comprises a compound according to claim 2 and a second pharmaceutical agent.

10. A method for increasing the secretion of an incretin in an individual or increasing a blood incretin level in an individual, the method comprising administering to said individual in need thereof a therapeutically effective amount of a compound according to claim 2.

11. A method for the treatment of a disorder selected from: a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; the method comprising administering to said individual in need thereof a therapeutically effective amount of a compound according to claim 2.

12. A method for increasing the secretion of an incretin in an individual or increasing a blood incretin level in an individual, or for treating a disorder selected from a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; the method comprising administering to said individual in need thereof a compound according to claim 2 in combination with a second pharmaceutical agent.

13. A method for increasing the secretion of an incretin in an individual or increasing a blood incretin level in an individual, or for treating a disorder selected from a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; the method comprising prescribing to said individual in need thereof, a compound according to claim 2 in combination with a second pharmaceutical agent.

14. A method for treating type 2 diabetes in an individual, comprising administering to said individual in need thereof, a compound according to claim 2 in combination with a second pharmaceutical agent.

15. The method according to claim 14, wherein said compound and said second pharmaceutical agent are administered simultaneously.

16. The method according to claim 10, wherein said incretin is GLP-1.

17. The method according to claim 10, wherein said incretin is GIP.

18. The method according to claim 10, wherein said incretin is PYY.

19. A method of treating a condition characterized by low bone mass selected from: osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height, wherein the method comprises administering to an individual in need of such treatment an effective amount of a compound according to claim 2.

20. A method of treating a neurological disorder selected from: stroke and Parkinson's disease, wherein the method comprises administering to an individual in need of such treatment an effective amount of a compound according to claim 2.

21. A method of treating a metabolic-related disorder selected from: diabetes, type 1 diabetes, type 2 diabetes, inadequate glucose tolerance, impaired glucose tolerance, insulin resistance, hyperglycemia, hyperlipidemia, hypertriglyceridemia, hypercholesterolemia, dyslipidemia, atherosclerosis, stroke, syndrome X, hypertension, pancreatic beta-cell insufficiency, enteroendocrine cell insufficiency, glycosuria, metabolic acidosis, a cataract, diabetic nephropathy, diabetic neuropathy, peripheral neuropathy, diabetic coronary artery disease, diabetic cerebrovascular disease, diabetic peripheral vascular disease, diabetic retinopathy, metabolic syndrome, a condition related to diabetes, myocardial infarction, learning impairment, memory impairment, a neurodegenerative disorder, a condition ameliorated by increasing a blood GLP-1 level in an individual with a neurodegenerative disorder, excitotoxic brain damage caused by severe epileptic seizures, Alzheimer's disease, Parkinson's disease, Huntington's disease, prion-associated disease, stroke, motor-neuron disease, traumatic brain injury, spinal cord injury, and obesity, wherein the method comprises administering to an individual in need of such treatment an effective amount of a compound according to claim 2.

22. A method of treating type 2 diabetes, wherein the method comprises administering to an individual in need of such treatment an effective amount of a compound according to claim 2.

23. The method according to claim 14 wherein said second pharmaceutical agent is selected from: a DPP-IV inhibitor, a biguanide, an alpha-glucosidase inhibitor, an insulin analogue, a sulfonylurea, an SGLT2 inhibitor, a meglitinide, a thiazolidinedione, and an anti-diabetic peptide analogue.

24. The method according to claim 14, wherein said second pharmaceutical agent is a DPP-IV inhibitor selected from the following DPP-IV inhibitors and pharmaceutically acceptable salts, solvates, and hydrates thereof:

- 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one;
- 1-[2-(3-hydroxyadamant-1-ylamino)acetyl]pyrrolidine-2(S)-carbonitrile;
- (1S,3S,5S)-2-[2(S)-amino-2-(3-hydroxyadamantan-1-yl)acetyl]-2-azabicyclo[3.1.0]hexane-3-carbonitrile;
- 2-[6-[3(R)-aminopiperidin-1-yl]-3-methyl-2,4-dioxo-1,2,3,4-tetrahydropyrimidin-1-ylmethyl]benzonitrile;
- 8-[3(R)-aminopiperidin-1-yl]-7-(2-butynyl)-3-methyl-1-(4-methylquinazolin-2-ylmethyl)xanthine;
- 1-[N-[3(R)-pyrrolidinyl]glycyl]pyrrolidin-2(R)-yl boronic acid;
- 4(S)-fluoro-1-[2-[(1R,3S)-3-(1H-1,2,4-triazol-1-ylmethyl)cyclopentylamino]acetyl]pyrrolidine-2(S)-carbonitrile;
- 1-[(2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one;
- (2S,4S)-2-cyano-4-fluoro-1-[(2-hydroxy-1,1-dimethyl)ethylamino]acetylpyrrolidine;
- 8-(cis-hexahydro-pyrrolo[3,2-b]pyrrol-1-yl)-3-methyl-7-(3-methyl-but-2-enyl)-1-(2-oxo-2-phenylethyl)-3,7-dihydro-purine-2,6-dione;
- 1-((3S,4S)-4-amino-1-(4-(3,3-difluoropyrrolidin-1-yl)-1,3,5-triazin-2-yl)pyrrolidin-3-yl)-5,5-difluoropiperidin-2-one;
- (R)-2-((6-(3-aminopiperidin-1-yl)-3-methyl-2,4-dioxo-3,4-dihydropyrimidin-1(2H)-yl)methyl)-4-fluorobenzonitrile;
- 5-{(S)-2-[2-((S)-2-cyano-pyrrolidin-1-yl)-2-oxo-ethylamino]-propyl}-5-(1H-tetrazol-5-yl)10,11-dihydro-5H-dibenzo[a,d]cycloheptene-2,8-dicarboxylic acid bis-dimethylamide;
- ((2S,4S)-4-(4-(3-methyl-1-phenyl-1H-pyrazol-5-yl)piperazin-1-yl)pyrrolidin-2-yl)(thiazolidin-3-yl)methanone;

(2S,4S)-1-[2-[(4-ethoxycarbonylbicyclo[2.2.2]oct-1-yl)
amino]acetyl]-4-fluoropyrrolidine-2-carbonitrile;

6-[(3R)-3-amino-piperidin-1-yl]-5-(2-chloro-5-fluoro-
benzyl)-1,3-dimethyl-1,5-dihydro-pyrrolo[3,2-d]py-
rimidine-2,4-dione;

2-({6-[(3R)-3-amino-3-methylpiperidin-1-yl]-1,3-dim-
ethyl-2,4-dioxo-1,2,3,4-tetrahydro-5H-pyrrolo[3,2-d]
pyrimidin-5-yl}methyl)-4-fluorobenzonitrile;

(2S)-1-{[2-(5-methyl-2-phenyl-oxazol-4-yl)-ethyl-
amino]-acetyl}-pyrrolidine-2-carbonitrile;

(2S)-1-{[1,1-dimethyl-3-(4-pyridin-3-yl-imidazol-1-yl)-
propylamino]-acetyl}-pyrrolidine-2-carbonitrile;

(3,3-difluoropyrrolidin-1-yl)-((2S,4S)-4-(4-(pyrimidin-2-
yl)piperazin-1-yl)pyrrolidin-2-yl)methanone;

(2S,4S)-1-[(2S)-2-amino-3,3-bis(4-fluorophenyl)pro-
panoyl]-4-fluoropyrrolidine-2-carbonitrile;

(2S,5R)-5-ethynyl-1-{N-(4-methyl-1-(4-carboxy-pyri-
din-2-yl)piperidin-4-yl)glycyl}pyrrolidine-2-carboni-
trile; and (1S,6R)-3-{[3-(trifluoromethyl)-5,6-dihydro[1,2,4]tri-
azolo[4,3-a]pyrazin-7(8H)-yl]carbonyl}-6-(2,4,5-trif-
luorophenyl)cyclohex-3-en-1-amine.

25. The method according to claim 14, wherein said second pharmaceutical agent is a biguanide selected from the following biguanides and pharmaceutically acceptable salts, solvates, and hydrates thereof:
(phenylethyl)biguanide,
dimethylbiguanide,
butylbiguanide, and
1-(p-chlorophenyl)-5-isopropylbiguanide.

26. The method according to claim 14, wherein said second pharmaceutical agent is an alpha-glucosidase inhibitor selected from the following alpha-glucosidase inhibitors and pharmaceutically acceptable salts, solvates, and hydrates thereof:
(2R,3R,4R,5R)-4-((2R,3R,4R,5S,6R)-5-((2R,3R,4S,5S,
6R)-3,4-dihydroxy-6-methyl-5-((1S,4R,5S,6S)-4,5,6-
trihydroxy-3-(hydroxymethyl)cyclohex-2-enylamino)
tetrahydro-2H-pyran-2-yloxy)-3,4-dihydroxy-6-
(hydroxymethyl)tetrahydro-2H-pyran-2-yloxy)-2,3,5,
6-tetrahydroxyhexanal; and
(2R,3R,4R,5S)-1-(2-hydroxyethyl)-2-(hydroxymethyl)
piperidine-3,4,5-triol;
(1S,2S,3R,4S,5S)-5-(1,3-dihydroxypropan-2-ylamino)-1-
(hydroxymethyl)cyclohexane-1,2,3,4-tetraol.

27. The method according to claim 14, wherein said second pharmaceutical agent is a sulfonylurea selected from the following sulfonylureas and pharmaceutically acceptable salts, solvates, and hydrates thereof:
N-(4-(N-(cyclohexylcarbamoyl)sulfamoyl)phenethyl)-5-
methylpyrazine-2-carboxamide;
5-chloro-N-(4-(N-(cyclohexylcarbamoyl)sulfamoyl)
phenethyl)-2-methoxybenzamide; and
3-ethyl-4-methyl-N-(4-(N-((1r,4r)-4-methylcyclohexyl-
carbamoyl)sulfamoyl)phenethyl)-2-oxo-2,5-dihydro-
1H-pyrrole-1-carboxamide.

28. The method according to claim 14, wherein said second pharmaceutical agent is an SGLT2 inhibitor selected from the following SGLT2 inhibitors and pharmaceutically acceptable salts, solvates, and hydrates thereof:
(2S,3R,4R,5S,6R)-2-(4-chloro-3-(4-ethoxybenzyl)phe-
nyl)-6-(hydroxymethyl)tetrahydro-2H-pyran-3,4,5-
triol;
ethyl ((2R,3S,4S,5R,6S)-3,4,5-trihydroxy-6-(4-(4-iso-
propoxybenzyl)-1-isopropyl-5-methyl-1H-pyrazol-3-
yloxy)tetrahydro-2H-pyran-2-yl)methyl carbonate; and
ethyl ((2R,3S,4S,5R,6S)-3,4,5-trihydroxy-6-(2-(4-
methoxybenzyl)phenoxy)tetrahydro-2H-pyran-2-yl)
methyl carbonate.

29. The method according to claim 14, wherein said second pharmaceutical agent is a meglitinide selected from the following meglitinides and pharmaceutically acceptable salts, solvates, and hydrates thereof:
(S)-2-ethoxy-4-(2-(3-methyl-1-(2-(piperidin-1-yl)phenyl)
butylamino)-2-oxoethyl)benzoic acid;
(R)-2-((1r,4R)-4-isopropylcyclohexanecarboxamido)-3-
phenylpropanoic acid; and
(S)-2-benzyl-4-((3aR,7aS)-1H-isoindol-2(3H,3aH,4H,
5H,6H,7H,7aH)-yl)-4-oxobutanoic acid.

30. The method according to claim 14, wherein said compound and said second pharmaceutical agent are administered separately or sequentially.

31. A method for increasing the secretion of an incretin in an individual or increasing a blood incretin level in an individual, or for treating a disorder selected from a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; the method comprising prescribing to said individual in need thereof, a compound according to claim 2.

32. A method according to claim 13, comprising determining that the individual is in need of the treatment prior to said prescribing.

33. A method according to claim 31, comprising determining that the individual is in need of the treatment prior to said prescribing.

34. A method for increasing the secretion of an incretin in an individual or increasing a blood incretin level in an individual, or for treating a disorder selected from a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; the method comprising prescribing to said individual in need thereof, a compound selected from 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide and pharmaceutically acceptable salts, solvates, and hydrates thereof, in combination with a second pharmaceutical agent, wherein the prescribing causes the compound to be administered to the individual.

35. A method for increasing the secretion of an incretin in an individual or increasing a blood incretin level in an individual, or for treating a disorder selected from a GPR119-receptor-related disorder; a condition ameliorated by increasing secretion of an incretin; a condition ameliorated by increasing a blood incretin level; a condition characterized by low bone mass; a neurological disorder; a metabolic-related disorder; and obesity; in an individual; the method comprising prescribing to said individual in need thereof, a compound from 3-fluoro-4-(5-fluoro-6-(4-(3-(2-fluoropropan-2-yl)-1,2,4-oxadiazol-5-yl)piperidin-1-yl)pyrimidin-4-ylamino)-N,N-dimethylbenzamide and pharmaceutically acceptable salts, solvates, and hydrates thereof, wherein the prescribing causes the compound to be administered to the individual.

* * * * *

UNITED STATES PATENT AND TRADEMARK OFFICE
CERTIFICATE OF CORRECTION

PATENT NO. : 10,894,787 B2  
APPLICATION NO. : 13/825601  
DATED : January 19, 2021  
INVENTOR(S) : Robert M. Jones et al.

Page 1 of 1

It is certified that error appears in the above-identified patent and that said Letters Patent is hereby corrected as shown below:

On the Title Page

Column 2, (57) Abstract, Line 4, delete "N-imethylbenzamide;" and insert
-- N-dimethylbenzamide; --.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*